(12) United States Patent
Dhanya et al.

(10) Patent No.: US 10,099,993 B2
(45) Date of Patent: Oct. 16, 2018

(54) METABOTROPIC GLUTAMATE RECEPTOR POSITIVE ALLOSTERIC MODULATORS (PAMS) AND USES THEREOF

(71) Applicant: Sanford-Burnham Medical Research Institute, La Jolla, CA (US)

(72) Inventors: Raveendra Panickar Dhanya, La Jolla, CA (US); Douglas J. Sheffler, La Jolla, CA (US); Nicholas D. P. Cosford, La Jolla, CA (US); Russell Dahl, La Jolla, CA (US)

(73) Assignee: SANFORD-BURNHAM MEDICAL RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 15/301,697

(22) PCT Filed: Apr. 6, 2015

(86) PCT No.: PCT/US2015/024554
§ 371 (c)(1),
(2) Date: Oct. 3, 2016

(87) PCT Pub. No.: WO2015/157187
PCT Pub. Date: Oct. 15, 2015

(65) Prior Publication Data
US 2017/0036987 A1 Feb. 9, 2017

Related U.S. Application Data

(60) Provisional application No. 61/975,870, filed on Apr. 6, 2014.

(51) Int. Cl.
| | |
|---|---|
| C07C 65/40 | (2006.01) |
| C07D 257/04 | (2006.01) |
| C07D 271/06 | (2006.01) |
| C07C 259/10 | (2006.01) |
| C07C 311/51 | (2006.01) |
| C07C 235/46 | (2006.01) |
| C07C 235/54 | (2006.01) |
| C07D 213/79 | (2006.01) |
| C07D 213/80 | (2006.01) |
| C07D 239/26 | (2006.01) |
| C07D 241/12 | (2006.01) |
| C07D 271/07 | (2006.01) |
| C07D 285/08 | (2006.01) |
| C07D 295/108 | (2006.01) |
| C07D 213/50 | (2006.01) |
| C07D 213/68 | (2006.01) |
| C07D 213/70 | (2006.01) |
| C07D 307/42 | (2006.01) |
| C07D 307/68 | (2006.01) |
| C07F 7/02 | (2006.01) |
| C07D 213/64 | (2006.01) |
| C07C 49/84 | (2006.01) |

(Continued)

(52) U.S. Cl.
CPC .............. *C07C 65/40* (2013.01); *C07C 49/84* (2013.01); *C07C 59/90* (2013.01); *C07C 69/92* (2013.01); *C07C 235/46* (2013.01); *C07C 235/54* (2013.01); *C07C 251/48* (2013.01); *C07C 255/56* (2013.01); *C07C 259/10* (2013.01); *C07C 311/51* (2013.01); *C07D 213/50* (2013.01); *C07D 213/55* (2013.01); *C07D 213/64* (2013.01); *C07D 213/68* (2013.01); *C07D 213/70* (2013.01); *C07D 213/79* (2013.01); *C07D 213/80* (2013.01); *C07D 239/26* (2013.01); *C07D 241/12* (2013.01); *C07D 241/24* (2013.01); *C07D 257/04* (2013.01); *C07D 271/06* (2013.01); *C07D 271/07* (2013.01); *C07D 277/24* (2013.01); *C07D 285/08* (2013.01); *C07D 285/12* (2013.01); *C07D 295/108* (2013.01); *C07D 295/16* (2013.01); *C07D 295/26* (2013.01); *C07D 307/42* (2013.01); *C07D 307/54* (2013.01); *C07D 307/68* (2013.01); *C07D 311/16* (2013.01); *C07D 333/24* (2013.01); *C07F 5/025* (2013.01); *C07F 5/04* (2013.01); *C07F 7/025* (2013.01); *C07C 2601/02* (2017.05); *C07C 2601/08* (2017.05)

(58) Field of Classification Search
CPC ......... C07D 65/38; C07D 65/40; C07D 65/42
See application file for complete search history.

(56) References Cited

U.S. PATENT DOCUMENTS 7,790,760 B2 9/2010 Cacciola et al.
8,748,632 B2 6/2014 Cosford et al.

FOREIGN PATENT DOCUMENTS

WO WO-2004018386 A2 3/2004
WO WO-2006014918 A2 2/2006

(Continued)

OTHER PUBLICATIONS

B.A. Rowe et al., 326 The Journal of Pharmacology and Experimental Therapeutics, 240-251 (2008).*

(Continued)

*Primary Examiner* — Alexander R Pagano
(74) *Attorney, Agent, or Firm* — Wilson, Sonsini, Goodrich & Rosati

(57) ABSTRACT

Provided herein are small molecule active metabotropic glutamate subtype-2 and -3 receptor positive allosteric modulators (PAMS), compositions comprising the compounds, and methods of using the compounds and compositions comprising the compounds.

24 Claims, 5 Drawing Sheets

(51) Int. Cl.

| | | |
|---|---|---|
| C07C 59/90 | (2006.01) | |
| C07C 69/92 | (2006.01) | |
| C07C 251/48 | (2006.01) | |
| C07C 255/56 | (2006.01) | |
| C07D 213/55 | (2006.01) | |
| C07D 241/24 | (2006.01) | |
| C07D 277/24 | (2006.01) | |
| C07D 285/12 | (2006.01) | |
| C07D 295/16 | (2006.01) | |
| C07D 295/26 | (2006.01) | |
| C07D 307/54 | (2006.01) | |
| C07D 311/16 | (2006.01) | |
| C07D 333/24 | (2006.01) | |
| C07F 5/02 | (2006.01) | |
| C07F 5/04 | (2006.01) | |

(56) References Cited

FOREIGN PATENT DOCUMENTS

| | | |
|---|---|---|
| WO | WO-2006015158 A1 | 2/2006 |
| WO | WO-2006057860 A1 | 6/2006 |
| WO | WO-2015157187 A1 | 10/2015 |

OTHER PUBLICATIONS

D.J. Cook et al., 483 Nature 213-218 (2012).*
S. Judge et al., 111 Pharmacology & Therapeutics, 224-259 (2006).*
V. Brinkmann et al., 9 Nature Reviews | Drug Discovery, 883-897 (2010).*
J.M. Zakrzewska et al., 87 Postgraduate medical journal, 410-416 (2011).*
G.A. Higgins et al., 46 Neuropharmacology, 907-917 (2004).*
M.J. Fell et al., 326 The Journal of Pharmacology and Experimental Therapeutics, 209-217 (2008).*
F. Caraci et al., 79 Molecular Pharmacology, 618-626 (2011).*
G. Marek et al., 4 Current Opinion in Pharmacology, 18-22 (2004).*
L.M. Rorick-Kehn et al., 316 The Journal of Pharmacology and Experimental Therapeutics, 905-913 (2005).*
J.T. O'Brien et al., 2 The Lancet Neurology, 89-98, 96 (2003).*
Adewale et al. Pharmacological stimulation of group II metabotropic glutamate receptors reduces Cocaine self-administration and cocaine-induced reinstatement of drug seeking in squirrel monkeys. J Pharmacol Exp Ther 318:922-931 (2006).
Ahnaou et al. Modulation of group II metabotropic glutamate receptor (mGlu2) elicits common changes in rat and mice sleep-wake architecture. Eur J Pharmacol 603:62-72 (2009).
Allen et al. Group II metabotropic glutamate receptor activation attenuates traumatic neuronal injury and improves neurological recovery after traumatic brain injury. J Pharmacol Exp Ther 290:112-120 (1999).
Anwyl. Metabotropic glutamate receptors: electrophysiological properties and role in plasticity. Brain Res Brain Res Rev 29:83-120 (1999).
Aujla et al. Rats with extended access to cocaine exhibit increased stress reactivity and sensitivity to the anxiolytic-like effects of the mGluR 2/3 agonist LY379268 during abstinence. Neuropsychopharmacology 33(8):1818-1826 (2008).
Baptista et al. Preferential effects of the metabotropic glutamate 2/3 receptor agonist LY379268 on conditioned reinstatement versus primary reinforcement: comparison between cocaine and a potent conventional reinforcer. J Neurosci 24:4723-4727 (2004).
Bonnefous et al. Allosteric potentiators of the metabotropic glutamate subtype 2 receptor. (7 pgs.) (2000).
Bonnefous et al. Biphenyl-indanones: allosteric potentiators of the metabotropic glutamate subtype 2 receptor. Bioorg Med Chem Lett 15(19):4354-4358 (2005).

Bossert et al. The mGluR 2/3 agonist. LY379268 attenuates context- and discrete cue-induced reinstatement of sucrose seeking but not sucrose self-administration in rats. Behav Brain Res 173:148-152 (2006).
Cartmell et al. Regulation of neurotransmitter release by metabotropic glutamate receptors. J. Neurochem 75:889-907 (2000).
Cartmell et al. The metabotropic glutamate 2/3 receptor agonists LY354740 and LY379268 selectively attenuate phencyclidine versus d-amphetamine motor behaviors in rats. J Pharmacol Exp Thor 291:161-170 (1999).
Chaki et al. mGlu2/3 and mGlu5 receptors: potential targets for novel antidepressants. Neuropharmacology 66:40-52 (2013).
Conn et al. Activation of metabotropic glutamate receptors as a novel approach for the treatment of schizophrenia. Trends Pharmacyl Sci. 30:25-31 (2009).
Corti et al. The use of knock-out mice unravels distinct roles for mGlu2 and mGlu3 metabotropic glutamate receptors in mechanisms of neurodegeneration/neuroprotection. J Neurosci 27:8297-8308 (2007).
Cube et al. 3-(2-Ethoxy-4-{4-[3-hydroxy-2-methyl-4-(3-methylbutanoyl)phenoxy]butoxy}phenyl)propanoic acid: a brain penetrant allosteric potentiator at the metabotropic glutamate receptor 2 (mGluR2). Bioorg Med Chem Lett 15:2389-2393 (2005).
Dhanya et al. Design and synthesis of an orally active metabotropic glutamate receptor subtype-2 (mGluR2) positive allosteric modulator (PAM) that decreases cocaine self-administration in rats. J Med Chem 54:342-353 (2011).
Dhanya et al. Design and synthesis of systemically active metabotropic glutamate subtype-2 and -3 (mGlu 2/3) receptor positive allosteric modulators (PAMs): pharmacological characterization and assessment in a rat model of cocaine dependence. J Med Chem 57(10):4154-4172 (2014).
Dominguez et al. Methyl substitution of 2-aminobicyclo[3.1.0]hexane 2,6-dicarboxylate (LY354740) determines functional activity at metabotropic glutamate receptors: identification of a subtype selective mGlu2 receptor agonist. J Med Chem 48:3605-3612 (2005).
Duplantier et al. 3-Benzyl-1,3-oxazolidin-2-ones as mGluR2 positive allosteric modulators: Hit-to lead and lead optimization. Bioorg Med Chem Lett 19(9):2524-2529 (2009).
Fell et al. N-(4-((2-(trifluoromethyl)-3-hydroxy-4-(isobutyryl)phenoxy)methyl)benzyl)-1-methyl-1H-imidazole-4-carboxamide (THIIC), a novel metabotropic glutamate 2 potentiator with potential anxiolytic/antidepressant properties: in vivo profiling suggests a link between behavioral and central nervous system neurochemical changes. J Pharmacol Exp Ther 336:165-177 (2011).
Flor et al. Neuroprotective activity of metabotropic glutamate receptor ligands. Adv Exp Med Biol 513:197-223 (2002).
Galici et al. Biphenyl-indanone A, a positive allosteric modulator of the metabotropic glutamate receptor subtype 2, has antipsychotic- and anxiolytic-tike effects in mice. J Pharmacol Exp Thor 318(1):173-185 (2006).
Govek et al. Benzazoles as allosteric potentiators of metabotropic glutamate receptor 2 (mGluR2): efficacy in an animal model for schizophrenia. Bioorg Med Chem Lett 15:4068-4072 (2005).
Hanna et al. Differentiating the roles of mGlu2 and mGlu3 receptors using LY541850, an mGlu2 agonist/mGlu3 antagonist. Neuropharmacology 66:114-121 (2013).
Hempstapat et al. A novel class of positive allosteric modulators of metabotropic glutamate receptor subtype 1 interact with a site distinct from that of negative allosteric modulators. Mol Pharmacol 70:616-626 (2006).
Jin et al. The mGluR2 positive allosteric modulator BINA decreases cocaine self-administration and cue-induced cocaine-seeking and counteracts cocaine-induced enhancement of brain reward function in rats. Neurophyschopharmacology 35:2021-2036 (2010).
Johnson et al. Discovery of allosteric potentiators for the metabotropic glutamate 2 receptor: synthesis and subtype selectivity of N-(4-(2-methoxyphenoxy)phenyl)-N-(2,2,2-trifluoroethylsulfonyl)pyrid-3-ylmethylamine. J Med Chem 46:3189-3192 (2003).
Kenny et al. The ups and downs of addiction: role of metabotropic glutamate receptors. Trends Pharmacol Sci 25:265-272 (2004).

(56) References Cited

OTHER PUBLICATIONS

Krystal et al. Potential psychiatric applications of metabotropic glutamate receptor agonists and antagonists. CNS Drugs 24:669-693 (2010).
Liechti et al. Metabotropic glutamate 2/3 receptors in the ventral tegmental area and the nucleus accumbens shell are involved in behaviors relating to nicotine dependence. J Neurosci 27:9077-9085 (2007).
Melancon et al. Allosteric modulation of seven transmembrane spanning receptors: theory, practice, and opportunities for central nervous system drug discovery. J Med Chem 55:1445-1464 (2012).
Monn et al. Synthesis, pharmacological characterization, and molecular modeling of heterobicyclic amino acids related to (+)-2-aminobicyclo[3.1.0] hexane-2,6-dicarboxylic acid (LY354740): identification of two new potent, selective, and systemically active agonists for group II metabotropic glutamate receptors. J Med Chem 42:1027-1040 (1999).
Morishima et al. Enhanced cocaine responsiveness and impaired motor coordination in metabotropic glutamate receptor subtype 2 knockout mice. PNAS USA 102:4170-4175 (2005).
Murray et al. Evaluation of the mGluR 2/3 agonist LY379268 in rodent models of Parkinson's disease. Pharmacol Biochem Behav 73:455-466 (2002).
Niswender et al. A novel assay of Gi/o-linked G protein-coupled receptor coupling to potassium channels provides new insights into the pharmacology of the group III metabotropic glutamate receptors. Mol Pharmacol 73:1213-1224 (2008).
PCT/US2015/024554 International Preliminary Report on Patentability dated Oct. 20, 2016.
PCT/US2015/024554 International Search Report and Written Opinion dated Jul. 16, 2015.
Peters et al. The group II metabotropic glutamate receptor agonist, LY379268, inhibits both cocaine- and food-seeking behavior in rats. Psychopharmacology (Beg) 186:143-149 (2006).
Pinkerton et al. Allosteric potentiators of the metabotropic glutamate receptor 2 (mCilu2). Part 1: Identification and synthesis of phenyl-tetrazolyl acetophenones. Bioorg Med Chem Lett 14:5329-5332 (2004).
Pinkerton et al. Allosteric Potentiators of the Metabotropic Glutamate Receptor 2 (mGglu2). Part 4: Synthesis and Biological Activity of 4-Thiopyridyl Indanone mGgluR2 Potentiators. (6 pgs.) (2003).
Pinkerton et al. Allosteric potentiators of the metabotropic glutamate receptor 2 (mGlu2). Part 2: 4-thiopyridyl acetophenones as non-tetrazole containing mGlu2 receptor potentiators. Bioorg Med Chem Lett 14(23):5867-5872 (2004).
Pinkerton et al. Allosteric potentiators of the metabotropic glutamate receptor 2 (mGlu2). Part 3: Identification and biological activity of indanone containing mGlu2 receptor potentiators. Bioorg Med Chem Lett 15:1565-1571 (2005).
Pinkerton et al. Phenyl-tetrazolyl acetophenones: discovery of positive allosteric potentiatiors for the metabotropic glutamate 2 receptor. J Med Chem 47:4595-4599 (2004).
Reiner et al. BDNF may play a differential role in the protective effect of the mGluR2/3 agonist LY379268 on striatal projection neurons in R6/2 Huntington's disease mice. Brain Res 1473:161-172 (2012).
Reiner et al. The group 2 metabotropic glutamate receptor agonist LY379268 rescues neuronal, neurochemical and motor abnormalities in R6/2 Huntington's disease mice. Neurobiol Dis 47:75-91 (2012).
Richards et al. Altered distribution of mGlu2 receptors in β-amyloid-affected brain regions of Alzheimer cases and aged PS2APP mice. Brain Res 1363:180-190 (2010).
Schann et al. Chemical switch of a metabotropic glutamate receptor 2 silent allosteric modulator into dual metabotropic glutamate receptor 2/3 negative/positive allosteric modulators. J Med Chem 53:8775-8779 (2010).
Schiefer et al. The metabotropic glutamate receptor 5 antagonist MPEP and the mGluR2 agonist LY379268 modify disease progression in a transgenic mouse model of Huntington's disease. Brain Res. 1019:246-254 (2004).
Sheffler et al. Activation of Group II Metabotropic Glutamate Receptors (mGluR2 and mGluR3) as a Novel Approach for Treatment of Schizophrenia. In Glutamate-based Therapies for Psychiatric Disorders. Skolnick, P., Ed. Birkhauser Basel. pp. 101-116 (2010).
Sheffler et al. Allosteric modulation of metabotropic glutamate receptors. Adv. Pharmacol 62:37-77 (2011).
Sheffler et al. Recent progress in the synthesis and characterization of group II metabotropic glutamate receptor allosteric modulators. ACS Chem Neurosci 2:382-393 (2011).
Sidique et al. Orally active metabotropic glutamate subtype .2 receptor positive allosteric modulators: structure-activity relationships and assessment in a rat model of nicotine dependence. J Med Chem 55(22):9434-9445 (2012).
Swanson et al. Metabotropic glutamate receptors as novel targets for anxiety and stress disorders. Nat Rev Drug Discov 4:131-144 (2005).
Tresadem et al. Scaffold hopping from pyridones to imidazo[1,2-a]pyridines. New positive allosteric modulators of metabotropic glutamate 2 receptor. Bioorg Med Chem Lett 20:175-179 (2010).
Wieronska et al. On the mechanism of anti-hyperthermic effects of LY379268 and LY487379, group II mGlu receptors activators, in the stress-induced hyperthermia in singly housed mice. Neuropharmacology 62(1):322-331 (2012).
Wright et al. [3H]LY341495 binding to group II metabotropic glutamate receptors in rat brain. J Pharmacol Exp Ther 298:453-460 (2001).
Xi et al. Group II metabotropic glutamate receptors modulate extracellular glutamate in the nucleus accumbens. J Pharmacol Exp Ther 300:162-171 (2002).
Xi et al. Modulation of group II metabotropic glutamate receptor signaling by chronic cocaine. J Pharmacol Exp Ther 303:608-615 (2002).
Xia et al. Classification of kinase inhibitors using a Bayesian model. J Med Chem 47:4463-4470 (2004).
Co-pending U.S. Appl. No. 15/820,194, filed Nov. 21, 2017.

* cited by examiner

\* Responding was significantly different from 0 mg/kg.
\# Responding was significantly different from cocaine.
@ Responding was significantly different from 0, 10, and 20 mg/kg.

METABOTROPIC GLUTAMATE RECEPTOR POSITIVE ALLOSTERIC MODULATORS (PAMS) AND USES THEREOF

PRIORITY CLAIM

This application is filed pursuant to 35 U.S.C. § 371 as a United States National Phase Application of International Application No. PCT/US2015/024554, filed Apr. 6, 2015, which claims benefit of U.S Provisional Application No. 61/975,870, filed on Apr. 6, 2014, which are herein incorporated by reference in their entirety.

STATEMENT OF GOVERNMENT SUPPORT

This invention was made in part with government support under grant R01 DA023926 awarded by the National Institute on Drug Abuse (NIDA). The government has certain rights in the invention.

FIELD OF THE INVENTION

Described herein are metabotropic glutamate subtype-2 and -3 (mGlu2/3) (collectively Group II mGlus) receptor positive allosteric modulators, methods of making such compounds, pharmaceutical compositions and medicaments comprising such compounds, and methods of using such compounds in the treatment of conditions, diseases, or disorders in which metabotropic glutamate receptors are involved.

SUMMARY OF THE INVENTION

Described herein are compounds and compositions, and methods of using these compounds and compositions, as positive allosteric modulators of the metabotropic glutamate receptor subtype 2 receptor (mGlu2), and of the metabotropic glutamate receptor subtype 3 receptor (mGlu3) (collectively Group II mGlus), and for treating CNS disorders associated with Group II mGlus.

In one aspect, described herein is a method for treating or preventing a disease or condition in a mammal that would benefit from the modulation of the metabotropic glutamate receptor subtype 2 receptor (mGlu2), and of the metabotropic glutamate receptor subtype 3 receptor (mGlu3) activities comprising administering a modulator of mGlu2 and mGlu3 to the mammal in need thereof. In some embodiments, the modulator of mGlu2 and mGlu3 is a small molecule. In some embodiments, the modulator of mGlu2 and mGlu3 is a positive allosteric modulator. In some embodiments, the positive allosteric modulator of mGlu2 and mGlu3 is a compound having the structure of Formula (I), Formula (Ia), Formula (Ib), Formula (II), Formula (IIa), Formula (IIb), Formula (IIc), or Formula (III), or a pharmaceutically acceptable salt thereof.

In one aspect, described herein is a compound that has the structure of Formula (I), or a pharmaceutically acceptable salt thereof:

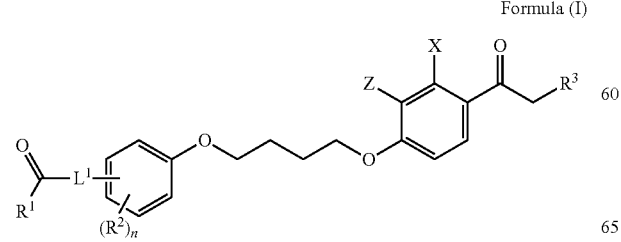

Formula (I)

wherein:
$R^1$ is —OH, —NHOR$^5$, —NHSO$_2$R$^4$, —NR$^4$R$^5$ or R$^4$;
$L^1$ is absent or $C_1$-$C_6$alkylene;
$R^2$ is hydrogen, halogen, nitro, —CN, —OH, —OR$^4$, substituted or unsubstituted $C_1$-$C_6$alkyl, substituted or unsubstituted $C_1$-$C_6$fluoroalkyl, or substituted or unsubstituted $C_3$-$C_6$cycloalkyl;
n is 0, 1, 2, 3, or 4;
$R^3$ is substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;
X is —OH, —OR$^4$, halogen, substituted or unsubstituted $C_1$-$C_6$alkyl, substituted or unsubstituted $C_1$-$C_6$fluoroalkyl, or substituted or unsubstituted $C_3$-$C_6$cycloalkyl;
Z is —OH, —OR$^4$, halogen, substituted or unsubstituted $C_1$-$C_6$alkyl, substituted or unsubstituted $C_1$-$C_6$fluoroalkyl, or substituted or unsubstituted $C_3$-$C_6$cycloalkyl;
$R^4$ is substituted or unsubstituted $C_1$-$C_6$alkyl, substituted or unsubstituted $C_3$-$C_6$cycloalkyl substituted or unsubstituted aryl or substituted or unsubstituted heteroaryl;
$R^5$ is hydrogen, substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;
or $R^4$ and $R^5$ taken together with the nitrogen to which they are attached to form a substituted or unsubstituted $C_2$-$C_8$heterocycloalkyl.

In some embodiments,

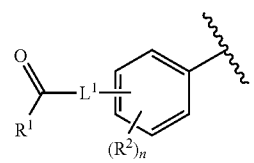

has the structure of

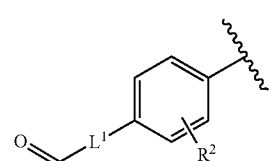

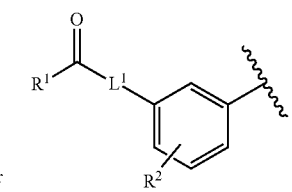

,   or   .

In some embodiments, $L^1$ is absent, —CH$_2$—, —CH$_2$CH$_2$—, —CH$_2$CH$_2$CH$_2$—, or —CH$_2$CH$_2$CH$_2$CH$_2$—. In some embodiments, $L^1$ is absent.
In some embodiments, Z is halogen, or $C_1$-$C_6$alkyl.
In some embodiments, Z is —CH$_3$, or —CH$_2$CH$_3$.

In some embodiments, the compound of Formula (I) has the structure of Formula (Ia):

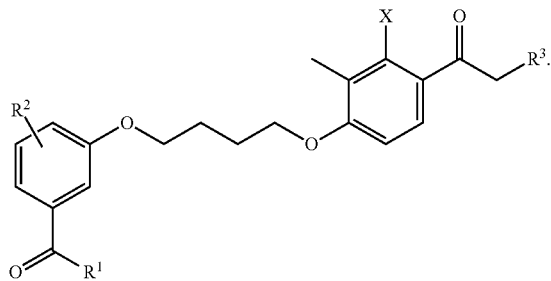

Formula (Ia)

In some embodiments, the compound of Formula (I) has the structure of Formula (Ib):

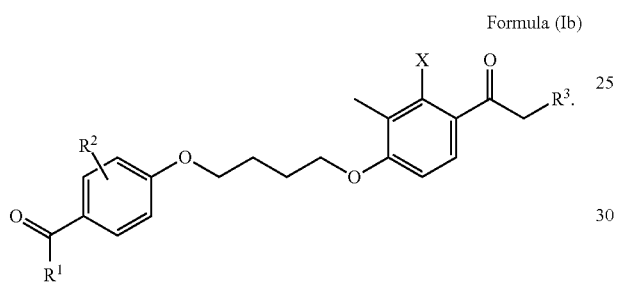

Formula (Ib)

In some embodiments, $R^1$ is —OH or —N($R^4R^5$).

In some embodiments, X is —OH, —$OR^4$, $C_1$-$C_6$alkyl, or $C_1$-$C_6$fluoroalkyl.

In some embodiments, $R^2$ is hydrogen, halogen, —CN, —OH, —$OR^4$, substituted or unsubstituted $C_1$-$C_6$alkyl, or substituted or unsubstituted $C_1$-$C_6$fluoroalkyl.

In some embodiments, $R^3$ is $C_1$-$C_6$alkyl, or $C_3$-$C_6$cycloalkyl.

In some embodiments, $R^3$ is —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2$CH($CH_3$)$_2$, —C($CH_3$)$_3$, cyclopropyl, cyclobutyl, cyclopentyl, or cyclohexyl.

In some embodiments, $R^3$ is —CH($CH_3$)$_2$, —C($CH_3$)$_3$, or cyclopentyl.

In some embodiments, $R^1$ is —OH; $R^2$ is F, Cl, —$CH_3$, or —$OCH_3$; and X is —OH.

In some embodiments, the compound is selected from the group consisting of:

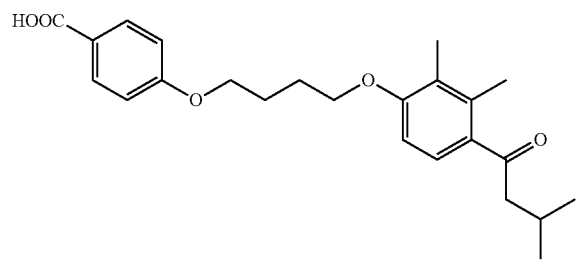

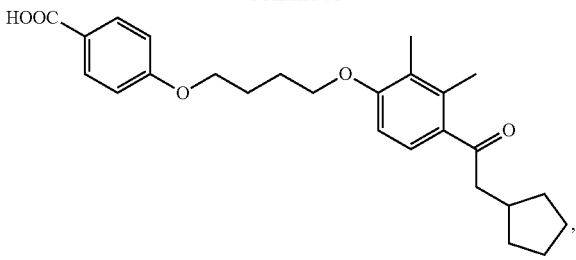

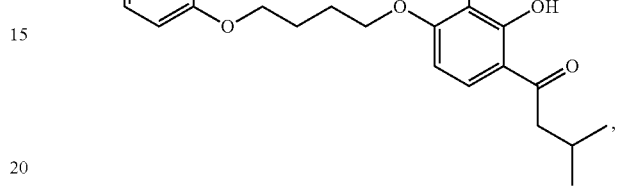

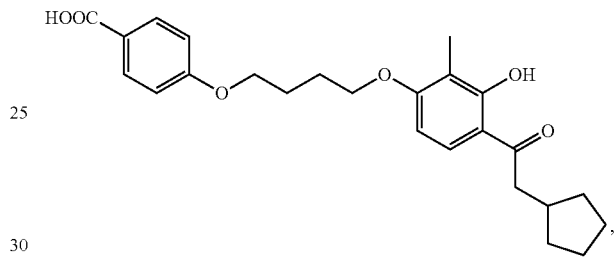

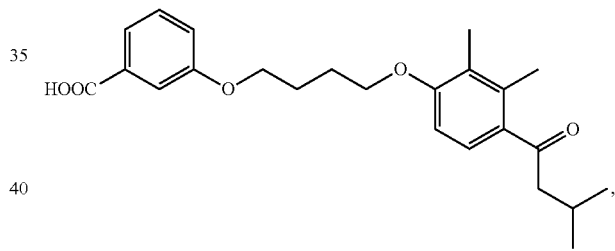

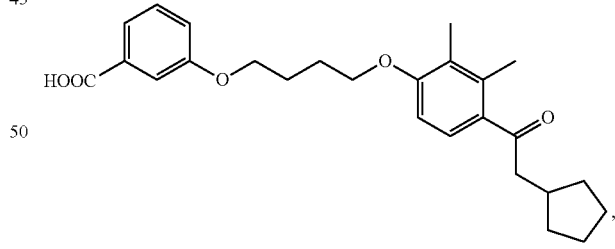

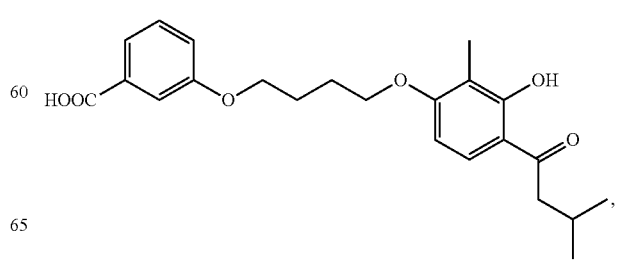

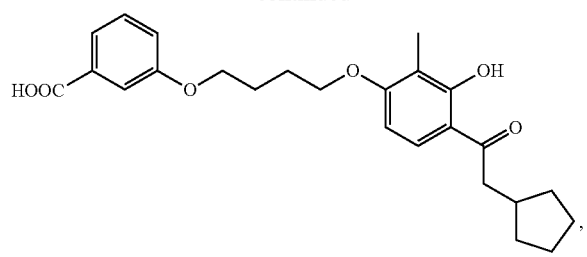
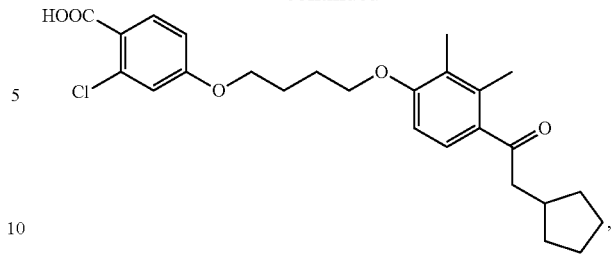
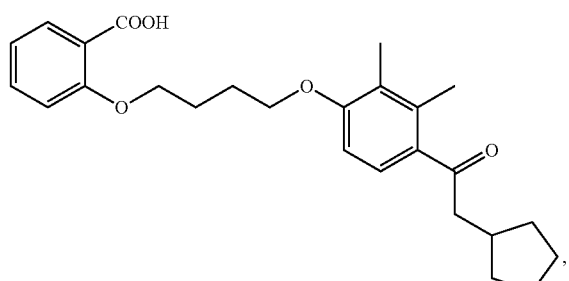
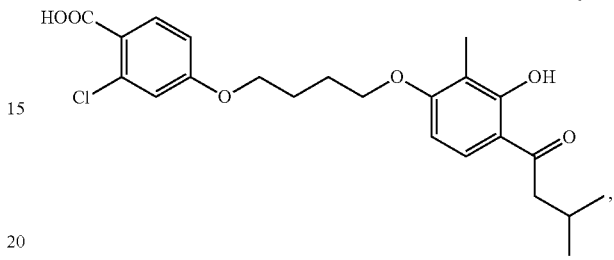
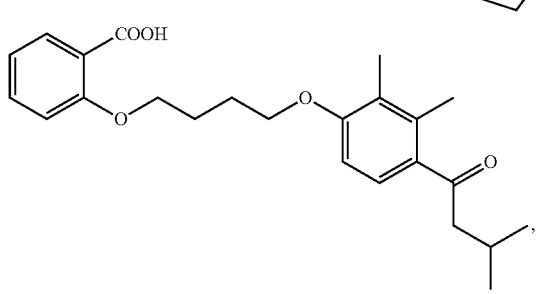
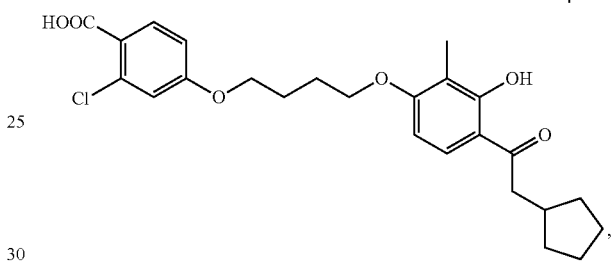
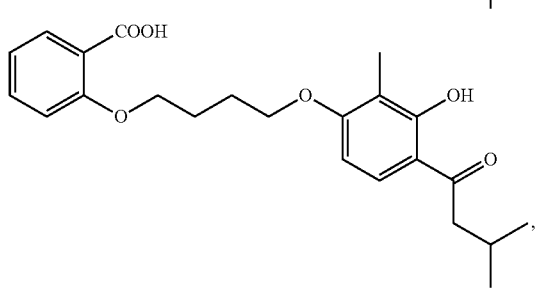
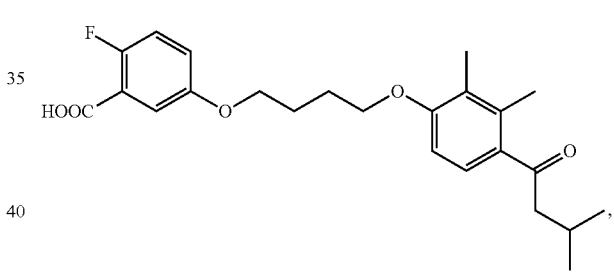
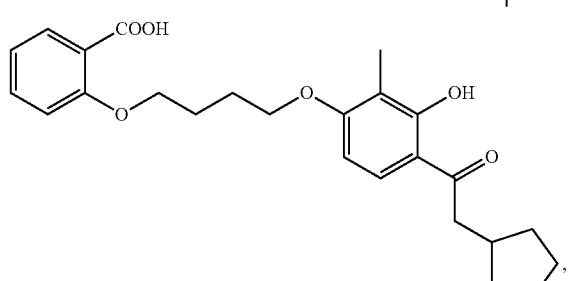
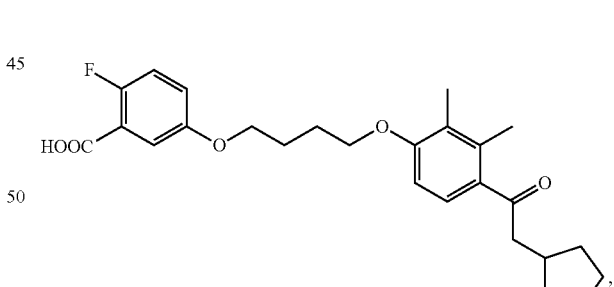
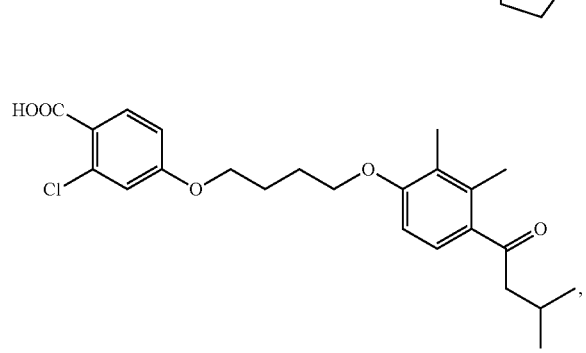
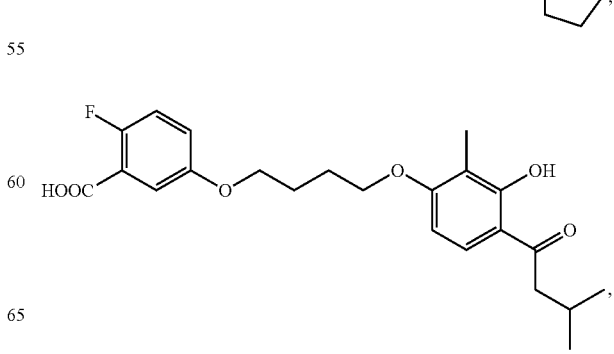

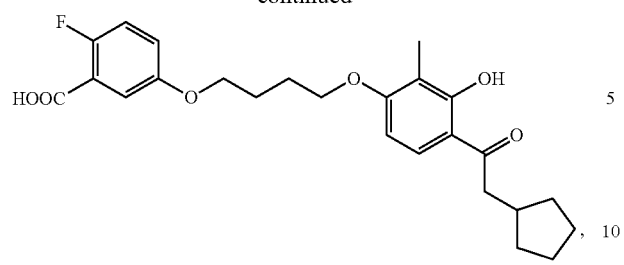
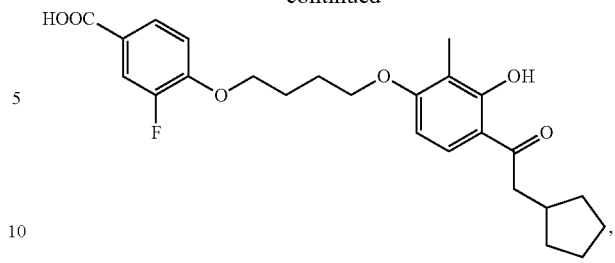
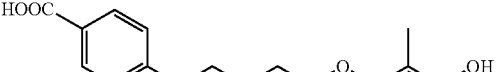

-continued
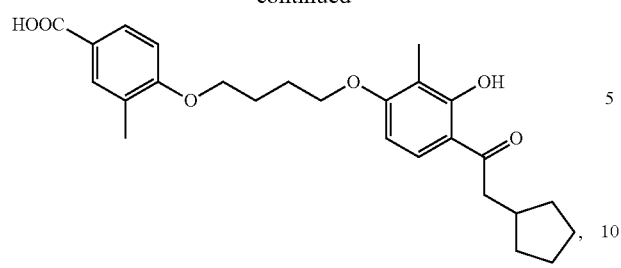
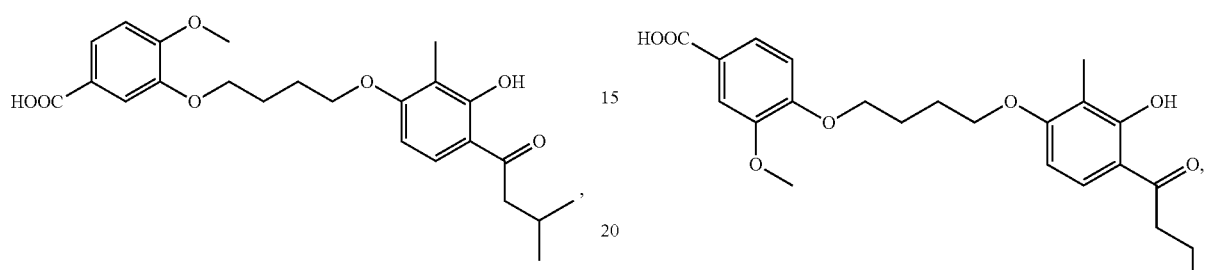
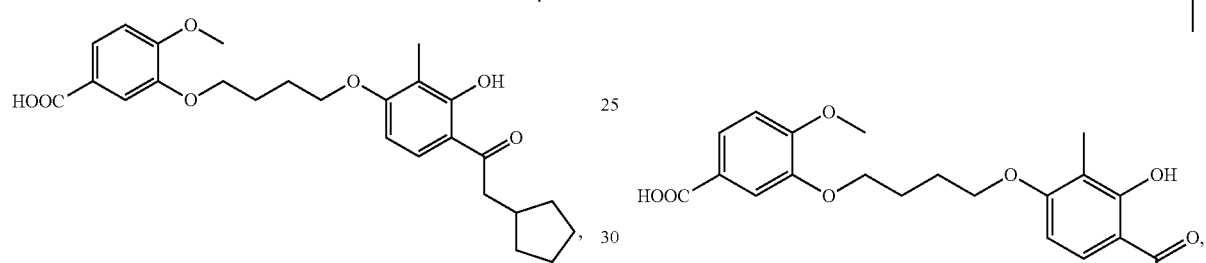
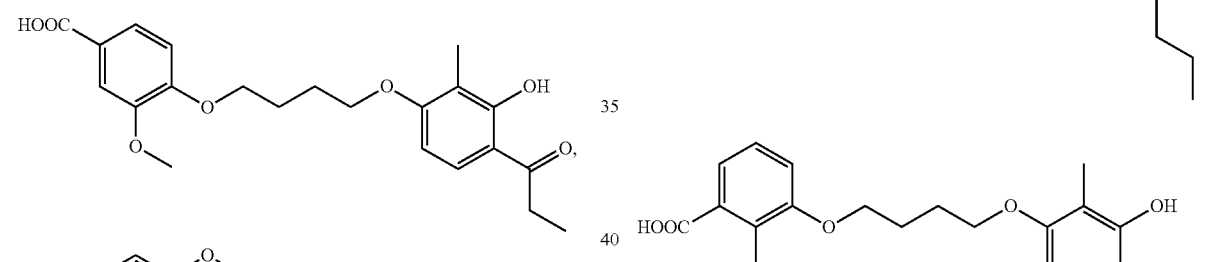
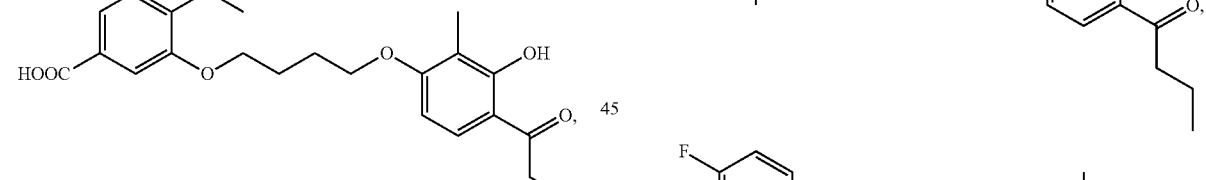
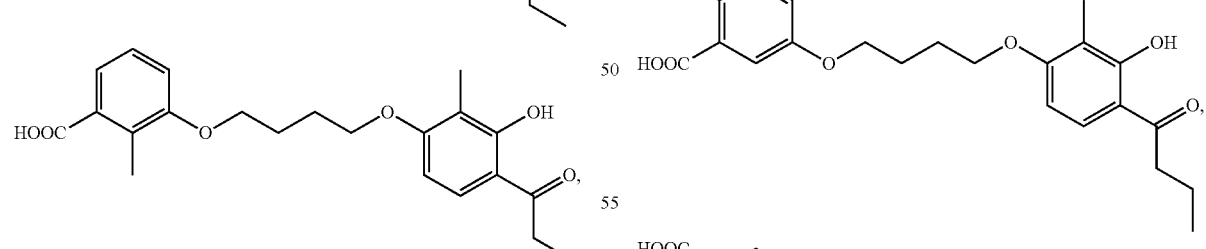
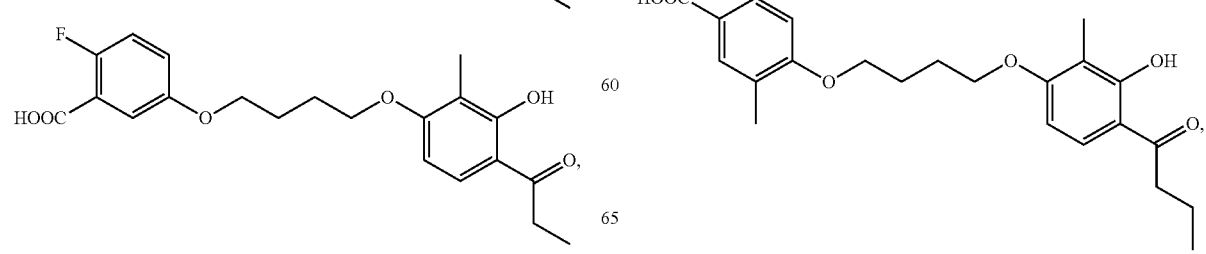

11
-continued
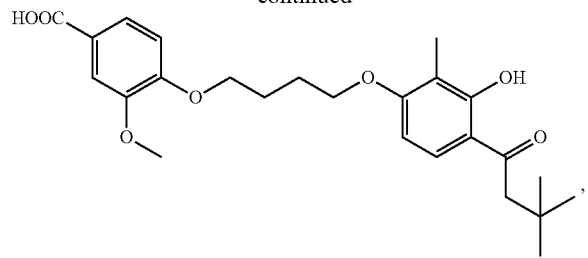
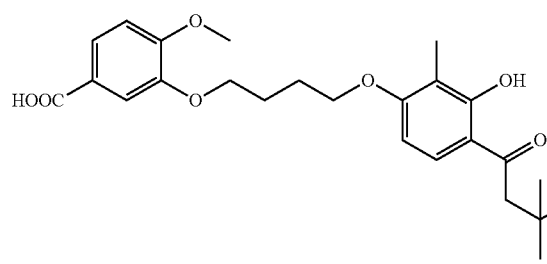
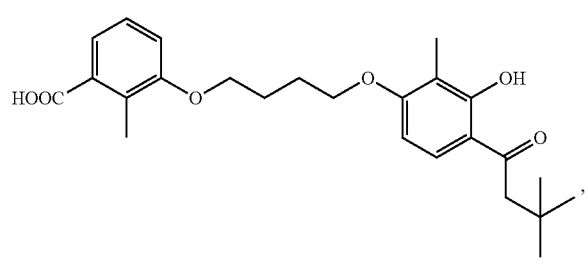
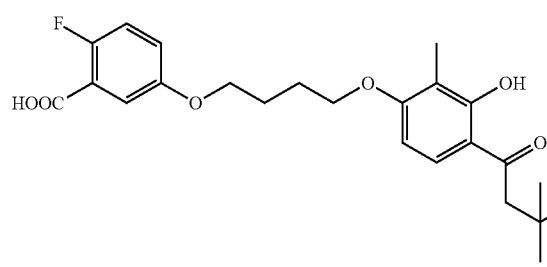
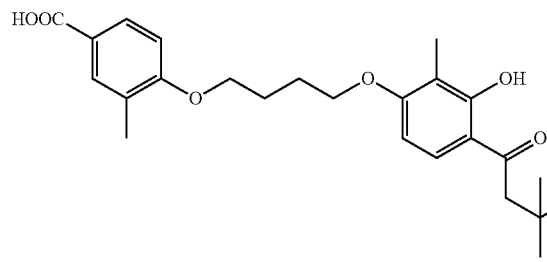
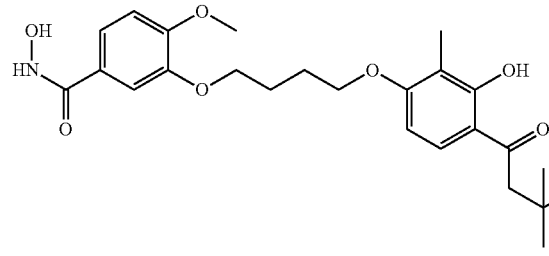
12
-continued
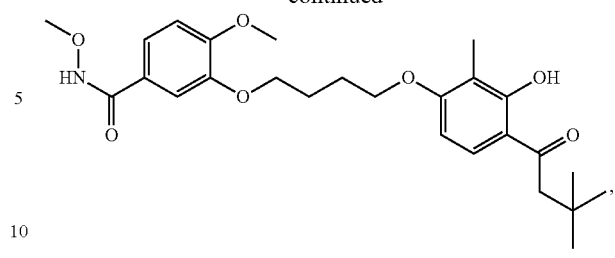
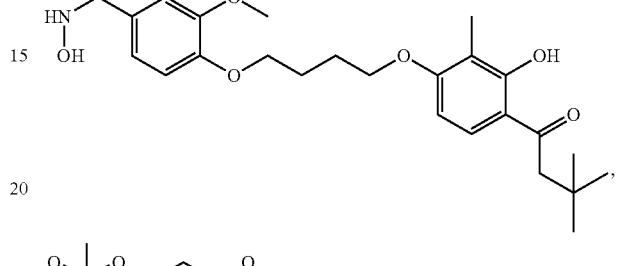
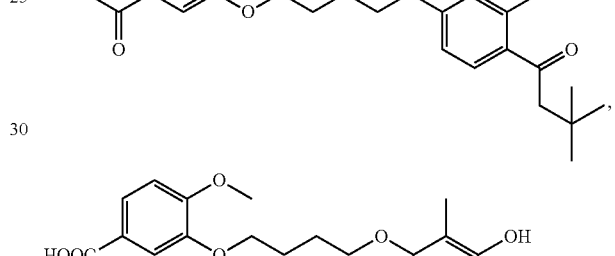
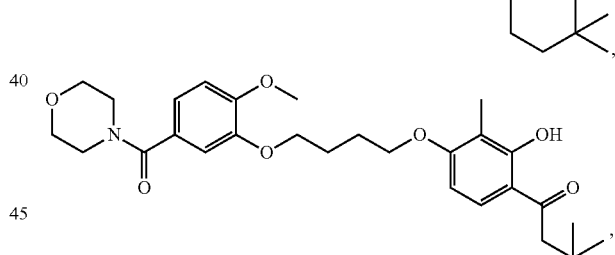
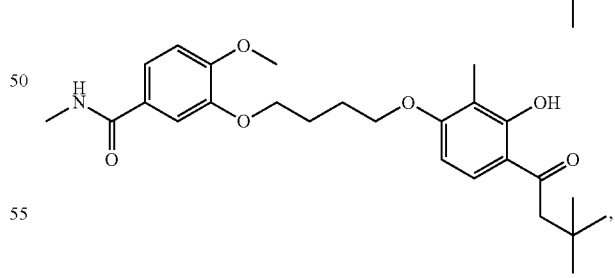
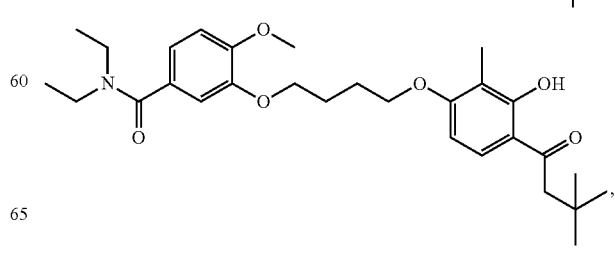

-continued

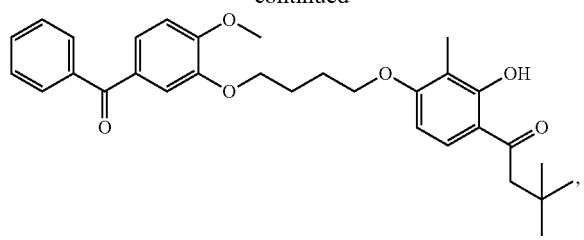

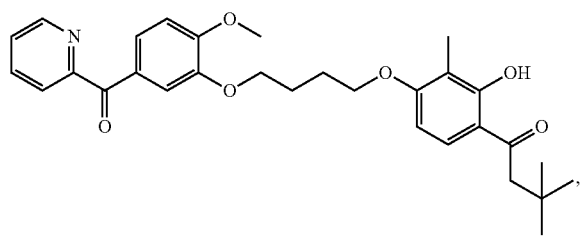

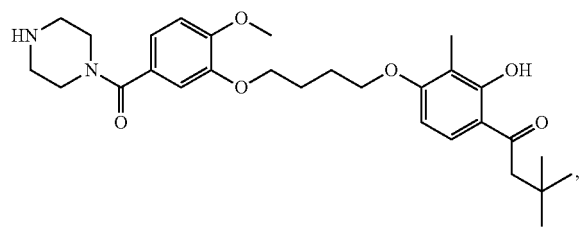

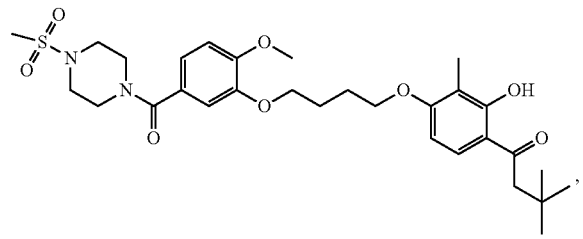

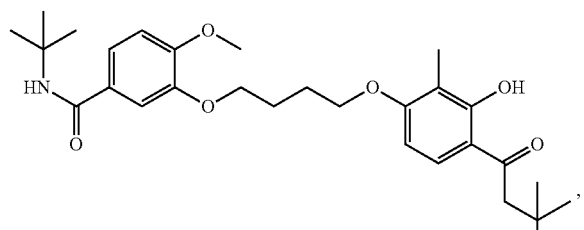

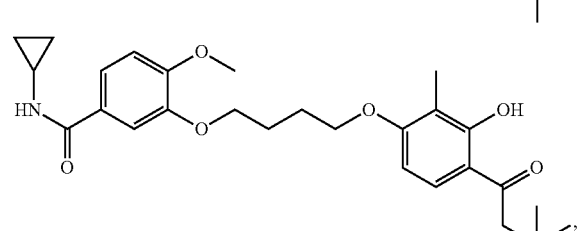

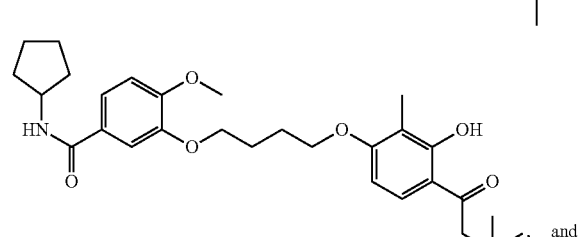

-continued

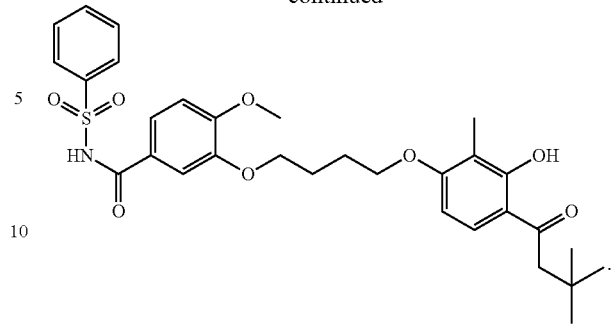

In another aspect, described herein is a compound that has the structure of Formula (II), or a pharmaceutically acceptable salt thereof:

Formula (II)

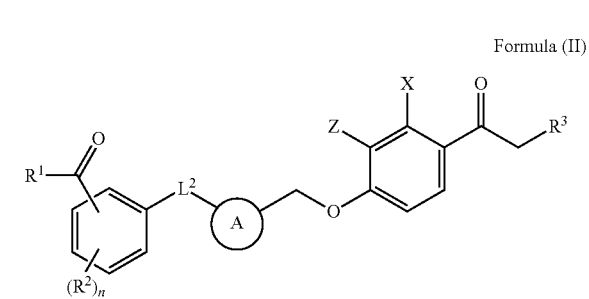

wherein:
$R^1$ is —OH, —OR$^4$, —NHOR$^5$, —NHSO$_2$R$^4$, —NR$^4$R$^5$ or R$^4$;
or —C(=O)R$^1$ is a carboxylic acid bioisostere having the structure

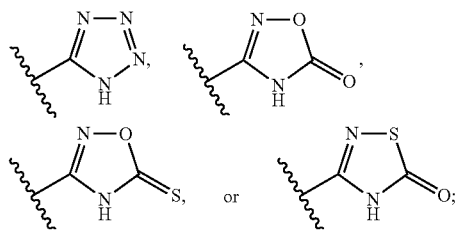

Ring A is substituted or unsubstituted aryl or substituted or unsubstituted heteroaryl;
$L^2$ is absent, —O—, —O—(C$_1$-C$_6$alkylene)-, —S—, or —S—(C$_1$-C$_6$alkylene)-;
$R^2$ is hydrogen, halogen, nitro, —CN, —OH, —OR$^4$, substituted or unsubstituted C$_1$-C$_6$alkyl, substituted or unsubstituted C$_1$-C$_6$fluoroalkyl, or substituted or unsubstituted C$_3$-C$_6$cycloalkyl;
n is 0, 1, 2, 3, or 4;
$R^3$ is substituted or unsubstituted C$_1$-C$_6$alkyl, substituted or unsubstituted C$_1$-C$_6$fluoroalkyl, substituted or unsubstituted C$_3$-C$_6$cycloalkyl, or substituted or unsubstituted aryl;
X is —OH, —OR$^4$, halogen, substituted or unsubstituted C$_1$-C$_6$alkyl, substituted or unsubstituted C$_1$-C$_6$fluoroalkyl, or substituted or unsubstituted C$_3$-C$_6$cycloalkyl;

Z is —OH, —OR$^4$, halogen, substituted or unsubstituted C$_1$-C$_6$alkyl, substituted or unsubstituted C$_1$-C$_6$fluoroalkyl, or substituted or unsubstituted C$_3$-C$_6$cycloalkyl;

R$^4$ is substituted or unsubstituted C$_1$-C$_6$alkyl, substituted or unsubstituted C$_3$-C$_6$cycloalkyl substituted or unsubstituted aryl, or substituted or unsubstituted heteroaryl;

R$^5$ is hydrogen, substituted or unsubstituted C$_1$-C$_6$alkyl, substituted or unsubstituted C$_1$-C$_6$fluoroalkyl, substituted or unsubstituted C$_3$-C$_6$cycloalkyl, or substituted or unsubstituted aryl;

or R$^4$ and R$^5$ taken together with the nitrogen to which they are attached to form a substituted or unsubstituted C$_2$-C$_8$heterocycloalkyl.

In some embodiments, Z is halogen, or C$_1$-C$_6$alkyl.

In some embodiments, Z is —CH$_3$, or —CH$_2$CH$_3$.

In some embodiments, L$^2$ is absent, —O—(CH$_2$)—, —S—(CH$_2$)—.

In some embodiments, Ring A is substituted or unsubstituted phenyl.

In some embodiments, Ring A is or

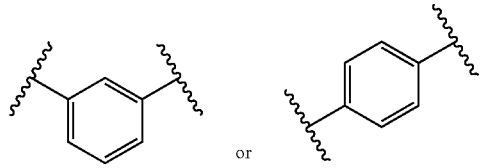

In some embodiments, the compound of Formula (II) has the structure of Formula (IIa):

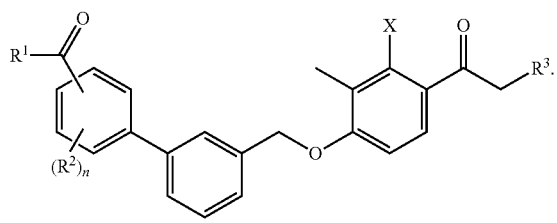

Formula (IIa)

In some embodiments, the compound of Formula (II) has the structure of Formula (IIb):

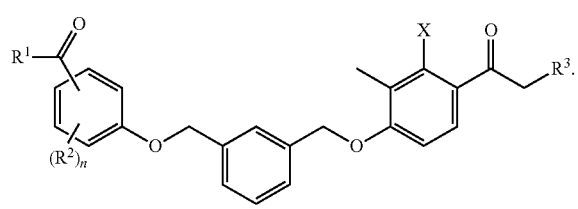

Formula (IIb)

In some embodiments, the compound of Formula (II) has the structure of Formula (IIc):

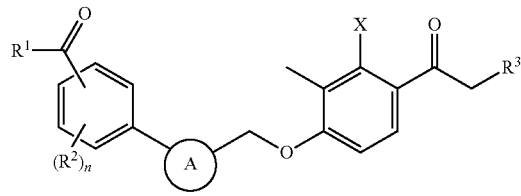

Formula (IIc)

wherein:

Ring A is a substituted or unsubstituted monocyclic 5-, or 6-heteroaryl.

In some embodiments, Ring A is selected from a group consisting of: furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl. In some embodiments, Ring A is selected from a group consisting of:

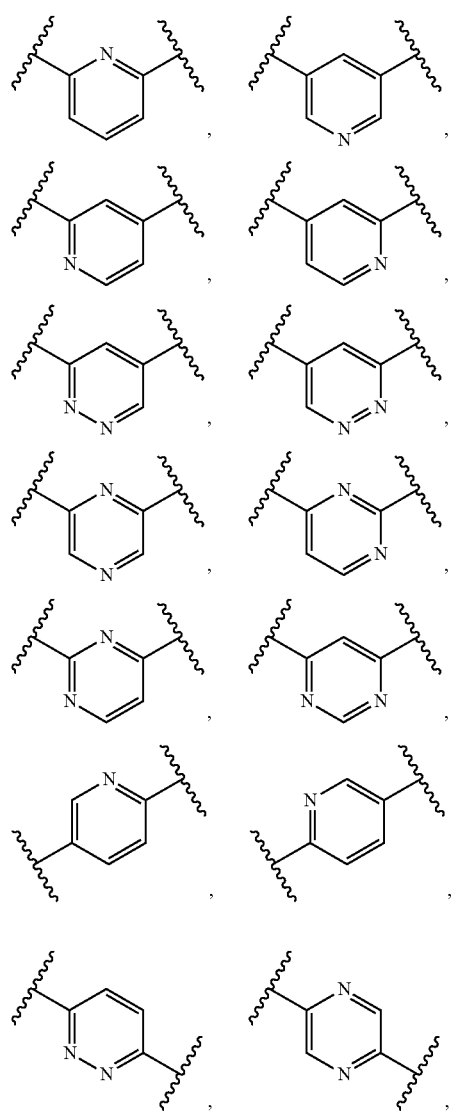

-continued

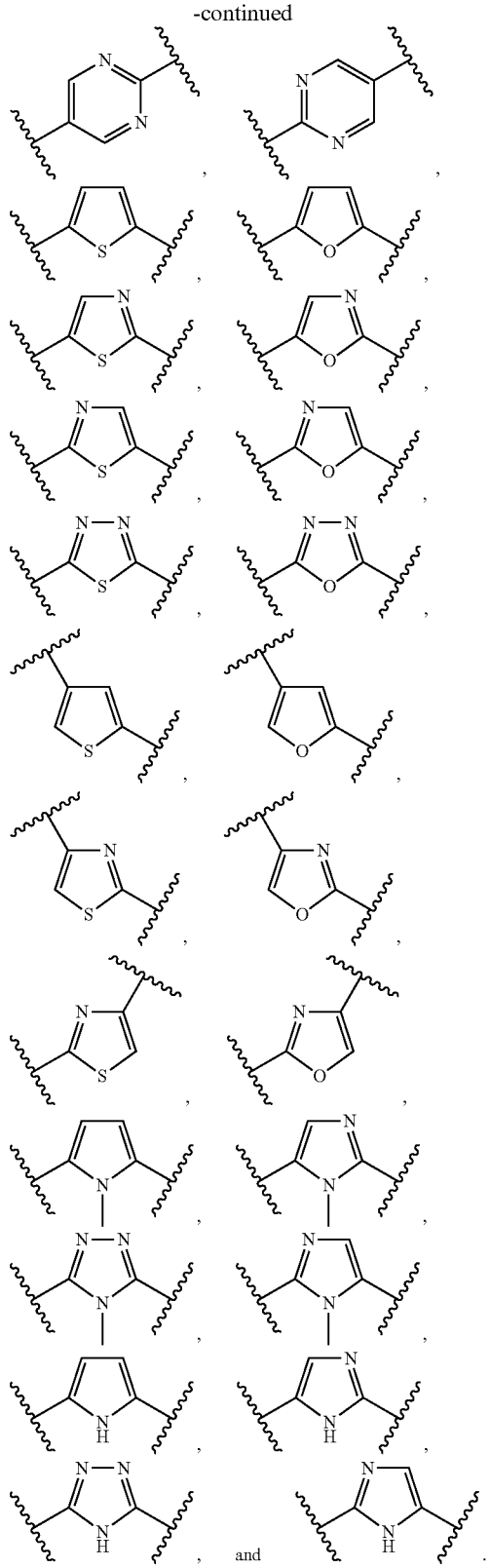

In some embodiments, $R^1$ is —OH, —OCH$_3$, —OCH$_2$CH$_3$, or —N(R$^4$R$^5$).

In some embodiments, X is —OH, —OR$^4$, C$_1$-C$_6$alkyl, or C$_1$-C$_6$fluoroalkyl.

In some embodiments, $R^2$ is hydrogen, halogen, —CN, —OH, —OR$^4$, substituted or unsubstituted C$_1$-C$_6$alkyl, or substituted or unsubstituted C$_1$-C$_6$fluoroalkyl.

In some embodiments, $R^2$ is F, Cl, —CH$_3$, or —OCH$_3$.

In some embodiments, $R^3$ is C$_1$-C$_6$alkyl, or C$_3$-C$_6$cycloalkyl.

In some embodiments, $R^3$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, cyclopropyl, cyclobutyl, cyclopentyl, or cyclohexyl.

In some embodiments, $R^3$ is —CH(CH$_3$)$_2$, —C(CH$_3$)$_3$, or cyclopentyl.

In some embodiments, the compound is selected from the group consisting of:

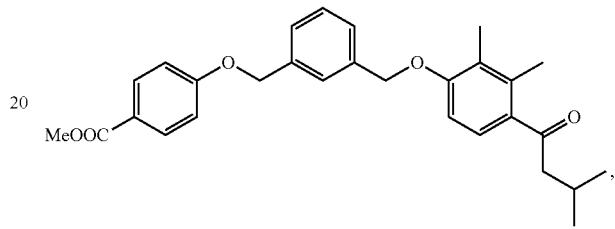

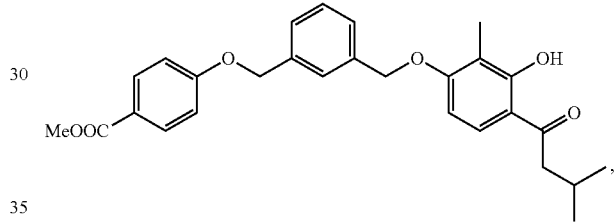

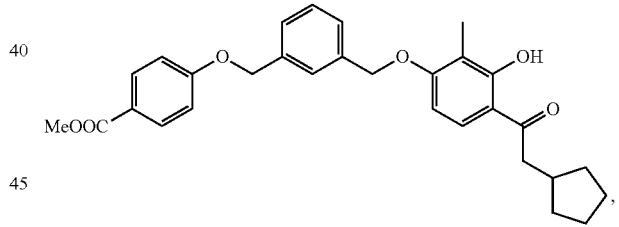

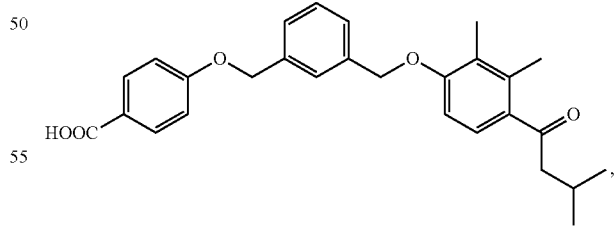

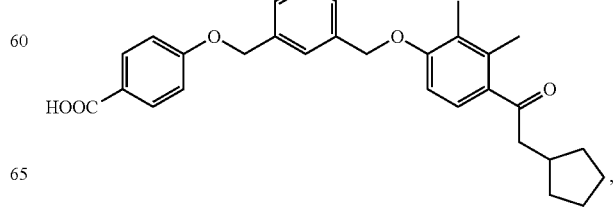

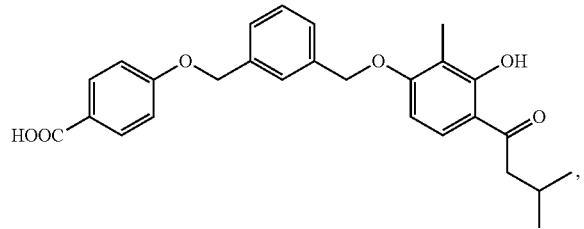
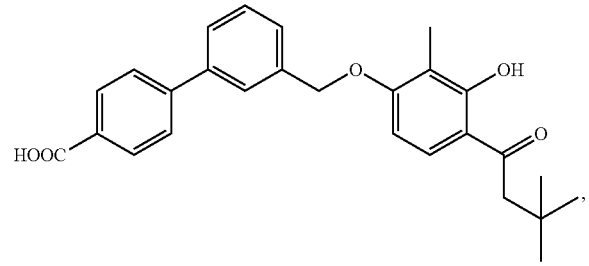
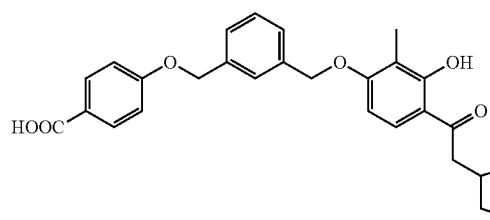
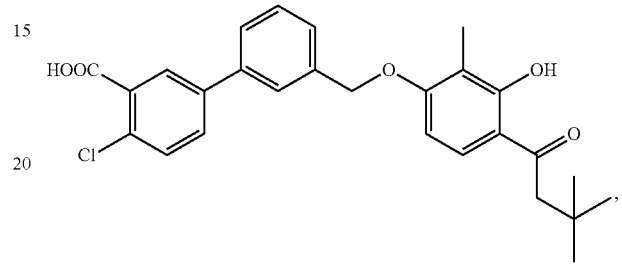
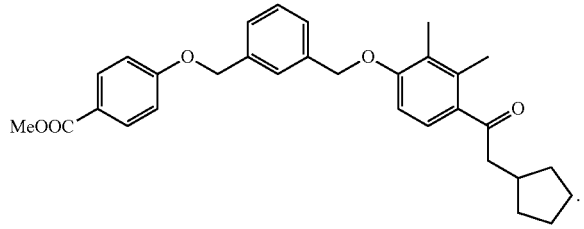 [SMILES: COC(=O)c1ccc(OCc2cccc(COc3ccc(C(=O)CC4CCCC4)c(C)c3C)c2)cc1]
In some embodiments, the compound is selected from the group consisting of:
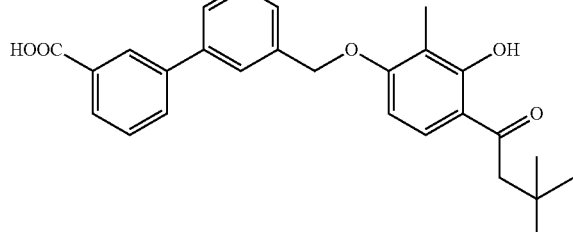
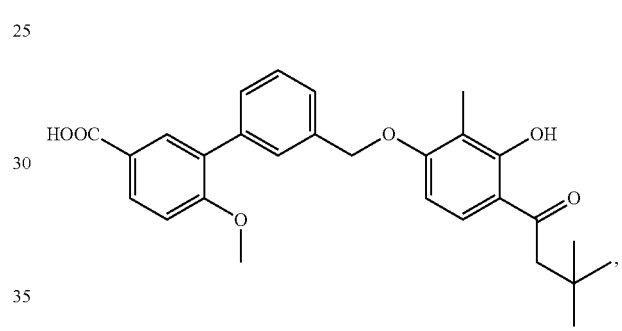
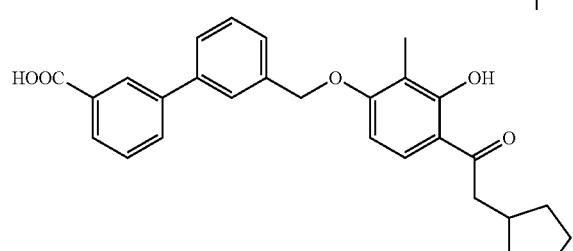
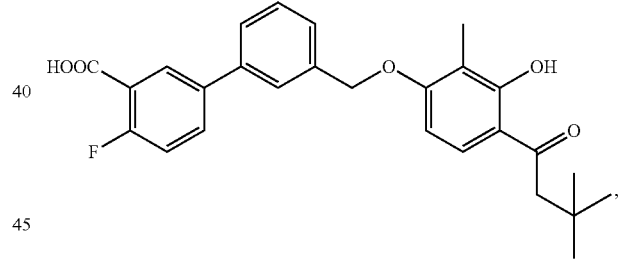
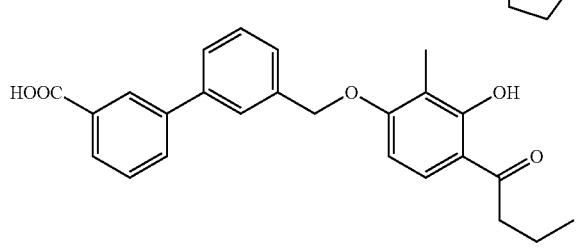
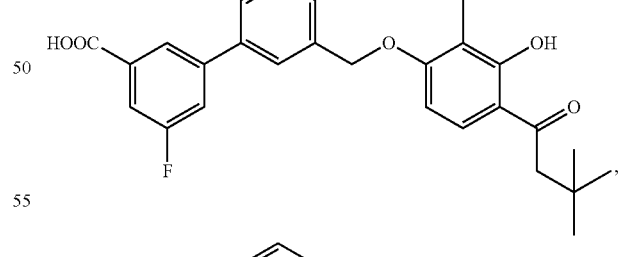
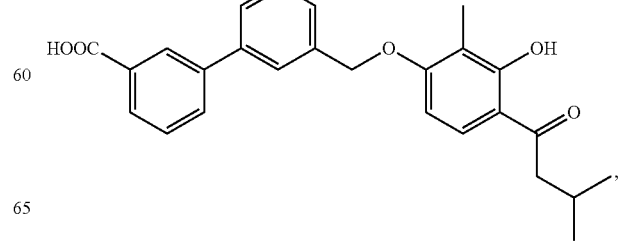

-continued
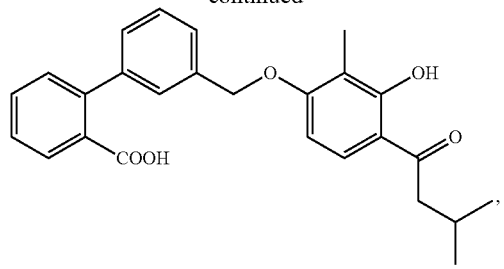
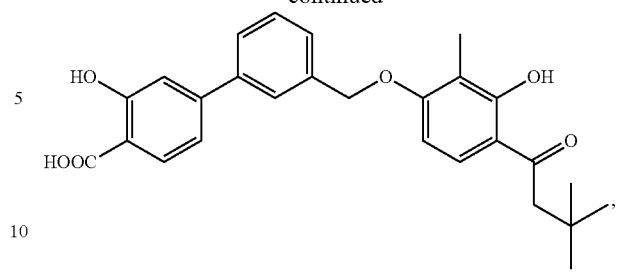
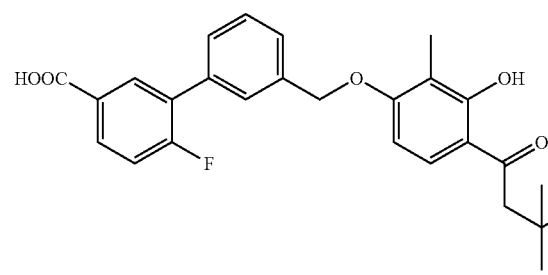
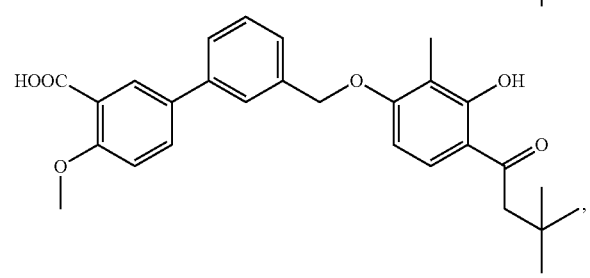
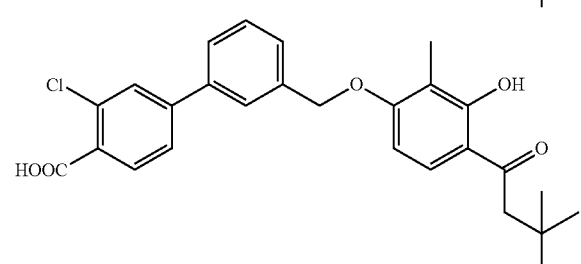
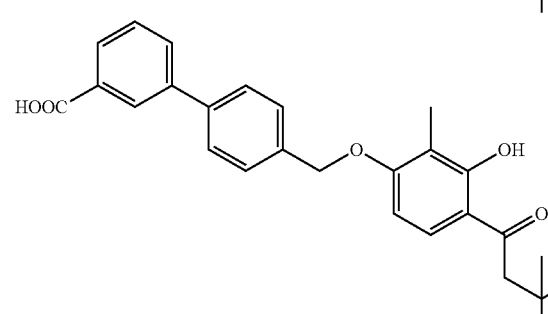
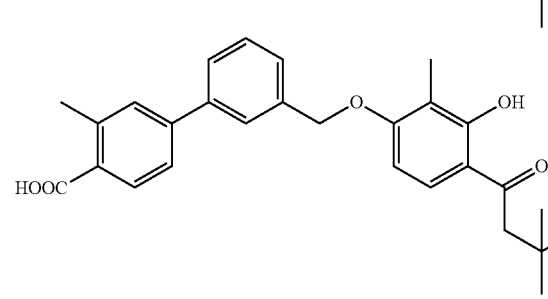
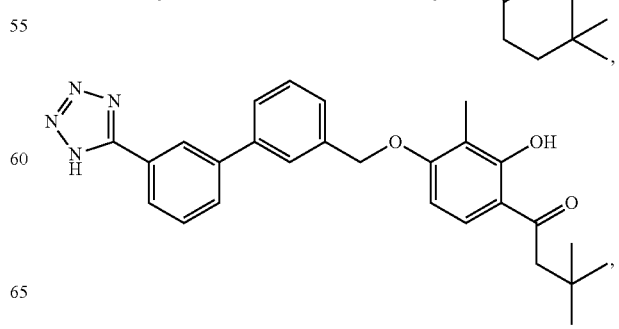

-continued
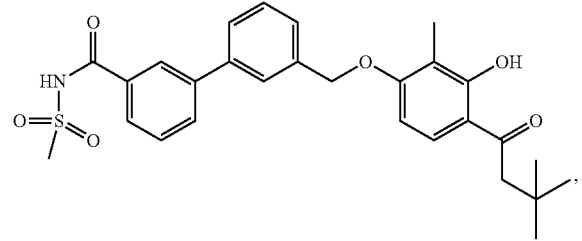
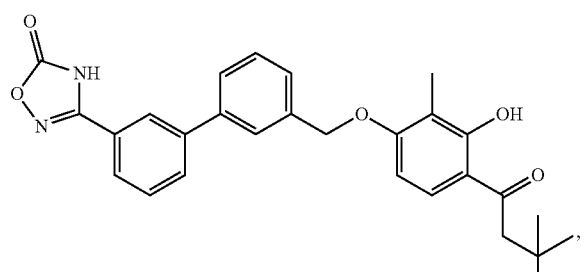
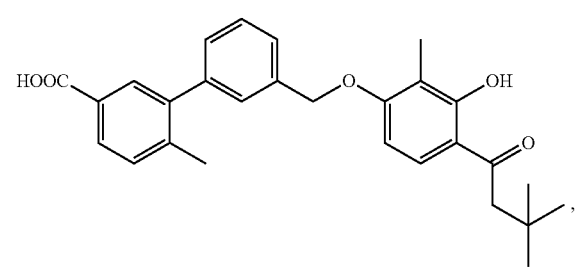
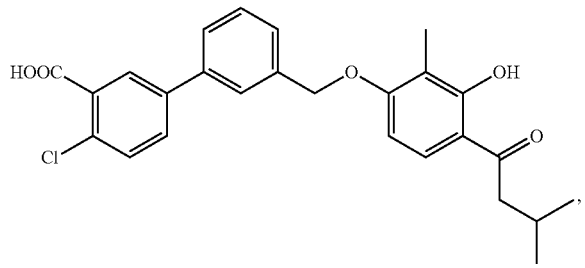
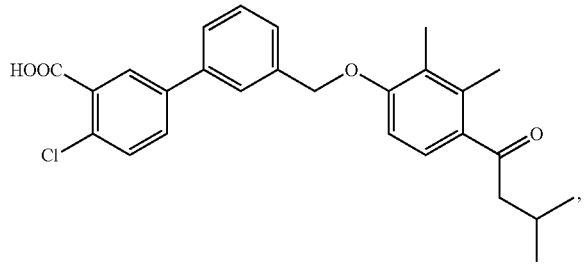
-continued
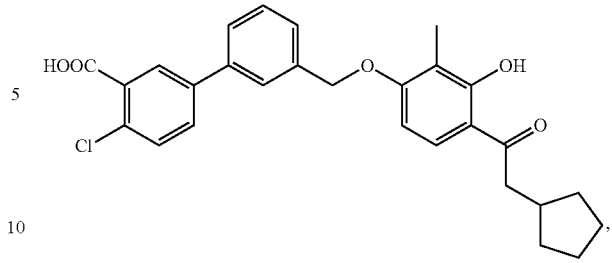
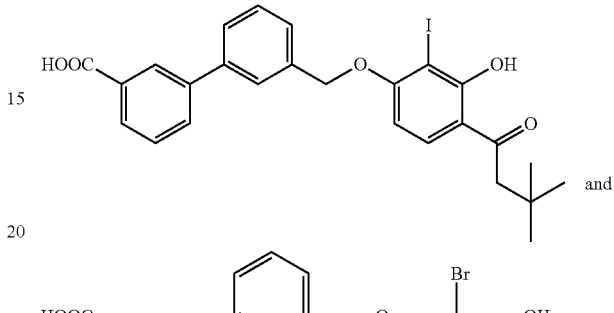
In some embodiments, the compound is selected from the group consisting of:
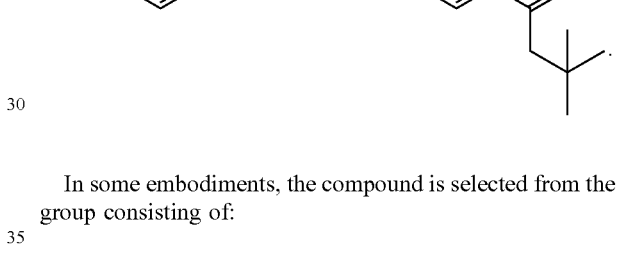
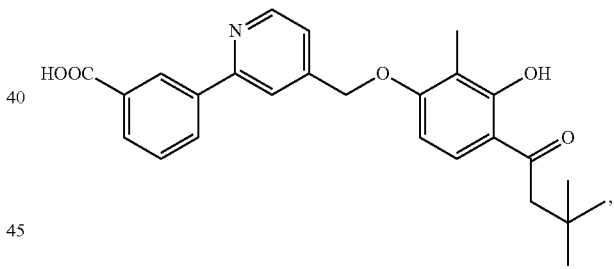
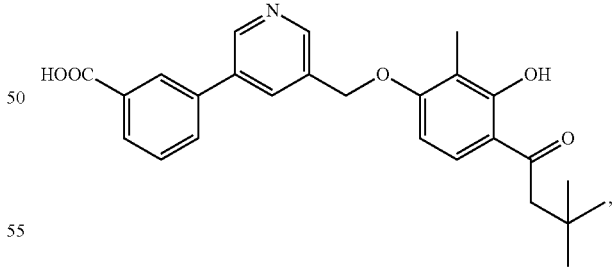

-continued

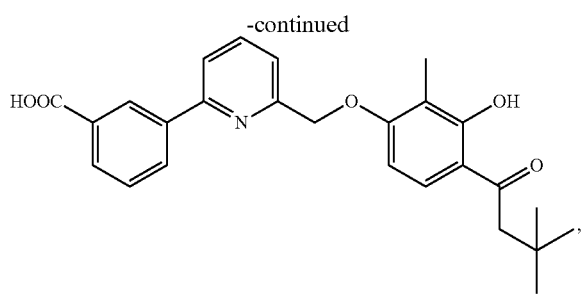

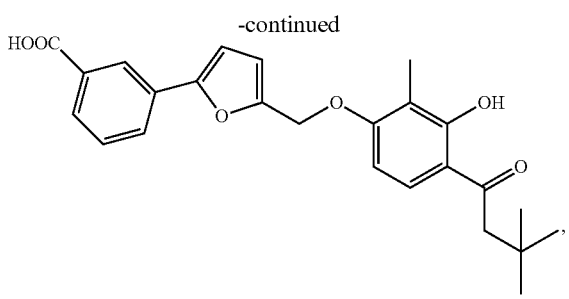

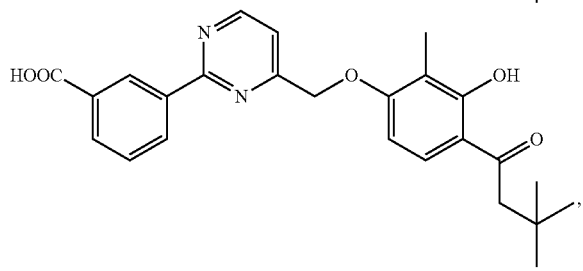

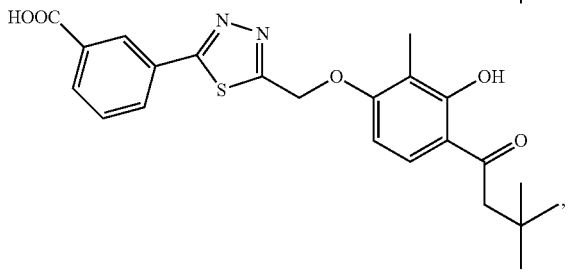

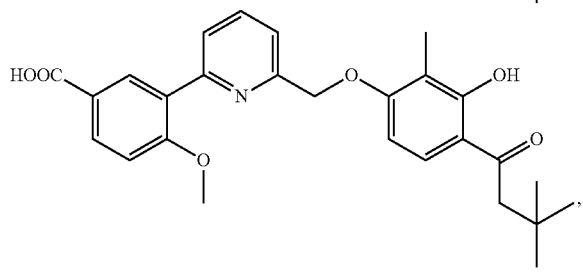

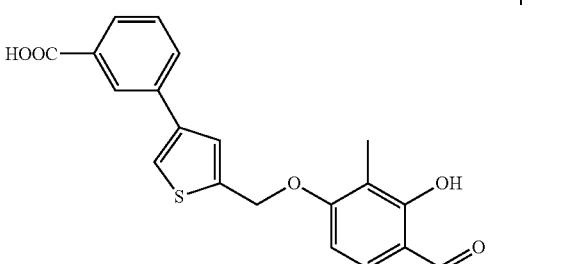

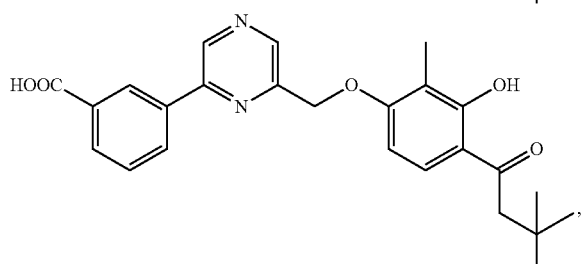

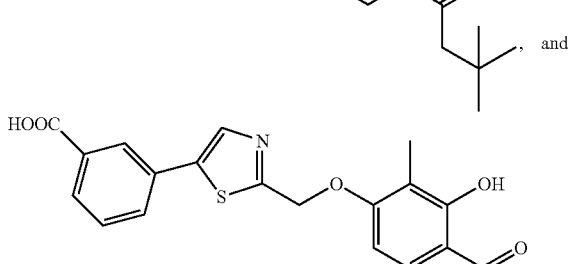

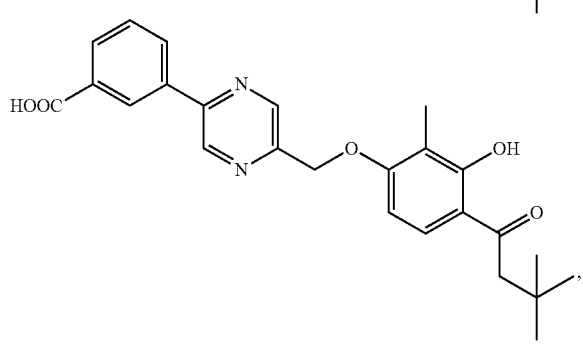

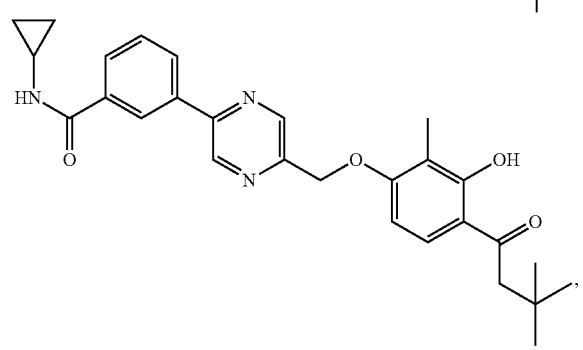

Any combination of the groups described above or below for the various variables is contemplated herein.

In one aspect, provided herein is a pharmaceutical composition comprising a compound of Formula (I), (Ia), (Ib), (II), (IIa), (IIb), (IIc), or (III), or a pharmaceutically acceptable salt thereof, and a pharmaceutically acceptable excipient.

In some embodiments, the compound of Formula (I), (Ia), (Ib), (II), (IIa), (IIb), (IIc), or (III), or a pharmaceutically acceptable salt thereof, is formulated for intravenous injection, subcutaneous injection, oral administration, inhalation, nasal administration, topical administration, ophthalmic administration or otic administration. In some embodiments, the compound of Formula (I), (Ia), (Ib), (II), (IIa), (IIb), (IIc), or (III), or a pharmaceutically acceptable salt thereof, is formulated as (i.e. incorporated into) a tablet, a pill, a capsule, a liquid, an inhalant, a nasal spray solution, a suppository, a suspension, a gel, a solution, an ointment, a lotion, an eye drop or an ear drop.

In one aspect, described herein is a method of treating a central nervous disorder (CNS) disorder, the method comprising the step of administering to a subject in need thereof, an effective amount of the compound of formula (I), (Ia), (Ib), (II), (IIa), (IIb), (IIc), or (III), thereby treating the disorder.

In some embodiments, the disorder is an addictive disorder.

In some embodiments, the addictive disorder is nicotine addiction, alcohol addiction, opiate addiction, amphetamine addiction, methamphetamine addiction, or cocaine addiction.

In some embodiments, the addictive disorder is nicotine addiction.

In some embodiments, the addictive disorder is cocaine addiction.

In some embodiments, the CNS disorder is schizophrenia.

In some embodiments, the CNS disorder is a neurodegenerative disease.

In some embodiments, the neurodegenerative disease is Alzheimer's disease, Parkinson's disease, Huntington's disease, or Lou Gehrig's disease (Amyotrophic Lateral Sclerosis or ALS).

In another aspect, described herein is a method of treating substance abuse, the method comprising the step of administering to a subject in need thereof, an effective amount of the compound of formula (I), (Ia), (Ib), (II), (IIa), (IIb), (IIc), or (III), wherein the effective amount is sufficient to diminish, inhibit or eliminate desire for and/or consumption of the substance in the subject.

In some embodiments, is a method of treating substance abuse, the method comprising the step of administering to a subject in need thereof, an effective amount of the compound of formula (I), (Ia), (Ib), (II), (IIa), (IIb), (IIc), or (III), wherein the effective amount is sufficient to diminish, inhibit or eliminate desire for and/or consumption of the substance in the subject and wherein the substance is nicotine, alcohol, opiates, amphetamines, methamphetamines, or cocaine.

In yet another aspect, described herein is a method for treating an addictive disorder, the method comprising the steps of: a) administering to a subject in need thereof, an effective amount of the compound of formula (I), (Ia), (Ib), (II), (IIa), (IIb), (IIc), or (III), during a first time period, wherein the first time period is a time period wherein the subject expects to be in an environment wherein, or exposed to stimuli in the presence of which, the subject habitually uses an addictive substance; and b) administering an effective amount of the compound of formula (I), (Ia), (Ib), (II), (IIa), (IIb), (IIc), or (III) during a second time period, wherein the second time period is a time period wherein the subject is suffering from withdrawal.

In one aspect, described herein is a method of treating a disease or condition by modulation of the mGlu2 receptor in a subject in need thereof, which method comprises administering to the subject a therapeutically effective amount of a compound of Formula (I), (Ia), (Ib), (II), (IIa), (IIb), (IIc), or (III), or a pharmaceutically acceptable salt thereof. In some embodiments, the disease or condition is a CNS disorder.

In another aspect, described herein is a method of treating a disease or condition by modulation of the mGlu3 receptor in a subject in need thereof, which method comprises administering to the subject a therapeutically effective amount of a compound of Formula (I), (Ia), (Ib), (II), (IIa), (IIb), (IIc), or (III), or a pharmaceutically acceptable salt thereof. In some embodiments, the disease or condition is a CNS disorder.

In one aspect, described herein is a method of treating a disease or condition by dual modulation of the mGlu2/3 receptors in a subject in need thereof, which method comprises administering to the subject a therapeutically effective amount of a compound of Formula (I), (Ia), (Ib), (II), (IIa), (IIb), (IIc), or (III), or a pharmaceutically acceptable salt thereof. In some embodiments, the disease or condition is a CNS disorder.

In any of the aforementioned aspects are further embodiments in which: (a) the effective amount of the compound of Formula (I), (Ia), (Ib), (II), (IIa), (IIb), (IIc), or (III), is systemically administered to the mammal; and/or (b) the effective amount of the compound of Formula (I), (Ia), (Ib), (II), (IIa), (IIb), (IIc), or (III) is administered orally to the mammal; and/or (c) the effective amount of the compound of Formula (I), (Ia), (Ib), (II), (IIa), (IIb), (IIc), or (III) is intravenously administered to the mammal; and/or (d) the effective amount of the compound of Formula (I), (Ia), (Ib), (II), (IIa), (IIb), (IIc), or (III) is administered by inhalation; and/or (e) the effective amount of the compound of Formula (I), (Ia), (Ib), (II), (IIa), (IIb), (IIc), or (III) is administered by nasal administration; or and/or (f) the effective amount of the compound of Formula (I), (Ia), (Ib), (II), (IIa), (IIb), (IIc), or (III) is administered by injection to the mammal; and/or (g) the effective amount of the compound of Formula (I), (Ia), (Ib), (II), (IIa), (IIb), (IIc), or (III) is administered topically to the mammal; and/or (h) the effective amount of the compound of Formula (I), (Ia), (Ib), (II), (IIa), (IIb), (IIc), or (III) is administered by ophthalmic administration; and/or (i) the effective amount of the compound of Formula (I), (Ia), (Ib), (II), (IIa), (IIb), (IIc), or (III) is administered rectally to the mammal; and/or (j) the effective amount is administered non-systemically or locally to the mammal.

In any of the aforementioned aspects are further embodiments comprising single administrations of the effective amount of the compound of Formula (I), (Ia), (Ib), (II), (IIa), (IIb), (IIc), or (III), including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound of Formula (I), (Ia), (Ib), (II), (IIa), (IIb), (IIc), or (III), including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the administration of a compound of Formula (I), (Ia), (Ib), (II), (IIa), (IIb), (IIc), or (III), or a pharmaceutically acceptable salt thereof, to a subject are further embodiments comprising administering at least one additional agent in addition to the administration of a compound having the structure of Formula (I), (Ia), (Ib), (II), (IIa), (IIb), (IIc), or (III), or a pharmaceutically acceptable salt thereof. In various embodiments, the compound of Formula (I), (Ia), (Ib), (II), (IIa), (IIb), (IIc), or (III) and the additional agent are administered in any order, including simultaneously. In some embodiments, the compound of Formula (I), (Ia), (Ib), (II), (IIa), (IIb), (IIc), or (III) and the additional agent are administered to the subject in the same pharmaceutical composition or in separate pharmaceutical compositions.

In any of the embodiments disclosed herein, the subject is a human.

In some embodiments, compounds and compositions provided herein are administered to a human.

In some embodiments, compounds and compositions provided herein are orally administered.

In other embodiments, compounds of Formula (I), (Ia), (Ib), (II), (IIa), (IIb), (IIc), or (III) provided herein are used in the manufacture of a medicament for the modulation of the mGlu2 receptor. In other embodiments, compounds of Formula (I), (Ia), (Ib), (II), (IIa), (IIb), (IIc), or (III) provided herein are used in the manufacture of a medicament for the modulation of the mGlu3 receptor. In other embodiments, compounds of Formula (I), (Ia), (Ib), (II), (IIa), (IIb), (IIc), or (III) provided herein are used in the manufacture of a medicament for the dual modulation of the mGlu2/3 receptors.

Articles of manufacture, which include packaging material, a compound of Formula (I), (Ia), (Ib), (II), (IIa), (IIb), (IIc), or (III), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for the treatment of diseases or conditions that would benefit from the modulation of the mGlu2 receptor, are provided.

Articles of manufacture, which include packaging material, a compound of Formula (I), (Ia), (Ib), (II), (IIa), (IIb), (IIc), or (III), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for the treatment of diseases or conditions that would benefit from the modulation of the mGlu3 receptor, are provided.

Articles of manufacture, which include packaging material, a compound of Formula (I), (Ia), (Ib), (II), (IIa), (IIb), (IIc), or (III), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for the treatment of diseases or conditions that would benefit from the dual modulation of the mGlu2/3 receptors, are provided Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1A:
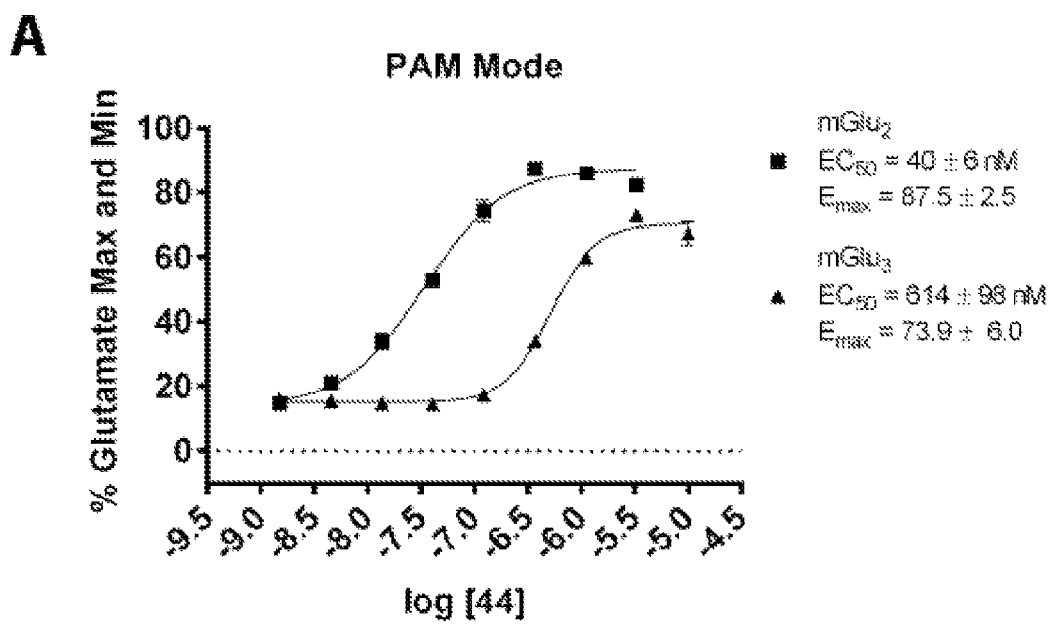
FIG. 1A shows Compound 44 displaying Ago-PAM activity toward mGlu2 and PAM activity toward mGlu3 in a G protein-coupled inwardly rectifying potassium (GIRK) channel thallium-flux assays. A concentration-response of 44 was performed in the presence of an $EC_{20}$ of glutamate in either the mGlu2 GIRK assay (squares) or mGlu3 GIRK assay (triangles).

Glutamate is the major excitatory neurotransmitter in the mammalian central nervous system (CNS), mediating fast synaptic transmission through ion channels, primarily the α-amino-3-hydroxy-5-methyl-4-isoxazolepropionic acid (AMPA) and kainate ionotropic glutamate receptor subtypes. The metabotropic glutamate (mGlu) receptors are a family of eight G protein-coupled receptors that are activated by glutamate and perform a modulatory function in the nervous system. The Group II mGlu receptors include the mGlu2 and mGlu3 receptor subtypes, which couple with $G_{i/o}$ proteins to negatively regulate the activity of adenylyl cyclase. Localization studies suggest that mGlu2 receptors act predominantly as presynaptic autoreceptors to modulate the release of glutamate into the synaptic cleft (Cartmell, J.; Schoepp, D. D. Regulation of neurotransmitter release by metabotropic glutamate receptors. *J. Neurochem.* 2000, 75, 889-907). On the other hand, mGlu3 receptors exhibit a broad distribution in the brain and have been shown to be present on astrocytes (Durand, D. et al. *Neuropharmacology* 2013, 66, 1-11). In addition, it has been shown that activation of mGlu3 receptors is required for the neuroprotective effects of mGlu2/3 agonists toward N-methyl-D-aspartate (NMDA) neurotoxicity in mixed cultures of astrocytes and neurons, whereas activation of mGlu2 receptors may be harmful (Corti, C. et al. *J. Neurosci.* 2007, 27, 8297-8308).

Various brain regions, including the cerebral cortex, hippocampus, striatum, amygdala, frontal cortex and nucleus accumbens, display high levels of mGlu2 and mGlu3 receptor binding. This distribution pattern suggests a role for the mGlu2/3 receptor subtypes in the pathology of neuropsychiatric disorders such as anxiety, schizophrenia, drug dependence, neuroprotection, Alzheimer's disease, and sleep/wake architecture. Thus there is significant potential for the development of selective Group II mGlu receptor activators, including agonists and positive allosteric modulators (PAMs), for the treatment of CNS diseases caused by aberrant glutamatergic signaling.

Positive Allosteric Modulator (PAM)

Allosteric modulators are substances which indirectly influence (modulates) the effects of an agonist or inverse agonist at a receptor. Allosteric modulators bind to a site distinct from that of the orthosteric agonist binding site. Usually they induce a conformational change within the protein structure. A positive allosteric modulator (PAM), which is also called an allosteric enhancer, induces an amplification of the agonist's effect. PAMs, through their interaction at allosteric sites on the mGlu receptor, positively modulate (i.e. potentiate) the effects of the endogenous orthosteric mGlu agonist glutamate. The advantages of PAMs compared with orthosteric agonists includes enhanced subtype-selectivity, the potential for spatial and temporal modulation of receptor activation, and ease of optimization and fine-tuning of drug-like properties. Studies showed that selectively activating mGlu2 receptors on cocaine or nicotine dependence, unlike mGlu2/3 orthosteric agonists, decreased cocaine self-administration in rats at doses that did not affect responding for food. Data suggests that mGlu2 receptor PAMs have the potential for therapeutic utility in the treatment of drug dependence.

There have been many accounts in the literature describing selective mGlu2 receptor PAMs, whereas very little has been reported on compounds which potentiate the effects of glutamate at mGlu3 receptors. This is somewhat surprising given the significant sequence homology (approximately 75%) within the transmembrane regions of mGlu2 and mGlu3 receptors. Considering the dearth of information on mixed mGlu2/3 receptor PAMs, the development of such compounds would provide valuable pharmacological tools. For example, a CNS penetrant mGlu2/3 receptor PAM could facilitate investigations into whether effects on food responding in rats are due to general activation of mGlu3 receptors or an effect specific to direct activation of the mGlu receptor by agonists that act at the mGlu orthosteric binding site.

In some embodiments, the compounds described herein are mGlu2/3 receptor PAMs.

In some embodiments, the compounds described herein are used to treat a CNS disorder. In some embodiments, the CNS disorder is anxiety. In some embodiments, the CNS disorder is schizophrenia. In another embodiment, the CNS disorder is an addictive disorder.

In some embodiments, the addictive disorder is nicotine addiction, alcohol addiction, opiate addiction, amphetamine addiction, methamphetamine addiction, or cocaine addiction.

In some embodiments, the addictive disorder is nicotine addiction. In some embodiments, the addictive disorder is cocaine addiction.

In another aspect the disclosure provides methods for treating substance abuse, by administering to a subject in need thereof, an effective amount of a compound having Formula I, wherein the effective amount is sufficient to diminish, inhibit or eliminate desire for and/or consumption of the substance in the subject.

In another aspect the disclosure provides methods for treating substance abuse, wherein the substance is nicotine, alcohol, opiates, amphetamines, methamphetamines, or cocaine.

In another aspect the disclosure provides a method for treating an addictive disorder, by a) administering to a subject in need thereof, an effective amount of a compound having Formula I, during a first time period, wherein the first time period is a time period wherein the subject expects to be in an environment wherein, or exposed to stimuli in the presence of which, the subject habitually uses an addictive substance; and b) administering an effective amount of a compound having Formula I during a second time period, wherein the second time period is a time period wherein the subject is suffering from withdrawal.

In some embodiments, the CNS disorder is a neurodegenerative disease.

In some embodiments, the neurodegenerative disease is Alzheimer's disease. In some embodiments, the neurodegenerative disease is Parkinson's disease. In some embodiments, the neurodegenerative disease is Huntington's disease. In some embodiments, the neurodegenerative disease is Lou Gehrig's disease (Amyotrophic Lateral Sclerosis or ALS).

In some embodiments, the compounds described herein provide neuroprotection.

Anxiety

Anxiety is an unpleasant state of inner turmoil, often accompanied by nervous behavior, such as pacing back and forth, somatic complaints and rumination. It is the subjectively unpleasant feelings of dread over anticipated events, such as the feeling of imminent death. Anxiety is a feeling of fear, worry, and uneasiness, usually generalized and unfocused as an overreaction to a situation that is only subjectively seen as menacing. It is often accompanied by muscular tension, restlessness, fatigue and problems in concentration. Anxiety can be appropriate, but when experienced regularly the individual may suffer from an anxiety disorder.

In some embodiments, the compounds described herein are mGlu2/3 receptor PAM used for treating anxiety symptoms. The method includes administering to a subject in need thereof, an effective amount of at least one mGlu2/3 receptor PAM, thereby treating the anxiety symptoms.

Nicotine Addiction

Nicotine dependence is an addiction to tobacco products caused by the drug nicotine. Nicotine dependence means a person can't stop using the substance, even though it's causing harm. Nicotine produces physical and mood-altering effects in the human brain that are temporarily pleasing. These effects increase the desire to use tobacco and lead to dependence. At the same time, stopping tobacco use causes withdrawal symptoms, including irritability and anxiety.

In certain aspects, the effective amount of at least one positive allosteric modulator is administered to decrease nicotine consumption. For example, in one aspect an effective amount of a positive allosteric modulator of mGlu2 and/or mGlu3, can be administered to decrease nicotine consumption. In certain aspects of the disclosure, a positive allosteric modulator of mGlu2 and/or mGlu3 is administered while a subject is experiencing withdrawal. In another aspect of the disclosure, a positive allosteric modulator of mGlu2 and/or mGlu3 is administered during a time period when a subject is actively using an addictive substance.

Cocaine Addiction

Cocaine addiction remains a major public health problem in the United States. There are several sources of motivation that contribute to the continuance of cocaine abuse, including: the positive reinforcing effects of cocaine; and the alleviation of the negative affective aspects of cocaine withdrawal. Conditioned stimuli previously associated with cocaine administration may also elicit conditioned "cravings" leading to the reinstatement of cocaine-seeking behavior even after a prolonged period of abstinence. Recent studies indicate that the neuronal mechanisms underlying various aspects of drug abuse may differ necessitating the use of different treatments for specific aspects of drug dependence. To date, a safe and effective pharmacological treatment for cocaine dependence has yet to be identified. Thus, there remains a need for the design of new chemical entities that can be used as novel medications for cocaine addiction.

It has been found that repeated cocaine exposure may alter the function of Group II metabotropic glutamate receptors (mGlu2 and mGlu3 receptors), pointing to a possible role of these mGlu subtypes in the development of cocaine dependence. The mGlu2/3 receptor positive modulators may decrease the reinforcing effects of self-administered cocaine in rats that had extended access to cocaine, a putative model of cocaine dependence while having no effect in rats with limited access to cocaine. Positive mGlu2/3 receptor modulators may attenuate discriminatory cue-induced reinstatement of cocaine self-administration. In contrast, mGlu2/3 receptor negative modulators may reverse the reward deficits associated with early cocaine abstinence.

Cocaine addiction is a chronic relapsing disorder and remains a major public health problem in the United States. The number of cases of cocaine abuse has steadily risen in the past decade. To date, a safe and effective pharmacological treatment for cocaine dependence has yet to be identified, which highlights the need to design new chemical entities that may become future novel medications for cocaine addiction. Recent evidence suggests that mGlus play a significant role in the abuse-related effects of cocaine. For example, repeated administration of cocaine has been shown to alter the function of mGlus, as well as their regulation by cysteine/glutamate exchange in the nucleus accumbens. These findings suggest that mGlu2/3 may be involved in the development of cocaine dependence and may represent a possible target for drug discovery against different aspects of cocaine abuse and dependence. There are several sources of motivation that contribute to the maintenance of cocaine abuse. These include the positive reinforcing effects of cocaine and alleviation of the negative affective aspects of cocaine withdrawal. Further, conditioned stimuli previously associated with cocaine administration may elicit conditioned "cravings" leading to the reinstatement of cocaine-seeking behavior even after a prolonged period of abstinence. Recent studies suggest that the neuronal mechanisms underlying drug self-administration are different from those mediating relapse vulnerability during abstinence, and different from those mediating the negative effects of early drug withdrawal. Therefore, it is important to explore concurrently the neurochemical mechanisms that contribute to the different aspects of cocaine dependence using animal models assessing the positive reinforcing effects of cocaine, the negative affective symptoms of early withdrawal, and cue-induced reinstatement of cocaine-seeking behavior after prolonged abstinence from drug intake. The discovery and preclinical testing of highly selective mGlu2/3 receptor modulators with good brain penetration may significantly contribute to the discovery of novel therapeutic treatments for different aspects cocaine dependence.

The intravenous drug self-administration procedure provides a reliable and robust model of human drug consumption. This procedure in animals provides a valid model of human drug abuse as studied in a controlled laboratory situation. Self-administration of drugs of abuse is thought to provide an operational measure of the rewarding effects of the drug. Increases in excitatory glutamatergic transmission are likely to contribute to the positive reinforcing properties of addictive drugs. Neurochemical studies indicate that systemic cocaine administration increase glutamate levels in the ventral tegmental area (VTA) and the nucleus accumbens, brain structures that are integral components of the extended amygdala, a brain circuit mediating the reward effects of all major drugs of abuse. The administration of a positive modulator of mGlu2/3 receptors may decrease cocaine self-administration in rats with extended access to cocaine by decreasing glutamate neurotransmission in limbic structures similar to the effects of mGlu2/3 agonists. In contrast, a negative modulator of mGlu2/3 receptors will most likely have no effect on cocaine self-administration, or possibly will shift the dose-response curve to the left, potentiating the reinforcing effects of cocaine.

Another challenge for the treatment of drug addiction is chronic vulnerability to relapse. One of the factors that precipitates drug craving and relapse to drug taking behavior in humans is environmental stimuli previously associated with drug-taking. These drug-associated stimuli can be divided into two categories: discrete drug cues (e.g., drug paraphernalia) that are associated with the rewarding effects of the drug, and discriminatory and contextual drug cues (e.g., specific environmental stimuli or specific environments) that predict drug availability. In animals, discrete, discriminative and contextual conditioned cues can reinstate drug-seeking behavior, measured by variables derived from the reinstatement procedure. Recent data showed that reinstatement of cocaine-seeking was attenuated by systemic injections of N-acetylcysteine that leads to a tonic increase in nucleus accumbens glutamate levels in rats. Preliminary results in humans suggest that N-acetylcysteine attenuated cocaine craving in addicted humans. Further, exposure to environmental cues previously paired with cocaine injections increased glutamate in the nucleus accumbens. A potential use for mGlu2/3 agonists as pharmacotherapeutic agents to inhibit relapse was recently shown using different rodent models of reinstatement. In some embodiments, mGlu2/3 agonists attenuate cocaine-seeking behavior induced by discriminative cocaine-associated cues or by cocaine priming. In addition, mGlu2/3 agonists have been shown to inhibit cue-induced reinstatement of heroin-seeking, alcohol-seeking, nicotine-seeking, and also inhibited food-seeking behavior. The decreases in cue-induced food responding suggest that the administration of mGlu2/3 agonist decreased motivation for a natural reinforcer also. Further, it has been hypothesized that susceptibility to relapse due to cue reactivity increases gradually over periods of weeks or months. Thus, the administration of a positive modulator of mGlu2/3 receptors during prolonged abstinence from cocaine self-administration will decrease, while a negative modulator of mGlu2/3 receptors will have no effect on cocaine-seeking behavior induced by discriminative stimuli associated with cocaine availability.

Avoidance and alleviation of the negative affective state of early drug withdrawal with further drug abuse is hypothesized to be an important source of motivation that contributes significantly to the development of compulsive drug use and relapse during early abstinence. It has been hypothesized that susceptibility to relapse due to affective withdrawal symptoms peaks within days of cessation reflecting early rise in withdrawal symptoms. Thus, pharmacological treatments that reverse aspects of cocaine early withdrawal would remove an important source of motivation that contributes to relapse to drug abuse shortly after the initial cessation of drug administration. Abrupt abstinence following chronic exposure to drugs of abuse, including cocaine results in a negative affective state reflected in significant elevations in intracranial self-stimulation (ICSS) thresholds. ICSS thresholds are thought to provide an operational measure of brain reward function; thus elevations in ICSS thresholds reflect deficits in brain reward function. This threshold elevation is opposite to the lowering of ICSS thresholds observed after cocaine administration that reflects an increase in brain reward function that most likely underlies, or at least relates to, cocaine's euphorigenic effects. This increase in brain reward function associated with cocaine consumption is considered essential for the establishment and maintenance of cocaine self-administration behavior. The mechanisms that contribute to withdrawal-induced reward deficits or reward facilitation remain unclear. Group II mGlus have been implicated in the synaptic adaptations that occur in response to chronic drug exposure and contribute to the aversive behavioral withdrawal syndrome. The role of glutamate transmission in the early phase of cocaine withdrawal has not been studied extensively. However, based on the nicotine dependence findings and the hypothesis of overlapping mechanisms of withdrawal from different drugs of abuse, one may hypothesize that decreased glutamatergic neurotransmission will also partly mediate cocaine withdrawal in cocaine-dependent subjects.

In some embodiments, the compounds described herein are mGlu2/3 receptor PAM used for treating cocaine addiction.

Schizophrenia

Schizophrenia is a devastating psychiatric illness that afflicts approximately 1% of the worldwide population. The core symptoms observed in schizophrenic patients include positive symptoms (thought disorder, delusions, hallucinations, and paranoia), negative symptoms (social withdrawal, anhedonia, apathy, and paucity of speech) and cognitive impairments such as deficits in perception, attention, learning, short- and long-term memory and executive function. The cognitive deficits in schizophrenia are one of the major disabilities associated with the illness and are considered a reliable predictor of long-term disability and treatment outcome. Currently available antipsychotics effectively treat the positive symptoms, but provide modest effects on the negative symptoms and cognitive impairments. Furthermore, some patients are unresponsive to current antipsychotic treatments and several of these agents are associated with adverse side effects, including disturbances in motor function, weight gain, and sexual dysfunction. Thus, there is a need for new treatment strategies for schizophrenia that provide major improvements in efficacy across multiple symptom clusters and have fewer adverse effects.

Although the underlying pathophysiology of schizophrenia remains unknown, accumulating evidence points to disruptions in multiple neurotransmitter systems that modulate neural circuits important for normal affect, sensory processing, and cognition. In particular, early clinical findings demonstrated that changes in glutamatergic transmission produced by antagonists of the N-methyl-D-aspartate (NMDA) subtype of ionotropic glutamate receptors, including phencyclidine (PCP), result in a state of psychosis in humans that is similar to that observed in schizophrenic patients. These studies suggest that agents that increase NMDA receptor function have potential as therapeutics for the treatment of all major symptom clusters (positive, negative, cognitive) of the disease. More recently, studies indicate that reduced NMDA receptor function induces complex changes in transmission through cortical and subcortical circuits that involve both glutamatergic and GABAergic synapses and include downstream increases in transmission at glutamatergic synapses in the prefrontal cortex. Importantly, these circuit changes might share common features with changes in brain circuit activities that occur in schizophrenia patients. One hypothesis is that NMDA receptors involved in these symptoms might reside at glutamatergic synapses on GABAergic projection neurons in midbrain regions as well as GABAergic interneurons and glutamatergic projection neurons in key cortical and limbic regions For example, under normal conditions the activation of NMDA receptors localized on GABAergic projection neurons in subcortical regions, such as the nucleus accumbens, provides inhibitory control on excitatory glutamatergic thalamocortical neurons that project to pyramidal neurons in the prefrontal cortex (PFC). Hypofunction or blockade of these NMDA receptors on midbrain inhibitory GABAergic neurons could result in a disinhibition of glutamatergic thalamocortical inputs to pyramidal neurons in the PFC. This disinhibition would lead to a subsequent increased activity of glutamatergic thalamic neurons and increased activity mediated by the DL-a-amino-3-hydroxy-5-methylisoxasole-4-propionate (AMPA) subtype of glutamate receptors at thalamocortical synapses in the PFC. Based on this model, manipulations that enhance NMDA receptor function, such as activation of metabotropic glutamate receptor subtype 5 (mGlu5) located on GABAergic neurons, have potential as a novel approach to the treatment of schizophrenia. An alternative approach might be to reduce excitatory glutamatergic transmission at key synapses, such as thalamocortical synapses in the PFC, by activation of metabotropic glutamate receptor subtypes 2 and 3 (mGlu2 and mGlu3) presynaptically located in these synapses. Although other viable models of circuit changes associated with schizophrenia exist, this hypothesis provides one possible framework within which to consider effects of ligands at mGlu receptors that might be relevant to schizophrenia.

A large number of preclinical and clinical studies provide strong evidence that agonists of mGlu2 and mGlu3 also have potential as a novel approach to the treatment of schizophrenia. Consistent with the animal studies, clinical studies reveal that a highly selective agonist of group II mGlu receptors has robust efficacy in improving ratings for positive and negative symptoms in patients with schizophrenia. Unlike currently marketed antipsychotic agents, there were no major adverse events reported for the mGlu2/3 agonist in the clinical studies to date. However, further clinical studies will be required to fully establish safety of these compounds after long-term dosing in schizophrenic patients, as well as assess possible efficacy on the cognitive impairments in these patients. Taken together, these findings represent an important breakthrough and could ultimately lead to introduction of group II mGlu receptor activators as a fundamentally novel approach to the treatment of schizophrenia. As mentioned above, animal studies reveal that the psychotomimetic agents increase activity of glutamatergic synapses in the PFC, and hyperactivity of glutamate neurotransmission in the PFC and limbic structures has been postulated to play a critical role in the pathophysiology of schizophrenia. Interestingly, effects of psychotomimetic agents on glutamatergic transmission in the PFC are blocked by group II mGlu receptor agonists. Although it is not yet clear whether this action of group II mGlu receptor agonists is mechanistically related to the antipsychotic actions of these compounds, these actions fit well with current models of disruptions in subcortical and cortical circuits that might be involved in the psychotomimetic effects of NMDA receptor antagonists and the range of symptoms observed in schizophrenia patients. Despite advances in development of group II mGlu receptor agonists, it is not yet clear whether orthosteric agonists of these receptors will reach the market for broad clinical use. Long-term administration of group II mGlu receptor agonists induces robust tolerance in at least one rodent model that has been used to predict antipsychotic efficacy. These orthosteric agonists also activate both mGlu2 and mGlu3 and do not provide insights into which of these group II mGlu receptor subtypes is most important for clinical efficacy. Although, recent findings demonstrate that the antipsychotic-like effects of mGlu2/3 receptor agonists are absent in mGlu2-knockout, but not mGlu3-knockout, mice. Thus, it is possible that positive allosteric modulators of mGlu2/3 might be an alternative approach that could provide greater selectivity and other potential advantages to orthosteric agonists.

In some embodiments, group II mGlu receptor agonists are useful in the treatment of schizophrenia. In some embodiments, selective mGlu2/3 PAMs represent a novel approach to the treatment of these disorders that is devoid of the adverse effects associated with currently available drugs.

In some embodiments, the compounds described herein are mGlu2/3 receptor PAM used for treating schizophrenia. The method includes administering to a subject in need thereof, an effective amount of at least one mGlu2/3 receptor PAM, thereby treating schizophrenia.

Alzheimer's Disease

Alzheimer's disease (AD), also known as Alzheimer disease, or just Alzheimer's, accounts for 60% to 70% of cases of dementia. It is a chronic neurodegenerative disease that usually starts slowly and gets worse over time. The most common early symptom is difficulty in remembering recent events (short term memory loss). As the disease advances, symptoms can include: problems with language, disorientation (including easily getting lost), mood swings, loss of motivation, not managing self-care, and behavioural issues. As a person's condition declines, she or he often withdraws from family and society. Gradually, bodily functions are lost, ultimately leading to death. Although the speed of progression can vary, the average life expectancy following diagnosis is three to nine years.

Various brain regions, including the cerebral cortex, hippocampus, striatum, amygdala, frontal cortex and nucleus accumbens, display high levels of mGlu2 and mGlu3 receptor binding. This distribution pattern suggests a role for the mGlu2/3 receptor subtypes in the pathology of neuropsychiatric disorders such as Alzheimer's disease.

In some embodiments, the compounds described herein are mGlu2/3 receptor PAM used for treating Alzheimer's disease. The method includes administering to a subject in need thereof, an effective amount of at least one mGlu2/3 receptor PAM, thereby treating Alzheimer's disease.

Huntington's Disease

Huntington's disease (HD) is a neurodegenerative genetic disorder that affects muscle coordination and leads to mental decline and behavioral symptoms. Symptoms of the disease can vary between individuals and affected members of the same family, but usually progress predictably. The earliest symptoms are often subtle problems with mood or cognition. A general lack of coordination and an unsteady gait often follows. As the disease advances, uncoordinated, jerky body movements become more apparent, along with a decline in mental abilities and behavioral symptoms. Physical abilities gradually worsen until coordinated movement becomes difficult. Mental abilities generally decline into dementia. Complications such as pneumonia, heart disease, and physical injury from falls reduce life expectancy to around twenty years from the point at which symptoms begin. Physical symptoms can begin at any age from infancy to old age, but usually begin between 35 and 44 years of age.

Excitotoxic injury to striatum by dysfunctional cortical input or aberrant glutamate uptake may contribute to Huntington's disease (HD) pathogenesis. Daily subcutaneous injection with a maximum tolerated dose (MTD) of the mGlu2/3 agonist LY379268 (20 mg/kg) beginning at 4 weeks has been found to dramatically improves the phenotype in R6/2 mice (the most commonly used animal model of Huntington's disease) (Reiner et al. Brain Research 1473 (2012) 161-172). For example, normalization of motor function in distance traveled, speed, the infrequency of pauses, and the ability to locomote in a straight line, and a rescue of a 15-20% striatal neuron loss at 10 weeks were observed.

In some embodiments, the compounds described herein are mGlu2/3 receptor PAM used for treating Huntington's disease. The method includes administering to a subject in need thereof, an effective amount of at least one mGlu2/3 receptor PAM, thereby treating Huntington's disease.

Lou Gehrig's Disease (ALS)

Amyotrophic lateral sclerosis (ALS) is a debilitating disorder characterized by rapidly progressive motor neuron degeneration, which results into weakness, muscle atrophy and spasticity. Riluzole is the only drug that improves survival of ALS patients, only to a modest extent. Thus, there is an urgent need for treatments that slow the progression of ALS. Familial ALS (FALS) is caused by mutations of several genes including SOD1 (type-1 superoxide dismutase). Although SOD1 mutations account for only 20% of FALS and about 2% of sporadic ALS, SOD1 mutant mice recapitulate several features of human ALS, and are widely employed as model for ALS. The validity of this model is strengthened by the evidence that SOD1 aggregates are detected in the spinal cord of people with sporadic ALS or with ALS caused by mutations of genes other than SOD1. The mechanisms by which SOD1 misfolding damages motor neurons are only partially elucidated and involve glutamate excitotoxicity, mitochondrial dysfunction, disruption of axonal transport, and abnormalities in astrocytes and microglia. One of the potential mechanisms of excitotoxicity in ALS is a reduced expression of the glutamate transporter, GLT-1, which clears glutamate from the synapses.

Enhancement of glial-derived neurotrophic factor (GDNF) is an established therapeutic target for amyotrophic lateral sclerosis (ALS). Activation of group II metabotropic glutamate (mGlu) receptors with the orthosteric agonist, LY379268, enhanced GDNF levels in cultured spinal cord astrocytes from wild-type mice and mGlu2 knockout mice, but not in astrocytes from mGlu3 knockout mice. LY379268 protected Sternberger monoclonal incorporated antibody-32 (SMI-32)+ motor neurons against excitotoxic death in mixed cultures of spinal cord cells, and its action was abrogated by anti-GDNF antibodies. Acute systemic injection of LY379268 (0.5, 1 or 5 mg/kg, i.p.) enhanced spinal cord GDNF levels in wild-type and mGlu2 knockout mice, but not in mGlu3 knockout mice. No tolerance developed to the GDNF-enhancing effect of LY379268 when the drug was continuously delivered for 28 days by means of s.c. osmotic minipumps (0.5-5 mg/day). Continuous infusion of LY379268 also enhanced the expression of the glutamate transporter GLT-1, in the spinal cord. Continuous treatment with 1 or 5 mg/kg/day with LY379268 had a beneficial effect on neurological disability in SOD1G93A mice. At day 40 of treatment, LY379268 enhanced spinal cord levels of GDNF and GLT-1, and rescued spinal cordmotor neurons, as assessed by stereologic counting of smi-32+ cells.

In some embodiments, the compounds described herein are mGlu2/3 receptor PAM used for treating ALS. The method includes administering to a subject in need thereof, an effective amount of at least one mGlu2/3 receptor PAM, thereby treating ALS.

Parkinson's Disease

Parkinson's disease (PD) is a chronic movement disorder resulting from a disturbance in the normal functioning of the basal ganglia, a collection of subcortical nuclei that are essential for the initiation and control of motor activity. The underlying pathology of the disease is a progressive degeneration of the dopaminergic nigrostriatal tract that manifests as a range of motor deficits including akinesia or bradykinesia, tremor, rigidity and postural instability. Current therapies for PD are essentially based on dopamine replacement and include levodapa (L-DOPA), a precursor of dopamine, and dopamine receptor agonists. These agents are effective in treating the symptoms of the disease in the early stages, but are less effective as the disease progresses when debilitating side-effects such as "on-off" fluctuations in efficacy and uncontrollable dyskinesias (involuntary muscle movements) ensue. More importantly, dopaminergic treatments do not halt the disease progression. For these reasons, several investigators have started to focus on nondopaminergic interventions as symptomatic and neuroprotecive strategies in PD.

Studies have shown that Group II mGlu receptors play some role in alleviating akinesia in the rat. In functional studies (Murray et al. Pharmacology, Biochemistry and Behavior 73 (2002) 455-466), intracerebroventricular administration of LY379268 (1, 5, 10, 20 nmol/2 μl) produced a dose-dependent increase in locomotor activity in the reserpine (5 mg/kg ip)-treated rat. In contrast, systemic administration of LY379268 (0.1, 1, 10 mg/kg ip) did not reverse reserpine-induced akinesia and failed to effect rotational behaviour 1 month after unilateral lesioning of the nigrostriatal tract by 6-hydroxydopamine (6-OHDA; 4 mg infused into the substantia nigra (SN)). These results suggest that mGlus may offer a nondopaminergic approach to the treatment of PD.

In some embodiments, the compounds described herein are mGlu2/3 receptor PAM used for treating Parkinson's disease. The method includes administering to a subject in need thereof, an effective amount of at least one mGlu2/3 receptor PAM, thereby treating Parkinson's disease.

Neuroprotection

In neuroprotective studies (Murray et al. Pharmacology, Biochemistry and Behavior 73 (2002) 455-466), animals were treated with LY379268 (10 mg/kg/day ip) either for 7 days following 6-OHDA injection into the SN (4 mg) or for 21 days following 6-OHDA injection into the striatum (10 mg) before measurement of tyrosine hydroxylase immunoreactivity in the striatum and/or SN as an index of neuroprotection. LY379268 provided some protection against nigral infusion of 6-OHDA and also some functional improvement and correction of dopamine turnover was observed. The compound also provided significant protection in the striatum and some protection in the SN against striatal infusion of 6-OHDA.

Low doses of the mGlu2/3 metabotropic glutamate receptor agonist, LY379268 (0.25-3 mg/kg, i.p.) increased glial cell line-derived neurotrophic factor (GDNF) mRNA and protein levels in the mouse brain, as assessed by in situ hybridization, real-time PCR, immunoblotting, and immunohistochemistry. This increase was prominent in the striatum, but was also observed in the cerebral cortex. GDNF mRNA levels peaked at 3 h and declined afterwards, whereas GDNF protein levels progressively increased from 24 to 72 h following LY379268 injection. The action of LY379268 was lost in mGlu3 receptor knockout mice, but not in mGlu2 receptor knockout mice. In pure cultures of striatal neurons, the increase in GDNF induced by LY379268 required the activation of the mitogen-activated protein kinase and phosphatidylinositol-3-kinase pathways, as shown by the use of specific inhibitors of the two pathways. Both in vivo and in vitro studies led to the conclusion that neurons were the only source of GDNF in response to mGlu3 receptor activation. Remarkably, acute or repeated injections of LY379268 at doses that enhanced striatal GDNF levels (0.25 or 3 mg/kg, i.p.) were highly protective against nigrostriatal damage induced by 1-methyl-4-phenyl-1,2,3,6-tetrahydropyridine in mice, as assessed by stereological counting of tyrosine hydroxylase-positive neurons in the pars compacta of the substantia nigra. It is speculated that selective mGlu3 receptor agonists or enhancers are potential candidates as neuroprotective agents in Parkinson's disease, and their use might circumvent the limitations associated with the administration of exogenous GDNF. Hence, selective mGlu3 receptor agonists or positive allosteric modulators (PAMs) would potentially be helpful in the treatment of chronic neurodegenerative disorder by providing neuroprotection.

Compounds

In one aspect, described herein is a compound that has the structure of Formula (I), or a pharmaceutically acceptable salt thereof:

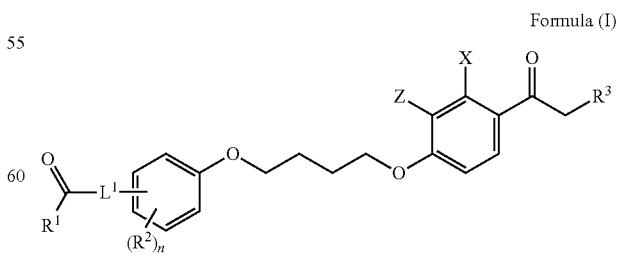

Formula (I)

wherein:
R$^1$ is —OH, —NHOR$^5$, —NHSO$_2$R$^4$, —NR$^4$R$^5$ or R$^4$;
L$^1$ is absent or C$_1$-C$_6$alkylene;

R² is hydrogen, halogen, nitro, —CN, —OH, —OR⁴, substituted or unsubstituted C₁-C₆alkyl, substituted or unsubstituted C₁-C₆fluoroalkyl, or substituted or unsubstituted C₃-C₆cycloalkyl;

n is 0, 1, 2, 3, or 4;

R³ is substituted or unsubstituted C₁-C₆alkyl, substituted or unsubstituted C₁-C₆fluoroalkyl, substituted or unsubstituted C₃-C₆cycloalkyl, or substituted or unsubstituted aryl;

X is —OH, —OR⁴, halogen, substituted or unsubstituted C₁-C₆alkyl, substituted or unsubstituted C₁-C₆fluoroalkyl, or substituted or unsubstituted C₃-C₆cycloalkyl;

Z is —OH, —OR⁴, halogen, substituted or unsubstituted C₁-C₆alkyl, substituted or unsubstituted C₁-C₆fluoroalkyl, or substituted or unsubstituted C₃-C₆cycloalkyl;

R⁴ is substituted or unsubstituted C₁-C₆alkyl, substituted or unsubstituted C₃-C₆cycloalkyl substituted or unsubstituted aryl or substituted or unsubstituted heteroaryl;

R⁵ is hydrogen, substituted or unsubstituted C₁-C₆alkyl, substituted or unsubstituted C₁-C₆fluoroalkyl, substituted or unsubstituted C₃-C₆cycloalkyl, or substituted or unsubstituted aryl;

or R⁴ and R⁵ taken together with the nitrogen to which they are attached to form a substituted or unsubstituted C₂-C₈heterocycloalkyl.

Throughout the specification, groups and substituents thereof are chosen by one skilled in the field to provide stable moieties and compounds. For example, in some embodiments, n is 0, 1, 2, 3, or 4. In some embodiments, n is 0. In some embodiments, n is 1. In some embodiments, n is 2. In some embodiments

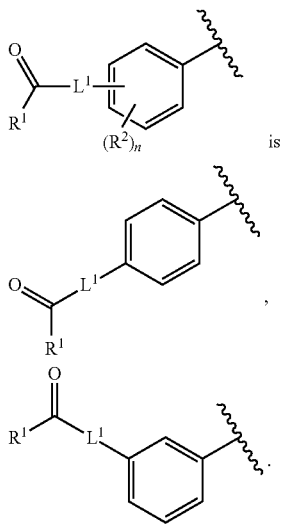

In some embodiments

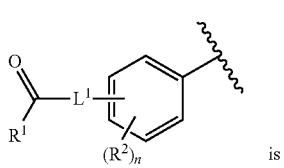

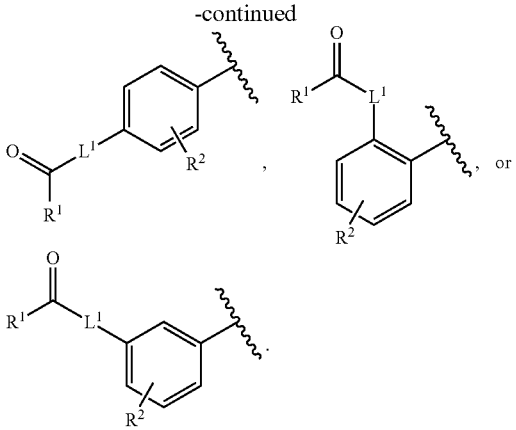

In some embodiments

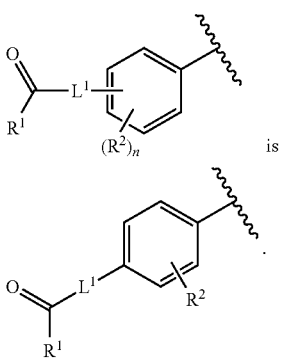

In some embodiments

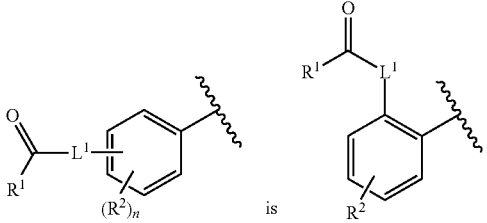

In some embodiments

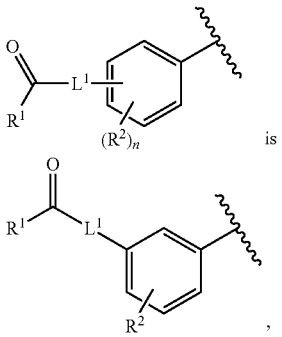

In some embodiments, $L^1$ is absent, —CH$_2$—, —CH$_2$CH$_2$—, —CH$_2$CH$_2$CH$_2$—, or —CH$_2$CH$_2$CH$_2$CH$_2$—. In some embodiments, $L^1$ is absent. In some embodiments, $L^1$ is —CH$_2$—, —CH$_2$CH$_2$—, —CH$_2$CH$_2$CH$_2$—, or —CH$_2$CH$_2$CH$_2$CH$_2$—. In some embodiments, $L^1$ is —CH$_2$CH$_2$—.

In some embodiments, Z is halogen, or $C_1$-$C_6$alkyl. In some embodiments, Z is F, Cl, Br, or I. In some embodiments, Z is Br, or I. In some embodiments, Z is F, or Cl. In some embodiments, Z is $C_1$-$C_6$alkyl. In some embodiments, Z is —CH$_3$, or —CH$_2$CH$_3$. In some embodiments, Z is —CH$_3$.

In some embodiments, the compound of Formula (I) has the structure of Formula (Ia):

Formula (Ia)

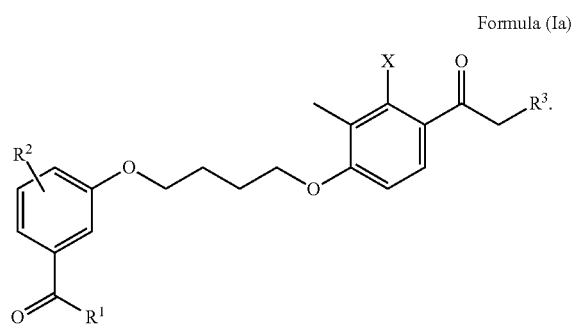

In some embodiments,

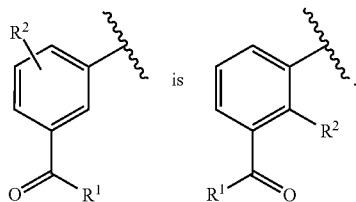

In some embodiments,

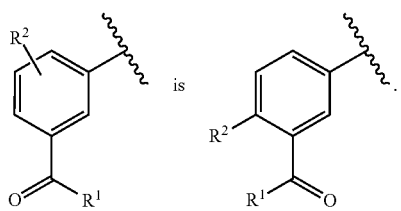

In some embodiments,

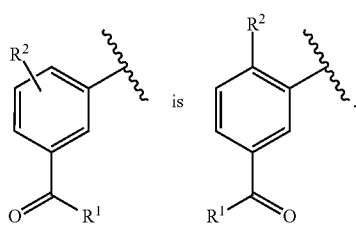

In some embodiments, the compound of Formula (I) has the structure of Formula (Ib):

Formula (Ib)

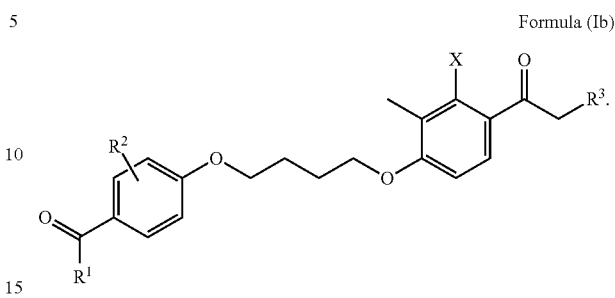

In some embodiments,

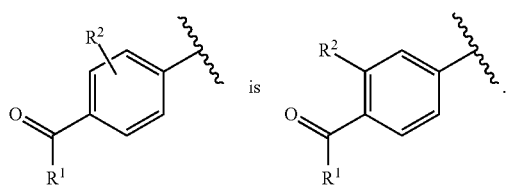

In some embodiments,

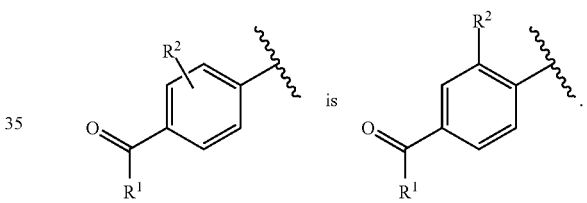

In some embodiments, $R^1$ is —OH, —NHOR$^5$, —NHSO$_2$R$^4$, —NR$^4$R$^5$ or R$^4$. In some embodiments, $R^1$ is —OH or —N(R$^4$R$^5$).

In some embodiments, $R^1$ is OH.

In some embodiments, $R^1$ is —N(R$^4$R$^5$). In some embodiments, $R^1$ is —N(R$^4$R$^5$), R$^4$ is $C_1$-$C_6$alkyl or $C_3$-$C_6$cycloalkyl; and R$^5$ is hydrogen or $C_1$-$C_6$alkyl. In some embodiments, $R^1$ is —N(R$^4$R$^5$) and R$^4$ and R$^5$ taken together with the nitrogen to which they are attached to form a substituted or unsubstituted $C_2$-$C_8$heterocycloalkyl. In some embodiments, R$^4$ and R$^5$ taken together with the nitrogen to which they are attached to form a substituted or unsubstituted $C_5$-$C_6$heterocycloalkyl. In some embodiments, R$^4$ and R$^5$ taken together with the nitrogen to which they are attached to form a substituted or unsubstituted $C_6$heterocycloalkyl. In some embodiments, R$^4$ and R$^5$ taken together with the nitrogen to which they are attached to form a pyrrolidinyl, morpholinyl, piperidinyl, or piperazinyl optionally substituted with $C_1$-$C_6$alkyl, halogen, or —SO$_2$CH$_3$.

In some embodiments, X is —OH, —OR$^4$, $C_1$-$C_6$alkyl, or $C_1$-$C_6$fluoroalkyl. In some embodiments, X is —OH. In some embodiments, X is $C_1$-$C_6$alkyl. In some embodiments, X is —CH$_3$. In some embodiments, Z is —CH$_3$ and X is —CH$_3$. In some embodiments, Z is —CH$_3$ and X is —OH.

In some embodiments, $R^2$ is hydrogen, halogen, —CN, —OH, —OR$^4$, substituted or unsubstituted $C_1$-$C_6$alkyl, or substituted or unsubstituted $C_1$-$C_6$fluoroalkyl. In some embodiments, $R^2$ is halogen. In some embodiments, $R^2$ is F or Cl. In some embodiments, $R^2$ is —OH or —OR$^4$. In some embodiments, $R^2$ is —OR$^4$. In some embodiments, $R^2$ is —OCH$_3$. In some embodiments, $R^2$ is C$_1$-C$_6$alkyl. In some embodiments, $R^2$ is —CH$_3$.

In some embodiments,

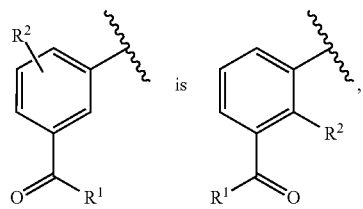

$R^2$ is —CH$_3$, —OCH$_3$, Cl, or F, and $R^1$ is —OH.

In some embodiments,

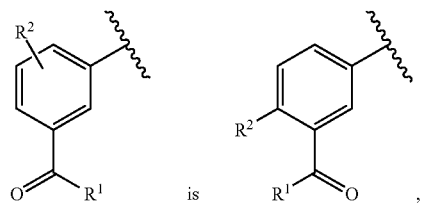

$R^2$ is —CH$_3$, —OCH$_3$, Cl, or F, and $R^1$ is —OH.

In some embodiments,

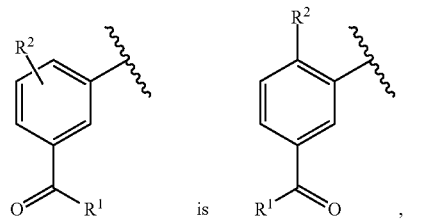

$R^2$ is —CH$_3$, —OCH$_3$, Cl, or F, and $R^1$ is —OH.

In some embodiments,

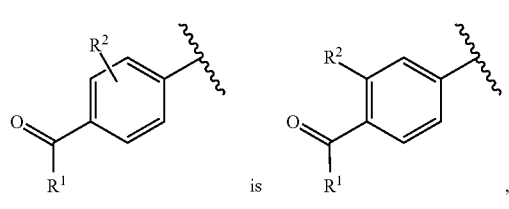

$R^2$ is —CH$_3$, —OCH$_3$, Cl, or F, and $R^1$ is —OH.

In some embodiments,

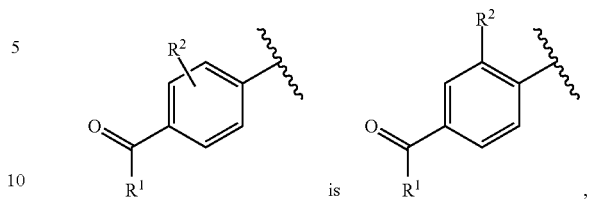

$R^2$ is —CH$_3$, —OCH$_3$, Cl, or F, and $R^1$ is —OH.

In some embodiments, $R^3$ is C$_1$-C$_6$alkyl, or C$_3$-C$_6$cycloalkyl.

In some embodiments, $R^3$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, cyclopropyl, cyclobutyl, cyclopentyl, or cyclohexyl.

In some embodiments, $R^3$ is —CH(CH$_3$)$_2$, —C(CH$_3$)$_3$, or cyclopentyl. In some embodiments, $R^3$ is —CH(CH$_3$)$_2$. In some embodiments, $R^3$ is —C(CH$_3$)$_3$. In some embodiments, $R^3$ is cyclopentyl.

In some embodiments, $R^1$ is —OH; $R^2$ is F, Cl, —CH$_3$, or —OCH$_3$; and X is —OH.

In some embodiments, $R^1$ is —OH; $R^2$ is F, Cl, —CH$_3$, or —OCH$_3$, X is —OH, Z is —CH$_3$, and $R^3$ is —CH(CH$_3$)$_2$, —C(CH$_3$)$_3$, or cyclopentyl.

In some embodiments, $R^1$ is —OH; $R^2$ is F, Cl, —CH$_3$, or —OCH$_3$, X is —OH, Z is —CH$_3$, and $R^3$ is —CH(CH$_3$)$_2$.

In some embodiments, $R^1$ is —OH; $R^2$ is F, Cl, —CH$_3$, or —OCH$_3$, X is —OH, Z is —CH$_3$, and $R^3$ is —C(CH$_3$)$_3$.

In some embodiments, $R^1$ is —OH; $R^2$ is F, Cl, —CH$_3$, or —OCH$_3$, X is —OH, Z is —CH$_3$, and $R^3$ is cyclopentyl.

In some embodiments, the compound is selected from the group consisting of:

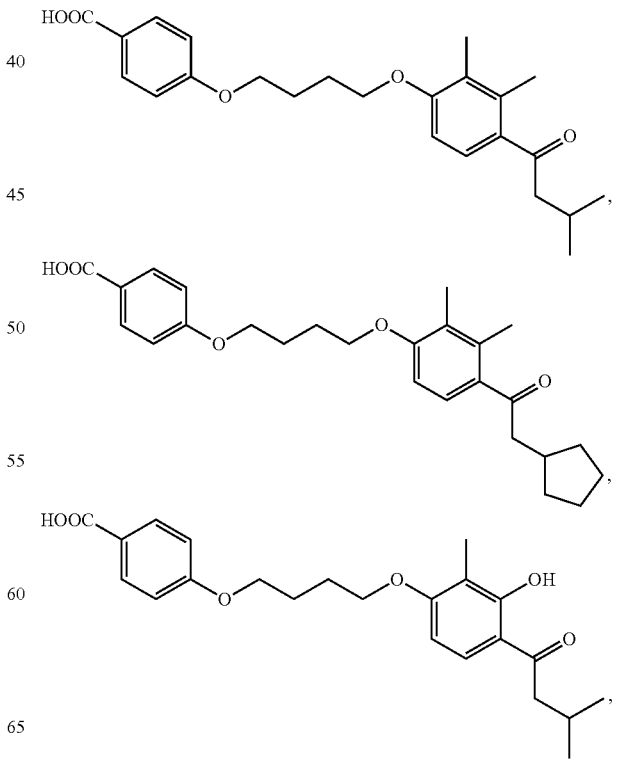

47
-continued
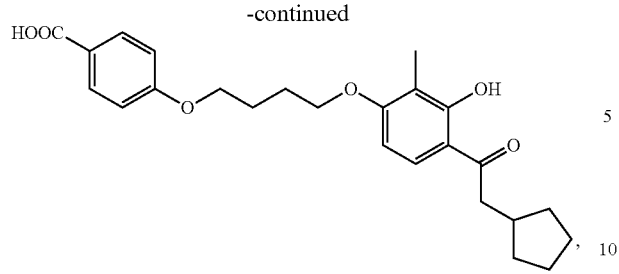
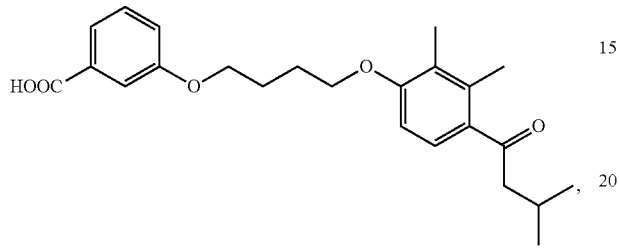
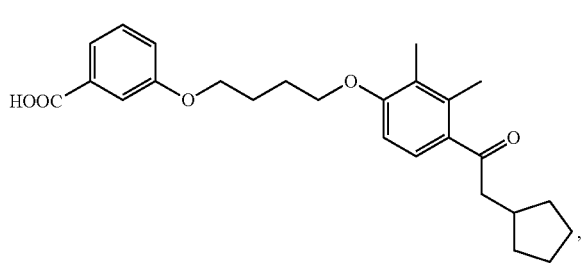
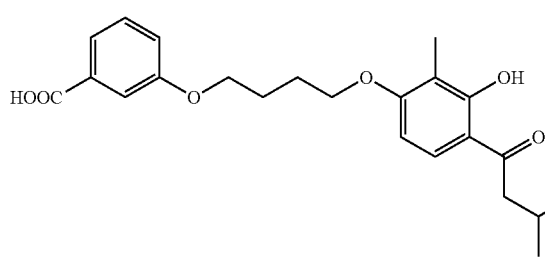
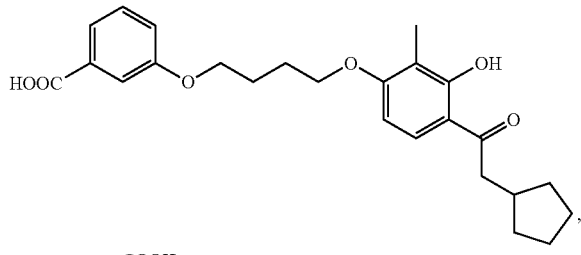
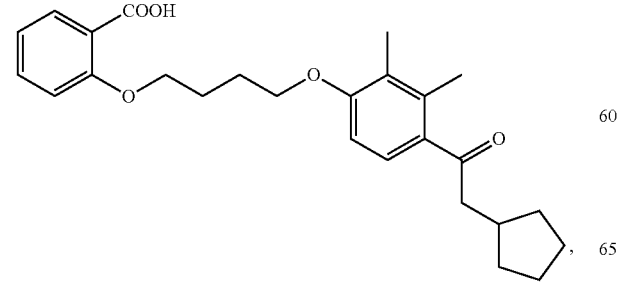
48
-continued
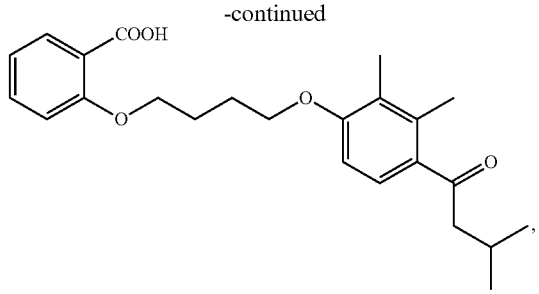
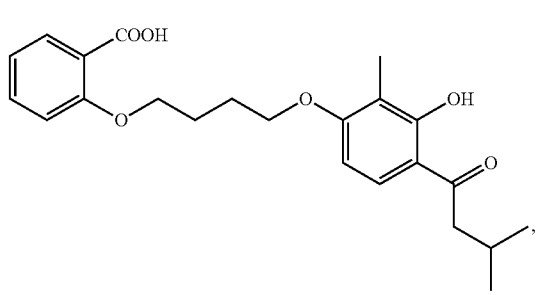
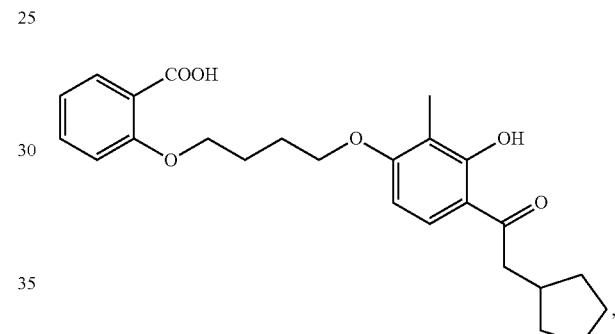
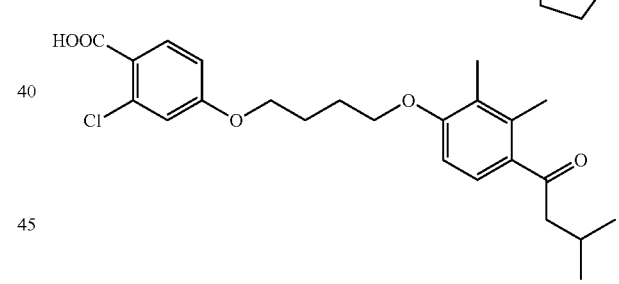
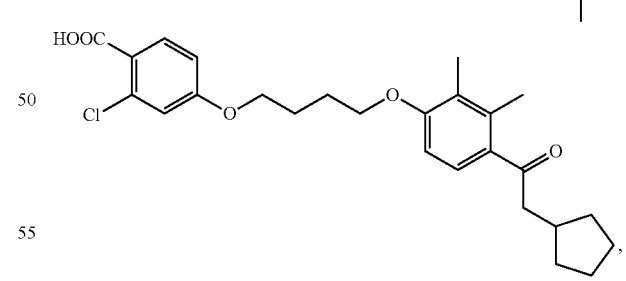
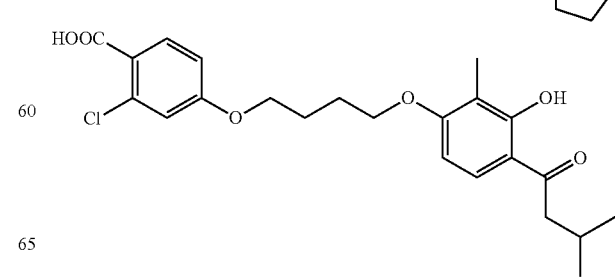

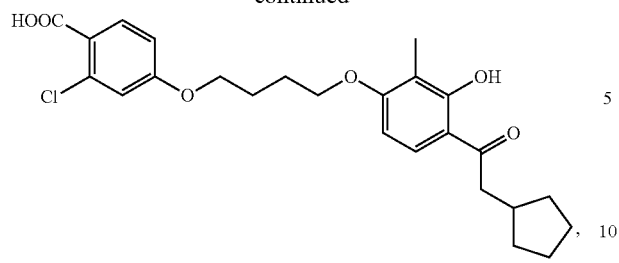
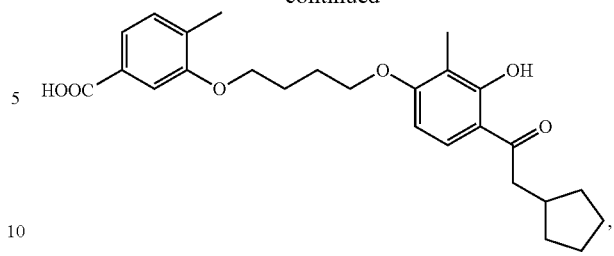

51
-continued
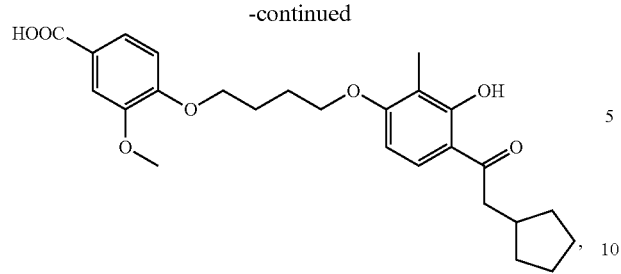
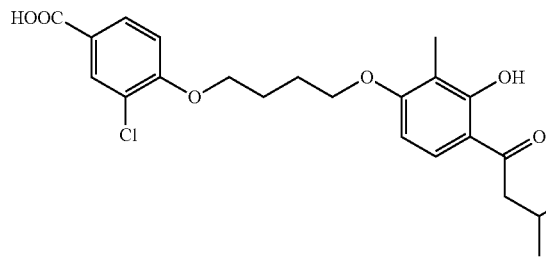
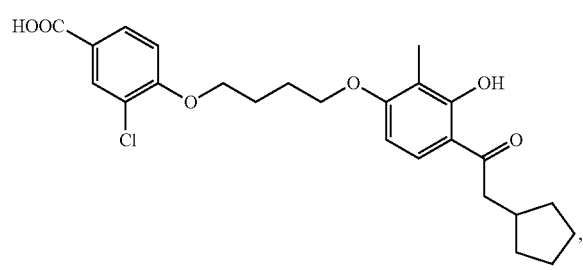
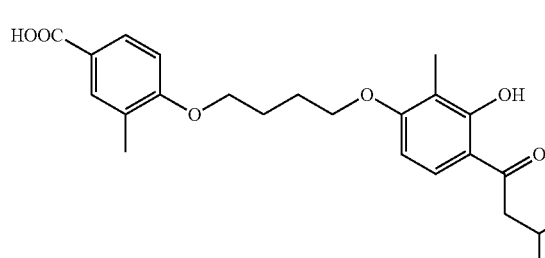
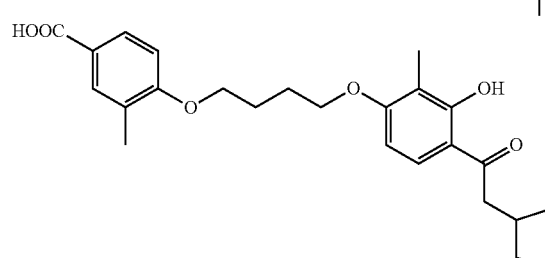
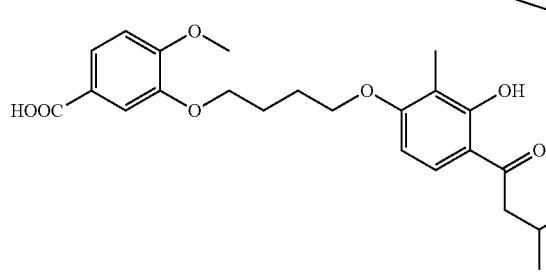
52
-continued
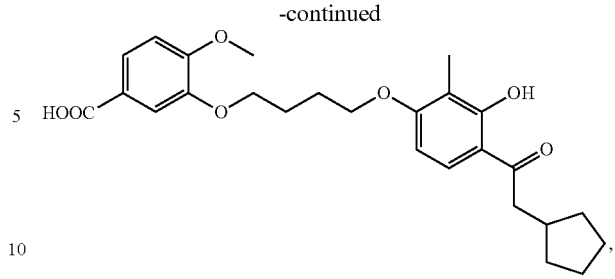
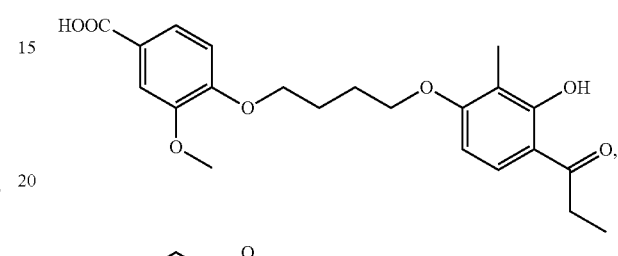
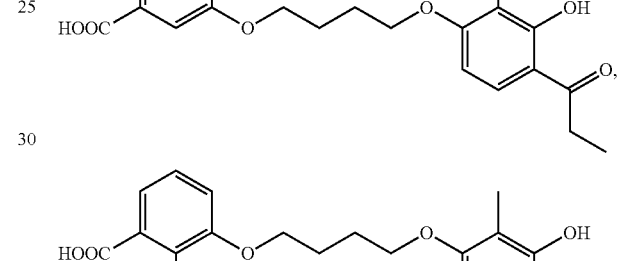
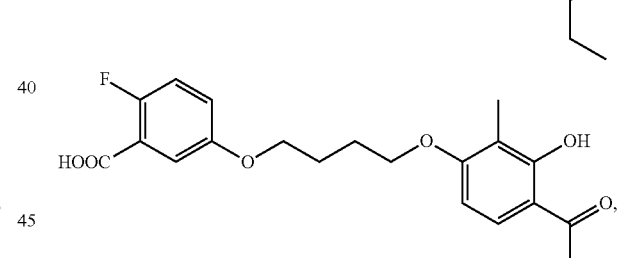
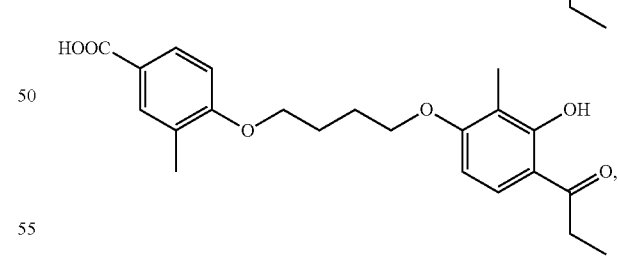
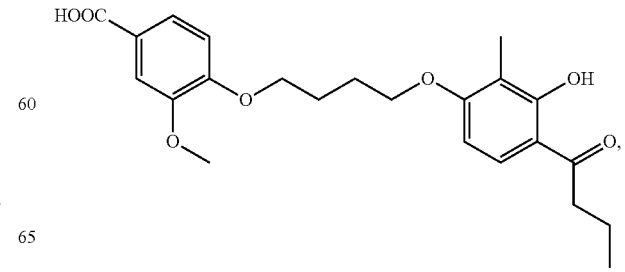

53
-continued
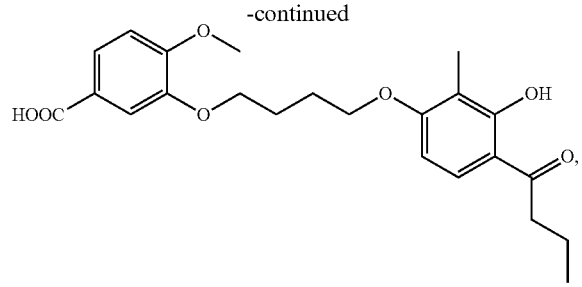
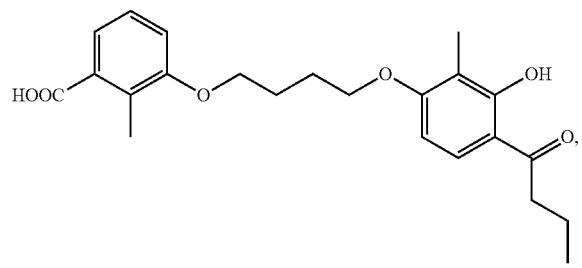
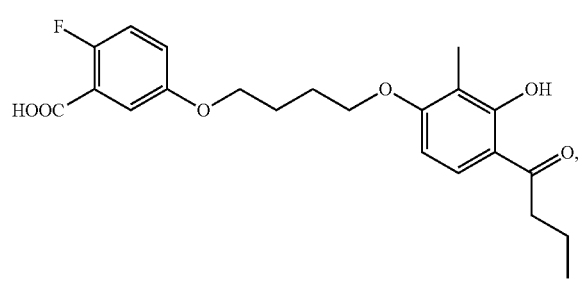
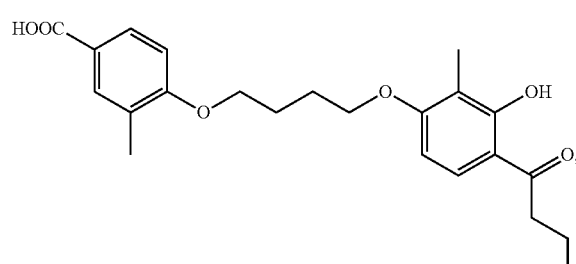
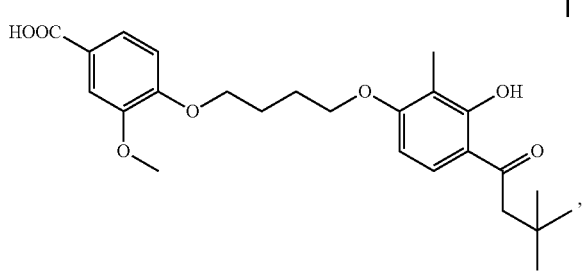
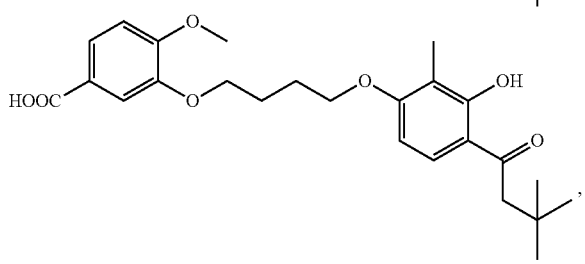
54
-continued
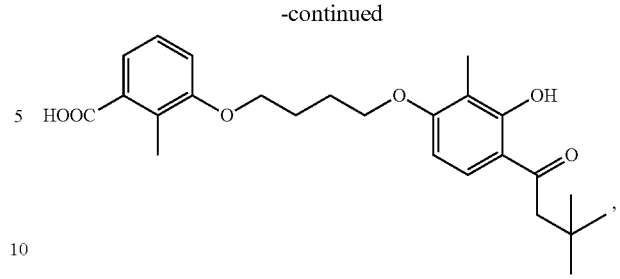
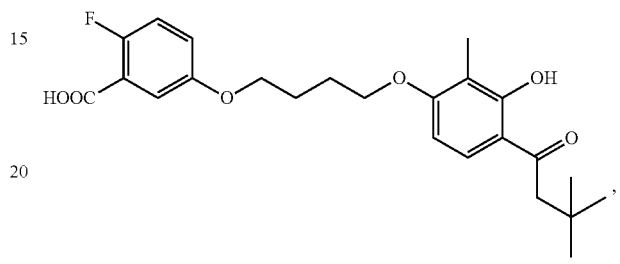
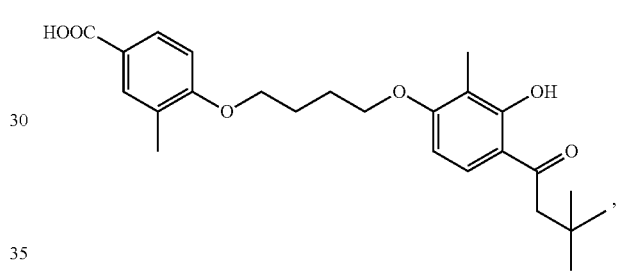
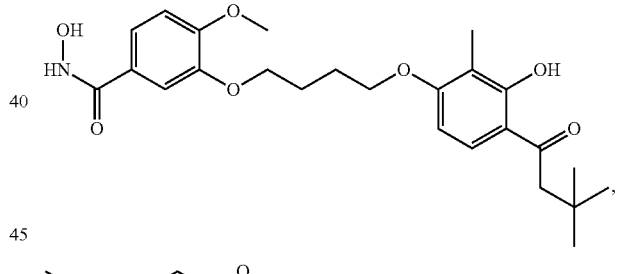
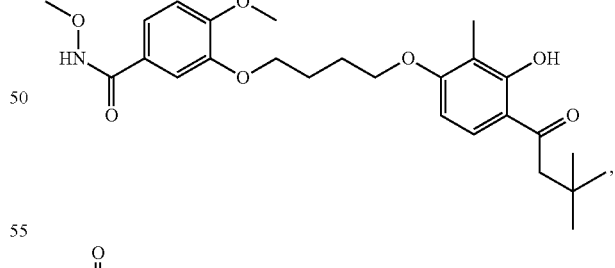
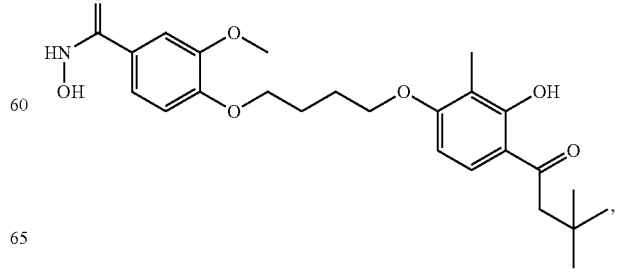

-continued
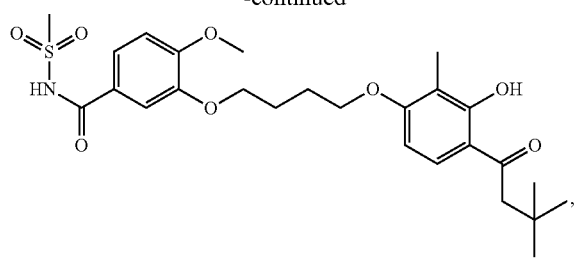
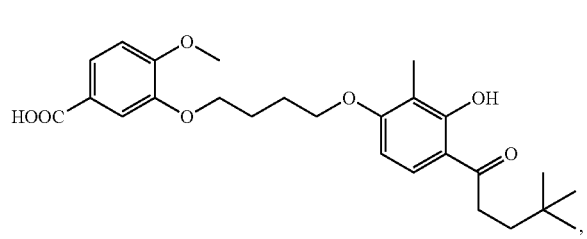
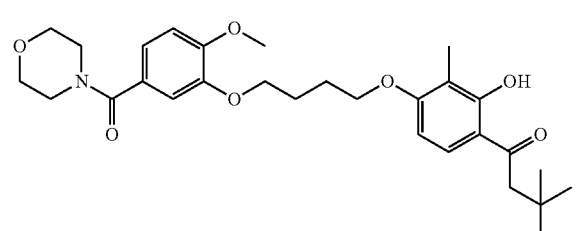
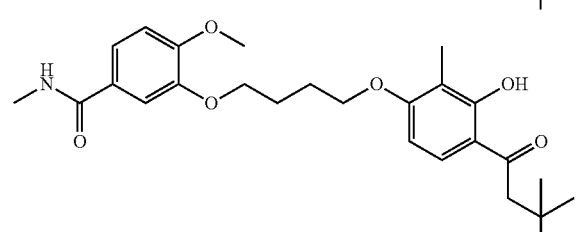
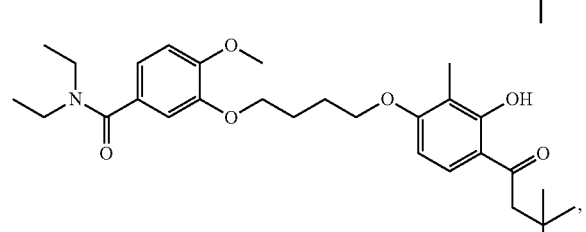
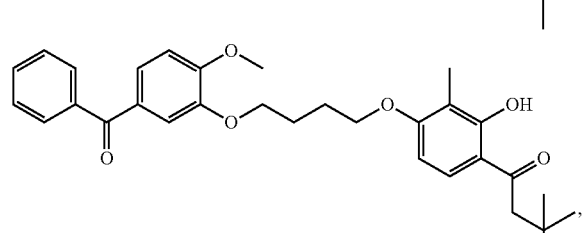
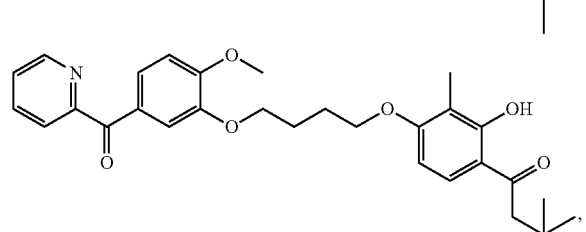
-continued
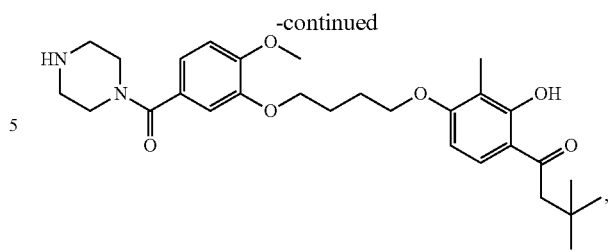
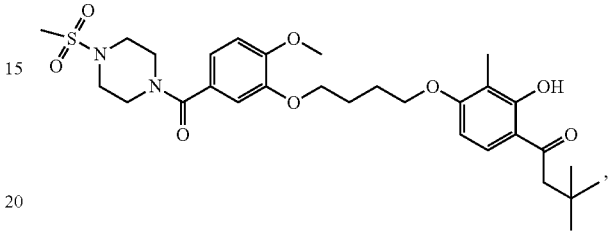
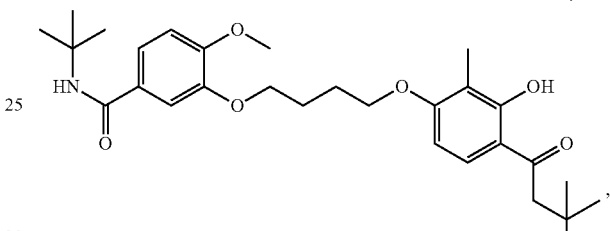
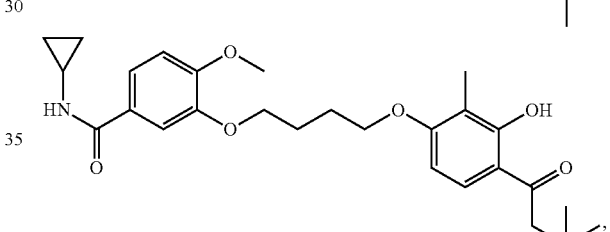
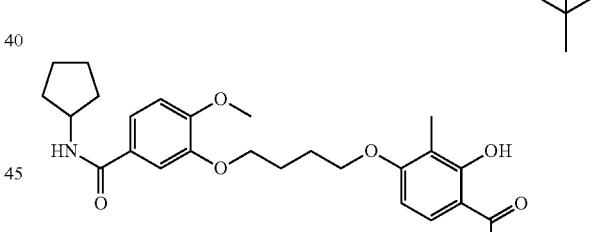, and
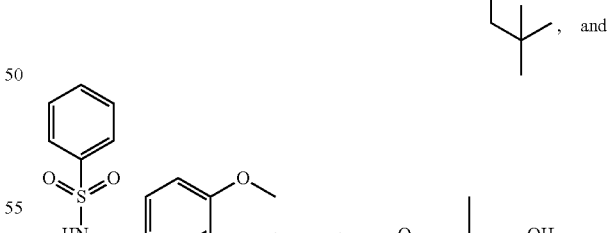
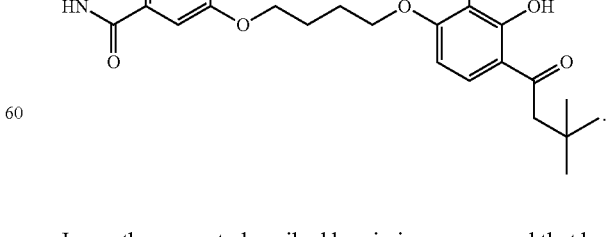
In another aspect, described herein is a compound that has the structure of Formula (II), or a pharmaceutically acceptable salt thereof:

Formula (II)

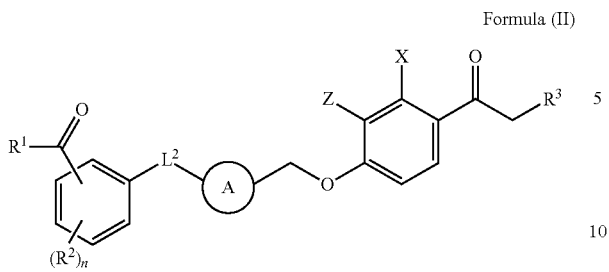

wherein:
$R^1$ is —OH, —OR⁴, —NHOR⁵, —NHSO₂R⁴, —NR⁴R⁵ or R⁴;
or —C(=O)R¹ is a carboxylic acid bioisostere having the structure

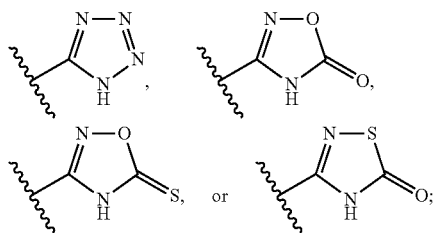

Ring A is substituted or unsubstituted aryl or substituted or unsubstituted heteroaryl;
$L^2$ is absent, —O—, —O—(C₁-C₆alkylene)-, —S—, or —S—(C₁-C₆alkylene)-;
$R^2$ is hydrogen, halogen, nitro, —CN, —OH, —OR⁴, substituted or unsubstituted C₁-C₆alkyl, substituted or unsubstituted C₁-C₆fluoroalkyl, or substituted or unsubstituted C₃-C₆cycloalkyl;
n is 0, 1, 2, 3, or 4;
$R^3$ is substituted or unsubstituted C₁-C₆alkyl, substituted or unsubstituted C₁-C₆fluoroalkyl, substituted or unsubstituted C₃-C₆cycloalkyl, or substituted or unsubstituted aryl;
X is —OH, —OR⁴, halogen, substituted or unsubstituted C₁-C₆alkyl, substituted or unsubstituted C₁-C₆fluoroalkyl, or substituted or unsubstituted C₃-C₆cycloalkyl;
Z is —OH, —OR⁴, halogen, substituted or unsubstituted C₁-C₆alkyl, substituted or unsubstituted C₁-C₆fluoroalkyl, or substituted or unsubstituted C₃-C₆cycloalkyl;
$R^4$ is substituted or unsubstituted C₁-C₆alkyl, substituted or unsubstituted C₃-C₆cycloalkyl substituted or unsubstituted aryl, or substituted or unsubstituted heteroaryl;
$R^5$ is hydrogen, substituted or unsubstituted C₁-C₆alkyl, substituted or unsubstituted C₁-C₆fluoroalkyl, substituted or unsubstituted C₃-C₆cycloalkyl, or substituted or unsubstituted aryl;
or $R^4$ and $R^5$ taken together with the nitrogen to which they are attached to form a substituted or unsubstituted C₂-C₈heterocycloalkyl.

In some embodiments, n is 0, 1, 2, 3, or 4. In some embodiments, n is 0. In some embodiments, n is 1. In some embodiments, n is 2. In some embodiments, n is 3. In some embodiments, n is 4.

In some embodiments,

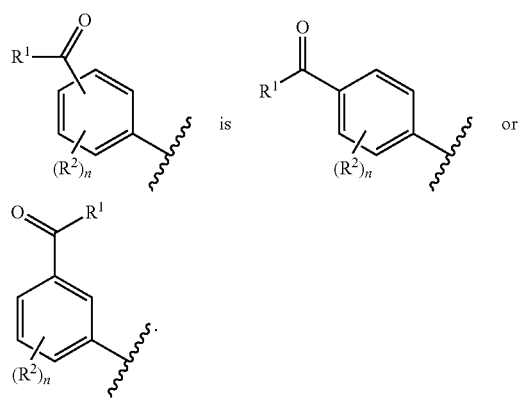

In some embodiments,

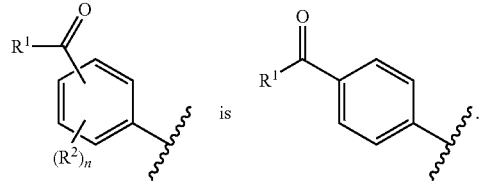

In some embodiments,

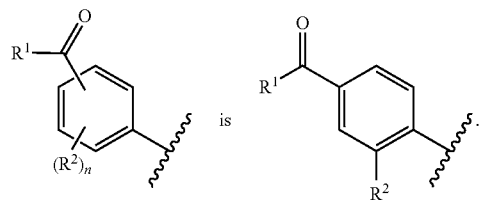

In some embodiments,

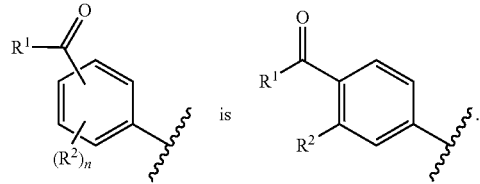

In some embodiments,

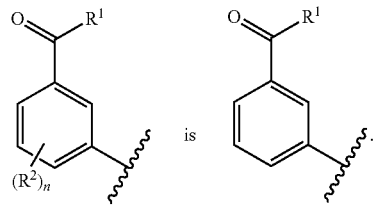

In some embodiments,

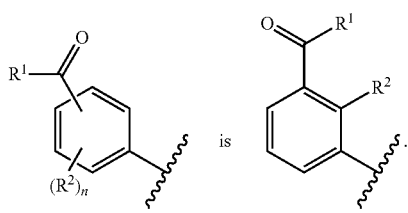 is 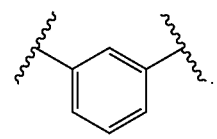.

In some embodiments,

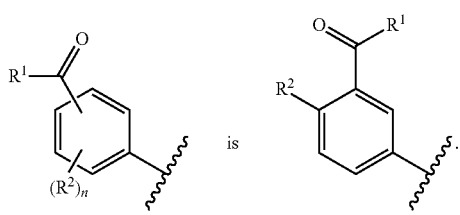 is 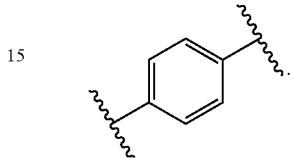.

In some embodiments,

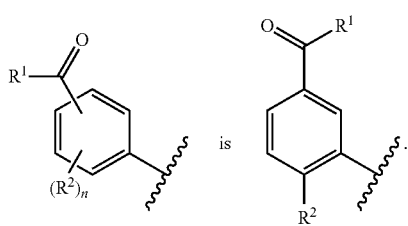 is 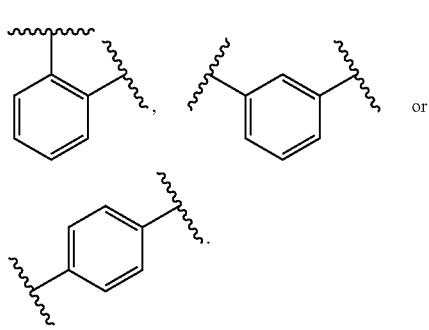.

In some embodiments, Z is halogen, or $C_1$-$C_6$alkyl. In some embodiments, Z is F, Cl, Br, or I. In some embodiments, Z is Br or I. In some embodiments, Z is Cl or F.

In some embodiments, Z is $C_1$-$C_6$alkyl. In some embodiments, Z is —$CH_3$, or —$CH_2CH_3$. In some embodiments, Z is —$CH_3$.

In some embodiments, $L^2$ is absent, —O—($CH_2$)—, —S—($CH_2$)—. In some embodiments, $L^2$ is absent.

In some embodiments, Ring A is substituted or unsubstituted aryl. In some embodiments, Ring A is unsubstituted aryl. In some embodiments, Ring A is substituted or unsubstituted phenyl.

In some embodiments, Ring A is

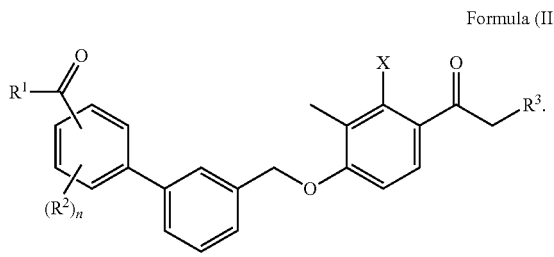

In some embodiments, Ring A is

In some embodiments, Ring A is

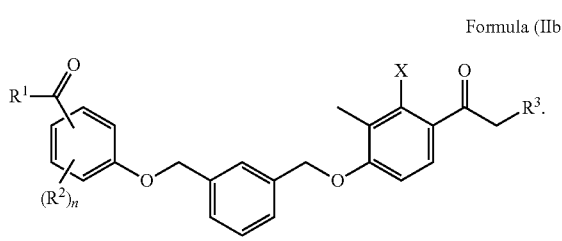

In some embodiments, the compound of Formula (II) has the structure of Formula (IIa):

Formula (IIa)

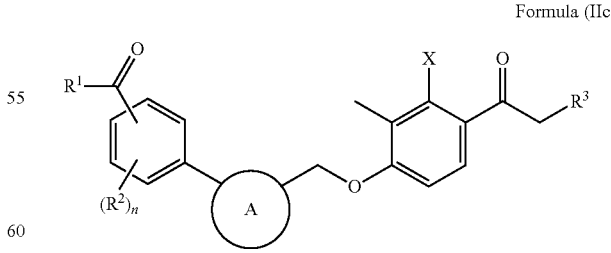

In some embodiments, the compound of Formula (II) has the structure of Formula (IIb):

Formula (IIb)

In some embodiments, the compound of Formula (II) has the structure of Formula (IIc):

Formula (IIc)

wherein:
Ring A is a substituted or unsubstituted monocyclic 5-, or 6-membered heteroaryl.

In some embodiments, Ring A is a substituted or unsubstituted monocyclic 5-membered heteroaryl. In some embodiments, Ring A is a substituted or unsubstituted monocyclic 6-membered heteroaryl.

In some embodiments, Ring A is selected from a group consisting of: furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl.

In some embodiments, Ring A is selected from a group consisting of:

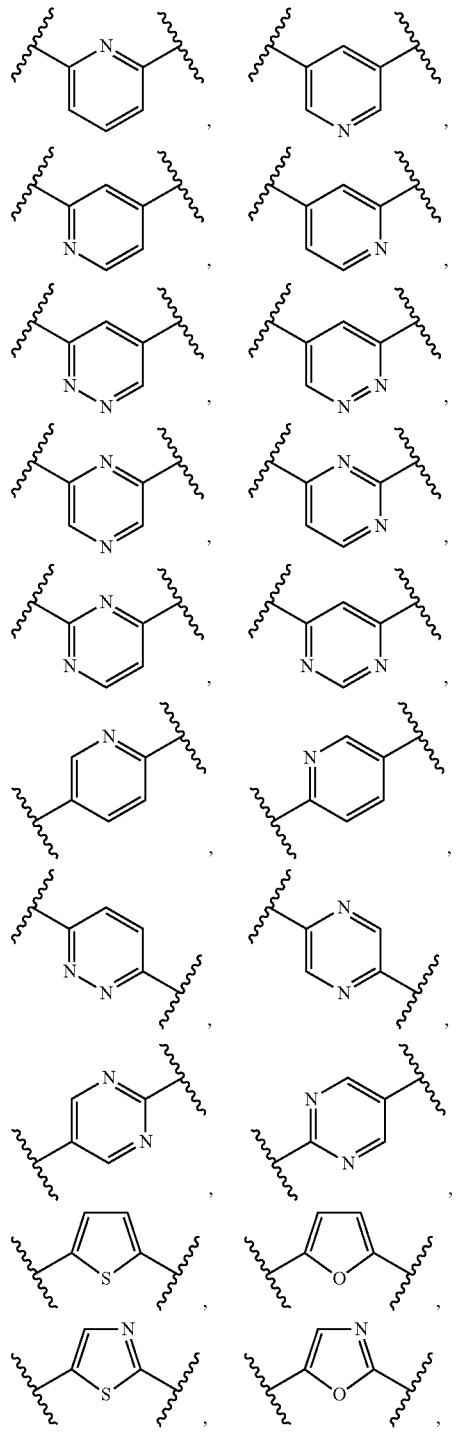

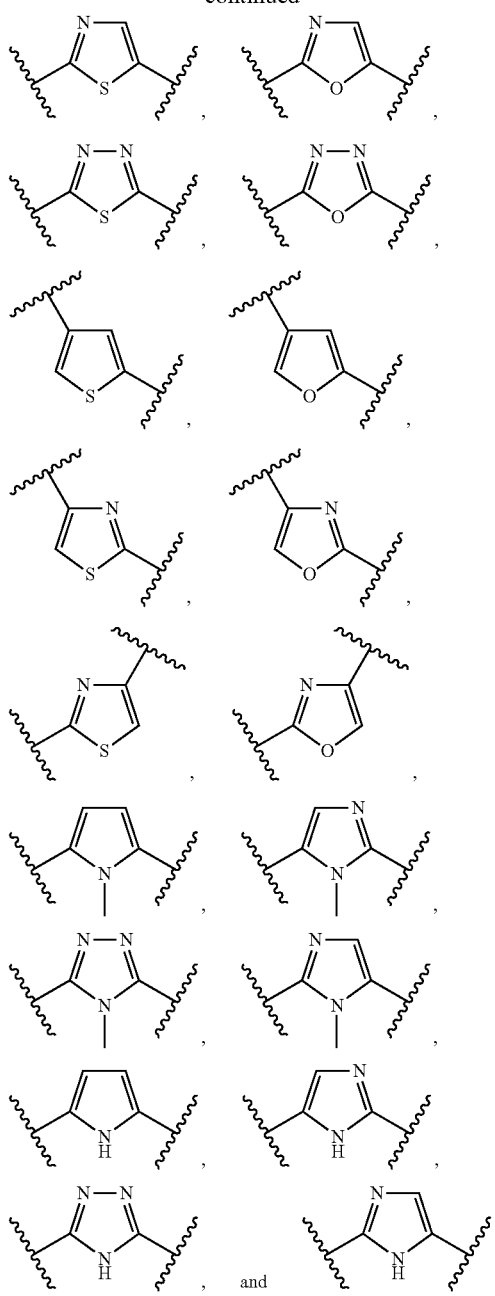

In some embodiments, Ring A is selected from a group consisting of:

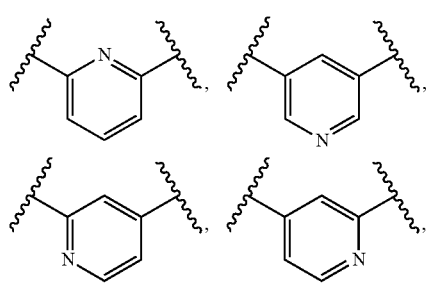

-continued

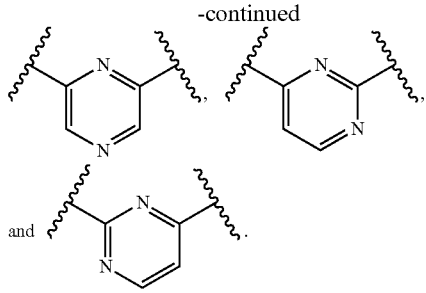

In some embodiments, Ring A is selected from a group consisting of:

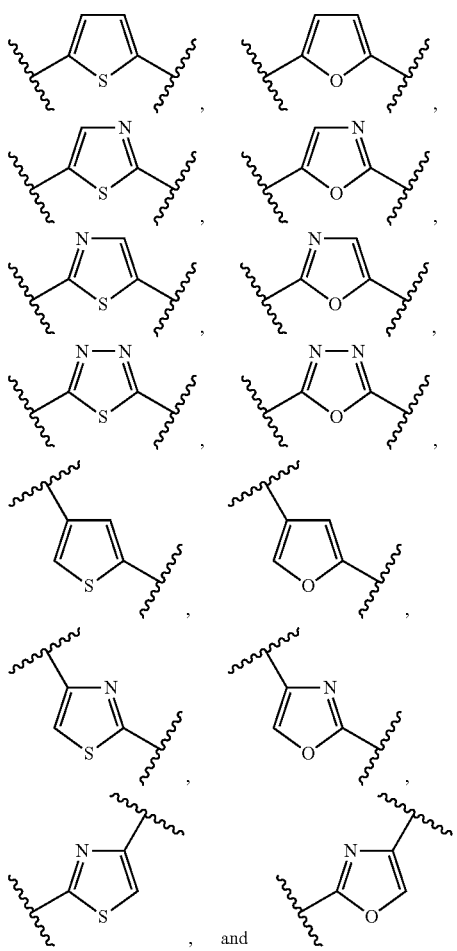

In some embodiments, $R^1$ is —OH, —OCH$_3$, —OCH$_2$CH$_3$, or —N(R$^4$R$^5$).

In some embodiments, $R^1$ is —OH or —N(R$^4$R$^5$).

In some embodiments, $R^1$ is OH.

In some embodiments, $R^1$ is —N(R$^4$R$^5$). In some embodiments, $R^1$ is —N(R$^4$R$^5$), $R^4$ is C$_1$-C$_6$alkyl or C$_3$-C$_6$cycloalkyl; and $R^5$ is hydrogen or C$_1$-C$_6$alkyl. In some embodiments, $R^1$ is —N(R$^4$R$^5$) and $R^4$ and $R^5$ taken together with the nitrogen to which they are attached to form a substituted or unsubstituted C$_2$-C$_8$heterocycloalkyl. In some embodiments, $R^4$ and $R^5$ taken together with the nitrogen to which they are attached to form a substituted or unsubstituted C$_5$-C$_6$heterocycloalkyl. In some embodiments, $R^4$ and $R^5$ taken together with the nitrogen to which they are attached to form a substituted or unsubstituted C$_6$heterocycloalkyl. In some embodiments, $R^4$ and $R^5$ taken together with the nitrogen to which they are attached to form a pyrrolidinyl, morpholinyl, piperidinyl, or piperazinyl optionally substituted with C$_1$-C$_6$alkyl, halogen, or —SO$_2$CH$_3$.

In some embodiments, —C(=O)R$^1$ is a carboxylic acid bioisostere having the structure

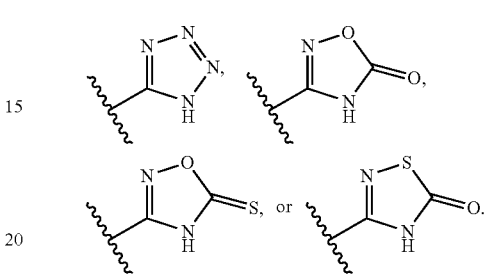

In some embodiments, —C(=O)R$^1$ is a carboxylic acid bioisostere having the structure

In some embodiments, —C(=O)R$^1$ is a carboxylic acid bioisostere having the structure

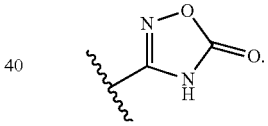

In some embodiments, —C(=O)R$^1$ is a carboxylic acid bioisostere having the structure

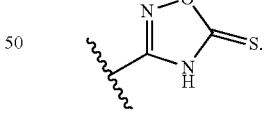

In some embodiments, —C(=O)R$^1$ is a carboxylic acid bioisostere having the structure

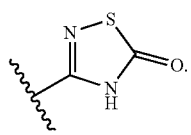 [SMILES: *c1nsc(=O)[nH]1]

In some embodiments, X is —OH, —OR$^4$, C$_1$-C$_6$alkyl, or C$_1$-C$_6$fluoroalkyl. In some embodiments, X is —OH. In some embodiments, X is C$_1$-C$_6$alkyl. In some embodiments, X is —CH$_3$. In some embodiments, Z is —CH$_3$ and X is —CH$_3$. In some embodiments, Z is —CH$_3$ and X is —OH.

In some embodiments, R$^2$ is hydrogen, halogen, —CN, —OH, —OR$^4$, substituted or unsubstituted C$_1$-C$_6$alkyl, or substituted or unsubstituted C$_1$-C$_6$fluoroalkyl.

In some embodiments, R$^2$ is hydrogen, F, Cl, —CH$_3$, or —OCH$_3$.

In some embodiments,

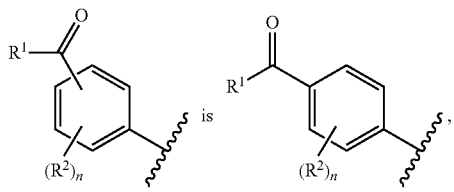

n is 1, R$^2$ is hydrogen, and R$^1$ is OH.

In some embodiments,

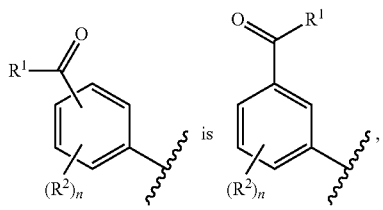

n is 1, R$^2$ is hydrogen, and R$^1$ is OH.

In some embodiments,

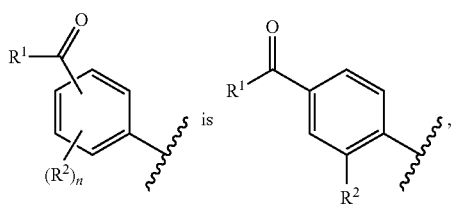

n is 1, R$^2$ is F, Cl, —CH$_3$, or —OCH$_3$, and R$^1$ is OH.

In some embodiments,

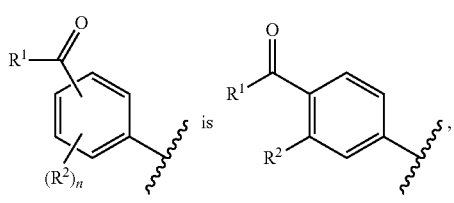

n is 1, R$^2$ is F, Cl, —CH$_3$, or —OCH$_3$, and R$^1$ is OH.

In some embodiments,

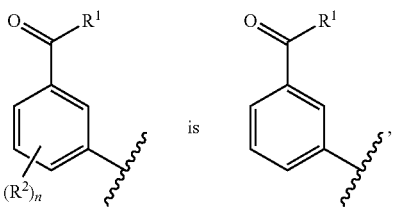

n is 1, R$^2$ is F, Cl, —CH$_3$, or —OCH$_3$, and R$^1$ is OH.

In some embodiments,

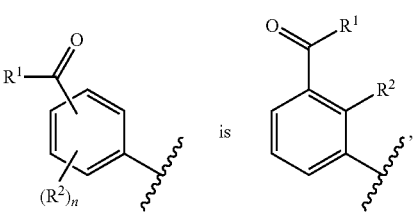

n is 1, R$^2$ is F, Cl, —CH$_3$, or —OCH$_3$, and R$^1$ is OH.

In some embodiments,

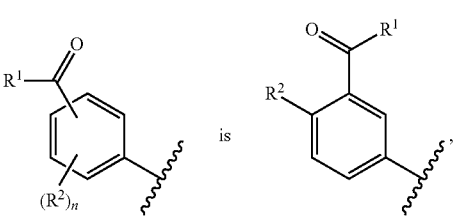

n is 1, R$^2$ is F, Cl, —CH$_3$, or —OCH$_3$, and R$^1$ is OH.

In some embodiments,

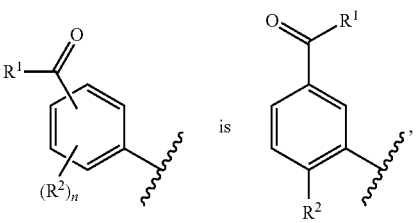

n is 1, R$^2$ is F, Cl, —CH$_3$, or —OCH$_3$, and R$^1$ is OH.

In some embodiments, R$^3$ is C$_1$-C$_6$alkyl, or C$_3$-C$_6$cycloalkyl.

In some embodiments, R$^3$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, cyclopropyl, cyclobutyl, cyclopentyl, or cyclohexyl.

In some embodiments, R$^3$ is —CH(CH$_3$)$_2$, —C(CH$_3$)$_3$, or cyclopentyl.

In some embodiments, R$^1$ is —OH; R$^2$ is hydrogen, F, Cl, —CH$_3$, or —OCH$_3$; and X is —OH. In some embodiments, R$^1$ is —OH; R$^2$ is hydrogen, X is —OH, Z is —CH$_3$, and R$^3$ is —CH(CH$_3$)$_2$, —C(CH$_3$)$_3$, or cyclopentyl. In some embodiments, R$^1$ is —OH; R$^2$ is hydrogen, X is —OH, Z is —CH$_3$, and R$^3$ is —CH(CH$_3$)$_2$. In some embodiments, R$^1$ is —OH; R$^2$ is hydrogen, X is —OH, Z is —CH$_3$, and R$^3$ is —C(CH$_3$)$_3$. In some embodiments, R$^1$ is —OH; R$^2$ is hydrogen, X is —OH, Z is —CH$_3$, and R$^3$ is cyclopentyl. In some embodiments, R$^1$ is —OH; R$^2$ is F, Cl, —CH$_3$, or —OCH$_3$, X is —OH, Z is —CH$_3$, and R$^3$ is —CH(CH$_3$)$_2$, —C(CH$_3$)$_3$, or cyclopentyl. In some embodiments, R$^1$ is —OH; R$^2$ is F, Cl, —CH$_3$, or —OCH$_3$, X is —OH, Z is —CH$_3$, and R$^3$ is —CH(CH$_3$)$_2$. In some embodiments, R$^1$ is —OH; R$^2$ is F, Cl, —CH$_3$, or —OCH$_3$, X is —OH, Z is —CH$_3$, and R$^3$ is —C(CH$_3$)$_3$. In some embodiments, R$^1$ is —OH; R$^2$ is F, Cl, —CH$_3$, or —OCH$_3$, X is —OH, Z is —CH$_3$, and R$^3$ is cyclopentyl.

In some embodiments, the compound is selected from the group consisting of:

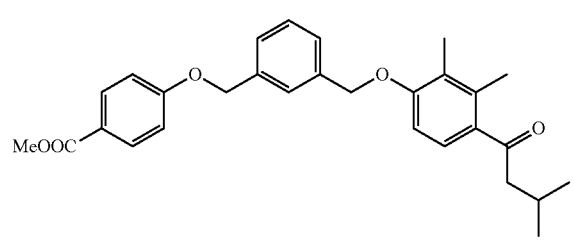

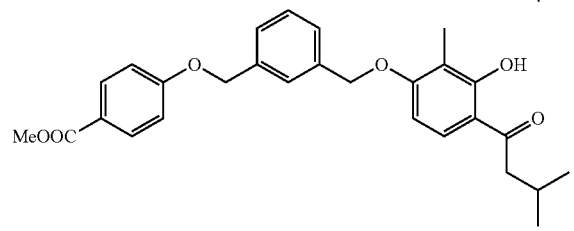

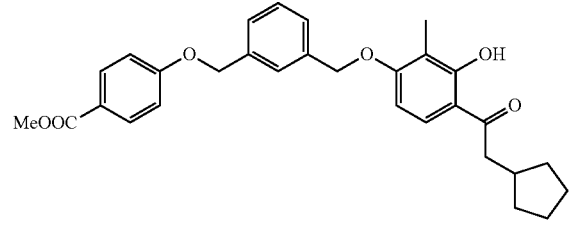

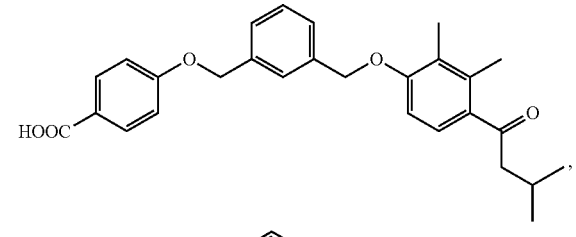

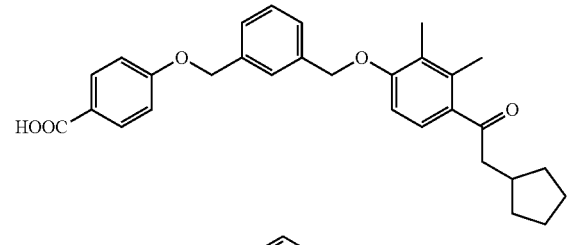

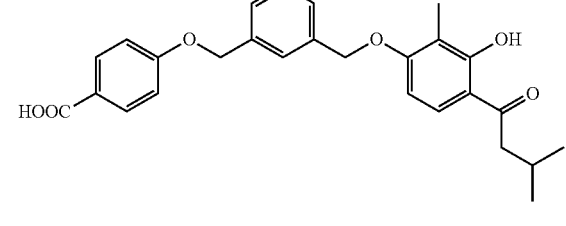

-continued

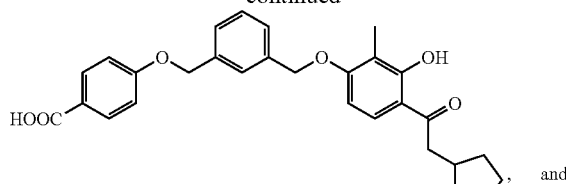

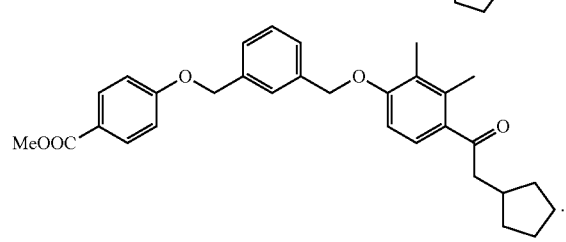

In some embodiments, the compound is selected from the group consisting of:

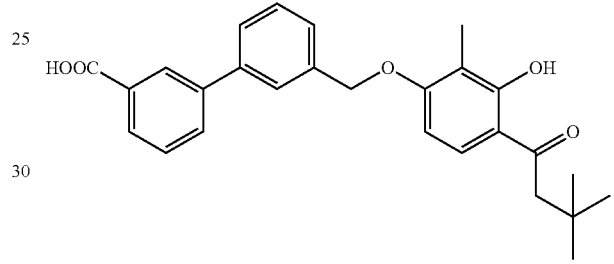

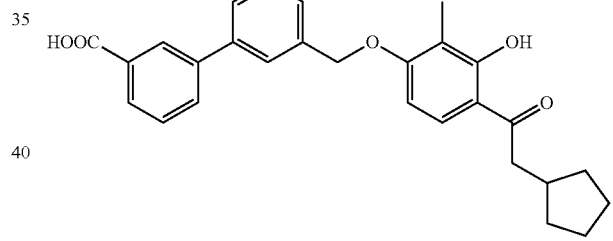

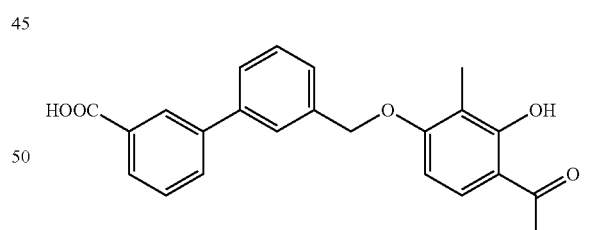

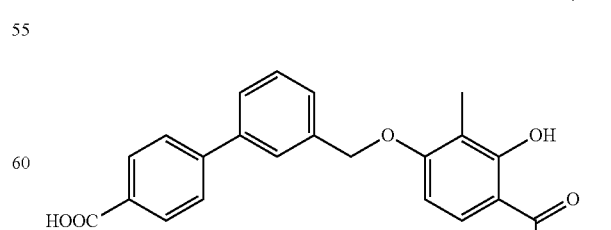

69
-continued
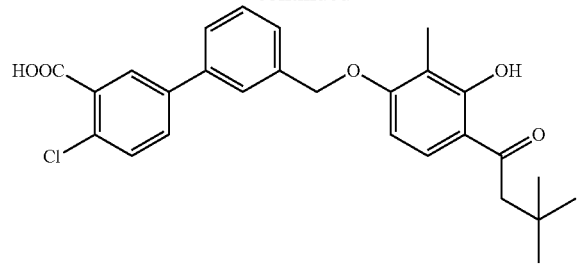
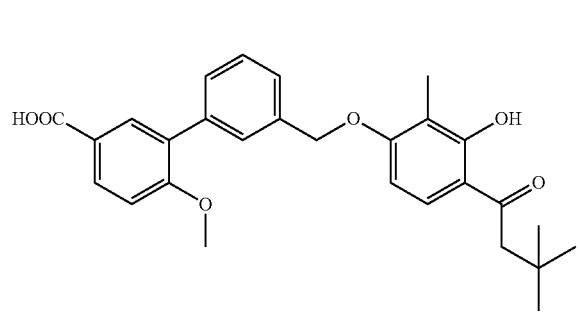
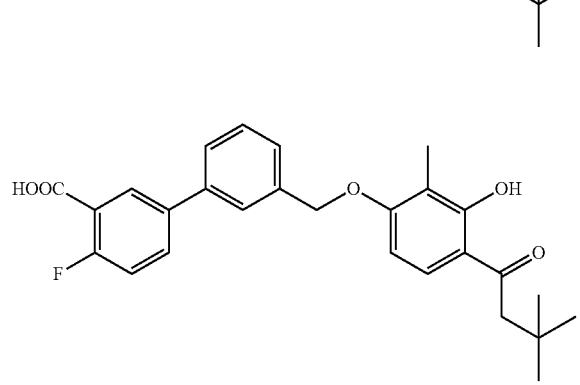
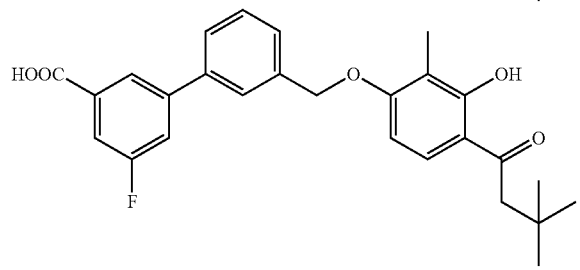
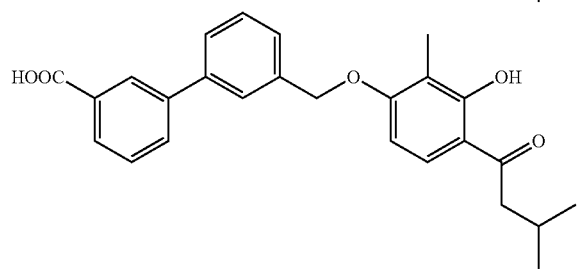
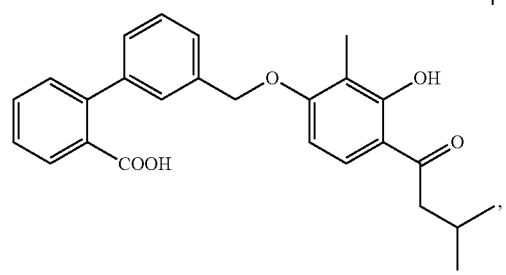
70
-continued
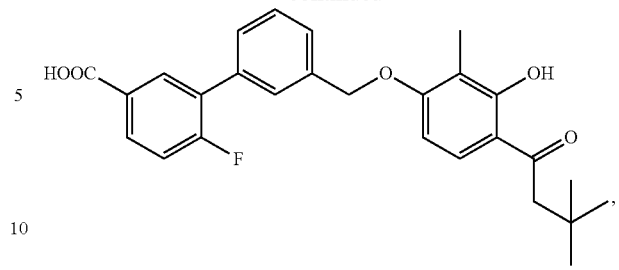
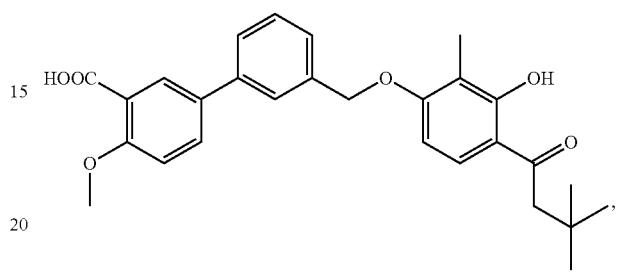
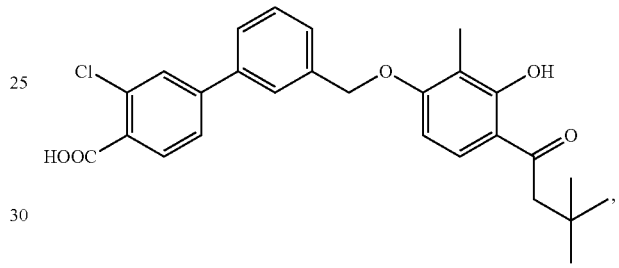
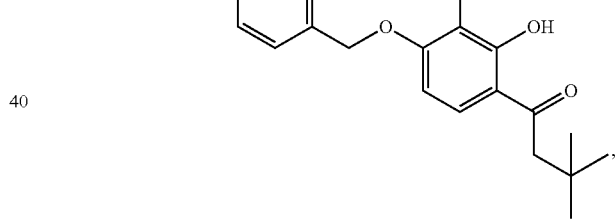
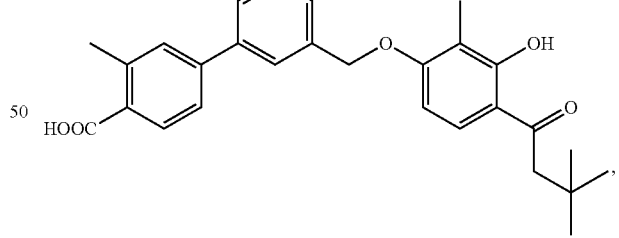
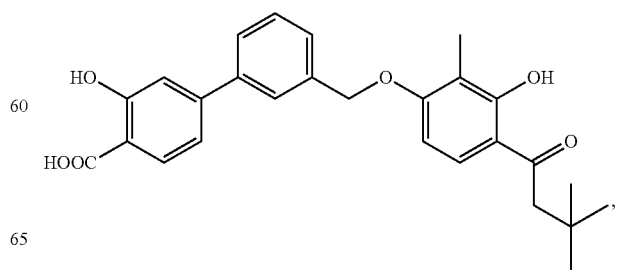

71
-continued
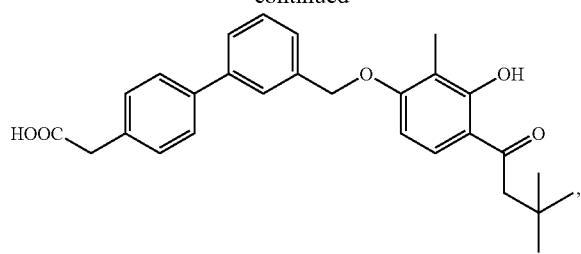
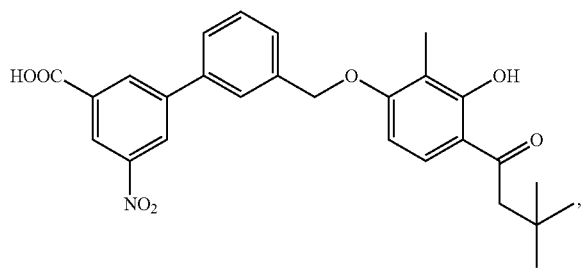 [SMILES: CC(C)CC(=O)c1ccc(OCc2cccc(-c3cccc(C(=O)O)c3)c2)c(Br)c1O]
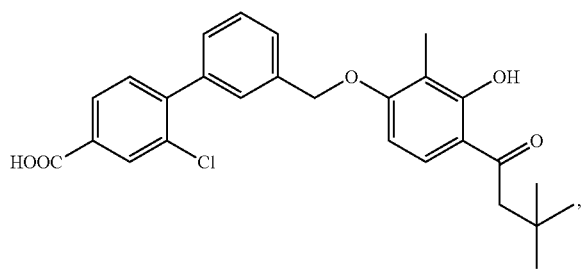
72
-continued
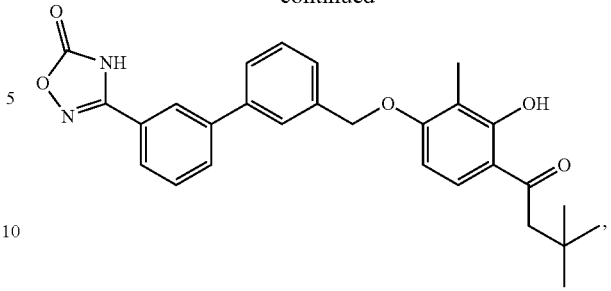
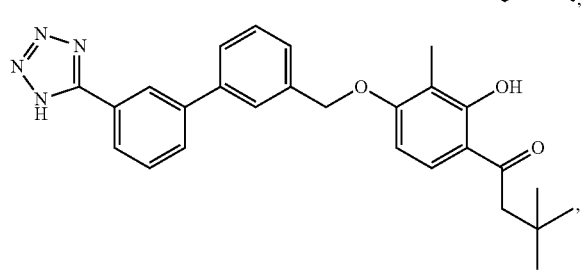
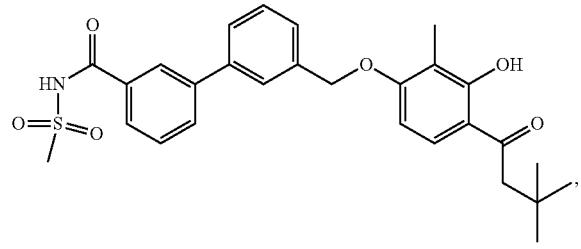

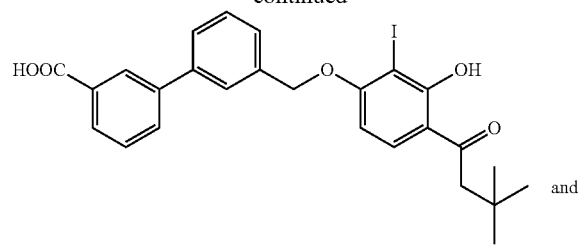
and
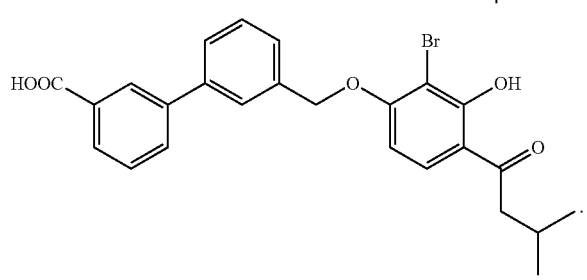
In some embodiments, the compound is selected from the group consisting of:
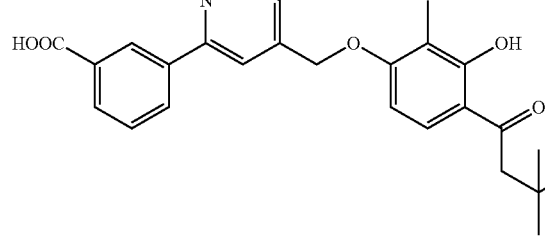
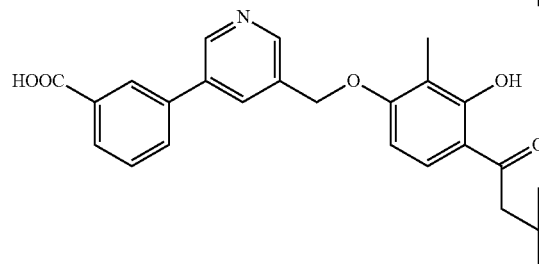
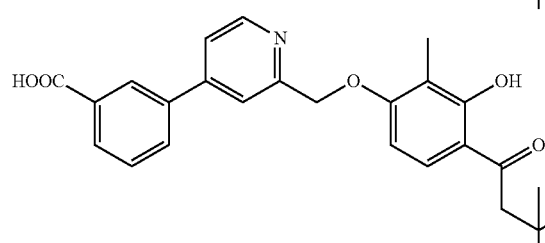
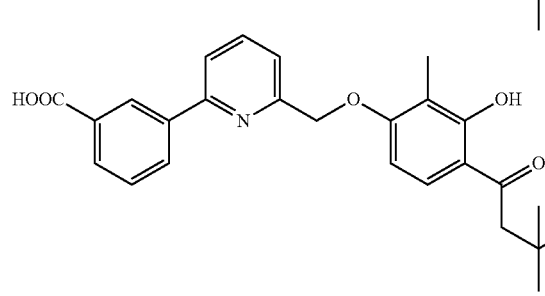
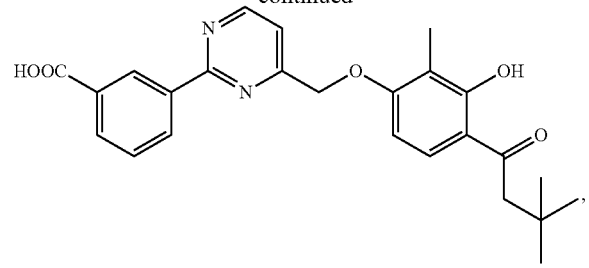
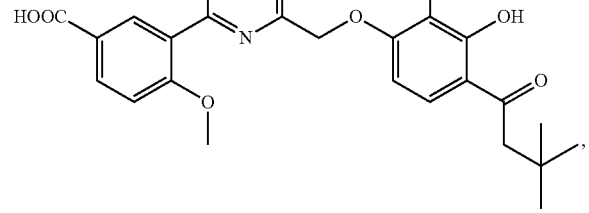
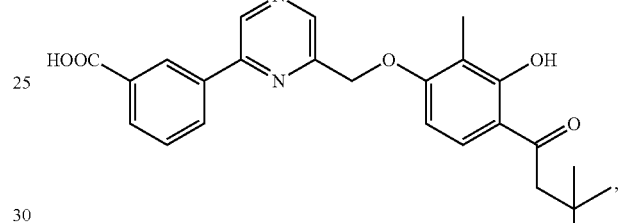
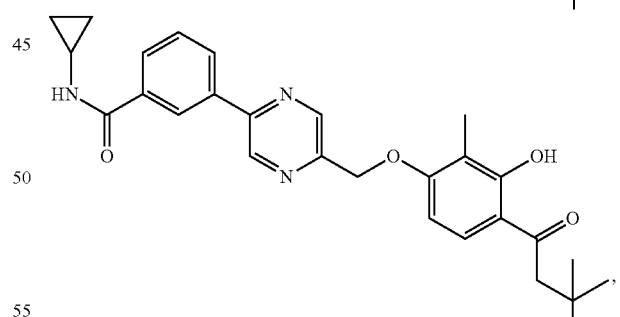
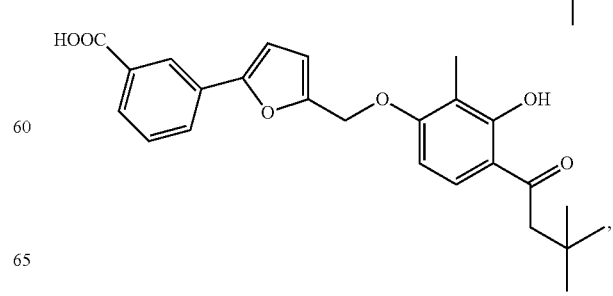

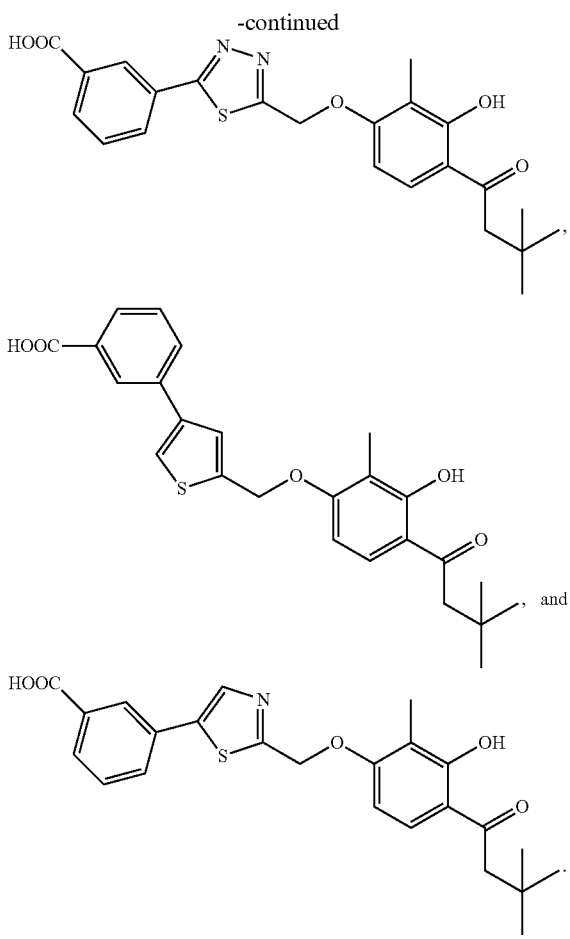

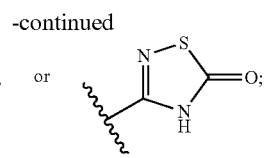

In another aspect, described herein is a compound that has the structure of Formula (III), or a pharmaceutically acceptable salt thereof:

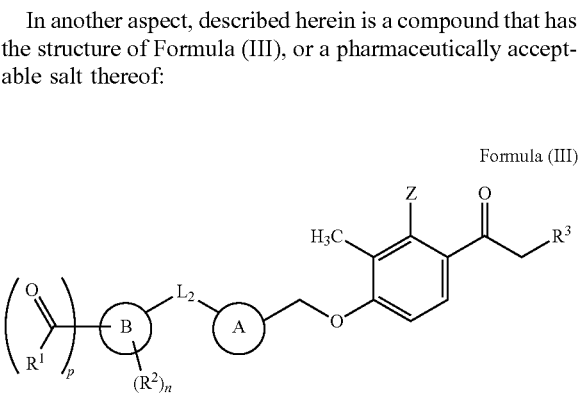

Formula (III)

wherein:

R¹ is —OH, —OR⁴, —NHOR⁵, —NHSO₂R⁴, —NR⁴R⁵ or R⁴;

or —C(=O)R¹ is a carboxylic acid bioisostere having the structure

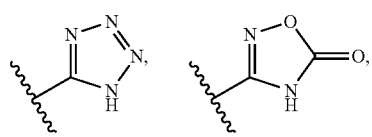

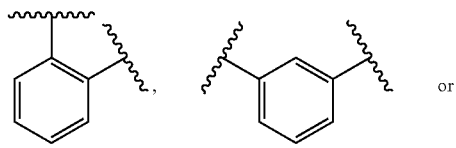

Ring A is substituted or unsubstituted aryl or substituted or unsubstituted heteroaryl;

Ring B is substituted or unsubstituted heteroarylaryl;

L² is absent, —O—, —O—(C₁-C₆alkylene)-, —S—, or —S—(C₁-C₆alkylene)-;

R² is hydrogen, halogen, nitro, —CN, —OH, —OR⁴, substituted or unsubstituted C₁-C₆alkyl, substituted or unsubstituted C₁-C₆fluoroalkyl, or substituted or unsubstituted C₃-C₆cycloalkyl;

R³ is substituted or unsubstituted C₁-C₆alkyl, substituted or unsubstituted C₁-C₆fluoroalkyl, substituted or unsubstituted C₃-C₆cycloalkyl, or substituted or unsubstituted aryl;

X is —OH, —OR⁴, halogen, substituted or unsubstituted C₁-C₆alkyl, substituted or unsubstituted C₁-C₆fluoroalkyl, or substituted or unsubstituted C₃-C₆cycloalkyl;

Z is —OH, —OR⁴, halogen, substituted or unsubstituted C₁-C₆alkyl, substituted or unsubstituted C₁-C₆fluoroalkyl, or substituted or unsubstituted C₃-C₆cycloalkyl;

R⁴ is substituted or unsubstituted C₁-C₆alkyl, substituted or unsubstituted C₃-C₆cycloalkyl substituted or unsubstituted aryl, or substituted or unsubstituted heteroaryl;

R⁵ is hydrogen, substituted or unsubstituted C₁-C₆alkyl, substituted or unsubstituted C₁-C₆fluoroalkyl, substituted or unsubstituted C₃-C₆cycloalkyl, or substituted or unsubstituted aryl;

or R⁴ and R⁵ taken together with the nitrogen to which they are attached to form a substituted or unsubstituted C₂-C₈heterocycloalkyl;

n is 0, 1, 2, 3, 4; and p is 0 or 1.

In some embodiments, n is 0, 1, 2, 3, or 4. In some embodiments, n is 0. In some embodiments, n is 1. In some embodiments, n is 2. In some embodiments, n is 3. In some embodiments, n is 4. In some embodiments, p is 0 and n is 0. In some embodiments, p is 1 and n is 0. In some embodiments, p is 1 and n is 1.

In some embodiments, Z is halogen, or C₁-C₆alkyl. In some embodiments, Z is F, Cl, Br, or I. In some embodiments, Z is Br or I. In some embodiments, Z is Cl or F.

In some embodiments, Z is C₁-C₆alkyl. In some embodiments, Z is —CH₃, or —CH₂CH₃. In some embodiments, Z is —CH₃.

In some embodiments, L² is absent, —O—(CH₂)—, —S—(CH₂)—. In some embodiments, L² is absent.

In some embodiments, Ring A is substituted or unsubstituted aryl. In some embodiments, Ring A is unsubstituted aryl.

In some embodiments, Ring A is substituted or unsubstituted phenyl.

In some embodiments, Ring A is

In some embodiments, Ring A is

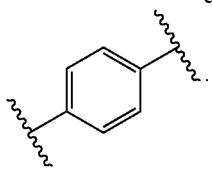

In some embodiments, Ring A is

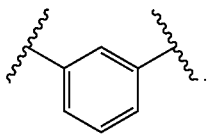 [SMILES: *c1cccc(*)c1]

In some embodiments, Ring A is

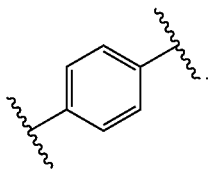 [SMILES: *c1ccc(*)cc1]

In some embodiments, Ring A is substituted or unsubstituted 5- or 6-membered heteroaryl. In some embodiments, Ring A is substituted or unsubstituted 5-membered heteroaryl. In some embodiments, Ring A is substituted or unsubstituted 6-membered heteroaryl. In some embodiments, Ring A is selected from a group consisting of: furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl.

In some embodiments, Ring B is substituted or unsubstituted 5- or 6-membered heteroaryl. In some embodiments, Ring B is substituted or unsubstituted 5-membered heteroaryl. In some embodiments, Ring B is substituted or unsubstituted 6-membered heteroaryl. In some embodiments, Ring B is selected from a group consisting of: furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl.

In some embodiments, Ring B is selected from a group consisting of:

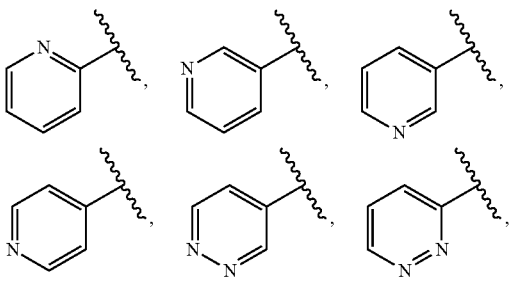

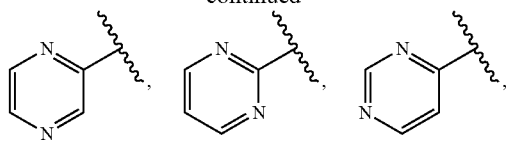

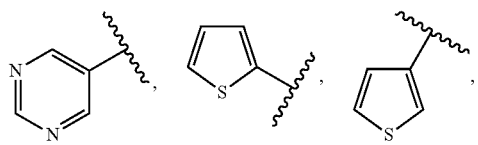

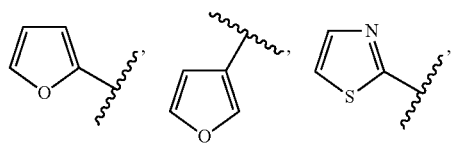

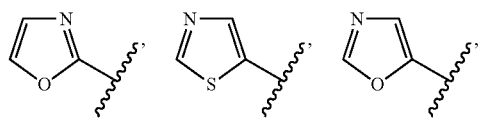

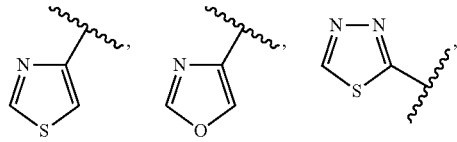

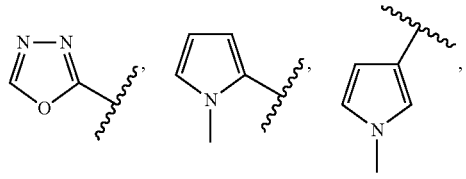

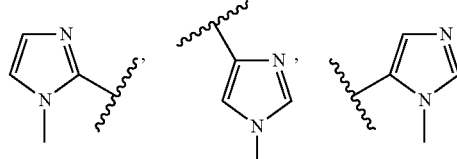

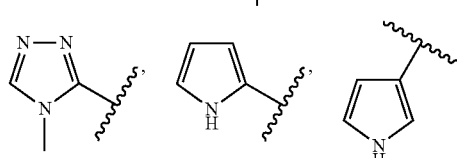, and

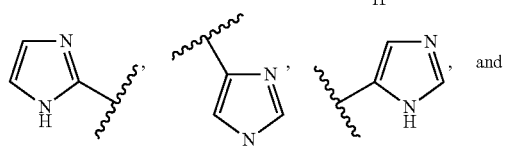

In some embodiments, Ring B is selected from a group consisting of:

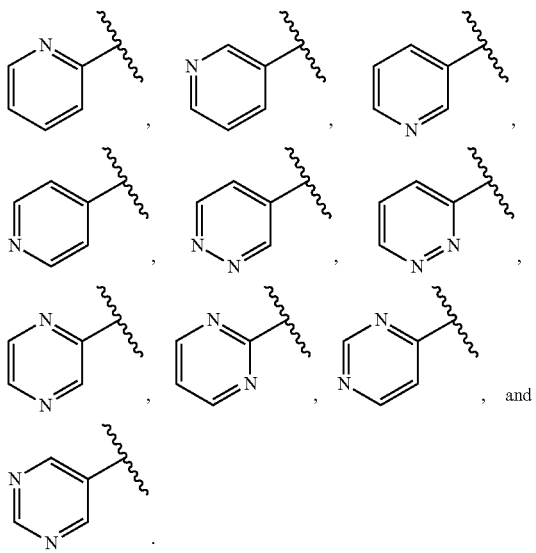

In some embodiments, Ring B is selected from a group consisting of:

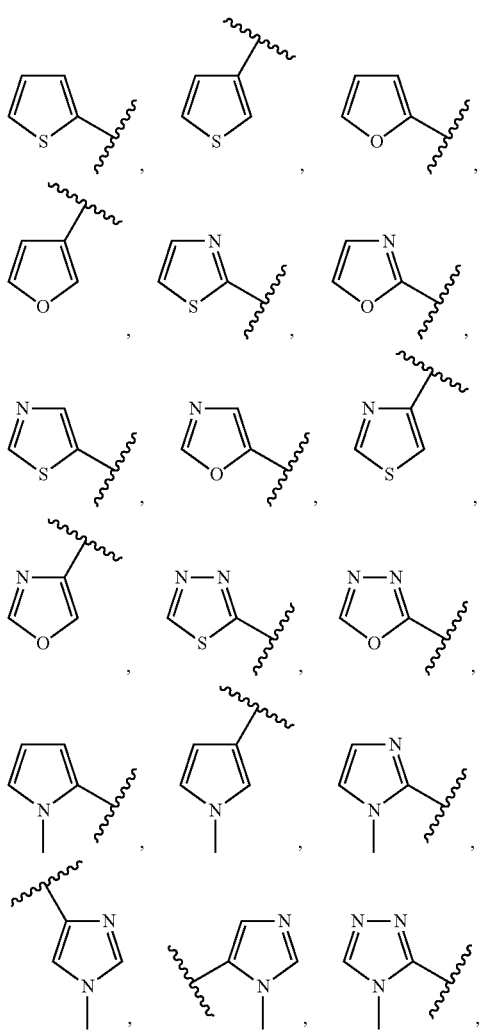

In some embodiments, $R^1$ is —OH, —OCH$_3$, —OCH$_2$CH$_3$, or —N(R$^4$R$^5$). In some embodiments, $R^1$ is —OH or —N(R$^4$R$^5$). In some embodiments, $R^1$ is OH.

In some embodiments, $R^1$ is —N(R$^4$R$^5$). In some embodiments, $R^1$ is —N(R$^4$R$^5$), $R^4$ is $C_1$-$C_6$alkyl or $C_3$-$C_6$cycloalkyl; and $R^5$ is hydrogen or $C_1$-$C_6$alkyl. In some embodiments, $R^1$ is —N(R$^4$R$^5$) and $R^4$ and $R^5$ taken together with the nitrogen to which they are attached to form a substituted or unsubstituted $C_2$-$C_8$heterocycloalkyl. In some embodiments, $R^4$ and $R^5$ taken together with the nitrogen to which they are attached to form a substituted or unsubstituted $C_5$-$C_6$heterocycloalkyl. In some embodiments, $R^4$ and $R^5$ taken together with the nitrogen to which they are attached to form a substituted or unsubstituted $C_6$heterocycloalkyl. In some embodiments, $R^4$ and $R^5$ taken together with the nitrogen to which they are attached to form a pyrrolidinyl, morpholinyl, piperidinyl, or piperazinyl optionally substituted with $C_1$-$C_6$alkyl, halogen, or —SO$_2$CH$_3$.

In some embodiments, —C(=O)R$^1$ is a carboxylic acid bioisostere. In some embodiments, —C(=O)R$^1$ is a carboxylic acid bioisostere having the structure

In some embodiments, X is —OH, —OR$^4$, $C_1$-$C_6$alkyl, or $C_1$-$C_6$fluoroalkyl. In some embodiments, X is —OH. In some embodiments, X is $C_1$-$C_6$alkyl. In some embodiments, X is —CH$_3$. In some embodiments, Z is —CH$_3$ and X is —CH$_3$. In some embodiments, Z is —CH$_3$ and X is —OH.

In some embodiments, $R^2$ is hydrogen, halogen, —CN, —OH, —OR$^4$, substituted or unsubstituted $C_1$-$C_6$alkyl, or substituted or unsubstituted $C_1$-$C_6$fluoroalkyl.

In some embodiments, $R^2$ is hydrogen, F, Cl, —CH$_3$, or —OCH$_3$. In some embodiments, $R^2$ is hydrogen.

In some embodiments, $R^3$ is $C_1$-$C_6$alkyl, or $C_3$-$C_6$cycloalkyl. In some embodiments, $R^3$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, cyclopropyl, cyclobutyl, cyclopentyl, or cyclohexyl. In some embodiments, $R^3$ is —CH(CH$_3$)$_2$, —C(CH$_3$)$_3$, or cyclopentyl.

In some embodiments, p is 1, $R^1$ is —OH; $R^2$ is hydrogen, F, Cl, —$CH_3$, or —$OCH_3$; and X is —OH.

In some embodiments, p is 0, $R^2$ is hydrogen, X is —OH, Z is —$CH_3$, and $R^3$ is —$CH(CH_3)_2$, —$C(CH_3)_3$, or cyclopentyl. In some embodiments, p is 0, $R^2$ is hydrogen, X is —OH, Z is —$CH_3$, and $R^3$ is —$CH(CH_3)_2$. In some embodiments, p is 0, $R^2$ is hydrogen, X is —OH, Z is —$CH_3$, and $R^3$ is —$C(CH_3)_3$. In some embodiments, p is 0, $R^2$ is hydrogen, X is —OH, Z is —$CH_3$, and $R^3$ is cyclopentyl.

In some embodiments, p is 1, $R^1$ is —OH; $R^2$ is hydrogen, X is —OH, Z is —$CH_3$, and $R^3$ is —$CH(CH_3)_2$, —$C(CH_3)_3$, or cyclopentyl. In some embodiments, p is 1, $R^1$ is —OH; $R^2$ is hydrogen, X is —OH, Z is —$CH_3$, and $R^3$ is —$CH(CH_3)_2$. In some embodiments, p is 1, $R^1$ is —OH; $R^2$ is hydrogen, X is —OH, Z is —$CH_3$, and $R^3$ is —$C(CH_3)_3$. In some embodiments, p is 1, $R^1$ is —OH; $R^2$ is hydrogen, X is —OH, Z is —$CH_3$, and $R^3$ is cyclopentyl.

In some embodiments, the compound is selected from the group consisting of:

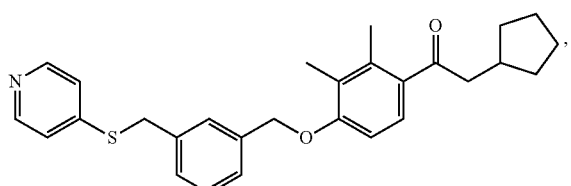

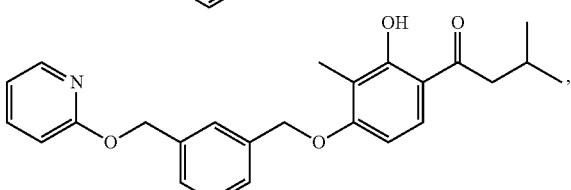

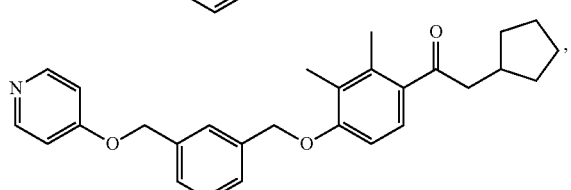

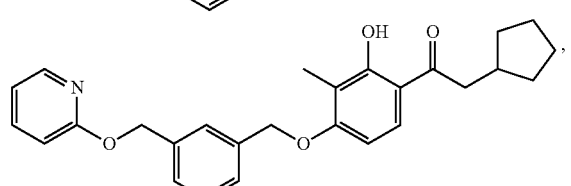

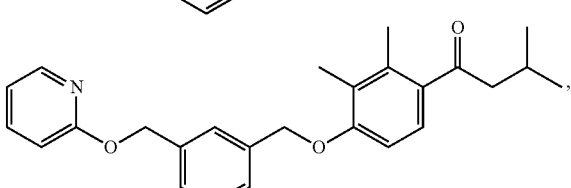

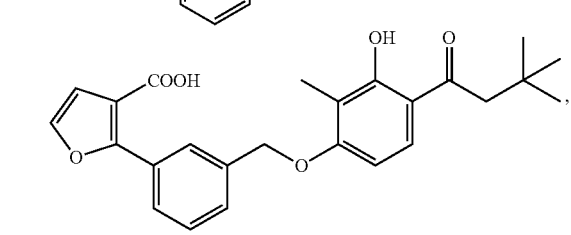

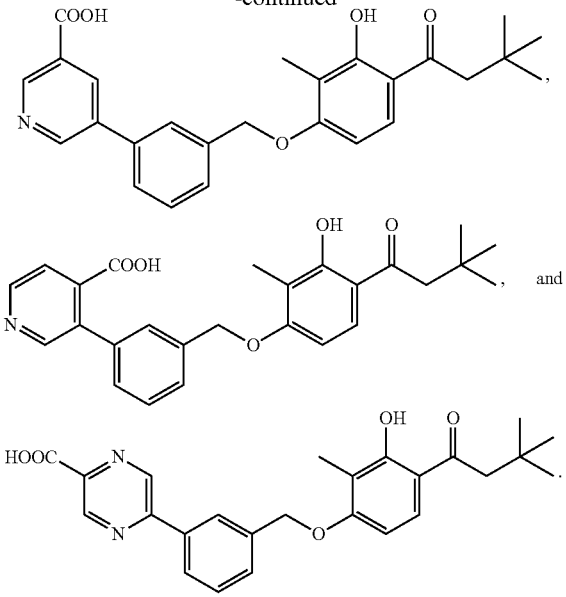

In some embodiments, compounds described herein have the following structure:

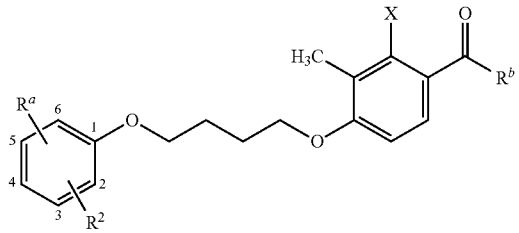

In some embodiments, $R^a$ is as described in Table 1. In some embodiments, $R^2$ is as described in Table 1. In some embodiments, $R^b$ is as described in Table 1. In some embodiments, X is as described in Table 1. In some embodiments, $R^a$, $R^2$, $R^b$ and X are as described in Table 1.

In some embodiments, compounds described herein have the following structure:

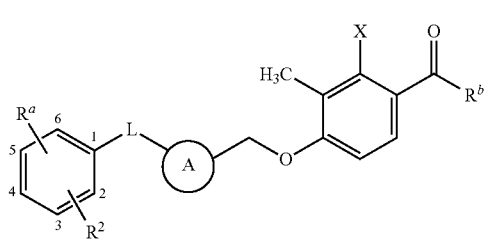

In some embodiments, $R^a$ is as described in Table 2. In some embodiments, $R^2$ is as described in Table 2. In some embodiments, $R^b$ is as described in Table 2. In some embodiments, X is as described in Table 2. In some embodiments, Ring A is as described in Table 2. In some embodiments, L is as described in Table 2. In some embodiments, $R^a$, $R^2$, $R^b$, X, and Ring A are as described in Table 2.

In some embodiments, compounds described herein have the following structure:

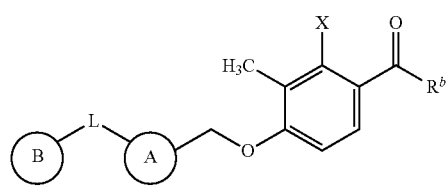

In some embodiments, Ring A is as described in Table 3. In some embodiments, Ring B is as described in Table 3. In some embodiments, L is as described in Table 3. In some embodiments, $R^b$ is as described in Table 3. In some embodiments, X is as described in Table 3. In some embodiments, Ring A, Ring B, $R^b$, X, and L are as described in Table 3.

Non-limiting examples of compounds described herein are presented in Tables 1 through Table 4.

TABLE 1

| Cmpd | $R^a$ | $R^2$ | X | $R^b$ |
|---|---|---|---|---|
| 5 | 4-CH₂CH₂CO₂H | 3-OH | OH | isobutyl |
| 6 | 4-CH=CHCOO-3 | | OH | isobutyl |
| 14 | 4-COOMe | H | CH₃ | isobutyl |
| 15 | 4-COOMe | H | CH₃ | cyclopentylmethyl |
| 16 | 4-COOMe | H | OH | isobutyl |
| 17 | 4-COOMe | H | OH | cyclopentylmethyl |
| 18 | 4-COOH | H | CH₃ | isobutyl |
| 19 | 4-COOH | H | CH₃ | cyclopentylmethyl |

TABLE 1-continued

| Cmpd | $R^a$ | $R^2$ | X | $R^b$ |
|---|---|---|---|---|
| 20 | 4-COOH | H | OH | isobutyl |
| 21 | 4-COOH | H | OH | cyclopentylmethyl |
| 22 | 3-COOH | H | CH₃ | isobutyl |
| 23 | 3-COOH | H | CH₃ | cyclopentylmethyl |
| 24 | 3-COOH | H | OH | isobutyl |
| 25 | 3-COOH | H | OH | cyclopentylmethyl |
| 26 | 2-COOH | H | CH₃ | isobutyl |
| 27 | 2-COOH | H | CH₃ | cyclopentylmethyl |
| 28 | 2-COOH | H | OH | isobutyl |
| 29 | 2-COOH | H | OH | cyclopentylmethyl |
| 30 | 4-COOH | 3-Cl | CH₃ | isobutyl |
| 31 | 4-COOH | 3-Cl | CH₃ | cyclopentylmethyl |

TABLE 1-continued
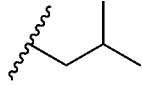 [SMILES: *CC(C)C]
| Cmpd | R$^a$ | R$^2$ | X | R$^b$ |
|---|---|---|---|---|
| 32 | 4-COOH | 3-Cl | OH | 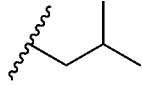 [SMILES: *CC(C)C] |
| 33 | 4-COOH | 3-Cl | OH | 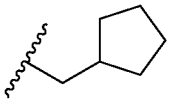 [SMILES: *CC1CCCC1] |
| 34 | 3-COOH | 4-F | CH$_3$ | 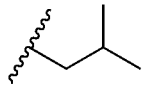 [SMILES: *CC(C)C] |
| 35 | 3-COOH | 4-F | CH$_3$ | 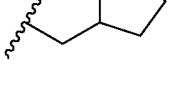 |
| 36 | 3-COOH | 4-F | OH | 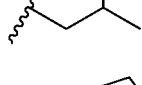 |
| 37 | 3-COOH | 4-F | OH | 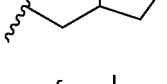 |
| 38 | 5-COOH | 2-CH$_3$ | OH | 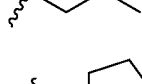 |
| 39 | 5-COOH | 2-CH$_3$ | OH | 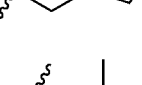 |
| 40 | 3-COOH | 2-CH$_3$ | OH | 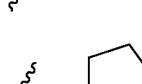 |
| 41 | 3-COOH | 2-CH$_3$ | OH |  |
| 42 | 4-COOH | 2-F | OH | 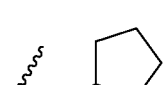 |
| 43 | 4-COOH | 2-F | OH |  |
TABLE 1-continued
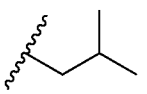
| Cmpd | R$^a$ | R$^2$ | X | R$^b$ |
|---|---|---|---|---|
| 44 | 4-COOH | 2-OMe | OH | 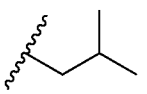 |
| 45 | 4-COOH | 2-OMe | OH | 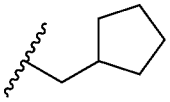 [SMILES: *CC1CCCC1] |
| 46 | 4-COOH | 2-Cl | OH | 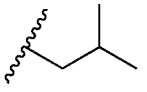 |
| 47 | 4-COOH | 2-Cl | OH | 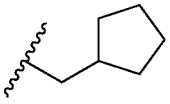 |
| 48 | 4-COOH | 3-CH$_3$ | OH | 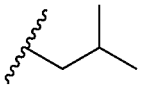 |
| 49 | 4-COOH | 3-CH$_3$ | OH | 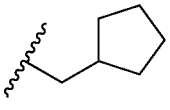 |
| 50 | 5-COOH | 2-OMe | OH | 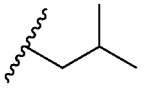 |
| 51 | 5-COOH | 2-OMe | OH | 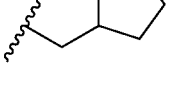 |
| 52 | 4-COOH | 2-OMe | OH |  |
| 53 | 5-COOH | 2-OMe | OH | 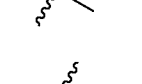 |
| 54 | 3-COOH | 2-CH$_3$ | OH |  |
| 55 | 3-COOH | 4-F | OH |  |

TABLE 1-continued

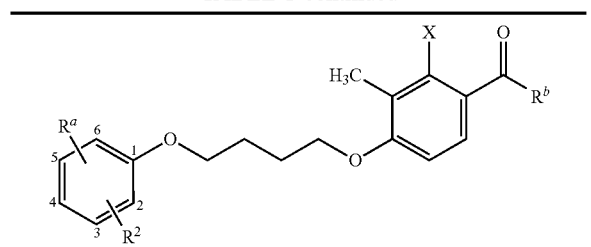

| Cmpd | $R^a$ | $R^2$ | X | $R^b$ |
|---|---|---|---|---|
| 56 | 4-COOH | 2-CH$_3$ | OH | (propyl branched) |
| 57 | 4-COOH | 2-OMe | OH | (propyl branched) |
| 58 | 5-COOH | 2-OMe | OH | (propyl branched) |
| 59 | 3-COOH | 2-CH$_3$ | OH | (propyl branched) |
| 60 | 3-COOH | 4-F | OH | (propyl branched) |
| 61 | 4-COOH | 2-CH$_3$ | OH | (propyl branched) |
| 62 | 4-COOH | 2-OMe | OH | (isopropyl) |
| 63 | 5-COOH | 2-OMe | OH | (isopropyl) |
| 64 | 3-COOH | 2-CH$_3$ | OH | (isopropyl) |
| 65 | 3-COOH | 4-F | OH | (isopropyl) |
| 66 | 4-COOH | 2-CH$_3$ | OH | (isopropyl) |
| 67 | 4-COOH | 2-OMe | OH | (butyl) |

TABLE 1-continued

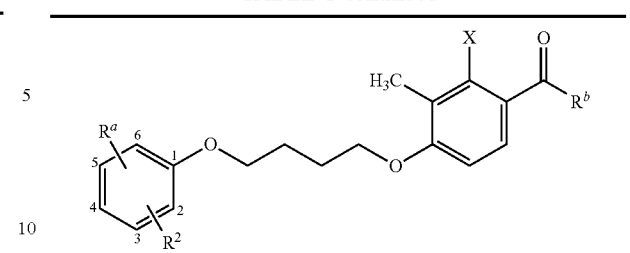

| Cmpd | $R^a$ | $R^2$ | X | $R^b$ |
|---|---|---|---|---|
| 68 | 5-COOH | 2-OMe | OH | (butyl) |
| 69 | 3-COOH | 2-CH$_3$ | OH | (butyl) |
| 70 | 3-COOH | 4-F | OH | (butyl) |
| 71 | 4-COOH | 2-CH$_3$ | OH | (butyl) |
| 72 | 5-COOH | 2-OMe | OH | (neopentyl) |
| 73 | 4-COOH | 2-OMe | OH | (neopentyl) |
| 74 | 3-COOH | 2-Me | OH | (neopentyl) |
| 75 | 3-COOH | 4-F | OH | (neopentyl) |
| 76 | 4-CN | H | CH$_3$ | (cyclopentylmethyl) |
| 77 | 4-CN | H | CH$_3$ | (isobutyl) |
| 78 | 4-tetrazoloyl | H | CH$_3$ | (cyclopentylmethyl) |
| 79 | 4-tetrazoloyl | H | CH$_3$ | (isobutyl) |

TABLE 1-continued

| Cmpd | R$^a$ | R$^2$ | X | R$^b$ |
|---|---|---|---|---|
| 80 | 4-CH=CHCOO-3 | | CH$_3$ | CH$_2$-cyclopentyl |
| 81 | 4-CH=CHCOO-3 | | CH$_3$ | isobutyl |
| 82 | 4-CN | H | OH | isobutyl |
| 83 | 4-CN | H | OH | CH$_2$-cyclopentyl |
| 84 | 4-CH=CHCOO-3 | | OH | CH$_2$-cyclopentyl |
| 85 | 3-CH$_2$CH$_2$CO$_2$Me | 4-OH | OH | isobutyl |
| 86 | 3-CH$_2$CH$_2$CO$_2$Me | 4-OH | OH | CH$_2$-cyclopentyl |
| 87 | 5-pinacol boronate | 2-OMe | OH | neopentyl |
| 88 | 4-CONHOH | 2-OMe | OH | neopentyl |
| 89 | 5-CONHOH | 2-OMe | OH | neopentyl |
| 90 | 5-CONHOMe | 2-OMe | OH | neopentyl |
| 91 | 5-CN | 2-OMe | OH | neopentyl |
| 92 | 5-tetrazolyl | 2-OMe | OH | neopentyl |
| 93 | 5-CONHSO$_2$Me | 2-OMe | OH | neopentyl |
| 94 | 4-CH$_2$OB(OH)-3 | | OH | neopentyl |
| 95 | 5-B(OH)$_2$ | 2-OMe | OH | neopentyl |
| 96 | 5-COOH | 2-OMe | OH | 3,3-dimethylbutyl |
| 97 | 5-C(NH$_2$)=NOH | 2-OMe | OH | neopentyl |
| 98 | 5-(1,2,4-oxadiazol-5(4H)-one-3-yl) | 2-OMe | OH | neopentyl |
| 99 | 5-(1,2,4-oxadiazol-5(4H)-thione-3-yl) | 2-OMe | OH | neopentyl |
| 100 | 5-(1,2,4-thiadiazol-5(4H)-one-3-yl) | 2-OMe | OH | neopentyl |

TABLE 1-continued

| Cmpd | Rᵃ | R² | X | Rᵇ |
|---|---|---|---|---|
| 101 | 5-(morpholin-4-ylcarbonyl) | 2-OMe | OH | neopentyl (CH₂C(CH₃)₃) |
| 102 | 5-CONHMe | 2-OMe | OH | neopentyl |
| 103 | 5-CONEt₂ | 2-OMe | OH | neopentyl |
| 104 | 5-(benzoyl) | 2-OMe | OH | neopentyl |
| 105 | 5-(piperazin-1-ylcarbonyl) | 2-OMe | OH | neopentyl |
| 106 | 5-(pyridin-2-ylcarbonyl) | 2-OMe | OH | neopentyl |
| 107 | 5-(4-methanesulfonylpiperazin-1-ylcarbonyl) | 2-OMe | OH | neopentyl |
| 108 | 5-(N-tert-butylcarbamoyl) | 2-OMe | OH | neopentyl |
| 109 | 5-(N-cyclopropylcarbamoyl) | 2-OMe | OH | neopentyl |
| 110 | 5-(N-isobutylcarbamoyl) | 2-OMe | OH | neopentyl |
| 111 | 4-CH₂CH₂CO₂H | 3-OH | CH₃ | isopentyl |
| 112 | 5-(N-cyclopentylcarbamoyl) | 2-OMe | OH | neopentyl |
| 113 | 5-CONHSO₂Phenyl | 2-OMe | OH | neopentyl |

TABLE 2

| Cmpd | L | Ring A | Rᵃ | R² | X | Rᵇ |
|---|---|---|---|---|---|---|
| 114 | —O—CH₂— | 1,3-phenylene | 4-CH=CHCOO-3 | | Me | CH₂-cyclopentyl |
| 115 | —O—CH₂— | 1,3-phenylene | 4-CN | H | Me | isobutyl |
| 116 | —O—CH₂— | 1,3-phenylene | 4-COOMe | H | Me | isobutyl |
| 117 | —O—CH₂— | 1,3-phenylene | 4-CH=CHCOO-3 | | Me | isobutyl |
| 118 | —O—CH₂— | 1,3-phenylene | 4-CN | H | OH | isobutyl |
| 119 | —O—CH₂— | 1,3-phenylene | 4-COOMe | H | OH | isobutyl |
| 120 | —O—CH₂— | 1,3-phenylene | 4-CH=CHCOO-3 | | OH | isobutyl |
| 121 | —O—CH₂— | 1,3-phenylene | 4-COOMe | H | OH | CH₂-cyclopentyl |
| 122 | —O—CH₂— | 1,3-phenylene | 4-CH=CHCOO-3 | | OH | CH₂-cyclopentyl |

TABLE 2-continued

| Cmpd | L | Ring A | R$^a$ | R$^2$ | X | R$^b$ |
|---|---|---|---|---|---|---|
| 123 | —O—CH$_2$— | 1,3-phenylene | 4-COOH | H | Me | isobutyl |
| 124 | —O—CH$_2$— | 1,3-phenylene | 4-COOH | H | Me | cyclopentylmethyl |
| 125 | —O—CH$_2$— | 1,3-phenylene | 4-COOH | H | OH | isobutyl |
| 126 | —O—CH$_2$— | 1,3-phenylene | 4-COOH | H | OH | cyclopentylmethyl |
| 127 | Absent | 1,3-phenylene | 3-COOH | H | OH | neopentyl |
| 128 | Absent | 1,3-phenylene | 3-COOH | H | OH | isopropyl |
| 129 | Absent | 1,3-phenylene | 3-COOH | H | OH | cyclopentylmethyl |
| 130 | Absent | 1,3-phenylene | 3-COOH | H | OH | n-butyl |
| 131 | Absent | 1,3-phenylene | 3-COOH | H | OH | isopropyl |

TABLE 2-continued

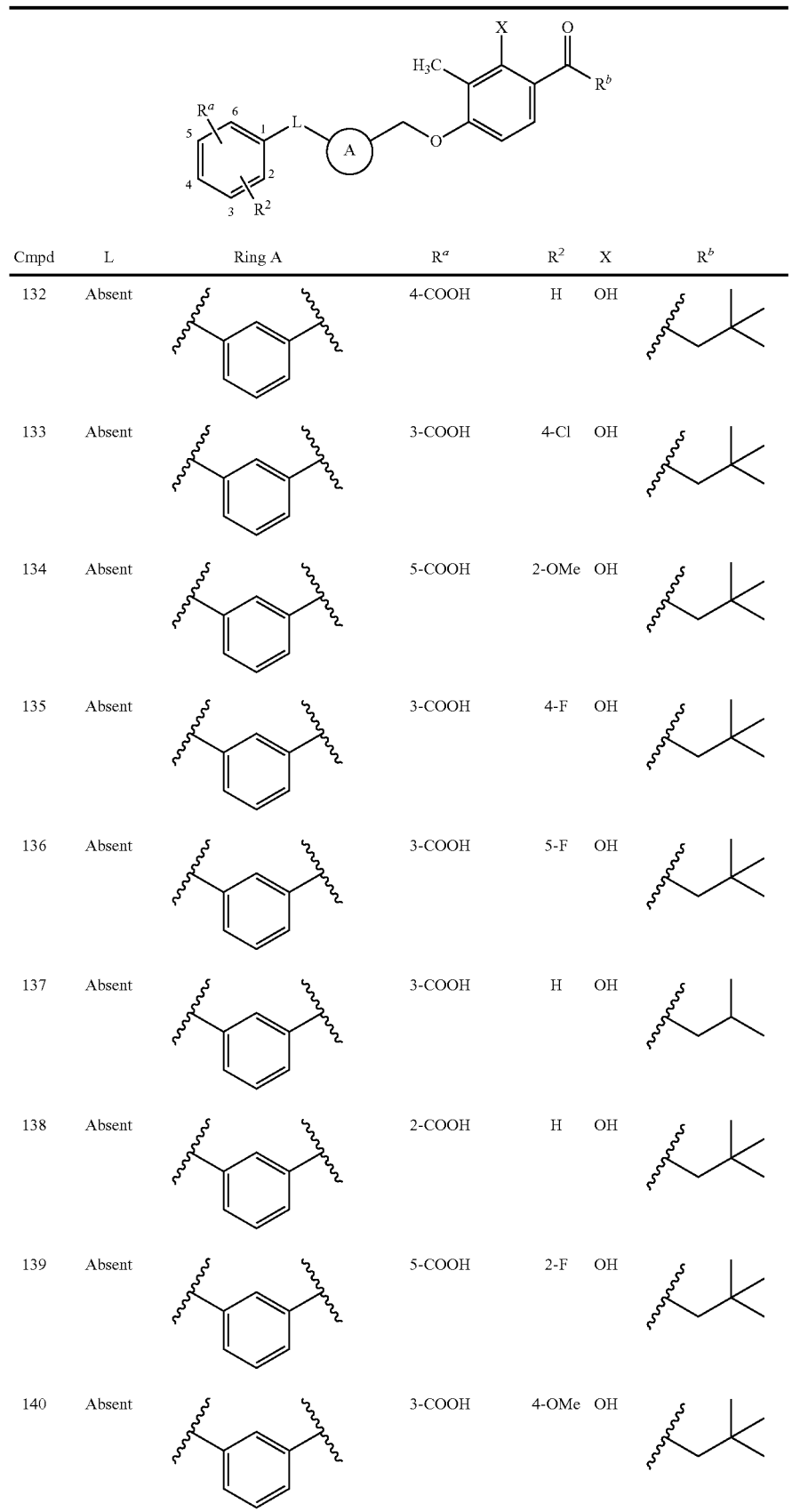

| Cmpd | L | Ring A | $R^a$ | $R^2$ | X | $R^b$ |
|---|---|---|---|---|---|---|
| 132 | Absent | 1,3-phenylene | 4-COOH | H | OH | neopentyl |
| 133 | Absent | 1,3-phenylene | 3-COOH | 4-Cl | OH | neopentyl |
| 134 | Absent | 1,3-phenylene | 5-COOH | 2-OMe | OH | neopentyl |
| 135 | Absent | 1,3-phenylene | 3-COOH | 4-F | OH | neopentyl |
| 136 | Absent | 1,3-phenylene | 3-COOH | 5-F | OH | neopentyl |
| 137 | Absent | 1,3-phenylene | 3-COOH | H | OH | isobutyl |
| 138 | Absent | 1,3-phenylene | 2-COOH | H | OH | neopentyl |
| 139 | Absent | 1,3-phenylene | 5-COOH | 2-F | OH | neopentyl |
| 140 | Absent | 1,3-phenylene | 3-COOH | 4-OMe | OH | neopentyl |

TABLE 2-continued

| Cmpd | L | Ring A | R$^a$ | R$^2$ | X | R$^b$ |
|---|---|---|---|---|---|---|
| 141 | Absent | 1,3-phenylene | 4-COOH | 3-Cl | OH | neopentyl |
| 142 | Absent | 1,4-phenylene | 3-COOH | H | OH | neopentyl |
| 143 | Absent | 1,3-phenylene | 4-COOH | 3-Me | OH | neopentyl |
| 144 | Absent | 1,3-phenylene | 3-COOH | 4-OH | OH | neopentyl |
| 145 | Absent | 1,3-phenylene | 3-CH$_2$COOH | H | OH | neopentyl |
| 146 | Absent | 1,3-phenylene | 3-COOH | 5-NO$_2$ | OH | neopentyl |
| 147 | Absent | 1,3-phenylene | 4-COOH | 2-Cl | OH | neopentyl |
| 148 | Absent | 1,3-phenylene | 3-COOH | H | OH | 3,3-dimethylbutyl |
| 149 | Absent | 2,4-pyridyl | 3-COOH | H | OH | neopentyl |

TABLE 2-continued

| Cmpd | L | Ring A | R$^a$ | R$^2$ | X | R$^b$ |
|---|---|---|---|---|---|---|
| 150 | Absent | 3,5-pyridinyl | 3-COOH | H | OH | neopentyl |
| 151 | Absent | 1,3-phenylene | 3-CN | H | OH | neopentyl |
| 152 | Absent | 1,3-phenylene | 3-tetrazoyl | H | OH | neopentyl |
| 153 | Absent | 2,4-pyridinyl | 3-COOH | H | OH | neopentyl |
| 154 | —O—CH$_2$— | 1,3-phenylene | 4-CN | H | Me | cyclopentylmethyl |
| 155 | —O—CH$_2$— | 1,3-phenylene | 4-COOMe | H | Me | cyclopentylmethyl |
| 156 | Absent | 1,3-phenylene | 3-CONHSO$_2$Me | H | OH | neopentyl |
| 157 | Absent | 1,3-phenylene | 3-(5-oxo-4,5-dihydro-1,2,4-oxadiazol-3-yl) | H | OH | neopentyl |
| 158 | Absent | 2,5-furanyl | 3-COOH | H | OH | neopentyl |

TABLE 2-continued
| Cmpd | L | Ring A | R$^a$ | R$^2$ | X | R$^b$ |
|---|---|---|---|---|---|---|
| 159 | Absent | 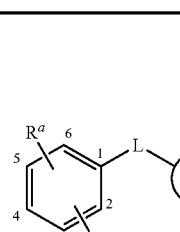 | 3-COOH | H | OH | 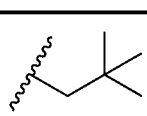 |
| 160 | Absent | 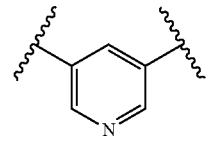 [SMILES: *c1cncc(*)c1] | 5-COOH | 2-OMe | OH | 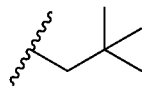 [SMILES: *CC(C)(C)C] |
| 161 | Absent | 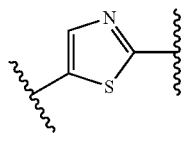 [SMILES: *c1cnc(*)s1] | 3-COOH | H | OH | 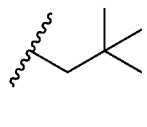 [SMILES: *CC(C)(C)C] |
| 162 | Absent | 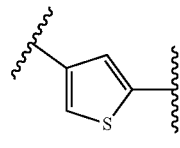 [SMILES: *c1csc(*)c1] | 3-COOH | H | OH | 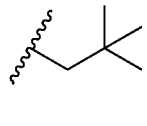 |
| 163 | Absent | 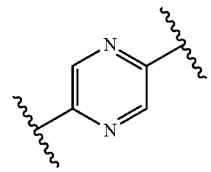 [SMILES: *c1cnc(*)cn1] | 3-COOH | H | OH | 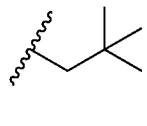 |
| 164 | Absent | 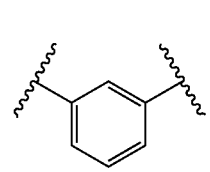 | 3-SO$_2$OH | H | OH | 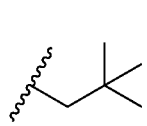 [SMILES: *CC(C)(C)C] |
| 165 | Absent | 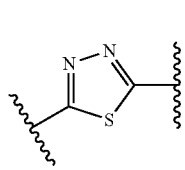 [SMILES: *c1nnc(*)s1] | 3-COOH | H | OH | 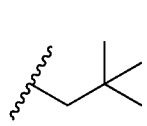 [SMILES: *CC(C)(C)C] |
| 166 | Absent | 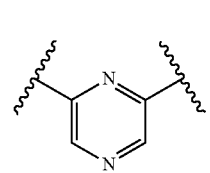 [SMILES: *c1cncc(*)n1] | 3-COOH | H | OH | 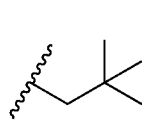 [SMILES: *CC(C)(C)C] |

TABLE 2-continued

| Cmpd | L | Ring A | $R^a$ | $R^2$ | X | $R^b$ |
|---|---|---|---|---|---|---|
| 167 | Absent | pyrazine (2,5) | 3- C(CH₃)₂C(O)NH-cyclopropyl | H | OH | neopentyl |
| 168 | Absent | 1,3-phenylene | 3-COOH | 2-Me | OH | neopentyl |
| 169 | Absent | 1,3-phenylene | 3-COOH | 4-Cl | OH | isobutyl |
| 170 | Absent | 1,3-phenylene | 3-COOH | 4-Cl | Me | isobutyl |
| 171 | Absent | 1,3-phenylene | 3-COOH | 4-Cl | Me | cyclopentylmethyl |
| 172 | Absent | 1,3-phenylene | 3-COOH | 4-Cl | OH | cyclopentylmethyl |
| 173 | Absent | pyrimidine (2,4) | 3-COOH | H | OH | neopentyl |

TABLE 3
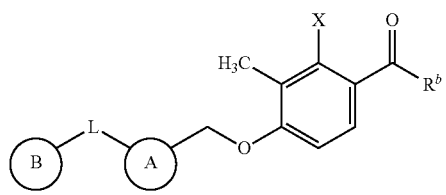
| Cmpd | L | Ring B | Ring A | X | R³ |
|---|---|---|---|---|---|
| 174 | —O—CH₂— | 2-Pyridyl | 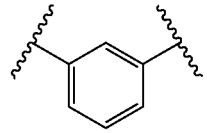 [SMILES: *c1cccc(*)c1] | Me | 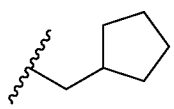 [SMILES: *CC1CCCC1] |
| 175 | —O—CH₂— | 2-Pyridyl | 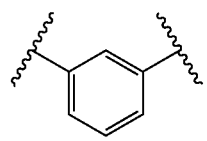 [SMILES: *c1cccc(*)c1] | Me | 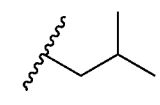 |
| 176 | —O—CH₂— | 2-Pyridyl | 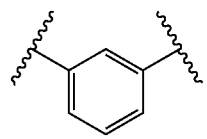 [SMILES: *c1cccc(*)c1] | OH | 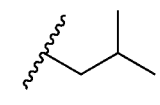 |
| 177 | —O—CH₂— | 2-Pyridyl | 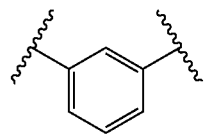 [SMILES: *c1cccc(*)c1] | OH | 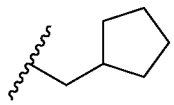 [SMILES: *CC1CCCC1] |
| 178 | Absent | 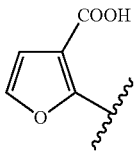 [SMILES: *c1occc1C(=O)O] | 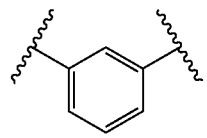 [SMILES: *c1cccc(*)c1] | OH | 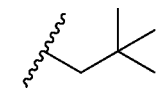 [SMILES: *CC(C)(C)C] |
| 179 | Absent | 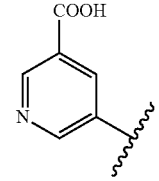 [SMILES: *c1cncc(C(=O)O)c1] | 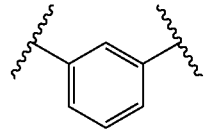 [SMILES: *c1cccc(*)c1] | OH | 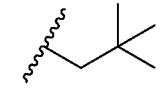 [SMILES: *CC(C)(C)C] |
| 180 | Absent | 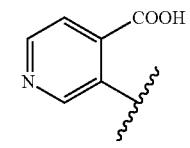 | 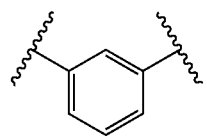 [SMILES: *c1cccc(*)c1] | OH | 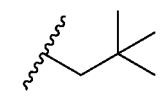 |
| 181 | Absent | 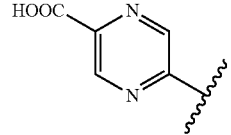 [SMILES: *c1cnc(C(=O)O)cn1] | 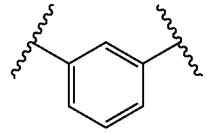 [SMILES: *c1cccc(*)c1] | OH | 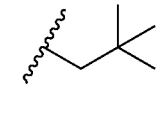 [SMILES: *CC(C)(C)C] |

TABLE 3-continued

| Cmpd | L | Ring B | Ring A | X | R³ |
|---|---|---|---|---|---|
| 182 | —S—CH₂— | 4-Pyridyl | (1,3-phenylene) | Me | (CH₂-cyclopentyl) |

TABLE 4

| Cmpd | Structure |
|---|---|
| 183 | 2-pyridyl-O-(CH₂)₄-O-(2,3-dimethylphenyl)-C(O)-CH₂-CH(CH₃)₂ |
| 184 | 2-pyridyl-S-(CH₂)₄-O-(3-methyl-2-hydroxyphenyl)-C(O)-CH₂-CH(CH₃)₂ |
| 185 | 2-pyridyl-O-(CH₂)₄-O-(3-methyl-2-hydroxyphenyl)-C(O)-CH₂-CH(CH₃)₂ |
| 186 | 2-pyridyl-O-(CH₂)₄-O-(3-methyl-2-hydroxyphenyl)-C(O)-CH₂-cyclopentyl |

TABLE 4-continued

| Cmpd | Structure |
|---|---|
| 187 | 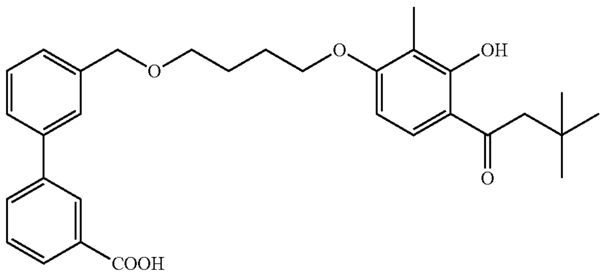 [SMILES: Cc1c(OCCCCOCc2cccc(-c3cccc(C(=O)O)c3)c2)ccc(C(=O)CC(C)(C)C)c1O] |
| 188 | 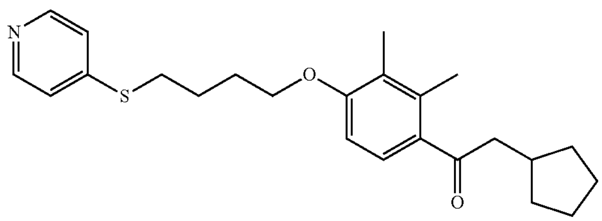 [SMILES: Cc1c(OCCCCSc2ccncc2)ccc(C(=O)CC2CCCC2)c1C] |
| 189 | 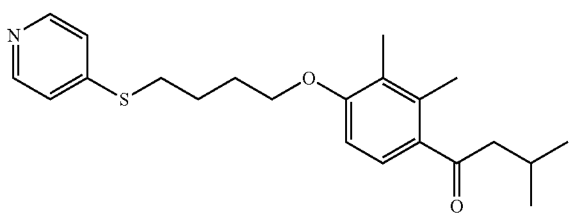 [SMILES: Cc1c(OCCCCSc2ccncc2)ccc(C(=O)CC(C)C)c1C] |
| 190 | 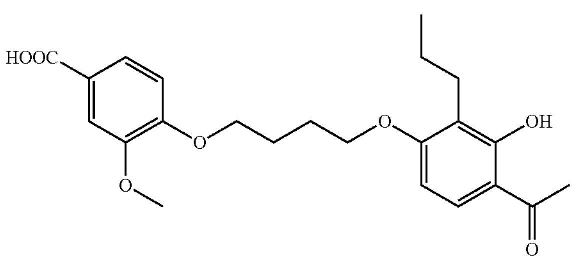 [SMILES: CCCc1c(OCCCCOc2ccc(C(=O)O)cc2OC)ccc(C(C)=O)c1O] |
| 191 | 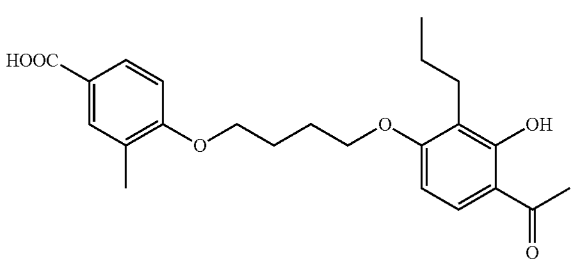 [SMILES: CCCc1c(OCCCCOc2ccc(C(=O)O)cc2C)ccc(C(C)=O)c1O] |
| 192 | 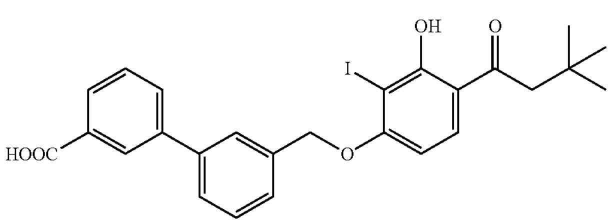 [SMILES: CC(C)(C)CC(=O)c1ccc(OCc2cccc(-c3cccc(C(=O)O)c3)c2)c(I)c1O] |

TABLE 4-continued

| Cmpd | Structure |
|---|---|
| 193 | 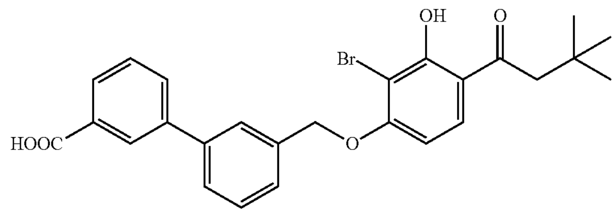 [SMILES: CC(C)(C)CC(=O)c1ccc(OCc2cccc(-c3cccc(C(=O)O)c3)c2)c(Br)c1O] |
| 194 | 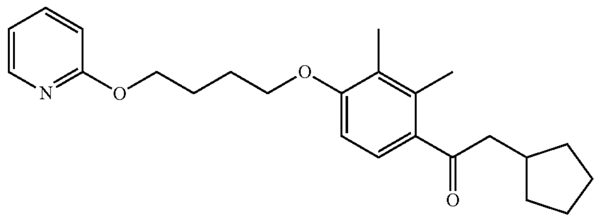 [SMILES: Cc1c(OCCCCOc2ccccn2)ccc(C(=O)CC2CCCC2)c1C] |

Further Forms of Compounds

In one aspect, the compound of Formula (I), (Ia), (Ib), (II), (IIa), (IIb), (IIc), or (III), possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design of prodrugs of the compound is possible. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews*, 56:53-102, 2004; Aesop Cho, "Recent Advances in Oral Prodrug Discovery", *Annual Reports in Medicinal Chemistry*, Vol. 41, 395-407, 2006; T. Higuchi and V. Stella, *Pro-drugs as Novel Delivery Systems*, Vol. 14 of the A.C.S. Symposium Series).

In some cases, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I), (Ia), (Ib), (II), (IIa), (IIb), (IIc), or (III) with acids. Pharmaceutically acceptable salts are also obtained by reacting a compound of Formula (I), (Ia), (Ib), (II), (IIa), (IIb), (IIc), or (III) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, Fisher Scientific (Fisher Chemicals), and Acros Organics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In some embodiments, compounds described herein are prepared as shown in Schemes A and B.

provide the key acetophenone derivatives 11. The phenol derivatives (12) were coupled with 1,4-dibromobutane by heating with potassium carbonate in acetonitrile to provide the corresponding bromobutoxybenzoate derivative (13).

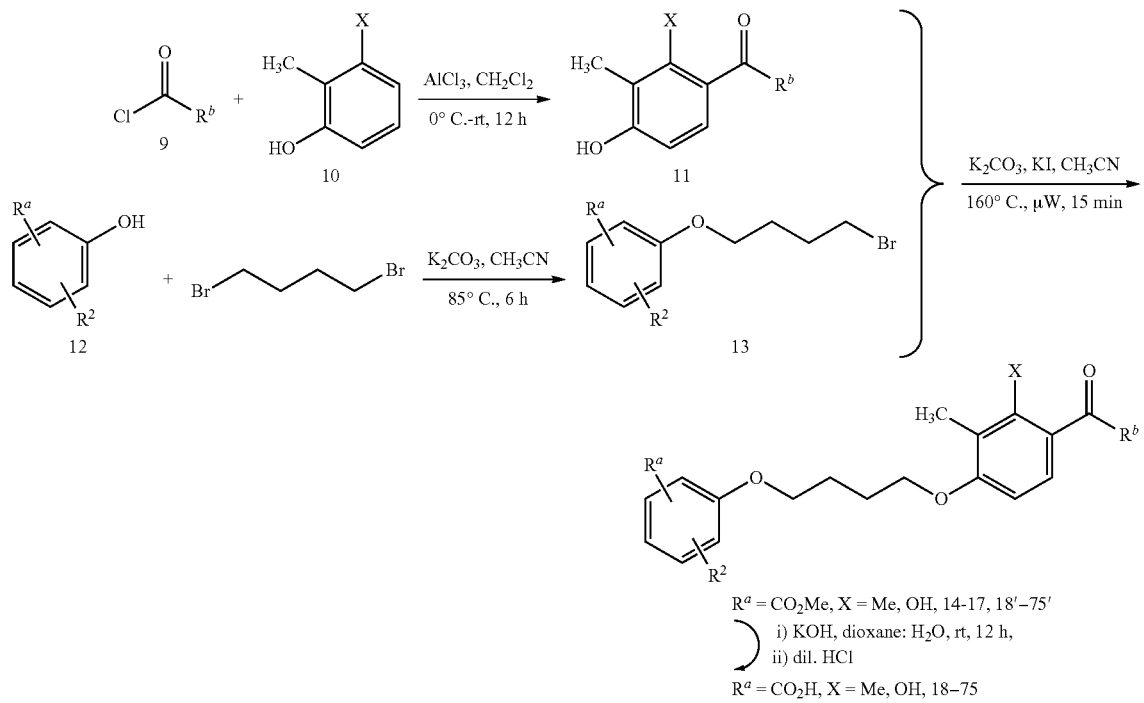

Scheme A

Commercially available carboxylic acids were converted to the corresponding acyl chloride derivatives (9) using oxalyl chloride in $CH_2Cl_2$. After removal of solvents, the acyl chlorides were employed in a Friedel-Crafts acylation of substituted phenols (10) using aluminum chloride to Finally, Finkelstein alkylation of intermediate 11 with 13 under microwave conditions delivered the ester derivatives (14-17 & 18'-75'), which were saponified with potassium hydroxide to provide the target carboxylic acid derivatives 18-75.

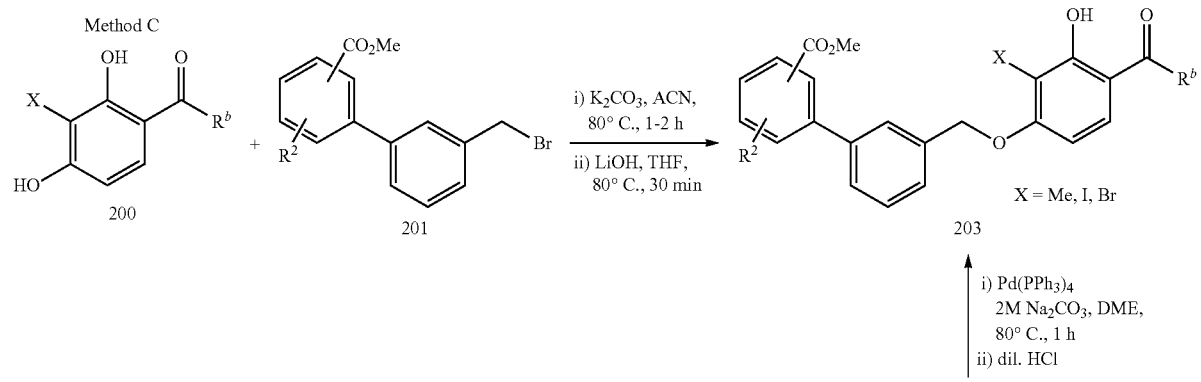

Scheme B

-continued

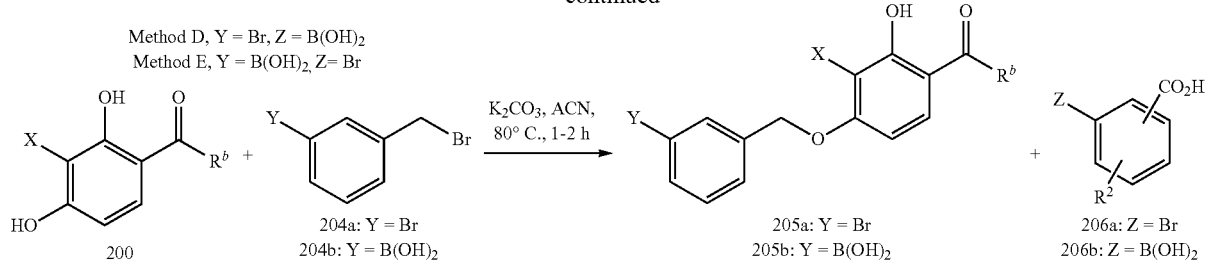

Commercially available resorcinol derivatives (200) and biphenyl derivatives (201) were reacted under basic conditions to afford the ester derivatives of 203 which were saponified to afford the acids 203. Alternatively, the commercially available resorcinol derivatives (200) were reacted with bromo-benzyl bromide derivatives (204a, Y=Br) or ((bromomethyl)phenyl)boronic acid (204b, Y=B(OH)$_2$) followed by a Suzuki cross coupling reaction of the intermediate 205a with borono benzoic acid derivatives (206b, Z=B(OH)$_2$) or 205b with bromo-benzoic acid derivatives (206a, Z=Br) to afford compounds 203.

It will be understood that the reactions shown above are illustrative.

In one aspect, compounds are synthesized as described in the Examples section.

DEFINITIONS

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Oxo" refers to the =O substituent.

"Thioxo" refers to the =S substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl.

Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —CH(CH$_3$)$_2$ or —C(CH$_3$)$_3$. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH$_2$OMe, —OCH$_2$CH$_2$OMe, or —OCH$_2$CH$_2$OCH$_2$CH$_2$NH$_2$. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthalenyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —CO₂H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

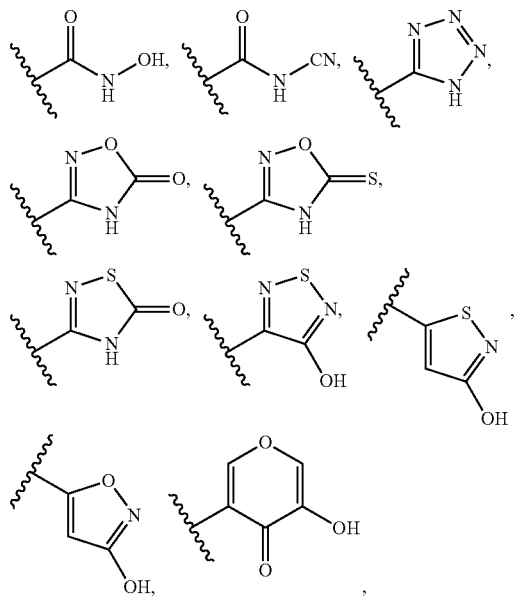

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloakyls having from three to ten carbon atoms, from three to eight carbon atoms, from three to six carbon atoms, or from three to five carbon atoms. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. In some embodiments, the monocyclic cyclcoalkyl is cyclopentyl. Polycyclic radicals include, for example, adamantyl, norbornyl, decalinyl, and 3,4-dihydronaphthalen-1 (2H)-one. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 13 carbon atoms and from one to 6 heteroatoms selected from the group consisting of nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, a bicyclic heteroaryl is a $C_6$-$C_9$heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2H$, —$CO_2$alkyl, nitro, and amino, including mono- and di-substituted amino groups (e.g. —$NH_2$, —NHR, —$N(R)_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2H$, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (Ia), (Ib), (II), (IIa), (IIb), (IIc), or (III) and a co-agent, are both administered to a patient simultaneously in the form of a single entity or dosage. The term "non-fixed combination" means that the active ingredients, e.g. a compound of Formula (I), (Ia), (Ib), (II), (IIa), (IIb), (IIc), or (III) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

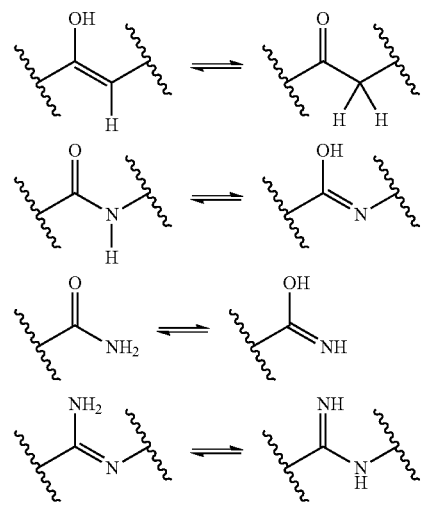

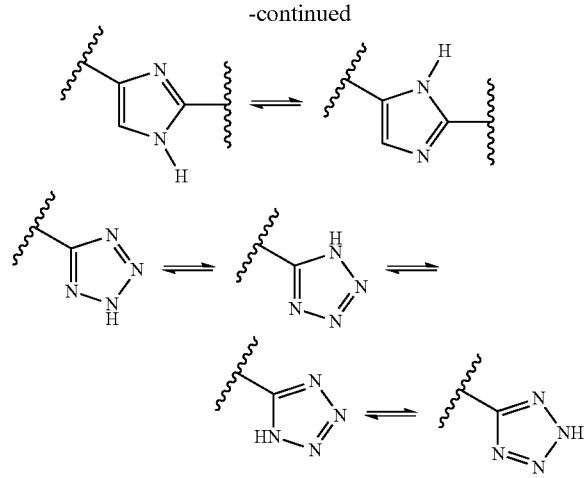

Administration and Pharmaceutical Composition

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), (Ia), (Ib), (II), (IIa), (IIb), (IIc), or (III) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I), (Ia), (Ib), (II), (IIa), (IIb), (IIc), or (III) are administered orally.

In some embodiments, the compounds of Formula (I), (Ia), (Ib), (II), (IIa), (IIb), (IIc), or (III) are administered topically. In such embodiments, the compound of Formula (I), (Ia), (Ib), (II), (IIa), (IIb), (IIc), or (III) is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds of Formula (I) are administered topically to the skin.

In another aspect, the compounds of Formula (I), (Ia), (Ib), (II), (IIa), (IIb), (IIc), or (III) are administered by inhalation.

In another aspect, the compounds of Formula (I), (Ia), (Ib), (II), (IIa), (IIb), (IIc), or (III) are formulated for intranasal administration. Such formulations include nasal sprays, nasal mists, and the like.

In another aspect, the compounds of Formula (I), (Ia), (Ib), (II), (IIa), (IIb), (IIc), or (III) are formulated as eye drops.

In any of the aforementioned aspects are further embodiments in which the effective amount of the compound of Formula (I), (Ia), (Ib), (II), (IIa), (IIb), (IIc), or (III) is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound of Formula (I), (Ia), (Ib), (II), (IIa), (IIb), (IIc), or (III), including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound of Formula (I), (Ia), (Ib), (II), (IIa), (IIb), (IIc), or (III), including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound of Formula (I), (Ia), (Ib), (II), (IIa), (IIb), (IIc), or (III) is temporarily suspended or the dose of the compound being administered is temporarily reduced; at the end of the drug holiday, dosing of the compound is resumed. In one embodiment, the length of the drug holiday varies from 2 days to 1 year.

In certain embodiments, the compound of Formula (I), (Ia), (Ib), (II), (IIa), (IIb), (IIc), or (III) is administered in a local rather than systemic manner.

In some embodiments, the compound of Formula (I), (Ia), (Ib), (II), (IIa), (IIb), (IIc), or (III) is administered topically.

In some embodiments, the compound of Formula (I), (Ia), (Ib), (II), (IIa), (IIb), (IIc), or (III) is administered systemically.

In some embodiments, the pharmaceutical formulation is in the form of a tablet. In other embodiments, pharmaceutical formulations of the compounds of Formula (I), (Ia), (Ib), (II), (IIa), (IIb), (IIc), or (III) are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound of Formula (I), (Ia), (Ib), (II), (IIa), (IIb), (IIc), or (III) is formulated for use as an aerosol, a mist or a powder.

For buccal or sublingual administration, the compositions may take the form of tablets, lozenges, or gels formulated in a conventional manner.

In some embodiments, compounds of Formula (I), (Ia), (Ib), (II), (IIa), (IIb), (IIc), or (III) are prepared as transdermal dosage forms.

In one aspect, a compound of Formula (I), (Ia), (Ib), (II), (IIa), (IIb), (IIc), or (III) is formulated into a pharmaceutical composition suitable for intramuscular, subcutaneous, or intravenous injection.

In some embodiments, the compound of Formula (I), (Ia), (Ib), (II), (IIa), (IIb), (IIc), or (III) is be administered topically and can be formulated into a variety of topically administrable compositions, such as solutions, suspensions, lotions, gels, pastes, medicated sticks, balms, creams or ointments.

In some embodiments, the compounds of Formula (I), (Ia), (Ib), (II), (IIa), (IIb), (IIc), or (III) are formulated in rectal compositions such as enemas, rectal gels, rectal foams, rectal aerosols, suppositories, jelly suppositories, or retention enemas.

Methods of Dosing and Treatment Regimens

In one embodiment, the compounds of Formula (I), (Ia), (Ib), (II), (IIa), (IIb), (IIc), or (III) are used in the preparation of medicaments for the treatment of diseases or conditions described herein. In addition, a method for treating any of the diseases or conditions described herein in a subject in need of such treatment, involves administration of pharmaceutical compositions that include at least one compound of Formula (I), (Ia), (Ib), (II), (IIa), (IIb), (IIc), or (III) or a pharmaceutically acceptable salt, active metabolite, prodrug, or solvate thereof, in therapeutically effective amounts to said subject.

In certain embodiments, the compositions containing the compounds of Formula (I), (Ia), (Ib), (II), (IIa), (IIb), (IIc), or (III) are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds of Formula (I), (Ia), (Ib), (II), (IIa), (IIb), (IIc), or (III) are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Combination Treatments

In certain instances, it is appropriate to administer at least one compound of Formula (I), (Ia), (Ib), (II), (IIa), (IIb), (IIc), or (III) in combination with another therapeutic agent.

In one specific embodiment, a compound of Formula (I), (Ia), (Ib), (II), (IIa), (IIb), (IIc), or (III) is co-administered with a second therapeutic agent, wherein the compound of Formula (I), (Ia), (Ib), (II), (IIa), (IIb), (IIc), or (III) and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

In some embodiments, compounds of Formula (I), (Ia), (Ib), (II), (IIa), (IIb), (IIc), or (III) are administered to a mammal in combination with one or more additional neurodegenerative disease or disorder therapeutic agent. In some embodiments, the neurodegenerative disease or disorder is Alzheimer's disease, Parkinson's disease, Huntington's disease, or Lou Gehrig's Disease (Amyotrophic Lateral Sclerosis or ALS). In some embodiments, compounds of Formula (I), (Ia), (Ib), (II), (IIa), (IIb), (IIc), or (III) are administered to a mammal in combination with one or more additional therapeutic agent that alleviate the symptoms or side effects of a neurodegenerative disease or disorder. In some embodiments the symptoms or side effects a neurodegenerative disease or disorder are dementia, memory loss, dyskinesias, cognitive impairment, tremors, rigidity, slowness of movement, postural instability, involuntary jerking or writhing movements (chorea), slow or abnormal eye movements, difficulty with the physical production of speech or swallowing, psychiatric disorders, muscle cramps and spasms, spasticity, constipation, fatigue, excessive salivation, excessive phlegm, pain, sleep problems, uncontrolled outbursts of laughing or crying.

In some embodiments, the additional therapeutic agent is an Alzheimer's disease therapeutic agent. In some embodiments, the additional therapeutic agent is a cholinesterase inhibitor. In some embodiments, the cholinesterase inhibitor is donepezil, galantamine, or rivastigmine. In some embodiments, the additional therapeutic agent is memantine. In some embodiments, the additional therapeutic agent is latrepirdine, idalopridine, or cerlapirdine.

In some embodiments, the additional therapeutic agent is a Parkinson's disease therapeutic agent. In some embodiments, the additional therapeutic agent is levodopa. In some embodiments, the additional therapeutic agent is carbidopa-levodopa. In some embodiments, the additional therapeutic agent is a Dopamine agonist. In some embodiments, the dopamine agonist is ropinirole, pramipexole, or rotigotine. In some embodiments, the additional therapeutic agent is a MAO-B inhibitor. In some embodiments, the MAO-B inhibitor is selegiline or rasagiline. In some embodiments, the additional therapeutic agent is a catechol O-methyltransferase (COMT) inhibitor. In some embodiments, the COMT inhibitor is entacapone or tolcapone. In some embodiments, the additional therapeutic agent is an Anticholinergic. In some embodiments, the anticholinergic is benztropine or trihexyphenidyl. In some embodiments, the additional therapeutic agent is amantadine.

In some embodiments, compounds of Formula (I), (Ia), (Ib), (II), (IIa), (IIb), (IIc), or (III) are administered to a mammal in combination with deep brain stimulation.

In some embodiments, the additional therapeutic agent is a Huntington's disease therapeutic agent. In some embodiments, the additional therapeutic agent is tetrabenazine. In some embodiments, the additional therapeutic agent is an antipsychotic drug. In some embodiments, the antipsychotic drug is haloperidol, chlorpromazine, risperidone, olanzapine or quetiapine. In some embodiments, the additional therapeutic agent is amantadine, levetiracetam, or clonazepam. In some embodiments, the additional therapeutic agent is an antidepressant. In some embodiments, the antidepressant is citalopram, fluoxetine, or sertraline. In some embodiments, the additional therapeutic agent is a mood-stabilizing drug. In some embodiments, the mood-stabilizing drug is valproate, carbamazepine, or lamotrigine.

In some embodiments, compounds of Formula (I), (Ia), (Ib), (II), (IIa), (IIb), (IIc), or (III) are administered to a mammal in combination with psychotherapy, speech therapy, physical therapy or occupational therapy.

In some embodiments, the additional therapeutic agent is a Lou Gehrig's Disease (Amyotrophic Lateral Sclerosis or ALS) therapeutic agent. In some embodiments, the additional therapeutic agent is riluzole. In some embodiments, the additional therapeutic agent is baclofen, diazepam, trihexyphenidyl or amitriptyline.

In some embodiments, compounds of Formula (I), (Ia), (Ib), (II), (IIa), (IIb), (IIc), or (III) are administered to a mammal in combination with one or more additional neuropsychiatric disease or disorder therapeutic agent. In some embodiments, the neuropsychiatric disease or disorder is schizophrenia, anxiety, sleep disorder, eating disorder, psychosis, or addictions.

In some embodiments, the additional therapeutic agent is an antipsychotic. In some embodiments, the antipsychotic is aripiprazole, asenapine, clozapine, iloperidone, lurasidone, olanzapine, paliperidone, quetiapine, risperidone, ziprasidone, chlorpromazine, fluphenazine, haloperidol, or perphenazine. In some embodiments, the additional therapeutic agent is an antidepressant. In some embodiments, the antidepressant is a selective serotonin reuptake inhibitor (SSRI) or a serotonin norepinephrine reuptake inhibitor (SNRI). In some embodiments, the antidepressant is escitalopram, duloxetine, venlafaxine, or paroxetine. In some embodiments, the additional therapeutic agent is an anti-anxiety medication. In some embodiments, the anti-anxiety medication is buspirone. In some embodiments, the additional therapeutic agent is a benzodiazepine. In some embodiments the benzodiazepine is alprazolam, chlordiazepoxide, diazepam, or lorazepam.

In some embodiments, the additional therapeutic agent is a medication used to treat dependence. In some embodiments, the medication used to treat dependence is subozone, methadone, naloxone, or acamprosate.

EXAMPLES

The following examples are intended to illustrate but not limit the disclosed embodiments.

All reactions were performed in oven-dried glassware under an atmosphere of argon with magnetic stirring. All solvents and chemicals used were purchased from Sigma-Aldrich or Acros, and were used as received without further purification. Purity of compounds was established by liquid chromatography-mass spectroscopy (HPLC-MS) and was >95% for all tested compounds. Silica gel column chromatography was carried out using prepacked silica cartridges from RediSep (ISCO Ltd.) and eluted using an Isco Companion system. $^1$H- and $^{13}$C-NMR spectra were obtained on a Jeol 400 spectrometer at 400 MHz and 100 MHz, respectively. Chemical shifts are reported in δ (ppm) relative to residual solvent peaks or TMS as internal standards. Coupling constants are reported in Hz. Melting points were obtained using a capillary melting point apparatus (MEL-TEMP®) and are uncorrected. High-resolution ESI-TOF mass spectra were acquired from the Mass Spectrometry Core at The Sanford-Burnham Medical Research Institute (Orlando, Fla.). HPLC-MS analyses were performed on a Shimadzu 2010EV LCMS using the following conditions: Kromisil C18 column (reverse phase, 4.6 mm×50 mm); a linear gradient from 10% acetonitrile and 90% water to 95% acetonitrile and 5% water over 4.5 min; flow rate of 1 mL/min; UV photodiode array detection from 200 to 300 nm.

General Methods for the Synthesis of mGlu2/3 Receptor PAMs.

General method A: To a stirred solution of methyl 4-hydroxybenzoate (1 mmol, 1 equiv.) and 1,4-dibromobutane (3 mmol, 3 equiv.) in ACN, potassium carbonate (2 mmol, 2 equiv.) was added. The reaction mixture was heated at reflux for 6 h at which time it was cooled to room temperature. The crude reaction mixture was diluted with $CH_2Cl_2$ and washed twice with 5% aq. HCl (200 mL). The organic layers were collected and washed twice with saturated $NaHCO_3$ solution (200 mL). The organic layers were collected, dried over $Na_2SO_4$ and evaporated to dryness. To a stirred solution of $AlCl_3$ (0.039 mol, 1 equivalent) in $CH_2Cl_2$ at 0° C. under nitrogen, the acyl chloride (0.039 mol, 1 equivalent) was dissolved in $CH_2Cl_2$ and added dropwise to the stirred solution. The phenol (0.039 mol, 1 equiv) was added to the reaction mixture, and the reaction was allowed to warm to room temperature over 12 h. The reaction was quenched with HCl (5% aq.) and $CH_2Cl_2$ was added (50 mL). The organic layer was separated and washed with saturated $NaHCO_3$ solution, then brine, and dried over $Na_2SO_4$. The solvents were removed by rotary evaporation and the products were isolated by flash chromatography [$SiO_2$, hexanes: EtOAc (4:1)] and concentrated in vacuo. To a crimp top microwave vial was added the phenol (1 mmol, 1 equiv.), bromobutoxy benzoate (1 mmol, 1 equiv.), potassium carbonate (2 mmol, 2 equiv.), potassium iodide (0.1 mmol, 0.1 equiv.), all dissolved in ACN (0.2 M). The reaction mixture was heated in the microwave at 160° C. for 15 min. Following filtration and evaporation of solvents, the products were isolated by flash chromatography or reverse phase HPLC and lyophilized to provide the final compounds which were determined to be >95% pure by HPLC-UV, HPLC-MS, and $^1$H NMR.

General method B: To a stirred solution of the product from "General Method A" (1 mmol, 1 equiv.) in dioxane at room temperature, KOH (6 mmol, 6 equiv.) was added in water (0.5 mL). The mixture was stirred continuously for an additional 12 h. The reaction was quenched with HCl (5% aq.) and $CH_2Cl_2$ (50 mL) was added. The organic layer was separated and dried over $Na_2SO_4$. The solvents were removed by rotary evaporation and the products were isolated by flash chromatography [$SiO_2$, hexanes: EtOAc (1:1)] or reverse phase HPLC and lyophilized to provide the final compounds which were determined to be >95% pure by HPLC-UV, HPLC-MS, and $^1$H NMR.

General method C: Potassium carbonate (1 mmol) was added to a solution of appropriate resorcinol derivative (0.5 mmol), methyl 3'-(bromomethyl)-biphenyl-3-carboxylate (0.5 mmol) and catalytic potassium iodide in $CH_3CN$ (5 mL). After stirring for 2 h at 80° C., the organic phase was evaporated under reduced pressure and the crude material was partioned between water and $CH_2Cl_2$. The aqueous layer was extracted with $CH_2Cl_2$ (3×15 mL). The organic layer was dried using $Na_2SO_4$ and evaporated to give the ester derivatives in quantitative yield. The crude ester derivative was used in the next step without further purification.

2M LiOH (0.25 mL g, 0.5 mmol) was added to a solution of the crude product (0.5 mmol) in THF (5 mL). The reaction mixture was heated under reflux for 1 h and then cooled to room temperature and acidified with dil. HCl. The precipitated product was collected by filtration or followed a usual work up ethyl acetate to afford the crude product. The product was purified by preparative HPLC using ACN:water as the solvent system to afford the acid derivatives.

General method D: Potassium carbonate (2.76 g, 20 mmol) was added to a solution of 1-(2,4-dihydroxy-3-methylphenyl)-3,3-dimethylbutan-1-one (2.23 g, 10 mmol) and 1-bromo-3-(bromomethyl)benzene (2.5 g, 10 mmol) in $CH_3CN$ (100 mL). After stirring for 2 h at 80° C., the organic phase was evaporated under reduced pressure and the crude material was partitioned between water and $CH_2Cl_2$. The aqueous layer was extracted with $CH_2Cl_2$ (3×50 mL). The organic phase was dried using $Na_2SO_4$ and evaporated to give 1-(4-(3-bromobenzyloxy)-2-hydroxy-3-methylphenyl)-3,3-dimethylbutan-1-one (3.87 g, 98%). The crude product was used for the next step without further purification. LC-MS m/z calcd for $C_{20}H_{23}BrO_3$ [M+H]$^+$: 391.08. Found: 391.00.

A mixture of 1-(4-(3-bromobenzyloxy)-2-hydroxy-3-methylphenyl)-3,3-dimethylbutan-1-one (0.100 g, 0.25 mmol), boronic acid (0.0.375 mmol) and Pd(PPh$_3$)$_4$(0.028 mg, 0.025 mmol) were taken in DME (2 mL). To this solution was added 2M Na$_2$CO$_3$ (0.5 mL) and the resulting mixture was heated at reflux under an atmosphere of N$_2$ for 1 h. The reaction mixture was cooled to room temperature, diluted with water and neutralized using 1M HCl. A usual work up with ethyl acetate followed by preparative HPLC yielded the desired compounds.

General method E: To a solution of 1-(2,4-dihydroxy-3-methylphenyl)-3,3-dimethylbutan-1-one (0.454 g, 2 mmol) in ACN (20 mL), K$_2$CO$_3$ (0.552 g, 4 mmol) and 3-(bromomethyl)phenylboronic acid (0.516 mg, 2.4 mmol) were added and refluxed for 3 h. The reaction mixture was filtered and solvent was evaporated in vacuo to obtain 3-((4-(3,3-dimethylbutanoyl)-3-hydroxy-2-methylphenoxy)methyl) phenylboronic acid as a yellow solid (0.659 g, 93%). The crude product was used for the next step without further purification. LC-MS m/z calcd for $C_{20}H_{25}BO_5$ [M+H]$^+$: 357.18. Found: 357.00.

A mixture of 3-((4-(3,3-dimethylbutanoyl)-3-hydroxy-2-methylphenoxy)methyl)phenylboronic acid (0.200 g, 0.56 mmol), 3-iodo-4-methylbenzoic acid (0.84 mmol) and Pd(PPh$_3$)$_4$(0.064 g, 0.056 mmol) were dissolved in DME (2 mL). To this solution was added 2M Na$_2$CO$_3$ (1.12 mL) and the resulting mixture was heated at reflux under an atmosphere of N$_2$ for 1 h. The reaction mixture was cooled to room temperature, diluted with water and neutralized using 1M HCl. A usual work up with ethyl acetate followed by preparative HPLC yielded the desired compound.

Compounds 5 and 6 were synthesized according to published procedures (Cube, R. V. et al. *Bioorg. Med. Chem. Lett.* 2005, 15, 2389-2393). The following compounds were prepared using the general procedures A-E from the appropriate starting materials.

Example 1

Methyl 4-(4-(2,3-dimethyl-4-(3-methylbutanoyl) phenoxy)butoxy)benzoate (Compound 14)

Prepared according to general procedure A. Colorless solid (0.070 g, 17%); mp 55-57° C. $^1$H NMR (CDCl$_3$): δ 7.86 (d, J=7.8 Hz, 2H), 7.17-6.94 (m, 4H), 4.05 (t, J=5.9 Hz, 2H), 3.88 (s, 3H), 3.80 (t, J=6.0 Hz, 2H), 2.81 (d, J=6.9 Hz, 2H), 2.29 (s, 3H), 2.20 (s, 3H), 2.10-2.01 (m, 1H), 1.88-1.84 (m, 4H), 0.93 (d, J=6.4 Hz, 6H). $^{13}$C NMR (CDCl$_3$): δ 203.3, 166.8, 162.7, 155.5, 142.3, 132.2, 131.5, 130.6, 125.7, 125.4, 122.5, 114.0, 75.1, 67.7, 51.8, 51.7, 26.9, 25.9, 25.1, 22.63, 20.0, 12.3. ESI-MS m/z 413 [M+H]$^+$. HRMS m/z calcd for $C_{25}H_{32}O_5$[M+H]$^+$: 413.2323. Found: 413.2256.

Example 2

Methyl 4-(4-(4-(2-cyclopentylacetyl)-2,3-dimethylphenoxy)butoxy)benzoate (Compound 15)

Prepared according to general procedure A. Colorless solid (0.039 g, 9%). $^1$H NMR (CDCl$_3$): δ 7.87 (d, J=9.2 Hz, 2H), 7.17 (d, J=7.8 Hz, 1H), 7.00-6.97 (m, 3H), 4.05 (t, J=5.9 Hz, 2H), 3.88 (s, 3H), 3.80 (t, J=5.9 Hz, 2H), 2.95 (d, J=6.9 Hz, 2H), 2.29 (s, 3H), 2.20 (s, 3H), 2.21-2.10 (m, 1H), 1.99-1.89 (m, 4H), 1.80-1.76 (m, 2H), 1.59-1.46 (m, 4H), 1.14-1.01 (m, 2H). $^{13}$C NMR (CDCl$_3$): δ 203.3, 166.8, 162.7, 155.5, 142.3, 132.2, 131.5, 130.6, 126.9, 126.2, 114.0, 74.7, 67.7, 51.8, 49.0, 36.1, 32.7, 26.9, 25.9, 24.9, 20.0, 12.3. ESI-MS m/z 439 [M+H]$^+$. HRMS m/z calcd for $C_{27}H_{34}O_5$[M+H]$^+$: 439.2479. Found: 439.2419.

Example 3

Methyl 4-(4-(3-hydroxy-2-methyl-4-(3-methylbutanoyl)phenoxy)butoxy)benzoate (Compound 16)

Prepared according to general procedure A. Colorless solid (0.112 g, 27%); mp 72-74° C. $^1$H NMR (CDCl$_3$): δ 7.98-7.96 (m, 2H), 7.58 (d, J=8.7 Hz, 1H), 6.90-6.88 (m, 2H), 6.41 (d, J=9.2 Hz, 1H), 4.09-4.03 (m, 4H), 3.86 (s, 3H), 2.76 (d, J=7.3 Hz, 2H), 2.20-2.15 (m, 1H), 2.09 (s, 3H), 1.96-1.94 (m, 4H), 0.97 (d, J=6.9 Hz, 6H). $^{13}$C NMR (CDCl$_3$): δ 205.1, 166.8, 162.6, 162.5, 162.3, 131.5, 129.3, 122.5, 114.0, 113.7, 102.4, 67.7, 67.5, 51.8, 46.8, 26.9, 26.8, 25.9, 22.7, 7.6. ESI-MS m/z 415 [M+H]$^+$. HRMS m/z calcd for $C_{24}H_{30}O_6$[M+H]$^+$: 415.2115. Found: 415.2137.

Example 4

Methyl 4-(4-(4-(2-cyclopentylacetyl)-3-hydroxy-2-methylphenoxy)butoxy)benzoate (Compound 17)

Prepared according to general procedure A. Colorless solid (0.277 g, 63%). $^1$H NMR (CDCl$_3$): δ 7.86 (d, J=8.7 Hz, 2H), 7.79 (d, J=8.7 Hz, 1H), 6.90 (d, J=9.2 Hz, 2H), 6.61 (d, J=9.2 Hz, 1H), 4.11-4.09 (m, 4H), 3.87 (s, 3H), 2.90 (d, J=7.3 Hz, 2H), 2.35-2.20 (m, 1H), 1.96 (s, 3H), 1.94-1.92 (m, 4H), 1.85-1.76 (m, 2H), 1.59-1.47 (m, 4H), 1.87-1.19 (m, 2H). $^{13}$C NMR (CDCl$_3$): δ205.3, 162.6, 162.5, 162.3, 131.6, 129.2, 122.5, 114.0, 113.8, 113.7, 102.4, 67.7, 67.5, 51.8, 44.0, 36.8, 32.6, 25.9, 24.8, 7.6. ESI-MS m/z 441 [M+H]$^+$. HRMS m/z calcd for C$_{26}$H$_{32}$O$_6$ [M+H]$^+$: 441.2272. Found: 441.2278.

Example 5

4-(4-(2,3-Dimethyl-4-(3-methylbutanoyl)phenoxy)butoxy)benzoic acid (Compound 18)

Colorless solid (0.159 g, 40%). $^1$H NMR (DMSO): δ 7.84 (d, J=8.7 Hz, 2H), 7.20 (d, J=8.2 Hz, 1H), 6.99 (d, J=8.7 Hz, 3H), 4.11 (t, J=5.5 Hz, 2H), 3.75 (t, J=5.5 Hz, 2H), 2.78 (d, J=6.9 Hz, 2H), 2.24 (s, 3H), 2.15 (s, 3H), 2.02-1.98 (m, 1H), 1.87-1.80 (m, 4H), 0.86 (d, J=6.9 Hz, 6H). $^{13}$C NMR (DMSO): δ 203.6, 167.0, 162.1, 155.1, 142.1, 131.7, 131.3, 130.4, 125.9, 125.2, 123.1, 114.2, 74.5, 67.5, 51.7, 27.2, 26.3, 25.3, 24.5, 22.3, 20.0, 12.0. ESI-MS m/z 399 [M+H]$^+$. HRMS m/z calcd for C$_{24}$H$_{30}$O$_5$[M+H]$^+$: 399.2166. Found: 399.2191.

Example 6

4-(4-(4-(2-Cyclopentylacetyl)-2,3-dimethylphenoxy)butoxy)benzoic acid (Compound 19)

Colorless solid (0.093 g, 22%). $^1$H NMR (DMSO): δ 7.83 (d, J=8.7 Hz, 2H), 7.21 (d, J=7.8 Hz, 1H), 6.98 (d, J=8.7 Hz, 3H), 4.12 (t, J=Hz, 2H), 3.75 (t, J=Hz, 2H), 2.90 (d, J=6.9 Hz, 2H), 2.25 (s, 3H), 2.14 (s, 3H), 2.09-2.07 (m, 1H), 1.86-1.84 (m, 4H), 1.69-1.62 (m, 2H), 1.51-1.37 (m, 4H), 1.04-0.98 (m, 2H). $^{13}$C NMR (DMSO): δ 207.8, 167.0, 162.3, 154.2, 142.1, 131.4, 130.4, 125.8, 125.6, 122.9, 114.3, 74.1, 67.9, 49.3, 35.6, 32.1, 25.6, 25.1, 24.5, 20.2, 12.1. ESI-MS m/z 425 [M+H]$^+$. HRMS m/z calcd for C$_{26}$H$_{32}$O$_5$[M+H]$^+$: 425.2323. Found: 425.2366.

Example 7

4-(4-(3-Hydroxy-2-methyl-4-(3-methylbutanoyl)phenoxy)butoxy)benzoic acid (Compound 20)

Colorless solid (0.208 g, 52%); mp 153-155° C. $^1$H NMR (DMSO): δ 7.84 (d, J=8.7 Hz, 2H), 7.76 (d, J=8.7 Hz, 1H), 6.96 (d, J=9.2 Hz, 2H), 6.60 (d, J=9.2 Hz, 1H), 4.11-4.06 (m, 4H), 2.79 (d, J=6.9 Hz, 2H), 2.10-2.08 (m, 1H), 1.93 (s, 3H), 1.89-1.86 (m, 4H), 0.89 (d, J=6.9 Hz, 6H). $^{13}$C NMR (DMSO): δ 206.2, 167.0, 162.5, 162.3, 161.4, 131.4, 130.4, 122.9, 114.3, 113.5, 112.0, 103.4, 67.7, 67.5, 51.8, 44.0, 36.8, 32.6, 25.4, 22.4, 7.6. ESI-MS m/z 401 [M+H]+. HRMS m/z calcd for C$_{23}$H$_{28}$O$_6$[M+H]$^+$: 401.1956. Found: 401.1966.

Example 8

4-(4-(4-(2-Cyclopentylacetyl)-3-hydroxy-2-methylphenoxy)butoxy)benzoic acid (Compound 21)

Colorless solid (0.192 g, 45%); mp 158-160° C. $^1$H NMR (DMSO): δ 7.83-7.81 (m, 3H), 6.69 (d, J=8.7 Hz, 2H), 6.59 (d, J=8.7 Hz, 1H), 4.11-4.08 (m, 4H), 2.97 (d, J=6.9 Hz, 2H), 2.22-2.01 (m, 1H), 1.96 (s, 3H), 1.89-1.86 (m, 4H), 1.72-1.71 (m, 2H), 1.59-1.55 (m, 2H), 1.45-1.53 (m, 2H), 1.15-1.12 (m, 2H). $^{13}$C NMR (DMSO): δ 207.8, 167.0, 162.5, 162.3, 161.4, 131.6, 131.3, 122.9, 114.2, 112.8, 111.9, 103.8, 69.0, 68.9, 43.8, 36.2, 31.1, 24.5, 22.4, 8.9. ESI-MS m/z 427 [M+H]$^+$. HRMS m/z calcd for C$_{25}$H$_{30}$O$_6$[M+H]$^+$: 427.2115. Found: 427.2120.

Example 9

3-(4-(2,3-Dimethyl-4-(3-methylbutanoyl)phenoxy)butoxy)benzoic acid (Compound 22)

Colorless solid (0.167 g, 42%). $^1$H NMR (DMSO): δ 7.49-7.46 (m, 2H), 7.41-7.39 (m, 2H), 7.16-7.14 (m, 1H), 6.73-6.69 (m, 1H), 4.04-4.03 (m, 4H), 2.74 (d, J=6.9 Hz, 2H), 2.11 (s, 3H), 2.03 (s, 3H), 1.90-1.87 (m, 1H), 1.86-1.84 (m, 4H), 0.82 (d, J=6.9 Hz, 6H). $^{13}$C NMR (DMSO): δ 205.6, 167.2, 162.9, 161.4, 158.6, 132.7, 131.4, 129.7, 124.7, 121.8, 119.8, 114.2, 109.8, 74.2, 67.6, 51.7, 25.6, 25.3, 22.4, 24.1, 19.9, 19.8, 12.0, 11.9. ESI-MS m/z 399 [M+H]$^+$. HRMS m/z calcd for C$_{24}$H$_{30}$O$_5$[M+H]$^+$: 399.2166. Found: 399.2239.

Example 10

3-(4-(4-(2-Cyclopentylacetyl)-2,3-dimethylphenoxy)butoxy)benzoic acid (Compound 23)

Colorless solid (0.114 g, 27%). $^1$H NMR (DMSO): δ 7.47-7.40 (m, 3H), 7.19-7.15 (m, 2H), 6.97 (d, J=7.8 Hz, 1H), 4.04 (t, J=5.6 Hz, 2H), 3.73 (t, J=5.9 Hz, 2H), 2.89 (d, J=6.9 Hz, 2H), 2.21 (s, 3H), 2.11-2.04 (overlapping singlet and multiplets, 4H), 1.85-1.83 (m, 4H), 1.66-1.64 (m, 2H), 1.48-1.39 (m, 4H), 1.04-1.01 (m, 2H). $^{13}$C NMR (DMSO): δ 205.6, 167.2, 167.2, 158.2, 155.2, 141.9, 132.7, 131.4, 130.2, 129.7, 125.9, 125.2, 121.8, 119.3, 114.5, 74.4, 67.6, 48.4, 35.5, 32.0, 26.3, 25.4, 24.5, 20.0, 11.9. ESI-MS m/z 425 [M+H]$^+$. HRMS m/z calcd for C$_{26}$H$_{32}$O$_5$[M+H]$^+$: 425.2323. Found: 425.2383.

Example 11

3-(4-(3-Hydroxy-2-methyl-4-(3-methylbutanoyl)phenoxy)butoxy)benzoic acid (Compound 24)

Colorless solid (0.148 g, 37%); mp 118-120° C. $^1$H NMR (DMSO): δ 7.81 (d, J=9.2 Hz, 1H), 7.46 (d, J=7.8 Hz, 1H), 7.39-7.34 (m, 2H), 7.14-7.13 (m, 1H), 6.58 (d, J=9.2 Hz, 1H), 4.13 (t, J=5.9 Hz, 2H), 4.07 (t, J=5.9 Hz, 2H), 2.81 (d, J=6.9 Hz, 2H), 2.11-2.08 (m, 1H), 1.95 (s, 3H), 1.88-1.86 (m, 4H), 0.91 (d, J=6.9 Hz, 6H). $^{13}$C NMR (DMSO): δ 205.6, 167.2, 162.5, 161.4, 158.6, 132.3, 130.4, 129.7, 121.6, 119.4, 114.5, 113.5, 112.0, 103.4, 67.9, 67.3, 46.0, 25.6, 25.4, 22.5, 7.5. ESI-MS m/z 401 [M+H]+. HRMS m/z calcd for C$_{23}$H$_{28}$O$_6$[M+H]+: 401.1959. Found: 401.1967.

Example 12

3-(4-(4-(2-Cyclopentylacetyl)-3-hydroxy-2-methyl-phenoxy)butoxy)benzoic acid (Compound 25)

Colorless solid (0.230 g, 54%); 125-127° C. $^1$H NMR (DMSO): δ 7.76 (d, J=9.2 Hz, 1H), 7.46 (d, J=7.8 Hz, 1H), 7.41-7.33 (m, 2H), 7.13-7.12 (m, 1H), 6.58 (d, J=9.2 Hz, 1H), 4.08-4.03 (m, 4H), 2.94 (d, J=7.3 Hz, 2H), 2.17-2.16 (m, 1H), 1.95 (s, 3H), 1.87-1.85 (m, 4H), 1.71-1.68 (m, 2H), 1.55-1.42 (m, 4H), 1.12-1.09 (m, 2H). $^{13}$C NMR (DMSO): δ 205.8, 162.5, 161.3, 158.6, 132.3, 130.3, 129.7, 121.6, 119.4, 114.6, 113.3, 112.0, 103.3, 67.9, 67.4, 43.6, 36.3, 32.1, 25.4, 24.5, 7.5. 167.2, ESI-MS m/z 427 [M+H]+. HRMS m/z calcd for C$_{25}$H$_{30}$O$_6$[M+H]+: 427.2115. Found: 427.2122.

Example 13

2-(4-(2,3-Dimethyl-4-(3-methylbutanoyl)phenoxy)butoxy)benzoic acid (Compound 26)

Colorless solid (0.207 g, 52%); mp 48-50° C. $^1$H NMR (DMSO): δ 7.58 (d, J=7.8 Hz, 1H), 7.45 (t, J=7.8 Hz, 1H), 7.11-6.99 (m, 3H), 6.73-6.68 (m, 1H), 4.09-4.04 (m, 4H), 2.77 (d, J=7.3 Hz, 2H), 2.24 (s, 3H), 2.18 (s, 3H), 2.01-2.00 (m, 1H), 1.89-1.86 (m, 4H), 0.86 (d, J=6.8 Hz, 6H). $^{13}$C NMR (DMSO): δ 205.8, 167.4, 157.5, 156.5, 137.2, 133.0, 130.7, 125.9, 121.9, 120.1, 113.5, 109.3, 67.9, 67.4, 51.2, 48.7, 25.6, 24.6, 22.4, 19.8, 12.1, 11.5. ESI-MS m/z 399 [M+H]+. HRMS m/z calcd for C$_{24}$H$_{30}$O$_5$[M+H]+: 399.2166. Found: 399.2284.

Example 14

2-(4-(4-(2-Cyclopentylacetyl)-2,3-dimethylphenoxy)butoxy)benzoic acid (Compound 27)

Colorless solid (0.199 g, 47%); mp 90-92° C. $^1$H NMR (DMSO): δ 7.59 (d, J=7.9 Hz, 1H), 7.46-7.44 (m, 2H), 7.06 (d, J=8.2 Hz, 1H), 6.92 (t, J=7.8 Hz, 1H), 6.81 (d, J=8.7 Hz, 1H), 4.05-4.04 (m, 4H), 2.79 (d, J=6.9 Hz, 2H), 2.24 (s, 3H), 2.19 (s, 3H), 2.11-2.04 (m, 1H) 1.89-1.86 (m, 4H), 1.66-1.64 (m, 2H), 1.51-1.40 (m, 4H), 1.05-1.02 (m, 2H). $^{13}$C NMR (DMSO): δ 204.1, 167.5, 158.1, 157.4, 136.7, 132.8, 132.2, 130.6, 127.4, 125.5, 121.7, 120.0, 113.4, 107.9, 67.8, 67.5, 47.6, 36.1, 32.0, 25.5, 24.5, 16.5, 11.5. ESI-MS m/z 425 [M+H]+. HRMS m/z calcd for C$_{26}$H$_{32}$O$_5$[M+H]+: 425.2323. Found: 425.2357.

Example 15

2-(4-(3-Hydroxy-2-methyl-4-(3-methylbutanoyl)phenoxy)butoxy)benzoic acid (Compound 28)

Colorless solid (0.164 g, 41%); mp 101-103° C. $^1$H NMR (DMSO): δ 7.78 (d, J=8.7 Hz, 1H), 7.59 (d, J=9.6 Hz, 1H), 7.42-7.41 (m, 1H), 7.06 (d, J=8.3 Hz, 1H), 6.95 (t, J=7.4 Hz, 1H), 6.60 (d, J=9.2 Hz, 1H), 4.11-4.07 (m, 4H), 2.79 (d, J=6.9 Hz, 2H), 2.09-2.02 (m, 1H), 1.95 (s, 3H), 1.89-1.86 (m, 4H), 0.90 (d, J=6.4 Hz, 6H). $^{13}$C NMR (CDCl$_3$): δ 205.6, 167.4, 162.5, 161.3, 157.4, 132.9, 130.6, 130.3, 121.6, 120.0, 113.4, 111.9, 103.3, 67.9, 67.8, 45.8, 36.3, 25.4, 22.4, 7.5. ESI-MS m/z 401 [M+H]+. HRMS m/z calcd for C$_{23}$H$_{28}$O$_6$[M+H]+: 401.1959. Found: 401.1990.

Example 16

2-(4-(4-(2-Cyclopentylacetyl)-3-hydroxy-2-methyl-phenoxy)butoxy)benzoic acid (Compound 29)

Colorless solid (0.158 g, 37%); mp 93-95° C. $^1$H NMR (DMSO): δ 7.78 (d, J=8.7 Hz, 1H), 7.62 (d, J=9.6 Hz, 1H), 7.45 (t, J=7.6 Hz, 1H), 7.10 (d, J=8.2 Hz, 1H), 6.69 (t, J=7.3 Hz, 1H), 6.63 (d, J=9.2 Hz, 1H), 4.14-4.11 (m, 4H), 2.98 (d, J=6.8 Hz, 2H), 2.23-2.18 (m, 1H), 1.97 (s, 3H), 1.92-1.87 (m, 4H), 1.75-1.71 (m, 2H), 1.58-1.47 (m, 4H), 1.15-1.11 (m, 2H). $^{13}$C NMR (DMSO): δ 205.8, 167.4, 162.5, 161.3, 157.4, 132.9, 130.6, 130.3, 121.6, 120.0, 113.4, 113.2, 103.3, 111.9, 67.8, 67.9, 43.9, 36.3, 32.0, 25.6, 24.4, 7.5. ESI-MS m/z 427 [M+H]+. HRMS m/z calcd for C$_{25}$H$_{30}$O$_6$ [M+H]+: 427.2115. Found: 427.2235.

Example 17

2-Chloro-4-(4-(2,3-dimethyl-4-(3-methylbutanoyl)phenoxy)butoxy)benzoic acid (Compound 30)

Colorless solid (0.078 g, 18%); mp 77-79° C. $^1$H NMR (DMSO): δ 7.72-7.68 (m, 1H), 7.09 (d, J=7.8 Hz, 1H), 6.91-4-6.91 (m, 3H), 4.06-4.03 (m, 4H), 2.62 (d, J=6.9 Hz, 2H), 2.11 (s, 3H), 2.01 (s, 3H), 1.88-1.86 (m, 4H), 1.74-1.72 (m, 1H), 0.78 (d, J=6.4 Hz, 6H). $^{13}$C NMR (DMSO): δ 204.1, 167.5, 162.0, 155.6, 143.3, 134.1, 133.9, 131.8, 131.7, 126.0, 125.9, 122.3, 117.1, 113.8, 75.8, 69.9, 51.7, 26.1, 25.8, 25.2, 22.8, 20.6, 12.5. ESI-MS m/z 433 [M+H]+. HRMS m/z calcd for C$_{24}$H$_{29}$ClO$_5$ [M+H]+: 433.1776. Found: 433.1799.

Example 18

2-Chloro-4-(4-(4-(2-cyclopentylacetyl)-2,3-dimethylphenoxy)butoxy)benzoic acid (Compound 31)

Colorless solid (0.115 g, 25%); mp 97-99° C. $^1$H NMR (DMSO): δ 7.68 (d, J=8.2 Hz, 1H), 7.38 (d, J=8.7 Hz, 1H), 6.88 (s, 1H), 6.88 (d, J=8.7 Hz, 1H), 6.74 (d, J=8.7 Hz, 1H), 4.07-4.03 (m, 4H), 2.71 (d, J=6.9 Hz, 2H), 2.10 (s, 3H), 1.98-1.94 (m, 1H), 1.95 (s, 3H), 1.79-1.77 (m, 4H), 1.66-1.64 (m, 2H), 1.51-1.40 (m, 4H), 1.05-1.02 (m, 2H). $^{13}$C NMR (DMSO): δ 205.8, 166.0, 162.5, 161.4, 133.2, 130.4, 122.3, 116.6, 113.5, 111.7, 103.4, 68.0, 67.8, 46.0, 26.1, 25.6, 25.3, 25.1, 22.5, 7.5. ESI-MS m/z 459 [M+H]+. HRMS m/z calcd for C$_{26}$H$_{31}$ClO$_5$ [M+H]+: 459.1933. Found: 459.1942.

Example 19

2-Chloro-4-(4-(3-hydroxy-2-methyl-4-(3-methylbutanoyl)phenoxy)butoxy)benzoic acid (Compound 32)

Colorless solid (0.191 g, 44%); mp 113-115° C. $^1$H NMR (DMSO): δ 7.78 (d, J=8.7 Hz, 2H), 7.00 (s, 1H), 6.94 (d, J=8.7 Hz, 1H), 6.60 (d, J=9.2 Hz, 1H), 4.10-4.08 (m, 4H), 2.80 (d, J=6.9 Hz, 2H), 2.13-2.01 (m, 1H), 1.92 (s, 3H), 1.89-1.86 (m, 4H), 0.90 (d, J=6.4 Hz, 6H). $^{13}$C NMR (DMSO): δ 205.8, 166.0, 162.5, 161.4, 133.2, 130.4, 122.3, 116.6, 113.5, 111.7, 103.4, 68.0, 67.8, 46.0, 26.1, 25.6, 25.3, 25.1, 22.5, 7.5. ESI-MS m/z 435 [M+H]+. HRMS m/z calcd for $C_{23}H_{27}ClO_6$ [M+H]+: 435.1569. Found: 435.1563.

Example 20

2-Chloro-4-(4-(4-(2-cyclopentylacetyl)-3-hydroxy-2-methylphenoxy)butoxy)benzoic acid (Compound 33)

Colorless solid (0.168 g, 30%); mp 130-132° C. $^1$H NMR (DMSO): δ 7.78 (d, J=8.7 Hz, 2H), 7.03 (s, 1H), 7.00 (d, J=9.2 Hz, 1H), 6.58 (d, J=9.2 Hz, 1H), 4.10-4.08 (m, 4H), 2.95 (d, J=7.3 Hz, 2H), 2.21-2.19 (m, 1H), 1.94 (s, 3H), 1.89-1.86 (m, 4H), 1.77-1.71 (m, 2H), 1.56-1.45 (m, 4H), 1.13.1.10 (m, 2H). $^{13}$C NMR (DMSO): δ 205.8, 166.0, 162.5, 161.4, 133.2, 130.4, 122.3, 116.6, 113.5, 111.7, 103.4, 68.0, 67.8, 46.0, 26.1, 25.6, 25.3, 25.1, 22.5, 7.5. ESI-MS m/z 461 [M+H]+. HRMS m/z calcd for $C_{25}H_{29}ClO_6$ [M+H]+: 461.1725. Found: 461.1721.

Example 21

5-(4-(2,3-Dimethyl-4-(3-methylbutanoyl)phenoxy) butoxy)-2-fluorobenzoic acid (Compound 34)

Colorless solid (0.133 g, 32%). $^1$H NMR (DMSO): δ 7.27-7.15 (m, 4H), 6.94 (d, J=7.8 Hz, 1H), 3.98-3.68 (m, 4H), 2.71 (d, J=6.9 Hz, 2H), 2.19 (s, 3H), 2.09 (s, 3H), 2.05-1.95 (m, 1H), 1.89-1.81 (m, 4H), 0.80 (d, J=6.4 Hz, 6H). $^{13}$C NMR (DMSO): δ 202.9, 155.2, 154.4, 142.2, 131.8, 130.5, 126.0, 125.3, 120.6, 118.0, 117.7, 116.1, 74.5, 68.1, 51.1, 26.3, 25.5, 24.6, 22.4, 20.1, 12.0. ESI-MS m/z 417 [M+H]+. HRMS m/z calcd for $C_{25}H_{29}FO_5$ [M+H]+: 417.2072. Found: 417.2116.

Example 22

5-(4-(4-(2-Cyclopentylacetyl)-2,3-dimethylphenoxy) butoxy)-2-fluorobenzoic acid (Compound 35)

Colorless solid (0.177 g, 40%); mp 118-120° C. $^1$H NMR (DMSO): δ 7.44 (d, J=8.2 Hz, 1H), 7.27-7.11 (m, 3H), 6.77 (d, J=8.7 Hz, 1H), 3.98-3.70 (m, 4H), 2.77 (d, J=7.3 Hz, 2H), 2.18 (s, 3H), 2.10-2.01 (m, 1H), 2.02 (s, 3H), 1.89-1.83 (m, 4H), 1.67-1.64 (m, 2H), 1.48-1.38 (m, 4H), 1.05-1.03 (m, 2H). $^{13}$C NMR (DMSO): δ 204.0, 165.0, 158.1, 154.3, 136.8, 132.2, 127.3, 125.6, 117.8, 117.6, 116.0, 107.9, 67.9, 67.4, 47.6, 36.1, 32.0, 25.6, 24.5, 16.5, 11.4. ESI-MS m/z 443 [M+H]+. HRMS m/z calcd for $C_{26}H_{31}FO_5$ [M+H]+: 443.2228. Found: 443.2214.

Example 23

2-Fluoro-5-(4-(3-hydroxy-2-methyl-4-(3-methylbutanoyl)phenoxy)butoxy)benzoic acid (Compound 36)

Colorless solid (0.188 g, 45%); mp 99-101° C. $^1$H NMR (DMSO): δ 7.76 (d, J=9.2 Hz, 1H), 7.28-7.15 (m, 3H), 6.58 (d, J=9.2 Hz, 1H), 4.10-4.03 (m, 4H), 2.78 (d, J=7.3 Hz, 2H), 2.10-2.01 (m, 1H), 1.94 (s, 3H), 1.87-1.84 (m, 4H), 0.89 (d, J=6.9 Hz, 6H). $^{13}$C NMR (DMSO): δ 205.7, 165.0, 162.5, 161.4, 154.4, 130.4, 121.3, 117.8, 116.0, 113.5, 112.0, 103.4, 67.9, 67.8, 46.0, 25.6, 25.5, 22.5, 7.5. ESI-MS m/z 419 [M+H]+. HRMS m/z calcd for $C_{23}H_{27}FO_6$ [M+H]+: 419.1864. Found: 419.1863.

Example 24

5-(4-(4-(2-Cyclopentylacetyl)-3-hydroxy-2-methylphenoxy)butoxy)-2-fluorobenzoic acid (Compound 37)

Colorless solid (0.208 g, 47%); mp 110-112° C. $^1$H NMR (DMSO): δ 7.76 (d, J=9.2 Hz, 1H), 7.28 (d, J=8.7 Hz, 1H), 7.15-7.13 (m, 2H), 6.59 (d, J=9.2 Hz, 1H), 4.10-4.03 (m, 4H), 2.94 (d, J=7.3 Hz, 2H), 2.20-2.10 (m, 1H), 1.94 (s, 3H), 1.87-1.84 (m, 4H), 1.72-1.70 (m, 2H), 1.56-1.44 (m, 4H), 1.12-1.01 (m, 2H). $^{13}$C NMR (DMSO): δ 206.5, 165.0, 162.5, 161.3, 154.4, 130.3, 121.3, 118.0, 117.8, 116.0, 113.3, 112.0, 103.3, 67.9, 67.8, 44.0, 36.0, 32.1, 25.5, 25.4, 24.5, 7.5. ESI-MS m/z 445 [M+H]+. HRMS m/z calcd for $C_{25}H_{29}FO_6$ [M+H]+: 445.2021. Found: 445.2027.

Example 25

3-{4-[3-Hydroxy-2-methyl-4-(3-methylbutanoyl) phenoxy]butoxy}-4-methylbenzoic acid (Compound 38)

Colorless solid (0.277 g, 67%); mp 151-153° C. $^1$H NMR (DMSO): δ 7.79 (d, J=9.2 Hz, 1H), 7.43-7.41 (m, 2H), 7.20 (d, J=7.8 Hz, 1H), 6.60 (d, J=8.7 Hz, 1H), 4.14-4.10 (m, 4H), 2.81 (d, J=6.9 Hz, 2H), 2.15 (s, 3H), 2.13-2.12 (m, 1H), 1.97 (s, 3H), 1.91-1.89 (m, 4H), 0.90 (d, J=6.9 Hz, 6H). $^{13}$C NMR (DMSO): δ 205.8, 167.4, 162.5, 161.3, 157.4, 132.9, 130.6, 130.3, 121.6, 120.0, 113.4, 113.2, 111.9, 103.3, 67.9, 67.8, 43.9, 36.3, 32.0, 25.6, 24.4, 7.5. ESI-MS m/z 415 [M+H]+. HRMS m/z calcd for $C_{24}H_{30}O_6$[M+H]+: 415.2115. Found: 415.2009.

Example 26

3-{4-[4-(2-Cyclopentylacetyl)-3-hydroxy-2-methylphenoxy]butoxy}-4-methylbenzoic acid (Compound 39)

Colorless solid (0.277 g, 63%). $^1$H NMR (DMSO): δ 7.79 (d, J=9.2 Hz, 1H), 7.42-7.40 (m, 2H), 7.20 (d, J=7.3 Hz, 1H), 6.59 (d, J=9.2 Hz, 1H), 4.16-4.08 (m, 4H), 2.95 (d, J=7.3 Hz, 2H), 2.23-2.21 (m, 1H), 2.15 (s, 3H), 1.96 (s, 3H), 1.94-1.90 (m, 4H), 1.73-1.71 (m, 2H), 1.57-1.45 (m, 4H), 1.17-1.14 (m, 2H). $^{13}$C NMR (DMSO): δ 205.8, 167.3, 162.4, 161.2, 156.4, 131.3, 130.3, 129.6, 121.4, 113.2, 111.9, 111.2, 103.3, 67.8, 67.2, 43.2, 36.3, 32.0, 25.4, 24.4, 16.1, 7.5. ESI-MS m/z 441 [M+H]+. HRMS m/z calcd for $C_{26}H_{32}O_6$[M+H]+: 441.2272. Found: 441.2245.

Example 27

4-{4-[3-Hydroxy-2-methyl-4-(3-methylbutanoyl) phenoxy]butoxy}-3-methylbenzoic acid (Compound 40)

Colorless solid (0.282 g, 68%); mp 125-127° C. $^1$H NMR (DMSO): δ 7.78 (d, J=9.2 Hz, 1H), 7.73-7.71 (m, 1H), 7.67 (d, J=1.4 Hz, 1H), 6.96 (d, J=8.7 Hz, 1H), 6.59 (d, J=9.2 Hz, 1H), 4.13-4.10 (m, 4H), 2.80 (d, J=6.9 Hz, 2H), 2.11 (s, 3H), 2.10-2.07 (m, 1H), 1.93 (s, 3H), 1.92-1.89 (m, 4H), 0.89 (d, J=6.4 Hz, 6H). $^{13}$C NMR (DMSO): δ 205.7, 167.2, 162.4, 161.3, 160.2, 131.5, 130.3, 129.2, 125.7, 122.3, 113.4, 111.9, 110.6, 103.3, 67.8, 67.4, 45.9, 25.4, 22.4, 15.8, 7.5. ESI-MS m/z 415 [M+H]+. HRMS m/z calcd for $C_{24}H_{30}O_6$[M+H]+: 415.2115. Found: 415.2084.

Example 28

4-{4-[4-(2-Cyclopentylacetyl)-3-hydroxy-2-methylphenoxy]butoxy}-3-methylbenzoic acid (Compound 41)

Colorless solid (0.273 g, 62%). $^1$H NMR (DMSO): δ 7.78 (d, J=8.7 Hz, 1H), 7.73 (d, J=8.7 Hz, 1H), 7.68 (s, 1H), 6.95 (d, J=8.7 Hz, 1H), 6.58 (d, J=8.7 Hz, 1H), 4.12-4.08 (m, 4H), 2.94 (d, J=6.9 Hz, 2H), 2.20-2.01 (m, 1H), 2.12 (s, 3H), 1.93 (s, 3H), 1.90-1.89 (m, 4H), 1.75-1.73 (m, 2H), 1.55-1.44 (m, 4H), 1.13-1.01 (m, 2H). $^{13}$C NMR (DMSO): δ 205.8, 167.2, 162.4, 161.2, 160.2, 131.5, 130.3, 129.2, 125.7, 122.3, 113.2, 111.9, 110.6, 103.3, 67.8, 67.4, 43.2, 36.3, 32.0, 25.4, 24.4, 15.8, 7.4. ESI-MS m/z 441 [M+H]+. HRMS m/z calcd for $C_{26}H_{32}O_6$[M+H]$^+$: 441.2272. Found: 441.2270.

Example 29

3-Fluoro-4-{4-[3-hydroxy-2-methyl-4-(3-methylbutanoyl)phenoxy]butoxy}benzoic acid (Compound 42)

Colorless solid (0.188 g, 45%). $^1$H NMR (DMSO): δ 7.80 (d, J=8.7 Hz, 1H), 7.70 (d, J=9.2 Hz, 1H), 7.61-7.59 (m, 1H), 7.23 (t, J=8.5 Hz, 1H), 6.60 (d, J=9.2 Hz, 1H), 4.18-4.13 (m, 4H), 2.81 (d, J=6.9 Hz, 2H), 2.20-2.10 (m, 1H), 1.93 (s, 3H), 1.89-1.87 (m, 4H), 0.90 (d, J=6.4 Hz, 6H). $^{13}$C NMR (DMSO): δ 206.3, 166.7, 163.0, 161.8, 150.8, 130.9, 127.2, 117.1, 114.7, 114.0, 112.5, 103.9, 69.0, 68.2, 46.5, 26.0, 25.7, 22.9, 8.0. ESI-MS m/z 419 [M+H]+. HRMS m/z calcd for $C_{23}H_{27}FO_6$ [M+H]$^+$: 419.1864. Found: 419.1848.

Example 30

4-{4-[4-(2-Cyclopentylacetyl)-3-hydroxy-2-methylphenoxy]butoxy}-3-fluorobenzoic acid (Compound 43)

Colorless solid (0.213 g, 48%); mp 160-162° C. $^1$H NMR (DMSO): δ 7.79 (d, J=9.2 Hz, 1H), 7.70-7.76 (m, 1H), 7.60-7.58 (m, 1H), 7.22 (t, J=8.7 Hz, 1H), 6.58 (d, J=9.2 Hz, 1H), 4.17-4.12 (m, 4H), 2.94 (d, J=7.3 Hz, 2H), 2.20-2.18 (m, 1H), 1.92 (s, 3H), 1.89-1.87 (m, 4H), 1.72-1.69 (m, 2H), 1.55-1.44 (m, 4H), 1.12-1.10 (m, 2H). $^{13}$C NMR (DMSO): δ 206.3, 166.7, 162.9, 161.8, 150.8, 130.8, 127.2, 123.8, 117.0, 114.7, 113.8, 112.5, 103.8, 69.0, 68.2, 43.8, 36.8, 32.6, 25.7, 25.0, 8.0. ESI-MS m/z 445 [M+H]$^+$. HRMS m/z calcd for $C_{25}H_{29}FO_6$ [M+H]$^+$: 445.2021. Found: 445.2014.

Example 31

4-{4-[3-Hydroxy-2-methyl-4-(3-methylbutanoyl)phenoxy]butoxy}-3-methoxybenzoic acid (Compound 44)

Colorless solid (0.301 g, 70%); mp 133-135° C. $^1$H NMR (DMSO): δ 7.78 (d, J=8.7 Hz, 1H), 7.53-7.51 (m, 1H), 7.40 (d, J=1.8 Hz, 1H), 7.00 (d, J=8.2 Hz, 1H), 6.59 (d, J=9.2 Hz, 1H), 4.13-4.07 (m, 4H), 3.76 (s, 3H), 2.83 (d, J=6.9 Hz, 2H), 2.12-2.10 (m, 1H), 1.94 (s, 3H), 1.90-1.88 (m, 4H), 0.89 (d, J=6.9 Hz, 6H). $^{13}$C NMR (DMSO): δ 205.7, 167.1, 162.5, 161.3, 151.9, 148.4, 130.3, 122.9, 113.4, 111.9, 103.5, 67.9, 67.8, 55.4, 45.9, 25.4, 22.4, 7.5. ESI-MS m/z 431 [M+H]$^+$. HRMS m/z calcd for $C_{24}H_{30}O_7$[M+H]$^+$: 431.2064. Found: 431.2061.

Example 32

4-{4-[4-(2-Cyclopentylacetyl)-3-hydroxy-2-methylphenoxy]butoxy}-methoxybenzoic acid (Compound 45)

Colorless solid (0.292 g, 64%). $^1$H NMR (DMSO): δ 7.80 (d, J=9.2 Hz, 1H), 7.50-7.49 (m, 1H), 7.39 (d, J=1.8 Hz, 1H), 7.00 (d, J=8.7 Hz, 1H), 6.60 (d, J=9.2 Hz, 1H), 4.14-4.07 (m, 4H), 3.75 (s, 3H), 2.95 (d, J=6.9 Hz, 2H), 2.21-2.19 (m, 1H), 1.94 (s, 3H), 1.89-1.87 (m, 4H), 1.74-1.72 (m, 2H), 1.56-1.45 (m, 4H), 1.14-1.12 (m, 2H). $^{13}$C NMR (DMSO): δ 205.8, 167.1, 162.4, 161.2, 151.8, 148.4, 130.3, 123.1, 113.2, 112.1, 111.9, 103.3, 67.9, 67.8, 55.5, 43.2, 36.3, 32.0, 25.5, 25.2, 24.4, 7.5. ESI-MS m/z 457 [M+H]$^+$. HRMS m/z calcd for $C_{26}H_{32}O_7$[M+H]$^+$: 457.2221. Found: 457.2218.

Example 33

3-Chloro-4-{4-[3-hydroxy-2-methyl-4-(3-methylbutanoyl)phenoxy]butoxy}benzoic acid (Compound 46)

Colorless solid (0.252 g, 58%); mp 147-149° C. $^1$H NMR (DMSO): δ 7.86-7.84 (m, 3H), 7.21 (d, J=8.7 Hz, 1H), 6.61 (d, J=9.2 Hz, 1H), 4.20-4.15 (m, 4H), 2.81 (d, J=6.9 Hz, 2H), 2.21-2.10 (m, 1H), 1.93 (s, 3H), 1.92-1.89 (m, 4H), 0.90 (d, J=6.4 Hz, 6H). $^{13}$C NMR (DMSO): δ 206.0, 166.6, 163.0, 161.8, 150.7, 130.9, 127.2, 117.1, 114.9, 114.0, 112.5, 103.8, 69.0, 68.1, 46.3, 26.0, 25.8, 22.4, 8.0. ESI-MS m/z 435 [M+H]$^+$. HRMS m/z calcd for $C_{23}H_{27}ClO_6$ [M+H]$^+$: 435.1569. Found: 435.1557.

Example 34

3-Chloro-4-{4-[4-(2-cyclopentylacetyl)-3-hydroxy-2-methylphenoxy]butoxy}benzoic acid (Compound 47)

Colorless solid (0.253 g, 55%). $^1$H NMR (DMSO): δ 7.87-7.82 (m, 3H)), 7.23 (d, J=8.2 Hz, 1H), 6.62 (d, J=9.2 Hz, 1H), 4.22-4.17 (m, 4H), 2.98 (d, J=6.9 Hz, 2H), 2.23-2.21 (m, 1H), 1.95 (s, 3H), 1.94-1.91 (m, 4H), 1.76-1.74 (m, 2H), 1.56-1.44 (m, 4H), 1.18-1.15 (m, 2H). $^{13}$C NMR (DMSO): δ 206.0, 166.7, 162.9, 161.8, 151.0, 130.8, 127.2, 123.7, 117.0, 114.6, 113.9, 112.5, 103.8, 69.1, 68.2, 43.7, 36.8, 32.7, 25.7, 25.1, 8.0. ESI-MS m/z 461 [M+H]$^+$. HRMS m/z calcd for $C_{25}H_{29}ClO_6$ [M+H]$^+$: 461.1725. Found: 461.1720.

Example 35

4-{4-[3-Hydroxy-2-methyl-4-(3-methylbutanoyl)phenoxy]butoxy}-2-methylbenzoic acid (Compound 48)

Colorless solid (0.269 g, 65%): mp 136-138° C. $^1$H NMR (DMSO): δ 7.79 (d, J=9.6 Hz, 2H), 6.78-6.76 (m, 2H), 6.59 (d, J=9.2 Hz, 1H), 4.11-4.06 (m, 4H), 2.80 (d, J=7.3 Hz, 2H), 2.45 (s, 3H), 2.10-2.01 (m, 1H), 1.94 (s, 3H), 1.86-1.84 (m, 4H), 0.89 (d, J=6.9 Hz, 6H). $^{13}$C NMR (DMSO): δ 205.7, 168.0, 162.4, 161.3, 161.1, 142.1, 132.8, 130.3, 122.0, 117.2, 113.4, 111.9, 111.5, 103.3, 67.7, 67.2, 45.9, 25.3, 22.4, 21.8, 7.5. ESI-MS m/z 415 [M+H]$^+$. HRMS m/z calcd for $C_{24}H_{30}O_6$[M+H]$^+$: 415.2115. Found: 415.2071.

Example 36

4-{4-[4-(2-Cyclopentylacetyl)-3-hydroxy-2-methylphenoxy]butoxy}-2-methylbenzoic acid (Compound 49)

Colorless solid (0.273 g, 62%). $^1$H NMR (DMSO): δ 7.78 (d, J=9.2 Hz, 2H), 6.77-6.76 (m, 2H), 6.58 (d, J=8.7 Hz, 1H), 4.11-4.05 (m, 4H), 2.94 (d, J=7.3 Hz, 2H), 2.46 (s, 3H), 2.20-2.01 (m, 1H), 1.94 (s, 3H), 1.86-1.84 (m, 4H), 1.74-1.71 (m, 2H), 1.56-1.45 (m, 4H), 1.13-1.01 (m, 2H). $^{13}$C NMR (DMSO): δ 205.8, 168.0, 162.4, 161.1, 142.1, 132.8, 130.3, 129.6, 122.0, 117.2, 113.2, 111.9, 111.5, 103.3, 67.7, 67.2, 43.2, 36.3, 32.0, 25.2, 24.4, 21.8, 7.5. ESI-MS m/z 441 [M+H]$^+$. HRMS m/z calcd for $C_{26}H_{32}O_6$[M+H]$^+$: 441.2272. Found: 441.2248.

Example 37

3-{4-[3-Hydroxy-2-methyl-4-(3-methylbutanoyl)phenoxy]butoxy}-4-methoxybenzoic acid (Compound 50)

Colorless solid (0.254 g, 59%); mp 143-145° C. $^1$H NMR (DMSO): δ 7.80 (d, J=8.7 Hz, 1H), 7.51 (d, J=8.2 Hz, 1H), 7.41 (d, J=2.3 Hz, 1H), 7.00 (d, J=8.7 Hz, 1H), 6.60 (d, J=9.2 Hz, 1H), 4.14-4.04 (m, 4H), 3.77 (s, 3H), 2.81 (d, J=6.9 Hz, 2H), 2.10-2.01 (m, 1H), 1.95 (s, 3H), 1.88-1.84 (m, 4H), 0.90 (d, J=6.9 Hz, 6H). $^{13}$C NMR (DMSO): δ 205.7, 167.1, 162.5, 161.3, 152.7, 147.5, 130.3, 123.0, 113.4, 111.9, 111.1, 103.3, 67.9, 55.7, 45.9, 25.5, 22.4, 7.5. ESI-MS m/z 431 [M+H]$^+$. HRMS m/z calcd for $C_{24}H_{30}O_7$[M+H]$^+$: 431.2064. Found: 431.2060.

Example 38

3-{4-[4-(2-Cyclopentylacetyl)-3-hydroxy-2-methylphenoxy]butoxy}-4-methoxybenzoic acid (Compound 51)

Colorless solid (0.273 g, 60%). $^1$H NMR (DMSO): δ 7.80 (d, J=9.2 Hz, 1H), 7.51 (d, J=8.2 Hz, 1H), 7.41 (d, J=1.8 Hz, 1H), 6.99 (d, J=8.7 Hz, 1H), 6.60 (d, J=9.2 Hz, 1H), 4.14-4.04 (m, 4H), 3.77 (s, 3H), 2.95 (d, J=6.9 Hz, 2H), 2.21-2.10 (m, 1H), 1.94 (s, 3H), 1.88-1.84 (m, 4H), 1.72-1.69 (m, 2H), 1.56-1.45 (m, 4H), 1.14-1.12 (m, 2H). $^{13}$C NMR (DMSO): δ 205.8, 167.1, 162.4, 161.2, 152.7, 147.5, 130.3, 123.1, 113.2, 111.9, 111.1, 103.3, 67.9, 55.7, 43.2, 36.3, 32.0, 25.4, 24.4, 7.5. ESI-MS m/z 457 [M+H]$^+$. HRMS m/z calcd for $C_{26}H_{32}O_7$[M+H]$^+$: 457.2221. Found: 457.2224.

Example 39

4-(4-(4-Acetyl-3-hydroxy-2-methylphenoxy)butoxy)-3-methoxybenzoic acid (Compound 52)

Colorless solid (0.255 g, 58%); mp 138-140° C. $^1$H NMR (DMSO): δ 7.75 (d, J=9.2 Hz, 1H), 7.48 (d, J=8.2 Hz, 1H), 7.39 (s, 1H), 7.02 (d, J=8.2 Hz, 1H), 6.62 (d, J=8.7 Hz, 1H), 4.13-4.07 (m, 4H), 3.75 (s, 3H), 2.53 (s, 3H), 1.93 (s, 3H), 1.89-1.87 (m, 4H). $^{13}$C NMR (DMSO): δ 204.4, 167.7, 163.1, 161.5, 152.3, 148.0, 131.4, 123.6, 11.0, 112.6, 112.4, 112.3, 103.9, 68.5, 68.3, 55.9, 26.9, 26.0, 25.7, 8.0. LC-MS (ESI) calcd for $C_{21}H_{24}O_7$[M+H]$^+$: 389.15. Found: 389.05. HRMS (ESI) calcd for $C_{21}H_{24}O_7$[M+H]$^+$: 389.1595. Found: 389.1587.

Example 40

3-(4-(4-Acetyl-3-hydroxy-2-methylphenoxy)butoxy)-4-methoxybenzoic acid (Compound 53)

Colorless solid (0.264 g, 68%); mp 135-136° C. $^1$H NMR (DMSO): δ 7.76 (d, J=9.2 Hz, 1H), 7.50 (d, J=10.0 Hz, 1H), 7.42 (s, 1H), 6.99 (d, J=8.7 Hz, 1H), 6.60 (d, J=9.2 Hz, 1H), 4.13-4.03 (m, 4H), 3.77 (s, 3H), 2.53 (s, 3H), 1.94 (s, 3H), 1.92-1.88 (m, 4H). $^{13}$C NMR (DMSO): δ 204.3, 167.6, 163.1, 161.5, 153.3, 148.0, 131.4, 123.7, 123.5, 114.0, 113.7, 112.3, 111.7, 103.9, 68.4, 56.2, 26.8, 25.9, 8.0. LC-MS (ESI) calcd for $C_{21}H_{24}O_7$[M+H]$^+$: 389.15. Found: 389.00. HRMS (ESI) calcd for $C_{21}H_{24}O_7$[M+H]$^+$: 389.1595. Found: 389.1585.

Example 41

3-(4-(4-Acetyl-3-hydroxy-2-methylphenoxy)butoxy)-2-methylbenzoic acid (Compound 54)

Colorless solid (0.204 g, 55%); mp 140-142° C. $^1$H NMR (DMSO): δ 7.73 (d, J=9.2 Hz, 1H), 7.27 (d, J=8.7 Hz, 1H), 7.16 (t, J=7.8 Hz, 1H), 7.16 (d, J=7.8 Hz, 1H), 6.58 (d, J=8.7 Hz, 1H), 4.11-4.02 (m, 4H), 2.52 (s, 3H), 2.28 (s, 3H), 1.93 (s, 3H), 1.89-1.87 (m, 4H). $^{13}$C NMR (DMSO): δ204.3, 169.7, 163.0, 161.5, 157.4, 133.2, 131.4, 127.1, 126.7, 121.9, 114.8, 114.0, 112.3, 103.8, 68.3, 68.1, 26.8, 25.9, 13.1, 8.0. LC-MS (ESI) calcd for $C_{21}H_{24}FO_6$ [M+H]$^+$: 373.16. Found: 373.00. HRMS (ESI) calcd for $C_{21}H_{24}O_6$ [M+Na]$^+$: 395.1465. Found: 395.1464.

Example 42

5-(4-(4-Acetyl-3-hydroxy-2-methylphenoxy)butoxy)-2-fluorobenzoic acid (Compound 55)

Colorless solid (0.229 g, 0.253 g, 61%); mp 102-104° C. $^1$H NMR (DMSO): δ 7.75 (d, J=8.7 Hz, 1H), 7.26-7.13 (m, 3H), 6.59 (d, J=9.2 Hz, 1H), 4.11-4.03 (m, 4H), 2.52 (s, 3H), 1.94 (s, 3H), 1.92-1.86 (m, 4H). $^{13}$C NMR (DMSO): δ 204.3, 165.4, 163.0, 161.5, 154.8, 154.6, 131.4, 118.4, 118.2, 116.5, 114.0, 112.3, 103.8, 68.3, 26.9, 25.8, 8.0. LC-MS (ESI) calcd for $C_{20}H_{21}FO_6$ [M+H]$^+$: 377.13. Found: 377.00. HRMS (ESI) calcd for $C_{20}H_{21}FO_6$ [M+H]$^+$: 377.1395. Found: 377.1395.

Example 43

4-(4-(4-Acetyl-3-hydroxy-2-methylphenoxy)butoxy)-3-methylbenzoic acid (Compound 56)

Colorless solid (0.201 g, 54%); mp 188-190° C. 1H NMR (DMSO): δ 7.70-7.65 (m, 2H), 7.64 (s, 1H), 6.93 (d, J=8.7 Hz, 1H), 6.57 (d, J=9.2 Hz, 1H), 4.09-4.04 (m, 4H), 2.49 (s, 3H), 2.08 (s, 3H), 1.89 (s, 3H), 1.88-1.86 (m, 4H). $^{13}$C NMR (DMSO): δ 204.4, 167.7, 163.0, 161.5, 160.8, 132.0, 131.4, 129.7, 126.2, 122.8, 114.0, 112.3, 112.2, 108.8, 68.3, 67.9, 26.8, 25.9, 25.8, 16.4, 8.0. LC-MS (ESI) calcd for $C_{21}H_{24}O_6$ [M+H]$^−$: 373.16. Found: 373.00. HRMS (ESI) calcd for $C_{21}H_{24}O_6$[M+Na]$^+$: 395.1465. Found: 395.1463.

Example 44

4-(4-(3-Hydroxy-2-methyl-4-propionylphenoxy)butoxy)-3-methoxybenzoic acid (Compound 57)

Colorless solid (0.253 g, 63%); mp 128-130° C. $^1$H NMR (DMSO): δ 7.80 (d, J=9.2 Hz, 1H), 7.49 (d, J=8.2 Hz, 1H), 7.40 (s, 1H), 7.01 (d, J=8.7 Hz, 1H), 6.60 (d, J=9.2 Hz, 1H), 4.13-4.03 (m, 4H), 3.74 (s, 3H), 2.99 (q, J=7.5 Hz, 2H), 1.96 (s, 3H), 1.90-1.88 (m, 4H), 1.07 (t, J=7.3 Hz, 3H). $^{13}$C NMR (DMSO): δ 206.8, 162.9, 161.5, 152.3, 148.9, 130.5, 123.6, 113.5, 112.6, 112.4, 103.9, 98.5, 68.5, 66.9, 66.2, 60.6, 60.0, 31.1, 26.0, 25.7, 8.9, 8.0. LC-MS (ESI) calcd for $C_{22}H_{26}O_7$ [M+H]$^+$: 403.17. Found: 403.00. HRMS (ESI) calcd for $C_{22}H_{26}O_7$[M+Na]$^+$: 425.1571. Found: 425.1568.

Example 45

3-(4-(3-Hydroxy-2-methyl-4-propionylphenoxy)butoxy)-4-methoxybenzoic acid (Compound 58)

Colorless solid (0.293 g, 73%); mp 120-122° C. $^1$H NMR (DMSO): δ 7.77 (d, J=8.6 Hz, 1H), 7.50 (d, J=10.5 Hz, 1H), 7.42 (s, 1H), 6.99 (d, J=8.7 Hz, 1H), 6.60 (d, J=9.1 Hz, 1H), 4.13-4.03 (m, 4H), 3.77 (s, 3H), 2.98 (q, J=7.5 Hz, 2H), 1.95 (s, 3H), 1.90-1.88 (m, 4H), 1.05 (t, J=7.3 Hz, 3H). $^{13}$C NMR (DMSO): δ 206.8, 167.7, 162.9, 161.5, 153.3, 148.0, 130.4, 123.7, 113.7, 113.4, 112.4, 111.6, 103.8, 68.5, 68.4, 56.2, 30.6, 25.5, 25.4, 8.9, 8.0. LC-MS (ESI) calcd for $C_{22}H_{26}O_7$ [M+H]$^+$: 403.17. Found: 403.35. HRMS (ESI) calcd for $C_{22}H_{26}O_7$[M+Na]$^+$: 425.1571. Found: 425.1569.

Example 46

3-(4-(3-Hydroxy-2-methyl-4-propionylphenoxy)butoxy)-2-methylbenzoic acid (Compound 59)

Colorless solid (0.228 g, 59%); 103-105° C. $^1$H NMR (DMSO): δ 7.77 (d, J=9.2 Hz, 1H), 7.24 (d, J=9.2 Hz, 1H), 7.16 (t, J=7.8 Hz, 1H), 7.08 (d, J=8.2 Hz, 1H), 6.59 (d, J=9.2 Hz, 1H), 4.12-4.02 (m, 4H), 3.00 (q, J=7.3 Hz, 2H), 2.28 (s, 3H), 1.94 (s, 3H), 1.90-1.89 (m, 4H), 1.05 (t, J=7.4 Hz, 3H). $^{13}$C NMR (DMSO): δ 206.8, 169.7, 162.8, 161.5, 157.4, 133.2, 130.4, 127.1, 126.8, 121.9, 114.8, 113.5, 112.4, 103.8, 63.3, 31.8, 24.6, 13.1, 8.9, 8.0. LC-MS (ESI) calcd for $C_{22}H_{26}O_6$[M+H]$^+$: 387.17. Found: 387.05. HRMS (ESI) calcd for $C_{22}H_{26}O_6$[M+H]$^+$: 387.1802. Found: 387.1802.

Example 47

2-Fluoro-5-(4-(3-hydroxy-2-methyl-4-propionylphenoxy)butoxy)benzoic acid (Compound 60)

Colorless solid (0.254 g, 65%); mp 123-125° C. $^1$H NMR (DMSO): δ 7.76 (d, J=8.7 Hz, 1H), 7.26-7.13 (m, 3H), 6.59 (d, J=9.2 Hz, 1H), 4.11-4.02 (m, 4H), 2.98 (q, J=7.3 Hz, 2H), 1.93 (s, 3H), 1.90-1.86 (m, 4H), 1.05 (t, J=7.3 Hz, 3H). $^{13}$C NMR (DMSO): δ 206.8, 165.5, 162.8, 161.5, 154.8, 154.6, 130.4, 118.4, 116.5, 113.5, 112.4, 103.8, 68.3, 31.1, 25.8, 8.9, 8.0. LC-MS (ESI) calcd for $C_{21}H_{23}FO_6$ [M+H]$^+$: 391.15. Found: 391.00. HRMS (ESI) calcd for $C_{21}H_{23}FO_6$ [M+Na]$^+$: 413.1371. Found: 413.1366.

Example 48

4-(4-(3-Hydroxy-2-methyl-4-propionylphenoxy)butoxy)-3-methylbenzoic acid (Compound 61)

Colorless solid (0.205 g, 53%); mp 178-180° C. $^1$H NMR (DMSO): δ 7.80-7.78 (m, 2H), 7.70 (s, 1H), 6.99 (d, J=8.7 Hz, 1H), 6.63 (d, J=9.2 Hz, 1H), 4.15-4.10 (m, 4H), 3.02 (q, J=7.3 Hz, 2H), 2.24 (s, 3H), 1.96 (s, 3H), 1.95-1.92 (m, 4H), 1.08 (t, J=7.3 Hz, 3H). $^{13}$C NMR (DMSO): δ 206.8, 167.7, 162.8, 161.5, 160.8, 132.0, 130.5, 129.7, 126.2, 122.8, 113.5, 112.4, 111.2, 103.8, 68.3, 67.9, 31.1, 25.9, 25.8, 16.4, 8.9, 8.0. LC-MS (ESI) calcd for $C_{22}H_{26}O_6$[M+H]$^+$: 387.17. Found: 387.05. HRMS (ESI) calcd for $C_{22}H_{26}O_6$[M+Na]$^+$: 409.1622. Found: 409.1625.

Example 49

4-(4-(3-Hydroxy-4-isobutyryl-2-methylphenoxy)butoxy)-3-methoxybenzoic acid (Compound 62)

Colorless solid (0.283 g, 68%); 118-120° C. $^1$H NMR (DMSO): δ 7.84 (d, J=8.7 Hz, 1H), 7.49 (d, J=10.5 Hz, 1H), 7.39 (s, 1H), 7.00 (d, J=8.2 Hz, 1H), 6.61 (d, J=9.2 Hz, 1H), 4.14-4.07 (m, 4H), 3.74 (s, 3H), 3.74-3.63 (m, 1H), 1.94 (s, 3H), 1.90-1.88 (m, 4H), 1.09 (d, J=6.9 Hz, 6H). $^{13}$C NMR (DMSO): δ 210.3, 167.6, 163.0, 162.3, 152.4, 148.9, 130.5, 123.6, 123.5, 112.7, 112.6, 112.4, 112.2, 103.9, 68.5, 56.0, 34.8, 26.0, 25.7, 20.0, 8.1. LC-MS (ESI) calcd for $C_{23}H_{28}O_7$ [M+H]$^+$: 417.18. Found: 417.05. HRMS (ESI) calcd for $C_{23}H_{28}O_7$[M+Na]$^+$: 439.1727. Found: 439.1725.

Example 50

3-(4-(3-Hydroxy-4-isobutyryl-2-methylphenoxy)butoxy)-4-methoxybenzoic acid (Compound 63)

Colorless solid (0.279 g, 67%); 82-84° C. $^1$H NMR (DMSO): δ 7.84 (d, J=9.2 Hz, 1H), 7.50 (d, J=10.5 Hz, 1H), 7.42 (s, 1H), 6.99 (d, J=8.7 Hz, 1H), 6.61 (d, J=9.2 Hz, 1H), 4.14 (brs, 2H), 4.07 (brs, 2H), 3.77 (s, 3H), 3.74-3.63 (m, 1H), 1.95 (s, 3H), 1.88 (brs, 4H), 1.08 (d, J=6.4 Hz, 6H). $^{13}$C NMR (DMSO): δ 210.2, 167.6, 163.0, 162.3, 153.3, 148.1, 130.4, 123.7, 113.7, 112.7, 112.2, 111.7, 103.9, 68.4, 56.2, 26.0, 19.9, 8.1. LC-MS (ESI) calcd for $C_{23}H_{28}O_7$ [M+H]$^+$: 417.18. Found: 417.05. HRMS (ESI) calcd for $C_{23}H_{28}O_7$ [M+H]$^+$: 417.1908. Found: 417.1895.

Example 51

3-(4-(3-Hydroxy-4-isobutyryl-2-methylphenoxy)butoxy)-2-methylbenzoic acid (Compound 64)

Colorless solid (0.264 g, 66%); mp 115-117° C. $^1$H NMR (DMSO): δ 7.85 (d, J=9.2 Hz, 1H), 7.28 (d, J=6.8 Hz, 1H), 7.18 (t, J=7.8 Hz, 1H), 7.10 (d, J=7.3 Hz, 1H), 6.64 (d, J=9.2 Hz, 1H), 4.16-4.05 (m, 4H), 3.66-3.54 (m, 1H), 2.03 (s, 3H), 1.93 (s, 3H), 1.91-1.88 (m, 4H), 1.10 (d, J=6.8 Hz, 6H). $^{13}$C NMR (DMSO): δ 210.2, 169.7, 162.9, 157.4, 133.2, 130.4, 127.1, 126.8, 121.9, 114.8, 112.7, 112.2, 103.9, 68.3, 68.1, 34.3, 26.0, 19.9, 13.1, 8.0. LC-MS (ESI) calcd for $C_{23}H_{28}O_6$ [M+H]$^+$: 401.19. Found: 401.05. HRMS (ESI) calcd for $C_{23}H_{28}O_6$[M+H]$^+$: 401.1959. Found: 401.1948.

Example 52

2-Fluoro-5-(4-(3-hydroxy-4-isobutyryl-2-methylphenoxy)butoxy)benzoic acid (Compound 65)

Colorless solid (0.234 g, 58%); mp 122-124° C. $^1$H NMR (DMSO): δ 7.82 (d, J=9.2 Hz, 1H), 7.27-7.13 (m, 3H), 6.61 (d, J=8.7 Hz, 1H), 4.12-4.02 (m, 4H), 3.64-3.46 (m, 1H), 1.94 (s, 3H), 1.90-1.86 (m, 4H), 1.08 (d, J=6.9 Hz, 6H). $^{13}$C NMR (DMSO): δ 210.2, 165.5, 162.9, 162.3, 154.8, 154.6, 130.5, 118.2, 116.4, 112.7, 112.2, 103.9, 68.3, 33.6, 19.9, 8.0. LC-MS (ESI) calcd for $C_{22}H_{25}FO_6$ [M+H]$^+$:

Example 53

4-(4-(3-Hydroxy-4-isobutyryl-2-methylphenoxy)butoxy)-3-methylbenzoic acid (Compound 66)

Colorless solid (0.224 g, 56%); mp 160-162° C. $^1$H NMR (DMSO): δ 7.84 (d, J=9.2 Hz, 1H), 7.75-7.71 (m, 1H), 7.76 (s, 1H), 6.98 (d, J=8.7 Hz, 1H), 6.61 (d, J=9.2 Hz, 1H), 4.14-4.09 (m, 4H), 3.71-3.61 (m, 1H), 2.12 (s, 3H), 1.94 (s, 3H), 1.94-1.90 (m, 4H), 1.08 (d, J=5.5 Hz, 6H). $^{13}$C NMR (DMSO): δ 210.2, 167.7, 162.9, 162.3, 160.8, 132.0, 130.5, 129.7, 126.2, 122.8, 1127, 112.3, 111.2, 103.9, 68.3, 67.9, 34.6, 25.9, 19.9, 16.4, 8.0. LC-MS (ESI) calcd for $C_{23}H_{28}O_6$ [M+H]$^+$: 401.19. Found: 401.05. HRMS (ESI) calcd for $C_{23}H_{28}O_6$[M+Na]$^+$: 423.1778. Found: 423.1778.

Example 54

(4-(4-Butyryl-3-hydroxy-2-methylphenoxy)butoxy)-3-methoxybenzoic acid (Compound 67)

Colorless solid (0.270 g, 65%); mp 148-150° C. $^1$H NMR (DMSO): δ 7.80 (d, J=9.2 Hz, 1H), 7.48 (d, J=10.5 Hz, 1H), 7.39 (s, 1H), 7.00 (d, J=8.2 Hz, 1H), 6.60 (d, J=8.7 Hz, 1H), 4.13-4.07 (m, 4H), 3.75 (s, 3H), 2.93 (t, J=7.5 Hz, 2H), 1.94 (s, 3H), 1.91-1.88 (m, 4H), 1.61-1.57 (m, 2H), 0.90 (t, J=7.3 Hz, 3H). $^{13}$C NMR (DMSO): δ 206.4, 167.4, 162.9, 161.7, 152.4, 148.9, 130.7, 123.6, 123.5, 112.5, 112.4, 103.8, 68.5, 68.3, 55.9, 26.0, 25.7, 18.4, 14.1, 8.0. LC-MS (ESI) calcd for $C_{23}H_{28}O_7$[M+H]$^+$: 417.18. Found: 417.00. HRMS (ESI) calcd for $C_{23}H_{28}O_7$[M+H]$^+$: 417.1908. Found: 417.1903.

Example 55

3-(4-(4-Butyryl-3-hydroxy-2-methylphenoxy)butoxy)-4-methoxybenzoic acid (Compound 68)

Colorless solid (0.279 g, 67%); mp 129-131° C. $^1$H NMR (DMSO): δ 7.79 (d, J=9.1 Hz, 1H), 7.43 (d, J=10.0 Hz, 1H), 7.43 (s, 1H), 7.02 (d, J=8.7 Hz, 1H), 6.63 (d, J=9.2 Hz, 1H), 4.13-4.07 (m, 4H), 3.79 (s, 3H), 2.99 (t, J=7.3 Hz, 2H), 1.96 (S, 3H), 1.89-1.86 (m, 4H), 1.63-1.61 (m, 2H), 0.92 (d, J=7.6 Hz, 3H). $^{13}$C NMR (DMSO): δ 206.4, 167.6, 162.9, 161.7, 153.3, 148.0, 130.6, 123.7, 123.4, 113.6, 112.4, 111.6, 103.8, 68.44, 68.41, 56.2, 26.0, 25.6, 18.4, 14.1, 8.0. LC-MS (ESI) calcd for $C_{23}H_{28}O_7$[M+H]$^+$: 417.18. Found: 417.00. HRMS (ESI) calcd for $C_{23}H_{28}O_7$[M+H]$^+$: 417.1908. Found: 417.1896.

Example 56

3-(4-(4-Butyryl-3-hydroxy-2-methylphenoxy)butoxy)-2-methylbenzoic acid (Compound 69)

Colorless solid (0.244 g, 61%); mp 97-99° C. $^1$H NMR (DMSO): δ 7.78 (d, J=8.7 Hz, 1H), 7.27 (d, J=7.3 Hz, 1H), 7.17 (t, J=8.2 Hz, 1H), 7.08 (d, J=7.8 8 Hz, 1H), 6.59 (d, J=9.2 Hz, 1H), 4.13-4.02 (m, 4H), 2.92 (t, J=7.3 Hz, 2H), 2.28 (s, 3H), 1.94 (s, 3H), 1.89-1.86 (m, 4H), 1.61-1.57 (m, 2H), 0.89 (t, J=7.8 Hz, 3H). $^{13}$C NMR (DMSO): δ 206.4, 169.6, 162.9, 161.7, 157.4, 133.1, 130.6, 127.1, 126.8, 121.8, 114.8, 113.7, 112.5, 103.8, 68.3, 68.2, 26.0, 18.4, 14.1, 13.1, 8.0. LC-MS (ESI) calcd for $C_{23}H_{28}O_6$[M+H]$^+$: 401.19. Found: 401.05. HRMS (ESI) calcd for $C_{23}H_{28}O_6$ [M+Na]$^+$: 439.1727. Found: 439.1727.

Example 57

5-(4-(4-Butyryl-3-hydroxy-2-methylphenoxy)butoxy)-2-fluorobenzoic acid (Compound 70)

Colorless solid (0.255 g, 63%); mp 88-90° C. $^1$H NMR (DMSO): δ 7.78 (d, J=8.7 Hz, 1H), 7.27-7.13 (m, 3H), 6.59 (d, J=9.2 Hz, 1H), 4.11-4.02 (m, 4H), 2.92 (t, J=7.3 Hz, 2H), 1.94 (s, 3H), 1.89-1.87 (m, 4H), 1.61-1.59 (m, 2H), 0.89 (t, J=7.3 Hz, 3H). $^{13}$C NMR (DMSO): δ 206.4, 165.4, 162.9, 161.7, 154.8, 154.6, 130.6, 118.2, 116.4, 113.6, 112.4, 103.8, 68.3, 25.8, 18.3, 14.1, 8.0. LC-MS (ESI) calcd for $C_{22}H_{25}FO_6$ [M+H]$^+$: 405.43. Found: 405.05. HRMS (ESI) calcd for $C_{22}H_{25}FO_6$ [M+Na]$^+$: 427.1527. Found: 427.1523.

Example 58

4-(4-(4-Butyryl-3-hydroxy-2-methylphenoxy)butoxy)-3-methylbenzoic acid (Compound 71)

Colorless solid (0.232 g, 58%); mp 161-163° C. $^1$H NMR (DMSO): δ 7.79 (d, J=9.2 Hz, 1H), 7.71 (d, J=8.7 Hz, 1H), 7.68 (s, 1H), 6.97 (d, J=8.7 Hz, 1H), 6.59 (d, J=8.7 Hz, 1H), 4.13-4.08 (m, 4H), 2.92 (t, J=7.3 Hz, 2H), 2.12 (s, 3H), 1.94 (s, 3H), 1.90-1.88 (m, 4H), 1.63-1.61 (m, 2H), 0.89 (t, J=7.3 Hz, 3H). $^{13}$C NMR (DMSO): δ 206.4, 167.7, 162.9, 161.7, 160.8, 132.0, 130.7, 129.7, 126.3, 122.8, 113.7, 112.5, 111.2, 103.9, 68.3, 67.9, 26.1, 25.9, 18.4, 16.3, 14.1, 8.0. LC-MS (ESI) calcd for $C_{23}H_{28}O_6$[M+H]$^+$: 401.19. Found: 401.05. HRMS (ESI) calcd for $C_{23}H_{28}O_6$[M+Na]$^+$: 423.1778. Found: 423.1778.

Example 59

3-(4-(4-(3,3-Dimethylbutanoyl)-3-hydroxy-2-methylphenoxy)butoxy)-4-methoxybenzoic acid (Compound 72)

Colorless solid (0.270 g, 61%); mp 140-142° C. $^1$H NMR (DMSO): δ 7.84 (d, J=9.2 Hz, 1H), 7.50 (d, J=10.0 Hz, 1H), 7.49 (s, 1H), 7.00 (d, J=8.7 Hz, 1H), 6.58 (d, J=9.2 Hz, 1H), 4.13-4.03 (m, 4H), 3.79 (s, 3H), 2.80 (s, 2H), 1.94 (s, 3H), 1.89-1.87 (m, 4H), 0.96 (s, 9H). $^{13}$C NMR (DMSO): δ 206.4, 167.6, 163.1, 162.1, 153.3, 148.1, 131.8, 123.7, 123.5, 114.9, 113.6, 111.6, 103.6, 68.4, 56.2, 49.1, 32.1, 30.5, 26.0, 25.8, 8.0. LC-MS (ESI) calcd for $C_{25}H_{32}O_7$[M+H]$^+$: 445.21. Found: 445.00. HRMS (ESI) calcd for $C_{25}H_{32}O_7$[M+Na]$^+$: 467.2040. Found: 467.2041.

Example 60

4-(4-(4-(3,3-Dimethylbutanoyl)-3-hydroxy-2-methylphenoxy)butoxy)-5-methoxycyclohexa-1,3-dienecarboxylic acid (Compound 73)

Colorless solid (0.258 g, 58%); mp 133-135° C. $^1$H NMR (DMSO): δ 7.86 (d, J=9.2 Hz, 1H), 7.48 (d, J=10.1 Hz, 1H), 7.39 (s, 1H), 7.01 (d, J=8.7 Hz, 1H), 6.58 (d, J=9.2 Hz, 1H), 4.13-4.07 (m, 4H), 3.77 (s, 3H), 2.80 (s, 2H), 1.94 (s, 3H), 1.89-1.87 (m, 4H), 0.96 (s, 9H). $^{13}$C NMR (DMSO): δ 206.4, 167.6, 163.1, 162.1, 152.4, 148.9, 131.8, 123.6, 114.9, 112.6, 112.4, 103.6, 68.4, 55.9, 49.1, 32.1, 30.5, 26.0, 25.8, 8.0. LC-MS (ESI) calcd for $C_{25}H_{32}O_7[M+H]^+$: 445.21. Found: 445.00. HRMS (ESI) calcd for $C_{25}H_{32}O_7[M+Na]^+$: 467.2040. Found: 467.2045.

Example 61

3-(4-(4-(3,3-Dimethylbutanoyl)-3-hydroxy-2-methylphenoxy)butoxy)-2-methylbenzoic acid (Compound 74)

Colorless solid (0.278 g, 65%); mp 123-125° C. $^1$H NMR (DMSO): δ 7.84 (d, J=8.7 Hz, 1H), 7.26 (d, J=7.8 Hz, 1H), 7.16 (t, J=8.2 Hz, 1H), 7.08 (d, J=7.3 Hz, 1H), 6.58 (d, J=9.2 Hz, 1H), 4.13-4.02 (m, 4H), 2.80 (s, 2H), 2.28 (s, 3H), 1.94 (s, 3H), 1.90-1.87 (m, 4H), 0.96 (s, 9H). $^{13}$C NMR (DMSO): δ 206.4, 169.7, 163.0, 162.1, 157.4, 131.1, 131.8, 127.1, 126.8, 121.9, 114.9, 114.8, 112.4, 103.6, 68.3, 66.8, 49.1, 32.1, 30.4, 13.1, 8.0. LC-MS (ESI) calcd for $C_{25}H_{32}O_7[M+H]^+$: 429.22. Found: 429.00. HRMS (ESI) calcd for $C_{25}H_{32}O_6[M+Na]^+$: 451.2091. Found: 451.2093.

Example 62

5-(4-(4-(3,3-Dimethylbutanoyl)-3-hydroxy-2-methylphenoxy)butoxy)-2-fluorobenzoic acid (Compound 75)

Colorless solid (0.258 g, 60%); mp 130-132° C. $^1$H NMR (DMSO): δ 7.83 (d, J=9.2 Hz, 1H), 7.27-7.13 (m, 3H), 6.57 (d, J=9.2 Hz, 1H), 4.11-4.02 (m, 4H), 2.79 (s, 2H), 1.94 (s, 3H), 1.86-1.85 (m, 4H), 0.96 (s, 9H). $^{13}$C NMR (DMSO): δ 206.4, 165.5, 163.0, 162.1, 154.8, 154.6, 131.7, 121.3, 118.5, 116.4, 114.9, 112.4, 103.6, 68.4, 66.8, 49.1, 32.2, 30.4, 8.0. LC-MS (ESI) calcd for $C_{24}H_{29}FO_6$ $[M+H]^+$: 433.19. Found: 433.00. HRMS (ESI) calcd for $C_{24}H_{29}FO_6$ $[M+Na]^+$: 455.1840. Found: 455.1840.

Example 63

4-(4-(4-Acetyl-3-hydroxy-2-propylphenoxy)butoxy)-3-methoxybenzoic acid (Compound 190)

Colorless solid (0.198 g, 47%). $^1$H NMR (400 MHz, DMSO-$d_6$): δ 7.76 (d, J=8.7 Hz, 1H), 7.50 (d, J=10.0 Hz, 1H), 7.42 (s, 1H), 6.99 (d, J=8.2 Hz, 1H), 6.60 (d, J=9.2 Hz, 1H), 4.14-4.09 (m, 4H), 3.78 (s, 3H), 2.52 (s, 3H), 2.46-2.42 (m, 2H), 1.88-1.86 (m, 4H), 1.41-1.37 (m, 2H), 0.79 (t, 7.3 Hz, 3H). LC-MS (ESI) calcd for $C_{23}H_{28}O_7[M+H]^+$: 417.18. Found: 417.05.

Example 64

4-(4-(4-Acetyl-3-hydroxy-2-propylphenoxy)butoxy)-3-methylbenzoic acid (Compound 191)

Colorless solid (0.204 g, 51%). $^1$H NMR (DMSO-$d_6$): δ 7.75-7.68 (m, 4H), 6.96 (d, J=8.7 Hz, 1H), 6.59 (d, J=9.2 Hz, 1H), 4.11-4.08 (m, 4H), 2.52 (s, 1H), 2.48-2.46 (m, 2H), 2.12 (s, 3H), 1.89-1.87 (m, 4H), 1.41-1.38 (m, 2H), 0.80 (t, J=7.3 Hz, 3H). LC-MS (ESI) calcd for $C_{23}H_{28}O_6$ $[M+H]^+$: 401.19. Found: 401.05.

Example 65

3-(4-(4-(4,4-Dimethylpentanoyl)-3-hydroxy-2-methylphenoxy)butoxy)-4-methoxybenzoic acid (Compound 96)

Colorless solid (0.247 g, 54%). $^1$H NMR (400 MHz, DMSO-$d_6$): δ 7.80 (d, J=8.7 Hz, 1H), 7.50 (d, J=9.2 Hz, 1H), 7.42 (s, 1H), 6.99 (d, J=8.2 Hz, 1H), 6.60 (d, J=9.2 Hz, 1H), 4.13-4.03 (m, 4H), 3.77 (s, 3H), 2.88 (t, J=8.2 Hz, 2H), 1.94 (s, 3H), 1.89-1.87 (m, 4H), 1.48 (t, J=8.2 Hz, 2H), 0.87 (s, 9H). LC-MS (ESI) calcd for $C_{26}H_{34}O_7[M+H]^+$: 459.23. Found: 459.00.

Example 66

3-(4-(4-(3,3-Dimethylbutanoyl)-3-hydroxy-2-methylphenoxy)butoxy)-4-methoxybenzonitrile (Compound 91)

White solid (0.185 g, 40%). $^1$H NMR (400 MHz, DMSO-$d_6$): δ 7.87 (d, J=9.2 Hz, 1H), 7.39-7.34 (m, 2H), 7.06 (d, J=8.7 Hz, 1H), 6.58 (d, J=9.2 Hz, 1H), 4.13-4.05 (m, 4H), 3.78 (s, 3H), 2.80 (s, 2H), 1.95 (s, 3H), 1.93-1.86 (m, 4H), 0.96 (s, 9H). LC-MS (ESI) calcd for $C_{25}H_{31}NO_5$ $[M+H]^+$: 426.22. Found: 426.00.

Example 67

1-(2-Hydroxy-4-(4-(2-methoxy-5-(1H-tetrazol-5-yl)phenoxy)butoxy)-3-methylphenyl)-3,3-dimethylbutan-1-one (Compound 92)

1-(2-Hydroxy-4-(4-(2-methoxy-5-(1H-tetrazol-5-yl)phenoxy)butoxy)-3-methylphenyl)-3,3-dimethylbutan-1-one (0.230 g, 0.54 mmol), sodium azide (0.421 g, 6.48 mmol), and ammonium chloride (0.347 g, 6.48 mmol) were taken in DMF (5 mL) and the resulting mixture was heated at 100° C. for 1 h. The reaction mixture cooled to room temperature and diluted with water. After extraction with EtOAc, the organic layer was washed with water and brine and dried over $Na_2SO_4$. The residue after rotary evaporation was purified by reverse phase HPLC. White solid (0.110 g, 43.5%). $^1$H NMR (400 MHz, DMSO-$d_6$): δ 7.87 (d, J=9.2 Hz, 1H), 7.56 (m, 2H), 7.14 (d, J=8.7 Hz, 1H), 6.59 (d, J=9.2 Hz, 1H), 4.15-4.10 (m, 4H), 3.79 (s, 3H), 2.81 (s, 2H), 1.95 (s, 3H), 1.94-1.91 (m, 4H), 0.97 (s, 9H). LC-MS (ESI) calcd for $C_{25}H_{32}N_4O_5$ $[M+H]^+$: 469.24. Found: 469.00.

Example 68

4-(4-(4-(3,3-Dimethylbutanoyl)-3-hydroxy-2-methylphenoxy)butoxy)-N-hydroxy-3-methoxybenzamide (Compound 88)

To a solution of 4-(4-(4-(3,3-dimethylbutanoyl)-3-hydroxy-2-methylphenoxy)butoxy)-3-methoxybenzoic acid (0.050 g, 0.112 mmol) in DCM (2 mL), was added carbonyl diimidazole (0.020 g, 0.124 mmol). The resulting mixture was stirred at room temperature for 1 h. Hydroxylamine hydrochloride (0.012 g, 0.169 mmol) was added to the same reaction mixture and stirring was continued for another 1 h after that time solvent was removed under reduced pressure. The crude product was purified by reverse phase HPLC. Colorless solid (0.027 g, 52.2%). $^1$H NMR (400 MHz, DMSO-$d_6$): δ 11.05 (s, 1H), 8.89 (s, 1H), 7.90 (d, J=9.2 Hz, 1H), 7.33 (s, 2H), 7.00 (d, J=8.7 Hz, 1H), 6.62 (d, J=9.2 Hz, 1H), 4.17-4.08 (m, 4H), 3.78 (s, 3H), 2.88 (s, 2H), 1.98 (s, 3H), 1.97-1.90 (m, 4H), 1.01 (s, 9H). LC-MS (ESI) calcd for $C_{25}H_{33}NO_7$ [M+H]$^+$: 460.23. Found: 460.00.

Example 69

3-(4-(4-(3,3-Dimethylbutanoyl)-3-hydroxy-2-methylphenoxy)butoxy)-N-hydroxy-4-methoxybenzamide (Compound 89)

Prepared in a similar manner described for 4-(4-(4-(3,3-dimethylbutanoyl)-3-hydroxy-2-methylphenoxy)butoxy)-N-hydroxy-3-methoxybenzamide. Colorless solid (0.022 g, 42%). $^1$H NMR (400 MHz, DMSO-d$_6$): δ 11.05 (s, 1H), 8.89 (s, 1H), 7.91 (d, J=9.2 Hz, 1H), 7.37 (s, 2H), 7.01 (d, J=8.7 Hz, 1H), 6.64 (d, J=9.2 Hz, 1H), 4.18-4.07 (m, 4H), 3.77 (s, 3H), 2.80 (s, 2H), 1.98 (s, 3H), 1.92-1.90 (m, 4H), 1.00 (s, 9H). LC-MS (ESI) calcd for $C_{26}H_{35}NO_7$ [M+H]$^+$: 474.57 Found: 474.00.

Example 70

3-(4-(4-(3,3-Dimethylbutanoyl)-3-hydroxy-2-methylphenoxy)butoxy)-N,4-dimethoxybenzamide (Compound 90)

Prepared in a similar manner described for 4-(4-(4-(3,3-dimethylbutanoyl)-3-hydroxy-2-methylphenoxy)butoxy)-N-hydroxy-3-methoxybenzamide. Colorless solid (0.043 g, 82%). $^1$H NMR (DMSO-d$_6$): δ 11.58 (s, 1H), 7.90 (d, J=9.2 Hz, 1H), 7.37-7.35 (s, 2H), 7.01 (d, J=8.2 Hz, 1H), 6.63 (d, J=9.2 Hz, 1H), 4.18-4.07 (m, 4H), 3.79 (s, 3H), 3.69 (s, 3H), 2.85 (s, 2H), 1.98 (s, 3H), 1.93-1.90 (m, 4H), 1.00 (s, 9H). LC-MS (ESI) calcd for $C_{26}H_{35}NO_7$ [M+H]$^+$: 474.24. Found: 474.20.

Example 71

3-(4-(4-(3,3-Dimethylbutanoyl)-3-hydroxy-2-methylphenoxy)butoxy)-4-methoxy-N-(methylsulfonyl)benzamide (Compound 93)

To a stirred solution of carboxylic acid (0.050 g, 0.112 mmol) and Et$_3$N (0.011 g, 0.112 mmol) in anhyd MeCN (4 mL) was added trichlorotriazine (0.006 g, 0.034 mmol) followed by the addition of alumina (0.003 g, 0.034 mmol) and the mixture was stirred at rt for 5 min. A soln of sulfonamide (0.010 g, 0.112 mmol) and Et$_3$N (0.011 g, 0.112 mmol) in anhyd MeCN (1 mL) was added and the solution stirred for a further 2 h. The reaction was filtered and the filtrate was concentrated under vacuum and the residue was dissolved in CHCl$_3$. The organic layer was washed with H$_2$O (2×10 mL), dried over anhyd. Na$_2$SO$_4$, and evaporated in vacuo to give the crude product which was purified by reverse phase HPLC to yield the desired product. White solid (0.010 g, 17%). $^1$H NMR (400 MHz, DMSO-d$_6$): δ 7.86 (d, J=9.2 Hz, 1H), 7.51 (d, J=8.7 Hz, 1H), 7.41 (s, 1H), 7.02 (t, J=8.2 Hz, 1H), 6.62 (d, J=9.2 Hz, 1H), 4.14-4.06 (m, 4H), 3.81 (s, 3H), 3.29 (s, 3H), 2.81 (s, 2H), 1.96 (s, 3H), 1.94-1.89 (m, 4H), 1.04 (s, 9H). LC-MS (ESI) calcd for $C_{26}H_{35}NO_8S$[M+H]$^+$: 522.21. Found: 522.00.

Example 72

3-(4-(4-(3,3-Dimethylbutanoyl)-3-hydroxy-2-methylphenoxy)butoxy)-4-methoxy-N-(phenylsulfonyl)benzamide (Compound 113)

Prepared in a similar manner described for 3-(4-(4-(3,3-dimethylbutanoyl)-3-hydroxy-2-methylphenoxy)butoxy)-4-methoxy-N-(methylsulfonyl)benzamide. White solid (0.010 g, 15%). $^1$H NMR (400 MHz, DMSO-d$_6$): δ 7.93 (d, J=7.8 Hz, 2H), 7.85 (d, J=8.7 Hz, 1H), 7.64-7.55 (m, 3H), 7.48 (d, J=8.3 Hz, 1H), 7.44 (s, 1H), 6.98 (d, J=8.7 Hz, 1H), 6.58 (d, J=9.2 Hz, 1H), 4.13-4.03 (m, 4H), 3.81 (s, 3H), 2.81 (s, 2H), 1.93 (s, 3H), 1.94-1.89 (m, 4H), 0.96 (s, 9H). LC-MS (ESI) calcd for $C_{31}H_{37}NO_8S$[M+H]$^+$: 584.22. Found: 584.00.

Example 73

1-(2-Hydroxy-4-(4-((1-hydroxy-1,3-dihydrobenzo[c][1,2]oxaborol-6-yl)oxy)butoxy)-3-methylphenyl)-3,3-dimethylbutan-1-one (Compound 94)

Benzo[c][1,2]oxaborole-1,6(3H)-diol (0.075 g, 0.5 mmol) was dissolved in DMF (2 mL) and cooled to 0° C. To this solution under nitrogen were added in sequence NaH (0.048 g, 2.0 mmol) and 1-(4-(4-bromobutoxy)-2-hydroxy-3-methylphenyl)-3,3-dimethylbutan-1-one (0.715 g, 2 mmol). The reaction mixture was stirred for 2 h and then treated with 1M HCl (5 mL). After extraction with EtOAc, the organic layer was washed with water and brine and dried over anhydrous Na$_2$SO$_4$. The residue after rotary evaporation was purified by reverse phase HPLC. Tan solid (0.030 g, 14%). $^1$H NMR (400 MHz, DMSO-d$_6$): δ 9.08 (s, 1H), 7.87 (d, J=8.7 Hz, 1H), 7.29-7.23 (m, 2H), 7.04-7.01 (m, 1H), 6.61 (d, J=9.2 Hz, 1H), 4.90 (s, 2H), 4.16-4.05 (m, 4H), 2.84 (s, 2H), 1.98 (s, 3H), 1.95-1.91 (m, 4H), 0.99 (s, 9H). LC-MS (ESI) calcd for $C_{24}H_{31}BO_6$ [M+H]$^+$: 426.22. Found: 426.00.

Example 74

1-(2-Hydroxy-4-(4-(2-methoxy-5-(4,4,5,5-tetramethyl-1,3,2-dioxaborolan-2-yl)phenoxy)butoxy)-3-methylphenyl)-3,3-dimethylbutan-1-one (Compound 87)

Prepared according to general method A. Colorless solid (0.184 g, 35.4%). $^1$H NMR (400 MHz, DMSO-d$_6$): δ 7.60 (d, J=8.7 Hz, 1H), 7.40 (d, J=7.8 Hz, 1H)., 7.29-7.25 (m, 2H), 6.41 (dd, J=9.2 Hz, 4.6 Hz, 1H), 4.13-4.07 (m, 4H), 3.85 (s, 3H), 2.76 (s, 2H), 2.09 (s, 3H), 2.03-2.02 (m, 4H), 1.31 (s, 12H), 1.05 (s, 9H). LC-MS (ESI) calcd for $C_{30}H_{43}BO_7$ [M+H]$^+$: 527.47. Found: 527.00.

Example 75

(3-(4-(4-(3,3-Dimethylbutanoyl)-3-hydroxy-2-methylphenoxy)butoxy)-4-methoxyphenyl)boronic acid (Compound 95)

To a solution of 1-(2-hydroxy-4-(4-(2-methoxy-5-(4,4,5,5-tetramethyl-1,3,2-dioxaborolan-2-yl)phenoxy)butoxy)-3-methylphenyl)-3,3-dimethylbutan-1-one (0.290 g, 0.551 mmol) in MeOH (5 mL) was added KHF$_2$ (4.5 M solution in water, 3 mmol). The resulting mixture was stirred at rt for 30 min. after that removed the solvent under reduced pressure. The crude material was dissolved in hot acetone and filtered, the filtrate was concentrated in vacuo to afford the crude potassium trifluoroborate as a while solid. To a solution of potassiumtrifluoro borate in acetonitrile (5 mL) was added water (29 μL, 1.653 mmol) and TMS-Cl (0.178 g, 1.653 mmol). The resulting suspension was stirred at rt for 1 h, quenched by saturated NaHCO$_3$ solution and dried over anhyd. Na$_2$SO$_4$. Filtration followed by removal of the solvent afforded the crude boronic acid, which was purified by reverse phase HPLC. Colorless solid (0.130 g, 53%). $^1$H NMR (400 MHz, DMSO-d$_6$): δ 7.87 (d, J=9.2 Hz, 1H), 7.84 (s, 2H), 7.37 (s, 1H), 7.35 (d, J=8.2 Hz, 1H), 6.90 (d, J=7.8 Hz, 1H), 6.61 (d, J=9.2 Hz, 1H), 4.17-4.02 (m, 4H), 3.73 (s, 3H), 2.83 (s, 2H), 1.97 (s, 3H), 1.90-1.89 (m, 4H), 0.94 (s, 9H). LC-MS (ESI) calcd for C$_{24}$H$_{33}$BO$_7$ [M+H]$^+$: 445.23. Found: 445.00.

Example 76

(Z)-3-(4-(4-(3,3-Dimethylbutanoyl)-3-hydroxy-2-methylphenoxy)butoxy)-N'-hydroxy-4-methoxybenzimidamide (Compound 97)

1-(2-Hydroxy-4-(4-(2-methoxy-5-(1H-tetrazol-5-yl)phenoxy)butoxy)-3-methylphenyl)-3,3-dimethylbutan-1-one (0.851 g, 2 mmol) and hydroxylamine (50% aqueous solution, 0.28 mL) were heated at 100° C. for 30 min. in presence of AcOH (few drops), cooled and diluted with water. The precipitated product was collected by filtration and purified by column silica gel column chromatography (Hexanes:Ethylacetate, 4:1). White solid (0.51 g, 47.2%). $^1$H NMR (400 MHz, DMSO-d$_6$): δ 11.01 (brs, 1H), 8.73 (brs, 2H), 7.86 (d, J=9.2 Hz, 1H), 7.32-7.28 (m, 2H), 7.10 (d, J=8.7 Hz, 1H), 6.58 (d, J=9.2 Hz, 1H), 4.14-4.07 (m, 4H), 3.79 (s, 3H), 2.81 (s, 2H), 1.98 (s, 3H), 1.94-1.89 (m, 4H), 0.96 (s, 9H). LC-MS (ESI) calcd for C$_{25}$H$_{34}$N$_2$O$_6$[M+H]$^+$: 459.24. Found: 459.00.

Example 77

3-(3-(4-(4-(3,3-Dimethylbutanoyl)-3-hydroxy-2-methylphenoxy)butoxy)-4-methoxyphenyl)-1,2,4-oxadiazol-5(4H)-one (Compound 98)

A mixture of (Z)-3-(4-(4-(3,3-Dimethylbutanoyl)-3-hydroxy-2-methylphenoxy)butoxy)-N'-hydroxy-4-methoxybenzimidamide (0.1 g, 0.218 mmol), carbonyl diimidazole (0.053 g, 0.327 mmol) and DBU (0.133 g, 0.872 mmol) in dioxane (5 mL) was heated at reflux for 3 h. Removed the solvent under vacuum. diluted with water and pH adjusted to 4-5 using dil. HCl, and extracted with ethylacetate, removal of solvent followed by reverse phase HPLC afforded the title compound. Colorless solid (0.032 g, 30%). $^1$H NMR (400 MHz, DMSO-d$_6$): δ 7.83 (d, J=9.2 Hz, 1H), 7.36-7.32 (m, 2H), 7.08 (d, J=8.2 Hz, 1H), 6.57 (d, J=9.2 Hz, 1H), 4.13-4.05 (m, 4H), 3.78 (s, 3H), 2.79 (s, 2H), 1.93 (s, 3H), 1.89-1.87 (m, 4H), 0.96 (s, 9H). LC-MS (ESI) calcd for C$_{26}$H$_{32}$N$_2$O$_7$[M+H]$^+$: 485.22. Found: 485.00.

Example 78

1-(2-Hydroxy-4-(4-(2-methoxy-5-(5-thioxo-4,5-dihydro-1,2,4-oxadiazol-3-yl)phenoxy)butoxy)-3-methylphenyl)-3,3-dimethylbutan-1-one (Compound 99)

A mixture of (Z)-3-(4-(4-(3,3-Dimethylbutanoyl)-3-hydroxy-2-methylphenoxy)butoxy)-N'-hydroxy-4-methoxybenzimidamide (0.1 g, 0.218 mmol), thiocarbonyl diimidazole (0.058 g, 0.327 mmol) and DBU (0.133 g, 0.872 mmol) in acetonitrile (5 mL) was stirred at rt for 4 h. The solvent was removed under vacuum, diluted with water and the pH adjusted to 4-5 using dil. HCl, and extracted with ethylacetate (3×10 mL), after the extract was concentrated in vacuo, the residue was dissolved in 1N NaOH and washed with ether. The aqueous layer was adjusted to pH 4 with 1N HCl and extracted again with ethyl acetate, removal of solvent followed by reverse phase HPLC afforded the title compound. Colorless solid (0.058 g, 53%). $^1$H NMR (400 MHz, DMSO-d$_6$): δ 7.84 (d, J=9.2 Hz, 1H), 7.45 (d, J=8.2 Hz, 1H), 7.39 (s, 1H), 7.11 (d, J=8.2 Hz, 1H), 6.57 (d, J=9.2 Hz, 1H), 4.14-4.05 (m, 4H), 3.79 (s, 3H), 2.79 (s, 2H), 1.94 (s, 3H), 1.92-1.88 (m, 4H), 0.96 (s, 9H). LC-MS (ESI) calcd for C$_{26}$H$_{32}$N$_2$O$_6$S[M+H]$^+$: 501.20. Found: 501.00.

Example 79

3-(3-(4-(4-(3,3-Dimethylbutanoyl)-3-hydroxy-2-methylphenoxy)butoxy)-4-methoxyphenyl)-1,2,4-thiadiazol-5(4H)-one (Compound 100)

A mixture of (Z)-3-(4-(4-(3,3-Dimethylbutanoyl)-3-hydroxy-2-methylphenoxy)butoxy)-N'-hydroxy-4-methoxybenzimidamide (0.1 g, 0.218 mmol), thiocarbonyl diimidazole (0.058 g, 0.327 mmol) in THF (5 mL) was stirred at rt for 30 min. The mixture was diluted with water and extracted with ethyl acetate (3×10 mL), extract was concentrated in vacuo, the residue was dissolved in THF (5 mL) and BF$_3$.OEt$_2$ (0.155 g, 1 mmol) was added to it and stirred at rt for 1 h. The reaction mixture was diluted with water and extracted with ethyl acetate. Organic phase washed with 1N HCl, dried over anhydrous sodium sulfate. Removal of the solvent followed by reverse phase HPLC afforded the title compound. Yellow solid (0.020 g, 18%). $^1$H NMR (400 MHz, DMSO-d$_6$): δ 7.84 (d, J=9.2 Hz, 1H), 7.51 (d, J=8.7 Hz, 1H), 7.48 (s, 1H), 7.04 (d, J=8.2 Hz, 1H), 6.58 (d, J=9.2 Hz, 1H), 4.14-4.06 (m, 4H), 3.77 (s, 3H), 2.80 (s, 2H), 1.94 (s, 3H), 1.92-1.88 (m, 4H), 0.96 (s, 9H). LC-MS (ESI) calcd for C$_{26}$H$_{32}$N$_2$O$_6$S[M+H]$^+$: 501.20. Found: 501.00.

Example 80

3'-((4-(4-(3,3-Dimethylbutanoyl)-3-hydroxy-2-methylphenoxy)butoxy)methyl)-[1,1'-biphenyl]-3-carboxylic acid (Compound 187)

To an ice cooled solution of benzylalcohol (0.105 g, 0.56 mmol) in DMF (3 mL), was added NaH (0.027 g, 1.12 mmol) in small portions and the resulting mixture was stirred for 10 min. To this 1-(4-(4-bromobutoxy)-3-hydroxy-2-methylphenyl)-3,3-dimethylbutan-1-one (0.220 g, 0.616 mmol) was added and stirring was continued for additional 12 h. Reaction mixture was diluted with water and extracted with ethylacetate. The combined organic layer was washed with brine and dried over anhydrous sodium sulfate. Removal of the solvent under vacuum afforded crude product which was used for the next step without further purification. Colorless solid (0.220 g, 85%). LC-MS (ESI) calcd for C$_{24}$H$_{31}$BrO$_4$[M+H]$^+$: 464.412. Found: 464.00.

A mixture of 1-(4-(4-((3-bromobenzyl)oxy)butoxy)-3-hydroxy-2-methylphenyl)-3,3-dimethylbutan-1-one (0.220 g, 0.475 mmol), 3-borono benzoic acid (0.118 g, 0.712 mmol) and tetrakistriphenylphosphinepalladium(0) (0.055 g, 0.047 mmol) were taken 4 mL of DME. To this 2M Na$_2$CO$_3$ (0.95 mL) solution was added and the resulting solution was refluxed in an atmosphere of N$_2$ for 6 h. The reaction mixture cooled to room temperature and diluted with water and then acidified using 1N HCl. The product was extracted with ethyl acetate and washed with brine and the organic layer was dried over anhydrous Na$_2$SO$_4$. The solvent was evaporated in vacuum to obtain the crude product. The crude product was purified using automated prep-HPLC to yield the desired compound as a white solid (0.150 g, 62.6%). $^1$H NMR (400 MHz, DMSO-d$_6$): δ 8.14 (s, 1H), 7.89 (d, J=7.3

Hz, 1H), 7.85 (d, J=7.8 Hz, 1H), 7.79 (d, J=9.2 Hz, 1H), 7.59-7.54 (m, 3H), 7.42 (t, J=7.3 Hz, 1H), 7.32-7.26 (m, 1H), 6.53 (d, J=9.2 Hz, 1H), 4.52 (s, 2H), 4.07 (t, J=5.9 Hz, 2H), 3.50 (t, J=6.4 Hz, 2H), 2.80 (s, 2H), 1.94 (s, 3H), 1.81-1.68 (m, 4H), 0.96 (s, 9H). LC-MS m/z calcd for $C_{31}H_{36}O_6[M+H]^+$: 505.623. Found: 505.00.

Example 81

Preparation of 3-(4-(4-(3,3-Dimethylbutanoyl)-3-hydroxy-2-methylphenoxy)butoxy)-4-methoxy-N-methylbenzamide (Compound 102)

3-(4-(4-(3,3-Dimethylbutanoyl)-3-hydroxy-2-methylphenoxy)butoxy)-4-methoxybenzoic acid (0.045 g, 0.1 mmol) was dissolved in DMF (2 mL) at room temperature. HOBt (0.020 g, 0.15 mmol) was added in one portion followed by EDC (0.029 g, 0.15 mmol). The resulting mixture was stirred at room temperature for 30 min. To this methylamine hydrogen chloride (0.010 g, 0.12) and triethylamine (0.02 mL, 0.12 mmol) were added and stirred for 2 h, after that time the organic phase was removed under reduced pressure and the crude material was partitioned between water and ethyl acetate. The aqueous layer was extracted with ethyl acetate (3×5 mL). The organic phase was dried using $Na_2SO_4$ and evaporated to give 3-(4-(4-(3,3-dimethylbutanoyl)-3-hydroxy-2-methylphenoxy)butoxy)-4-methoxy-N-methylbenzamide. The crude product was purified by HPLC using acetonitrile:water as the solvent system to afford amide as a colorless solid (0.027 g, 59%). $^1$H NMR (400 MHz, DMSO-$d_6$): δ8.22 (q, J=4.6 Hz, 1H), 7.85 (d, J=8.7 Hz, 1H), 7.41-7.39 (m, 2H), 6.95 (d, J=9.2 Hz, 1H), 6.58 (d, J=8.5 Hz, 1H), 4.14-4.03 (m, 4H), 3.75 (s, 3H), 2.81 (s, 2H), 2.72 (d, J=4.6 Hz, 3H), 1.94 (s, 3H), 1.88-1.81 (m, 4H), 0.97 (s, 9H). LC-MS (ESI) Calcd for $C_{22}H_{35}NO_6$ $[M+H]^+$: 458.25. Found: 458.00.

Example 82

1-(2-Hydroxy-4-(4-(2-methoxy-5-(morpholine-4-carbonyl)phenoxy)butoxy)-3-methylphenyl)-3,3-dimethylbutan-1-one (Compound 101)

The title compound was synthesized as described in Example 81 to afford a white solid (0.029 g, 58%). $^1$H NMR (400 MHz, DMSO-$d_6$): δ7.85 (d, J=8.7 Hz, 1H), 7.00-6.91 (m, 3H), 6.59 (d, J=9.1 Hz, 1H), 4.14-4.03 (m, 4H), 3.73 (s, 3H), 3.52-3.43 (m, 8H), 2.81 (s, 2H), 1.94 (s, 3H), 1.87-1.86 (m, 4H), 0.96 (s, 9H). LC-MS (ESI) Calcd for $C_{29}H_{39}NO_7$ $[M+H]^+$: 514.28. Found: 514.00.

Example 83

3-(4-(4-(3,3-Dimethylbutanoyl)-3-hydroxy-2-methylphenoxy)butoxy)-N,N-diethyl-4-methoxybenzamide (Compound 103)

The title compound was synthesized as described in Example 81 to afford a white solid (0.030 g, 60%). $^1$H NMR (400 MHz, DMSO): δ 7.85 (d, J=9.2 Hz, 1H), 6.93-6.85 (m, 3H), 6.59 (d, J=9.2 Hz, 1H), 4.15-4.05 (m, 4H), 3.76 (s, 3H), 3.52-3.22 (m, 2H), 2.81 (s, 2H), 1.94 (s, 3H), 1.93-1.86 (m, 4H), 1.06 (t, J=8.8 Hz, 6H), 0.96 (s, 9H). LC-MS (ESI) Calcd for $C_{29}H_{41}NO_6[M+H]^+$: 500.29. Found: 500.35.

Example 84

3-(4-(4-(3,3-Dimethylbutanoyl)-3-hydroxy-2-methylphenoxy)butoxy)-4-methoxy-N-phenylbenzamide (Compound 104)

The title compound was synthesized as described in Example 81 to afford a white solid (0.026 g, 50%). $^1$H NMR (400 MHz, DMSO-$d_6$): δ10.00 (s, 1H), 7.85 (d, J=9.2 Hz, 1H), 7.71 (d, J=8.7 Hz, 2H), 7.57 (d, J=9.2 Hz, 1H), 7.52 (s, 1H), 7.30 (t, J=7.8 Hz, 2H), 7.06-7.03 (m, 2H), 6.59 (d, J=9.2 Hz, 1H), 4.15-4.05 (m, 4H), 3.79 (s, 3H), 2.81 (s, 2H), 1.95 (s, 3H), 1.90-1.89 (m, 4H), 0.96 (s, 9H). LC-MS (ESI) Calcd for $C_{31}H_{37}NO_6[M+H]^+$: 520.26 Found: 519.90.

Example 85

1-(2-Hydroxy-4-(4-(2-methoxy-5-(piperazine-1-carbonyl)phenoxy)butoxy)-3-methylphenyl)-3,3-dimethylbutan-1-one (Compound 105)

The title compound was synthesized as described in Example 81 to afford a white solid (0.018 g, 35%). $^1$H NMR (400 MHz, DMSO-$d_6$): δ 8.25 (s, 1H), 7.85 (d, J=9.2 Hz, 1H), 6.95-6.89 (m, 3H), 6.58 (d, J=9.2 Hz, 1H), 4.15-4.05 (m, 4H), 3.79 (s, 3H), 3.37-3.30 (m, 4H), 2.81 (s, 2H), 2.71-2.63 (m, 4H), 1.94 (s, 3H), 1.87-1.86 (m, 4H), 0.96 (s, 9H). LC-MS (ESI) Calcd for $C_{29}H_{40}N_2O_6$ $[M+H]^+$: 513.29. Found: 513.00.

Example 86

3-(4-(4-(3,3-Dimethylbutanoyl)-3-hydroxy-2-methylphenoxy)butoxy)-4-methoxy-N-(pyridin-2-yl)benzamide (Compound 106)

The title compound was synthesized as described in Example 81 to afford an off-white solid (0.018 g, 34%). $^1$H NMR (400 MHz, DMSO-$d_6$): δ10.60 (s, 1H), 8.33 (d, J=4.6 Hz, 1H), 8.14 (t, J=8.7 Hz, 1H), 7.85 (d, J=9.2 Hz, 1H), 7.79 (t, J=8.2 Hz, 1H), 7.65 (s, 1H), 7.12-7.03 (m, 3H), 6.59 (d, J=9.2 Hz, 1H), 4.15-4.07 (m, 4H), 3.77 (s, 3H), 2.81 (s, 2H), 1.95 (s, 3H), 1.90-1.89 (m, 4H), 0.96 (s, 9H). LC-MS (ESI) Calcd for $C_{30}H_{36}N_2O_6S[M+H]^+$: 521.26. Found: 520.95.

Example 87

1-{2-Hydroxy-4-[4-(2-methoxy-5-{[4-(methylsulfonyl)piperazinyl]carbonyl}phenoxy)butoxy]-3-methylphenyl}-3,3-dimethylbutan-1-one (Compound 107)

The title compound was synthesized as described in Example 81 to afford a white solid (0.032 g, 54%). $^1$H NMR (400 MHz, DMSO-$d_6$): δ 7.85 (d, J=9.2 Hz, 1H), 6.98-6.96 (m, 3H), 6.59 (d, J=9.2 Hz, 1H), 4.14-4.02 (m, 4H), 3.77 (s, 3H), 3.54-3.52 (m, 4H), 3.19-3.10 (m, 4H), 2.85 (s, 3H), 2.81 (s, 2H), 1.94 (s, 3H), 1.88-1.87 (m, 4H), 0.96 (s, 9H). LC-MS (ESI) Calcd for $C_{30}H_{42}N_2O_8S$ $[M+H]^+$: 591.27. Found: 590.95.

Example 88

N-(tert-Butyl)-3-(4-(4-(3,3-dimethylbutanoyl)-3-hydroxy-2-methylphenoxy)butoxy)-4-methoxybenzamide (Compound 108)

The title compound was synthesized as described in Example 81 to afford a white solid (0.029 g, 58%). $^1$H NMR (400 MHz, DMSO): δ 7.85 (d, J=9.2 Hz, 1H), 7.51 (s, 1H), 7.38 (d, J=8.2 Hz, 1H), 7.34 (s, 1H), 6.91 (d, J=8.2 Hz, 1H), 6.60 (d, J=8.7 Hz, 1H), 4.15-4.04 (m, 4H), 3.74 (s, 3H), 2.81 (s, 2H), 1.95 (s, 3H), 1.88-1.87 (m, 4H), 1.33 (s, 9H), 0.96 (s, 9H). LC-MS (ESI) Calcd for $C_{29}H_{41}NO_6$ [M+H]$^+$: 500.30. Found: 500.30.

Example 89

N-Cyclopropyl-3-(4-(4-(3,3-dimethylbutanoyl)-3-hydroxy-2-methylphenoxy)butoxy)-4-methoxybenzamide (Compound 109)

The title compound was synthesized as described in Example 81 to afford a yellow solid (0.030 g, 62%). $^1$H NMR (400 MHz, DMSO-d$_6$): δ 8.22 (s, 1H), 7.85 (d, J=9.2 Hz, 1H), 7.40-7.38 (m, 2H), 6.94 (d, J=8.2 Hz, 1H), 6.59 (d, J=8.7 Hz, 1H), 4.14-4.03 (m, 4H), 3.76 (s, 3H), 2.81 (s, 2H), 2.78-2.73 (m, 1H), 1.95 (s, 3H), 1.94-1.87 (m, 4H), 0.96 (s, 9H), 0.66-0.62 (m, 2H), 0.52-0.47 (m, 2H). LC-MS (ESI) Calcd for $C_{28}H_{37}NO_6$ [M+H]$^+$: 484.26. Found: 484.00.

Example 90

3-(4-(4-(3,3-Dimethylbutanoyl)-3-hydroxy-2-methylphenoxy)butoxy)-N-isobutyl-4-methoxybenzamide (Compound 110)

The title compound was synthesized as described in Example 81 to afford a white solid (0.022 g, 44%). $^1$H NMR (400 MHz, DMSO-d$_6$): δ 8.26 (t, J=6.0 Hz, 1H), 7.85 (d, J=9.2 Hz, 1H), 7.44-7.42 (m, 2H), 6.96 (d, J=8.2 Hz, 1H), 6.58 (d, J=9.2 Hz, 1H), 4.14-4.04 (m, 4H), 3.75 (s, 3H), 3.01 (t, J=6.4 Hz, 2H), 2.81 (s, 2H), 1.94 (s, 3H), 1.88-1.87 (m, 4H), 1.80-1.78 (m, 1H), 0.96 (s, 9H), 0.83 (d, J=6.9 Hz, 6H). LC-MS (ESI) Calcd for $C_{29}H_{41}NO_6$[M+H]$^+$: 500.29. Found: 500.00.

Example 91

N-Cyclopentyl-3-(4-(4-(3,3-dimethylbutanoyl)-3-hydroxy-2-methylphenoxy)butoxy)-4-methoxybenzamide (Compound 112)

The title compound was synthesized as described in Example 81 to afford a white solid (0.030 g, 59%). $^1$H NMR (400 MHz, DMSO-d$_6$): δ 8.04 (d, J=7.3 Hz, 1H), 7.86 (d, J=8.7 Hz, 1H), 7.44-7.39 (m, 2H), 6.94 (d, J=8.7 Hz, 1H), 6.59 (d, J=9.2 Hz, 1H), 4.21-4.04 (m, 5H), 3.75 (s, 3H), 2.81 (s, 2H), 1.95 (s, 3H), 1.88-1.87 (m, 6H), 1.65-1.46 (m, 6H), 0.96 (s, 9H). LC-MS (ESI) Calcd for $C_{30}H_{41}NO_6$ [M+H]$^+$: 512.30. Found: 512.30.

Example 92

3'-((4-(3,3-Dimethylbutanoyl)-3-hydroxy-2-methylphenoxy)methyl)-[1,1'-biphenyl]-3-carboxylic acid (Compound 127)

Prepared according to general method C. Colorless solid (0.150 g, 69%). $^1$H NMR (400 MHz, DMSO-d$_6$): δ 8.18 (s, 1H), 7.91-7.90 (m, 3H), 7.88 (s, 1H), 7.63-7.47 (m, 4H), 6.69 (d, J=9.2 Hz, 1H), 5.31 (s, 2H), 2.80 (s, 2H), 2.02 (s, 3H), 0.96 (s, 9H). HRMS m/z calcd for $C_{27}H_{28}O_5$[M+H]$^+$: 433.2010. Found: 433.2030.

Example 93

3'-((4-Acetyl-3-hydroxy-2-methylphenoxy)methyl)-[1,1'-biphenyl]-3-carboxylic acid (Compound 128)

Prepared according to general method C. Pale yellow solid (0.110 g, 59%). $^1$H NMR (400 MHz, DMSO-d$_6$): δ 8.18 (s, 1H), 7.90 (t, J=8.7 Hz, 1H), 7.78-7.75 (m, 1H), 7.64 (d, J=7.7 Hz, 1H), 7.54 (t, J=7.8 Hz, 7.49-7.46 (m, 1H), 6.73 (d, J=9.2 Hz, 1H), 5.32 (s, 2H), 2.53 (s, 2H), 2.03 (s, 3H). HRMS m/z calcd for $C_{23}H_{20}O_5$[M+H]$^+$: 377.1384. Found: 377.1393.

Example 94

3'-((4-(2-Cyclopentylacetyl)-3-hydroxy-2-methylphenoxy)methyl)-[1,1'-biphenyl]-3-carboxylic acid (Compound 129)

Prepared according to general method C. Colorless solid (0.120 g, 54%). $^1$H NMR (400 MHz, DMSO-d$_6$): δ 8.18 (s, 1H), 7.92 (t, J=8.7 Hz, 2H), 7.79-7.77 (m, 2H), 7.64 (d, J=7.3 Hz, 1H), 7.58 (t, J=7.8 Hz, 1H), 7.51-7.44 (m, 2H), 6.71 (d, J=9.2 Hz, 1H), 5.30 (s, 2H), 2.94 (d, J=6.9 Hz, 2H), 2.22-2.18 (m, 1H), 1.73-1.68 (m, 2H), 1.57-1.43 (m, 2H), 1.14-1.09 (m, 2H). HRMS m/z calcd for $C_{28}H_{28}O_5$[M+H]$^+$: 445.2010. Found: 445.2023.

Example 95

3'-((4-Butyryl-3-hydroxy-2-methylphenoxy)methyl)-[1,1'-biphenyl]-3-carboxylic acid (Compound 130)

Prepared according to general method C. Colorless solid (0.141 g, 69%). $^1$H NMR (400 MHz, DMSO-d$_6$): δ. 8.18 (s, 1H), 7.91 (t, J=9.2 Hz, 2H), 7.88-7.77 (m, 2H), 7.63 (d, J=7.8 Hz, 1H), 7.58 (t, J=9.2 Hz, 1H), 7.51-7.44 (m, 2H), 6.71 (d, J=9.2 Hz, 1H), 5.30 (s, 2H), 2.92 (t, J=7.3 Hz, 2H), 2.02 (s, 3H), 1.60-1.57 (m, 2H), 0.88 (t, J=7.3 Hz, 3H). HRMS m/z calcd for $C_{25}H_{24}O_5$[M+H]$^+$: 405.1697. Found: 405.1712.

Example 96

3'-((3-Hydroxy-4-isobutyryl-2-methylphenoxy)methyl)-[1,1'-biphenyl]-3-carboxylic acid (Compound 131)

Prepared according to general method C. Colorless solid (0.110 g, 54%). $^1$H NMR (400 MHz, DMSO-d$_6$): δ 8.18 (s, 1H), 7.93-7.83 (m, 3H), 7.77 (s, 1H), 7.64 (d, J=7.3 Hz, 1H), 7.58 (t, J=7.8 Hz, 1H), 7.51-7.44 (m, 2H), 6.73 (d, J=9.2 Hz, 1H), 3.65-3.62 (m, 1H), 2.03 (s, 1H), 1.08 (d, J=6.9 Hz, 6H). HRMS m/z calcd for $C_{25}H_{24}O_5$[M+H]$^+$: 405.1697. Found: 405.1710.

Example 97

3'-((4-(3,3-Dimethylbutanoyl)-3-hydroxy-2-methylphenoxy)methyl)-[1,1'-biphenyl]-4-carboxylic acid (Compound 132)

Prepared according to general method C. Colorless solid (0.098 g, 45%). $^1$H NMR (400 MHz, DMSO-d$_6$): δ 8.00 (d, J=8.2 Hz, 2H), 7.86 (d, J=8.7 Hz, 1H), 7.78 (d, J=7.3 Hz, 3H), 7.68-7.65 (m, 1H), 7.52-7.46 (m, 2H), 6.70 (d, J=9.2

Hz, 1H), 5.30 (s, 2H), 2.80 (s, 2H), 2.02 (s, 3H), 0.96 (s, 9H). HRMS m/z calcd for $C_{27}H_{28}O_5[M+H]^+$: 433.2010. Found: 433.2027.

Example 98

4-Chloro-3'-((4-(3,3-dimethylbutanoyl)-3-hydroxy-2-methylphenoxy)methyl)-[1,1'-biphenyl]-3-carboxylic acid (Compound 133)

Prepared according to general method D. Colorless solid (0.187 g, 80%). $^1$H NMR (400 MHz, DMSO-$d_6$): δ 8.02 (d, J=2.3 Hz, 1H), 7.86 (d, J=9.2 Hz, 1H), 7.81-7.78 (m, 2H), 7.65-7.64 (m, 1H), 7.61 (d, J=8.7 Hz, 1H), 7.50-7.46 (m, 2H), 6.69 (d, J=9.2 Hz, 1H), 5.28 (s, 2H), 2.80 (s, 2H), 2.02 (s, 3H), 0.96 (s, 9H). HRMS m/z calcd for $C_{27}H_{27}ClO_5$ $[M+H]^+$: 467.1620. Found: 467.1662.

Example 99

3'-((4-(3,3-Dimethylbutanoyl)-3-hydroxy-2-methylphenoxy)methyl)-6-methoxy-[1,1'-biphenyl]-3-carboxylic acid (Compound 134)

Prepared according to general method D. Colorless solid (0.064 g, 56%). $^1$H NMR (400 MHz, DMSO-$d_6$): δ 7.93 (dd, J=2.3 Hz, 8.7 Hz, 1H), 7.87 (d, J=9.2 Hz, 1H), 7.82 (d, J=2.3 Hz, 1H), 7.55 (s, 1H), 7.43-7.40 (m, 3H), 7.18 (d, J=8.7 Hz, 1H), 6.69 (d, J=9.2 Hz, 1H0, 3.79 (s, 3H), 2.80 (s, 2H), 2.02 (s, 3H), 0.96 (s, 9H). HRMS m/z calcd for $C_{28}H_{30}O_6[M+H]^+$: 463.2115. Found: 463.2133.

Example 100

3'-((4-(3,3-Dimethylbutanoyl)-3-hydroxy-2-methylphenoxy)methyl)-4-fluoro-[1,1'-biphenyl]-3-carboxylic acid (Compound 135)

Prepared according to general method D. Off-white solid (0.065 g, 58%). $^1$H NMR (400 MHz, DMSO-$d_6$): δ 8.08 (dd, J=2.3 Hz, 6.9 Hz, 1H), 7.92-7.85 (m, 2H), 7.75 (s, 1H), 7.62 (d, J=7.3 Hz, 1H), 7.50-7.36 (m, 3H), 6.70 (d, J=9.2 Hz, 1H), 5.30 (s, 2H), 2.80 (s, 2H), 2.02 (s, 3H), 0.96 (s, 9H). HRMS m/z calcd for $C_{27}H_{27}FO_5$ $[M+H]^+$: 451.1915. Found: 451.1930.

Example 101

3'-((4-(3,3-Dimethylbutanoyl)-3-hydroxy-2-methylphenoxy)methyl)-5-fluoro-[1,1'-biphenyl]-3-carboxylic acid (Compound 136)

Prepared according to general method D. Colorless solid (0.062 g, 55%). $^1$H NMR (400 MHz, DMSO-$d_6$): δ 8.04 (s, 1H), 7.87-7.77 (m, 3H), 7.68-7.67 (m, 1H), 7.62 (d, J=7.8 Hz, 1H), 7.52-7.49 (m, 2H), 6.70 (d, J=9.2 Hz, 1H), 5.30 (s, 2H), 2.80 (s, 2H), 2.01 (s, 3H), 0.96 (s, 9H). HRMS m/z calcd for $C_{27}H_{27}FO_5$ $[M+H]^+$: 451.1915. Found: 451.1931.

Example 102

3'-((3-Hydroxy-2-methyl-4-(3-methylbutanoyl)phenoxy)methyl)-[1,1'-biphenyl]-3-carboxylic acid (Compound 137)

Prepared according to general method D. Colorless solid (0.150 g, 72%). $^1$H NMR (400 MHz, DMSO-$d_6$): δ 8.18 (s, 1H), 7.93-7.89 (m, 2H), 7.80 (t, J=8.7 Hz, 2H), 7.63 (d, J=7.3 Hz, 1H), 7.58 (t, J=7.8 Hz, 1H), 7.51-7.44 (m, 2H), 6.71 (d, J=9.2 Hz, 1H), 5.31 (s, 2H), 2.80 (d, J=6.9 Hz, 2H), 2.13-2.06 (m, 1H), 2.03 (s, 3H), 0.89 (d, J=6.9 Hz, 6H). HRMS m/z calcd for $C_{26}H_{26}O_5[M+H]^+$: 419.1853. Found: 419.1873.

Example 103

3'-((4-(3,3-Dimethylbutanoyl)-3-hydroxy-2-methylphenoxy)methyl)-[1,1'-biphenyl]-2-carboxylic acid (Compound 138)

Prepared according to general method D. Off white solid (0.032 g, 29%). $^1$H NMR (400 MHz, DMSO-$d_6$): δ 7.89 (d, J=9.2 Hz, 1H), 7.70 (d, J=7.2 Hz, 1H), 7.55 (t, J=7.3 Hz, 1H), 7.44-7.40 (m, 4H), 7.35 (d, J=7.8 Hz, 1H), 7.28-7.26 (m, 1H), 6.70 (d, J=9.2 Hz, 1H), 2.82 (s, 2H), 2.02 (s, 3H), 0.97 (s, 9H). HRMS m/z calcd for $C_{27}H_{28}O_5[M+H]^+$: 433.2010. Found: 433.2042.

Example 104

3'-((4-(3,3-Dimethylbutanoyl)-3-hydroxy-2-methylphenoxy)methyl)-6-fluoro-[1,1'-biphenyl]-3-carboxylic acid (Compound 139)

Prepared according to general method D. Colorless solid (0.050 g, 45%). $^1$H NMR (400 MHz, DMSO-$d_6$): δ 8.03 (dd, J=2.3 Hz, 7.8 Hz, 1H), 7.97-7.94 (m, 1H), 7.86 (d, J=9.2 Hz, 1H), 7.66 (s, 1H), 7.52-7.49 (m, 3H), 7.44-7.39 (m, 1H), 6.69 (d, J=9.2 Hz, 1H), 5.30 (s, 2H), 2.80 (s, 2H), 2.01 (s, 3H), 0.96 (s, 9H). HRMS m/z calcd for $C_{27}H_{27}FO_5$ $[M+H]^+$: 451.1915. Found: 451.1939.

Example 105

3'-((4-(3,3-Dimethylbutanoyl)-3-hydroxy-2-methylphenoxy)methyl)-4-methoxy-[1,1'-biphenyl]-3-carboxylic acid (Compound 140)

Prepared according to general method D. Off-white solid (0.063 g, 54%). $^1$H NMR (400 MHz, DMSO-$d_6$): δ 7.92 (d, J=2.3 Hz, 1H), 7.82 (d, J=9.2 Hz, 1H), 7.77 (dd, J=2.2 Hz, 8.7 Hz, 1H), 7.70 (s, 1H), 7.56 (d, J=7.8 Hz, 1H), 7.44-7.36 (m, 2H), 7.17 (d, J=8.7 Hz, 1H), 6.67 (d, J=9.2 Hz, 1H), 5.25 (s, 2H), 3.82 (s, 3H), 2.77 (s, 2H), 2.01 (s, 3H), 0.95 (s, 9H). HRMS m/z calcd for $C_{28}H_{30}O_6[M+H]^+$: 463.2115. Found: 463.2151.

Example 106

3-Chloro-3'-((4-(3,3-dimethylbutanoyl)-3-hydroxy-2-methylphenoxy)methyl)-[1,1'-biphenyl]-4-carboxylic acid (Compound 141)

Prepared according to general method D. Brown solid (0.068 g, 58%). $^1$H NMR (400 MHz, DMSO-$d_6$): δ 7.85-7.80 (m, 4H), 7.70-7.66 (m, 2H), 7.48 (d, J=5.0 Hz, 2H), 6.68 (d, J=9.2 Hz, 1H), 5.27 (s, 2H), 2.79 (s, 2H), 2.01 (s, 3H), 0.95 (s, 9H). HRMS m/z calcd for $C_{27}H_{27}ClO_5$ $[M+H]^+$: 467.1610. Found: 467.1648.

Example 107

2-(3-((4-(3,3-Dimethylbutanoyl)-3-hydroxy-2-methylphenoxy)methyl)phenyl)furan-3-carboxylic acid (Compound 178)

Prepared according to general method D. Brown solid (0.020 g, 19%). $^1$H NMR (400 MHz, DMSO-$d_6$): δ 8.00 (s, 1H), 7.89-7.86 (m, 2H), 7.79 (d, J=1.8 Hz, 1H), 7.79-7.43 (m, 2H), 6.81 (d, J=1.8 Hz, 1H), 6.70 (d, J=9.2 Hz, 1H), 2.80 (s, 2H), 2.10 (s, 3H), 0.95 (s, 9H). HRMS m/z calcd for $C_{25}H_{26}O_6$[M+H]$^+$: 423.1802. Found: 423.1811.

Example 108

3'-((4-(3,3-Dimethylbutanoyl)-3-hydroxy-2-iodophenoxy)methyl)-[1,1'-biphenyl]-3-carboxylic acid (Compound 192)

Prepared according to general method D. Brown solid (0.082 g, 30%). $^1$H NMR (400 MHz, DMSO-$d_6$): δ 8.22 (s, 1H), 7.93-7.88 (m, 3H), 7.70 (s, 1H), 7.61-7.50 (m, 5H), 6.89 (d, J=8.7 Hz, 1H), 5.42 (s, 2H), 3.52 (s, 2H), 0.92 (s, 9H). HRMS m/z calcd for $C_{26}H_{25}IO_5$ [M+H]$^+$: 545.0819. Found: 545.0815.

Example 109

3'-((2-Bromo-4-(3,3-dimethylbutanoyl)-3-hydroxyphenoxy)methyl)-[1,1'-biphenyl]-3-carboxylic acid (Compound 193)

Prepared according to general method D. Colorless solid (0.093 g, 36%). $^1$H NMR (400 MHz, DMSO-$d_6$): δ 8.20 (s, 1H), 8.05 (d, J=9.2 Hz, 1H), 7.91-7.83 (m, 3H), 7.58-7.48 (m, 4H), 6.83 (d, J=9.2 Hz, 1H), 5.41 (s, 2H), 2.85 (s, 2H), 0.96 (s, 9H). HRMS m/z calcd for $C_{26}H_{25}BrO_5$ [M+H]$^+$: 497.0958. Found: 497.0962.

Example 110

4'-((4-(3,3-Dimethylbutanoyl)-3-hydroxy-2-methylphenoxy)methyl)-[1,1'-biphenyl]-3-carboxylic acid (Compound 142)

Prepared according to general method C. Pale yellow solid (0.153 g, 71%). $^1$H NMR (400 MHz, DMSO-$d_6$): δ 8.16 (s, 1H), 7.89-7.87 (m, 3H), 7.70 (d, J=8.2 Hz, 2H), 7.57-7.53 (m, 3H), 6.70 (d, J=9.2 Hz, 1H), 5.29 (s, 2H), 2.82 (s, 2H), 2.04 (s, 3H), 0.97 (s, 9H). HRMS m/z calcd for $C_{27}H_{28}O_5$[M+H]$^+$: 433.2010. Found: 433.2025.

Example 111

3'-((4-(3,3-Dimethylbutanoyl)-3-hydroxy-2-methylphenoxy)methyl)-3-methyl-[1,1'-biphenyl]-4-carboxylic acid (Compound 143)

Prepared according to general method E. Colorless solid (0.035 g, 31%). $^1$H NMR (400 MHz, DMSO-$d_6$): δ 7.88 (s, 1H), 7.86 (d, J=6.9 Hz, 2H), 7.77 (d, J=9.2 Hz, 1H), 7.48-7.46 (m, 2H), 7.42 (s, 1H), 7.32-7.28 (m, 2H), 6.69 (d, J=9.2 Hz, 1H), 5.31 (s, 2H), 2.83 (s, 2H), 2.45 (s, 3H), 2.02 (s, 3H), 0.98 (s, 9H). HRMS m/z calcd for $C_{28}H_{30}O_5$[M+H]$^+$: 447.2166. Found: 447.2174.

Example 112

3'-((4-(3,3-dimethylbutanoyl)-3-hydroxy-2-methylphenoxy)methyl)-4-hydroxy-[1,1'-biphenyl]-3-carboxylic acid (Compound 144)

Prepared according to general method E. Colorless solid (0.050 g, 45%). $^1$H NMR (400 MHz, DMSO-$d_6$): δ 8.04 (s, 1H), 7.82-7.80 (m, 2H), 7.67 (s, 1H), 7.42 (d, J=7.8 Hz, 1H), 7.42-7.38 (m, 2H), 7.03 (d, J=8.7 Hz, 1H), 6.66 (d, J=9.2 Hz, 1H), 5.24 (s, 2H), 2.76 (s, 2H), 2.01 (s, 3H), 0.96 (s, 9H). HRMS m/z calcd for $C_{27}H_{28}O_6$[M+H]$^+$: 449.1959. Found: 449.1974.

Example 113

2-(3'-((4-(3,3-dimethylbutanoyl)-3-hydroxy-2-methylphenoxy)methyl)-[1,1'-biphenyl]-3-yl)acetic acid (Compound 145)

Prepared according to general method E. Colorless solid (0.052 g, 46%). $^1$H NMR (400 MHz, DMSO-$d_6$): δ 7.87 (d, J=8.7 Hz, 1H), 7.72 (s, 1H), 7.58 (d, J=7.3 Hz, 1H), 7.53-7.36 (m, 4H), 7.24 (d, J=7.8 Hz, 1H), 6.70 (d, J=9.2 Hz, 1H), 5.31 (s, 2H), 3.64 (s, 2H), 2.83 (s, 2H), 2.03 (s, 3H), 0.99 (s, 9H). HRMS m/z calcd for $C_{28}H_{30}O_5$[M+H]$^+$: 447.2166. Found: 447.2232.

Example 114

3'-((4-(3,3-Dimethylbutanoyl)-3-hydroxy-2-methylphenoxy)methyl)-5-nitro-[1,1'-biphenyl]-3-carboxylic acid (Compound 146)

Prepared according to general method D. Pale yellow solid (0.042 g, 36%). $^1$H NMR (400 MHz, DMSO-$d_6$): δ 8.63 (s, 1H), 8.54 (d, J=8.2 Hz, 2H), 7.89 (s, 1H), 7.84 (d, J=8.7 Hz, 1H), 7.77-7.74 (m, 1H), 7.53 (d, J=4.6 Hz, 2H), 6.69 (d, J=9.2 Hz, 1H), 5.33 (s, 2H), 2.82 (s, 2H), 2.03 (s, 3H), 0.97 (s, 9H). HRMS m/z calcd for $C_{27}H_{27}NO_7$ [M+H]$^+$: 478.1860. Found: 478.1870.

Example 115

2-Chloro-3'-((4-(3,3-dimethylbutanoyl)-3-hydroxy-2-methylphenoxy)methyl)-[1,1'-biphenyl]-4-carboxylic acid (Compound 147)

Prepared according to general method D. Colorless solid (0.055 g, 47%). $^1$H NMR (400 MHz, DMSO-$d_6$): δ 7.99 (d, J=1.4 Hz, 1H), 7.92 (dd, J=1.4 Hz, 7.8 Hz, 1H), 7.86 (d, J=9.2 Hz, 1H), 7.53-7.49 (m, 6H), 6.68 (d, J=9.2 Hz, 1H), 5.29 (s, 2H), 2.80 (s, 2H), 2.10 (s, 3H), 0.96 (s, 9H). HRMS m/z calcd for $C_{27}H_{27}ClO_5$ [M+H]$^+$: 467.1620. Found: 467.1632.

Example 116

3'-((4-(3,3-Dimethylbutanoyl)-3-hydroxy-2-methylphenoxy)methyl)-2-methyl-[1,1'-biphenyl]-3-carboxylic acid (Compound 168)

Prepared according to general method E. Colorless solid (0.115 g, 45%). $^1$H NMR (400 MHz, DMSO-$d_6$): δ 7.90 (d, J=9.2 Hz, 1H), 7.75-7.71 (m, 1H), 7.49-7.27 (m, 7H), 6.72 (d, J=9.2 Hz, 1H), 5.31 (s, 2H), 2.84 (s, 2H), 2.30 (s, 3H), 2.04 (s, 3H), 0.99 (s, 9H). LC-MS m/z calcd for $C_{28}H_{31}O_5$ [M+H]$^+$: 447.21. Found: 447.00.

Example 117

3'-((4-(3,3-Dimethylbutanoyl)-3-hydroxy-2-methylphenoxy)methyl)-[1,1'-biphenyl]-3-carbonitrile (Compound 151)

Prepared according to general method D using 1-(4-((3-bromobenzyl)oxy)-2-hydroxy-3-methylphenyl)-3,3-dimethylbutan-1-one (1.8 g, 4.6 mmol), (3-cyanophenyl)boronic acid (1.014 g, 6.90 mmol), Pd(PPh$_3$)$_4$ (0.532 g, 0.460 mmol) and 2M sodium carbonate solution. White solid (1.87 g, 98%). $^1$H NMR (400 MHz, DMSO-d$_6$): δ 8.12 (s, 1H), 8.00 (d, J=8.7 Hz, 1H), 7.88-7.79 (m, 3H), 7.69-7.62 (m, 3H), 7.50-7.48 (m, 2H), 6.70 (d, J=8.7 Hz, 1H), 5.28 (s, 2H), 2.81 (s, 2H), 2.02 (s, 3H), 0.96 (s, 9H). LC-MS(ESI) calcd for $C_{27}H_{27}NO_3$ [M+H]$^+$: 414.20. Found: 414.00.

Example 118

3-(4-((4-(3,3-Dimethylbutanoyl)-3-hydroxy-2-methylphenoxy)methyl)pyridin-2-yl)benzoic acid (Compound 149)

Prepared according to general method D using 1-(4-((2-bromopyridin-4-yl)methoxy)-2-hydroxy-3-methylphenyl)-3,3-dimethylbutan-1-one (0.26 g, 0.663 mmol), 3-boronobenzoic acid (0.132 g, 0.795 mmol), Pd(PPh$_3$)$_4$ (0.077 g, 0.66 mmol) and 2M sodium carbonate solution. White solid (0.110 g, 38%). $^1$H NMR (400 MHz, DMSO-d$_6$): δ 8.68-8.64 (m, 2H), 8.28 (d, J=7.8 Hz, 1H), 8.07 (s, 1H), 7.98 (d, J=7.8 Hz, 1H), 7.88 (d, J=9.2 Hz, 1H), 7.60 (t, J=7.8 Hz, 1H), 7.42 (d, J=4.6 Hz, 1H), 6.66 (d, J=9.2 Hz, 1H), 5.37 (s, 2H), 2.81 (s, 2H), 2.08 (s, 3H), 0.96 (s, 9H). LC-MS(ESI) calcd for $C_{26}H_{27}NO_5$ [M+H]$^+$: 434.19. Found: 434.40.

Example 119

3-(5-((4-(3,3-Dimethylbutanoyl)-3-hydroxy-2-methylphenoxy)methyl)pyridin-3-yl)benzoic acid (Compound 150)

Prepared according to general method D using 1-(4-((5-bromopyridin-3-yl)methoxy)-2-hydroxy-3-methylphenyl)-3,3-dimethylbutan-1-one (0.140 g, 0.357 mmol), 3-boronobenzoic acid (0.089 g, 0.535 mmol), Pd(PPh$_3$)$_4$ (0.041 g, 0.036 mmol) and 2M sodium carbonate solution. White solid (0.065 g, 42%). $^1$H NMR (400 MHz, DMSO-d$_6$): δ 8.88 (s, 1H), 8.69 (s, 1H), (m, 2H), 8.21-8.20 (m, 2H), 7.96 (d, J=7.8 Hz, 1H), 7.91 (d, J=9.2 Hz, 1H), 7.88 (d, J=9.2 Hz, 1H), 7.61 (t, J=7.8 Hz, 1H), 6.74 (d, J=9.2 Hz, 1H), 5.35 (s, 2H), 2.82 (s, 2H), 2.00 (s, 3H), 0.96 (s, 9H). LC-MS (ESI) calcd for $C_{26}H_{27}NO_5$ [M+H]$^+$: 434.19. Found: 434.00.

Example 120

3-(2-((4-(3,3-Dimethylbutanoyl)-3-hydroxy-2-methylphenoxy)methyl)pyridin-4-yl)benzoic acid (Compound 153)

Prepared according to general method D using 1-(4-((4-bromopyridin-3-yl)methoxy)-2-hydroxy-3-methylphenyl)-3,3-dimethylbutan-1-one (0.160 g, 0.408 mmol), 3-boronobenzoic acid (0.102 g, 0.612 mmol), Pd(PPh$_3$)$_4$ (0.047 g, 0.041 mmol) and 2M sodium carbonate solution. White solid (0.098 g, 55%). $^1$H NMR (400 MHz, DMSO-d$_6$): δ 8.64 (d, J=5.0 Hz, 1H), 8.26 (s, 1H), 8.00 (d, J=7.8 Hz, 2H), 7.88-7.85 (m, 2H), 7.69 (d, J=4.6 Hz, 1H), 7.64 (t, J=7.8 Hz, 1H), 6.71 (d, J=9.2 Hz, 1H), 5.35 (s, 2H), 2.81 (s, 2H), 2.05 (s, 3H), 0.96 (s, 9H). LC-MS(ESI) calcd for $C_{26}H_{27}NO_5$ [M+H]$^+$: 434.19. Found: 434.10.

Example 121

3-(5-((4-(3,3-Dimethylbutanoyl)-3-hydroxy-2-methylphenoxy)methyl)furan-2-yl)benzoic acid (Compound 158)

Prepared according to general method D using 1-(4-((5-bromofuran-2-yl)methoxy)-2-hydroxy-3-methylphenyl)-3,3-dimethylbutan-1-one (0.191 g, 0.5 mmol), 3-boronobenzoic acid (0.124 g, 0.750 mmol), Pd(PPh$_3$)$_4$ (0.058 g, 0.050 mmol) and 2M sodium carbonate solution. Off-white solid (0.110 g, 47%). $^1$H NMR (400 MHz, DMSO-d$_6$): δ 8.22 (t, J=3.2 Hz, 1H), 7.93-7.84 (m, 3H), 7.54 (t, J=7.6 Hz, 1H), 7.06 (d, J=3.2 Hz, 1H), 6.84 (d, J=9.2 Hz, 1H), 6.72 (d, J=3.2 Hz, 1H), 5.29 (s, 2H), 2.85 (s, 2H), 1.98 (s, 3H), 0.99 (s, 9H). LC-MS(ESI) calcd for $C_{25}H_{26}O_6$ [M+H]$^+$: 423.16. Found: 423.00.

Example 122

3-(6-((4-(3,3-Dimethylbutanoyl)-3-hydroxy-2-methylphenoxy)methyl)pyridin-2-yl)benzoic acid (Compound 159)

Prepared according to general method D using 1-(4-((6-bromopyridin-2-yl)methoxy)-2-hydroxy-3-methylphenyl)-3,3-dimethylbutan-1-one (0.196 g, 0.5 mmol), 3-boronobenzoic acid (0.124 g, 0.750 mmol), Pd(PPh$_3$)$_4$ (0.058 g, 0.050 mmol) and 2M sodium carbonate solution. White solid (0.050 g, 23%). $^1$H NMR (400 MHz, DMSO-d$_6$): δ 8.70 (s, 1H), 8.30 (d, J=7.8 Hz, 1H), 8.02-7.96 (m, 3H), 7.89 (d, J=9.2 Hz, 1H), 7.62 (t, J=9.2 Hz, 1H), 7.51 (d, J=6.0 Hz, 1H), 6.74 (d, J=8.7 Hz, 1H), 5.42 (s, 2H), 2.83 (s, 2H), 2.11 (s, 3H), 0.99 (s, 9H). LC-MS(ESI) calcd for $C_{26}H_{27}NO_5$ [M+H]$^+$: 434.19. Found: 434.00.

Example 123

3-(5-((4-(3,3-Dimethylbutanoyl)-3-hydroxy-2-methylphenoxy)methyl)pyridin-3-yl)-4-methoxybenzoic acid (Compound 160)

Prepared according to general method D using 1-(4-((5-bromopyridin-3-yl)methoxy)-2-hydroxy-3-methylphenyl)-3,3-dimethylbutan-1-one White (0.137 g, 0.349 mmol), 3-borono-4-methoxybenzoic acid (0.103 g, 0.524 mmol), Pd(PPh$_3$)$_4$ (0.040 g, 0.035 mmol) and 2M sodium carbonate solution. solid (0.045 g, 28%). $^1$H NMR (400 MHz, DMSO-d$_6$): δ 8.67-8.65 (m, 2H), 8.01-7.89 (m, 3H), 7.24 (d, J=8.7 Hz, 2H), 6.75 (d, J=9.2 Hz, 1H), 5.36 (s, 2H), 3.84 (s, 3H), 2.85 (s, 2H), 2.04 (s, 3H), 0.99 (s, 9H). LC-MS (ESI) calcd for $C_{27}H_{29}NO_6$ [M+H]$^+$: 464.20. Found: 464.00.

Example 124

3-(2-((4-(3,3-Dimethylbutanoyl)-3-hydroxy-2-methylphenoxy)methyl)thiazol-5-yl)benzoic acid (Compound 161)

Prepared according to general method D using 1-(4-((5-bromothiazol-2-yl)methoxy)-2-hydroxy-3-methylphenyl)-

3,3-dimethylbutan-1-one (0.25 g, 0.628 mmol), 3-boronobenzoic acid (0.156 g, 0.941 mmol), Pd(PPh$_3$)$_4$(0.073 g, 0.063 mmol) and 2M sodium carbonate solution. White solid (0.075 g, 27%). $^1$H NMR (400 MHz, DMSO-d$_6$): δ 8.30 (d, J=7.8 Hz, 1H), 8.11-7.90 (m, 4H), 7.56 (t, J=7.3 Hz, 1H), 6.80 (t, J=6.4 Hz, 1H), 5.59 (s, 2H), 2.86 (s, 2H), 2.10 (s, 3H), 1.00 (s, 9H). LC-Ms (ESI) calcd for C$_{24}$H$_{25}$NO$_5$S [M+H]$^+$: 440.15. Found: 440.00.

Example 125

3-(5-((4-(3,3-Dimethylbutanoyl)-3-hydroxy-2-methylphenoxy)methyl)thiophen-3-yl)benzoic acid (Compound 162)

Prepared according to general method D using 1-(4-((4-bromothiophene-2-yl)methoxy)-2-hydroxy-3-methylphenyl)-3,3-dimethylbutan-1-one (0.3 g, 0.755 mmol), 3-boronobenzoic acid (0.188 g, 1.133 mmol), Pd(PPh$_3$)$_4$(0.087 g, 0.076 mmol) and 2M sodium carbonate solution. White solid (0.150 g, 45%). $^1$H NMR (400 MHz, DMSO-d$_6$): δ 8.20 (d, J=1.4 Hz, 1H), 7.99 (s, 1H), 7.92 (t, J=8.7 Hz, 2H), 7.87 (d, J=8.7 Hz, 1H), 7.71 (s, 1H), 7.54 (t, J=7.8 Hz, 1H), 6.79 (d, J=9.2 Hz, 1H), 5.47 (s, 2H), 2.85 (s, 2H), 2.02 (s, 3H), 0.99 (s, 9H). LC-MS (ESI) calcd for C$_{25}$H$_{26}$O$_5$S [M+H]$^+$: 439.15. Found: 439.00.

Example 126

3-(5-((4-(3,3-Dimethylbutanoyl)-3-hydroxy-2-methylphenoxy)methyl)-1,3,4-thiadiazol-2-yl)benzoic acid (Compound 165)

Prepared according to general method D using 1-(4-((5-bromo-1,3,4-thiadiazol-2-yl)methoxy)-2-hydroxy-3-methylphenyl)-3,3-dimethylbutan-1-one (0.38 g, 0.952 mmol), 3-boronobenzoic acid (0.190 g, 1.142 mmol), Pd(PPh$_3$)$_4$ (0.110 g, 0.095 mmol) and 2M sodium carbonate solution. White solid (0.100 g, 24%). $^1$H NMR (400 MHz, DMSO-d$_6$): δ 8.49 (d, J=1.8 Hz, 1H), 8.24 (d, J=8.7 Hz, 1H), 8.12 (d, J=8.7 Hz, 1H), 7.94 (t, J=10.0 Hz, 2H), 6.74 (d, J=9.2 Hz, 1H), 5.78 (s, 2H), 2.86 (s, 2H), 2.07 (s, 3H), 0.99 (s, 9H). LC-MS (ESI) calcd for C$_{23}$H$_{24}$N$_2$O$_5$S[M+H]$^+$: 441.14. Found: 441.00.

Example 127

3-(5-((4-(3,3-Dimethylbutanoyl)-3-hydroxy-2-methylphenoxy)methyl)pyrazin-2-yl)benzoic acid (Compound 163)

Prepared according to general method D using 1-(4-((5-bromopyrazin-2-yl)methoxy)-2-hydroxy-3-methylphenyl)-3,3-dimethylbutan-1-one (0.38 g, 0.966 mmol), 3-boronobenzoic acid (0.241 g, 1.449 mmol), Pd(PPh$_3$)$_4$(0.112 g, 0.097 mmol) and 2M sodium carbonate solution. White solid (0.132 g, 31%). $^1$H NMR (400 MHz, DMSO-d$_6$): δ 9.33 (s, 1H), 8.90 (s, 1H), 8.71 (s, 1H), 8.33 (d, J=8.7 Hz, 1H), 8.05 (d, J=7.8 Hz, 1H), 7.92 (d, J=9.2 Hz, 1H), 7.68 (t, J=7.8 Hz, 1H), 6.77 (d, J=9.2 Hz, 1H), 5.45 (s, 2H), 2.85 (s, 2H), 2.08 (s, 3H), 0.99 (s, 9H). LC-MS (ESI) calcd for C$_{25}$H$_{26}$N$_2$O$_5$[M+H]$^+$: 435.18. Found: 435.00.

Example 128

3-(6-((4-(3,3-Dimethylbutanoyl)-3-hydroxy-2-methylphenoxy)methyl)pyrazin-2-yl)benzoic acid (Compound 166)

Prepared according to general method D using 1-(4-((6-bromopyrazin-2-yl)methoxy)-2-hydroxy-3-methylphenyl)-3,3-dimethylbutan-1-one (0.295 g, 0.75 mmol), 3-boronobenzoic acid (0.187 g, 1.25 mmol), Pd(PPh$_3$)$_4$(0.087 g, 0.075 mmol) and 2M sodium carbonate solution. White solid (0.130 g, 40%). LC-MS (ESI) calcd for C$_{25}$H$_{26}$N$_2$O$_5$ [M+H]$^+$: 435.18. Found: 435.00.

Example 129

3-(4-((4-(3,3-Dimethylbutanoyl)-3-hydroxy-2-methylphenoxy)methyl)pyrimidin-2-yl)benzoic acid (Compound 173)

Prepared according to general method D using 1-(4-((2-bromopyrimidin-4-yl)methoxy)-2-hydroxy-3-methylphenyl)-3,3-dimethylbutan-1-one (0.118 g, 0.3 mmol), 3-boronobenzoic acid (0.0.75 g, 0.450 mmol), Pd(PPh$_3$)$_4$(0.035 g, 0.035 mmol) and 2M sodium carbonate solution. White solid (0.062 g, 48%). LC-MS (ESI) calcd for C$_{25}$H$_{26}$N$_2$O$_5$ [M+H]$^+$: 435.18. Found: 435.00.

Example 130

5-(3-((4-(3,3-Dimethylbutanoyl)-3-hydroxy-2-methylphenoxy)methyl)phenyl)nicotinic acid (Compound 179)

Prepared according to general method E using (3-((4-(3,3-dimethylbutanoyl)-3-hydroxy-2-methylphenoxy)methyl)phenyl)boronic acid (0.089 g, 0.25 mmol), methyl 5-bromonicotinate (0.065 g, 0.3 mmol), Pd(PPh$_3$)$_4$(0.029 g, 0.025 mmol) and 2M sodium carbonate solution. White solid (0.025 g, 23%). $^1$H NMR (400 MHz, DMSO-d$_6$): δ 7.05 (d, J=6.0 Hz, 2H), 8.46 (s, 1H), 7.93-7.89 (m, 2H), 7.76 (d, J=6.4 Hz, 1H), 7.56-7.54 (m, 2H), 6.75 (d, J=9.2 Hz, 1H), 5.35 (s, 2H), 2.85 (s, 2H), 2.05 (s, 3H), 0.99 (s, 9H). LC-MS (ESI) calcd for C$_{26}$H$_{27}$NO$_5$[M+H]$^+$: 434.19. Found: 434.00.

Example 131

3-(3-((4-(3,3-Dimethylbutanoyl)-3-hydroxy-2-methylphenoxy)methyl)phenyl)isonicotinic acid (Compound 180)

Prepared according to general method E using (3-((4-(3,3-dimethylbutanoyl)-3-hydroxy-2-methylphenoxy)methyl)phenyl)boronic acid (0.089 g, 0.25 mmol), methyl 3-bromoisonicotinate (0.065 g, 0.3 mmol), Pd(PPh$_3$)$_4$(0.029 g, 0.025 mmol) and 2M sodium carbonate solution. White solid (0.039 g, 36%). $^1$H NMR (400 MHz, DMSO-d$_6$): δ 7.05 (d, J=6.0 Hz, 2H), 8.46 (s, 1H), 7.93-7.89 (m, 2H), 7.76 (d, J=6.4 Hz, 1H), 7.56-7.54 (m, 2H), 6.75 (d, J=9.2 Hz, 1H), 5.35 (s, 2H), 2.85 (s, 2H), 2.05 (s, 3H), 0.99 (s, 9H). LC-MS (ESI) calcd for $C_{26}H_{27}NO_5$[M+H]$^+$: 434.19. Found: 434.05.

Example 132

5-(3-((4-(3,3-Dimethylbutanoyl)-3-hydroxy-2-methylphenoxy)methyl)phenyl)pyrazine-2-carboxylic acid (Compound 181)

Prepared according to general method E using (3-((4-(3,3-dimethylbutanoyl)-3-hydroxy-2-methylphenoxy)methyl)phenyl)boronic acid (0.178 g, 0.5 mmol), methyl 5-chloropyrazine-2-carboxylate (0.104 g, 0.6 mmol), Pd(PPh$_3$)$_4$ (0.058 g, 0.05 mmol) and 2M sodium carbonate solution. White solid (0.112 g, 52%). $^1$H NMR (400 MHz, DMSO-d$_6$): δ 9.39 (s, 1H), 9.23 (s, 1H), 8.34 (s, 1H), 8.20 (d, J=7.3 Hz, 1H), 7.92-7.59 (m, 3H), 6.74 (d, J=9.2 Hz, 1H), 5.36 (s, 2H), 2.84 (s, 2H), 2.06 (s, 3H), 0.99 (s, 9H). LC-MS (ESI) calcd for $C_{26}H_{26}N_2O_5$[M+H]$^+$: 435.18. Found: 435.00.

Example 133

3'-((4-(3,3-Dimethylbutanoyl)-3-hydroxy-2-methylphenoxy)methyl)-[1,1'-biphenyl]-3-sulfonic acid (Compound 164)

Prepared according to general method E using (3-((4-(3,3-dimethylbutanoyl)-3-hydroxy-2-methylphenoxy)methyl)phenyl)boronic acid (0.178 g, 0.5 mmol), sodium 3-bromobenzenesulfonate (0.194 g, 0.75 mmol), Pd(PPh$_3$)$_4$(0.058 g, 0.05 mmol) and 2M sodium carbonate solution. Yellow solid (0.093 g, 40%). $^1$H NMR (400 MHz, DMSO-d$_6$): δ 7.99-7.88 (m, 2H), 7.74 (s, 1H), 7.61-7.59 (m, 3H), 7.50-7.43 (m, 3H), 6.74 (d, J=9.2 Hz, 1H), 5.35 (s, 2H), 2.84 (s, 2H), 2.06 (s, 3H), 0.99 (s, 9H). LC-MS (ESI) calcd for $C_{26}H_{28}O_6S$[M+H]$^+$: 469.17. Found: 469.00.

Example 134

1-(4-((3'-(2H-Tetrazol-5-yl)-[1,1'-biphenyl]-3-yl)methoxy)-2-hydroxy-3-methylphenyl)-3,3-dimethylbutan-1-one (Compound 152)

3'-((4-(3,3-Dimethylbutanoyl)-3-hydroxy-2-methylphenoxy)methyl)-[1,1'-biphenyl]-3-carbonitrile (0.207 g, 0.5 mmol), sodium azide (0.390 g, 6.00 mmol), and ammonium chloride (0.321 g, 6.00 mmol) were taken in DMF (5 mL) and the resulting mixture was heated at 100° C. for 1 h. The reaction mixture cooled to room temperature and diluted with water. After extraction with EtOAc, the organic layer was washed with water and brine and dried over Na$_2$SO$_4$. The residue after rotary evaporation was purified by reverse phase HPLC. White solid (0.170 g, 75%). $^1$H NMR (400 MHz, DMSO-d$_6$): δ 8.35 (d, J=1.4 Hz, 1H), 8.04 (d, J=7.1 Hz, 1H), 7.92-7.86 (m, 3H), 7.75-7.69 (m, 2H), 7.58-7.52 (m, 2H), 6.75 (d, J=9.2 Hz, 1H), 5.35 (s, 2H), 2.84 (s, 2H), 2.06 (s, 3H), 0.99 (s, 9H). LC-MS (ESI) calcd for $C_{27}H_{28}N_4O_4$ [M+H]$^+$: 457.21. Found: 457.00.

Example 135

3'-((4-(3,3-Dimethylbutanoyl)-3-hydroxy-2-methylphenoxy)methyl)-N-(methylsulfonyl)-[1,1'-biphenyl]-3-carboxamide (Compound 156)

To a stirred solution of 3'-((4-(3,3-dimethylbutanoyl)-3-hydroxy-2-methylphenoxy)methyl)biphenyl-3-carboxylic acid (0.100 g, 0.231 mmol) and Et$_3$N (0.023 g, 0.231 mmol) in anhyd MeCN (8 mL) was added trichlorotriazine (0.013 g, 0.069 mmol) followed by the addition of alumina (0.007 g, 0.069 mmol) and the mixture was stirred at rt for 5 min. A soln of sulfonamide (0.022 g, 0.231 mmol) and Et$_3$N (0.023 g, 0.231 mmol) in anhydrous MeCN (1 mL) was added and the solution stirred for a further 2 h. The reaction was filtered and the filtrate was concentrated under vacuum and the residue was dissolved in CHCl$_3$. The organic layer was washed with H$_2$O (2×10 mL), dried over anhyd Na$_2$SO$_4$, and evaporated in vacuo to give the crude product which was purified by reverse phase HPLC to yield the desired product. White solid (0.017 g, 14%). $^1$H NMR (400 MHz, DMSO-d$_6$): δ 8.25 (s, 1H), 7.93-7.83 (m, 4H), 7.74-7.73 (m, 1H), 7.62-7.52 (m, 3H), 6.73 (d, J=9.2 Hz, 1H), 5.34 (s, 2H), 3.36 (s, 3H), 2.83 (s, 2H), 2.06 (s, 3H), 0.98 (s, 9H). LC-MS (ESI) calcd for $C_{28}H_{31}NO_6S$ [M+H]$^+$: 510.19. Found: 510.00.

Example 136

3-(3'-((4-(3,3-Dimethylbutanoyl)-3-hydroxy-2-methylphenoxy)methyl)-[1,1'-biphenyl]-3-yl)-1,2,4-oxadiazol-5(4H)-one (Compound 157)

3'-((4-(3,3-Dimethylbutanoyl)-3-hydroxy-2-methylphenoxy)methyl)-[1,1'-biphenyl]-3-carbonitrile (0.330 g, 0.798 mmol) and hydroxylamine (50% aqueous solution, 0.1 mL) were heated at 100° C. for 30 min. in presence of AcOH (few drops), cooled and diluted with water. The precipitated 3'-((4-(3,3-dimethylbutanoyl)-3-hydroxy-2-methylphenoxy)methyl)-N'-hydroxy-[1,1'-biphenyl]-3-carboximidamide was collected by filtration and purified by column chromatography. White solid (0.325 g, 91%). LC-MS (ESI) calcd for $C_{27}H_{30}N_2O_4$[M+H]$^+$: 447.22. Found: 447.00. 3'-((4-(3,3-dimethylbutanoyl)-3-hydroxy-2-methylphenoxy)methyl)-N'-hydroxy-[1,1'-biphenyl]-3-carboximidamide (0.325 g, 0.728 mmol), carbonyl diimidazole (0.177 g, 1.092 mmol) and DBU (0.433 g, 2.91 mmol) in dioxane (10 mL) was heated at reflux for 3 h. Removed the solvent under vacuum. diluted with water and pH adjusted to 4-5 using dil. HCl, and extracted with ethylacetate, removal of solvent followed by reverse phase HPLC afforded the title compound. White solid (0.250 g, 73%). $^1$H NMR (400 MHz, DMSO-d$_6$): δ 8.01 (s, 1H), 7.89-7.86 (m, 2H), 7.81-7.78 (m, 2H), 7.69-7.63 (m, 2H), 7.54-7.48 (m, 2H), 6.71 (d, J=9.2 Hz, 1H), 5.30 (s, 2H), 2.81 (s, 2H), 2.04 (s, 3H), 0.96 (s, 9H). LCMS (ESI) calcd for $C_{28}H_{28}N_2O_5$ [M+H]$^+$: 473.20. Found: 473.00.

Example 137

N-Cyclopropyl-3-(5-((4-(3,3-dimethylbutanoyl)-3-hydroxy-2-methylphenoxy)methyl)pyrazin-2-yl) benzamide (Compound 167)

3-(5-((4-(3,3-Dimethylbutanoyl)-3-hydroxy-2-methylphenoxy)methyl)pyrazin-2-yl)benzoic acid (0.025 g, 0.058 mmol) was dissolved in DMF (2 mL) at room temperature. HOBt (0.012 g, 0.086 mmol) was added in one portion followed by EDC (0.013 g, 0.086 mmol). The resulting mixture was stirred at room temperature for 30 min. To this cyclopropyl amine (0.004 g, 0.069 mmol) and triethylamine (0.01 mL, 0.069 mmol) were added and stirred for 2 h, after that time the organic phase was removed under reduced pressure and the crude material was partitioned between water and ethyl acetate. The aqueous layer was extracted with ethyl acetate (3×5 mL). The organic phase was dried using Na$_2$SO$_4$ and evaporated to give 3-(4-(4-(3,3-dimethylbutanoyl)-3-hydroxy-2-methylphenoxy)butoxy)-4-methoxy-N-methylbenzamide. The crude product was purified by HPLC using acetonitrile:water as the solvent system to afford amide as a colorless solid (0.015 g, 55%). LC-MS (ESI) Calcd for C$_{28}$H$_{31}$N$_3$O$_4$ [M+H]$^+$: 474.23. Found: 474.00.

PHARMACEUTICAL COMPOSITION EXAMPLES

Example A1

Parenteral Composition

To prepare a parenteral pharmaceutical composition suitable for administration by injection, 100 mg of a water-soluble salt of a compound of Formula (I), (Ia), (Ib), (II), (IIa), (IIb), (IIc), or (III), or pharmaceutically acceptable salt, N-oxide, racemate or stereoisomer thereof, is dissolved in 2% HPMC, 1% Tween 80 in DI water, pH 2.2 with MSA, q.s. to at least 20 mg/mL. The mixture is incorporated into a dosage unit form suitable for administration by injection.

Example A2

Oral Composition

To prepare a pharmaceutical composition for oral delivery, 100 mg of a compound of Formula (I), (Ia), (Ib), (II), (IIa), (IIb), (IIc), or (III), or pharmaceutically acceptable salt, N-oxide, racemate or stereoisomer thereof, is mixed with 750 mg of starch. The mixture is incorporated into an oral dosage unit for, such as a hard gelatin capsule, which is suitable for oral administration.

BIOLOGY EXAMPLES

Example B1 mGlu Receptor In Vitro Assays

Human Embryonic Kidney (HEK-293) cell lines co-expressing rat mGlu receptors 2, 3, 4, 6, 7 or 8 and G protein-coupled inwardly-rectifying potassium (GIRK) channels were grown in Growth Media containing 45% DMEM, 45% F-12, 10% FBS, 20 mM HEPES, 2 mM L-glutamine, antibiotic/antimycotic, non-essential amino acids, 700 µg/ml G418, and 0.6 µg/ml puromycin at 37° C. in the presence of 5% CO$_2$. Cells expressing rat mGlu$_1$ and mGlu$_5$ receptor were cultured as described in Hemstapat et al (*Mol. Pharmacol.* 2006, 70, 616-626). All cell culture reagents were purchased from Invitrogen Corp. (Carlsbad, Calif.) unless otherwise noted. Calcium assays were used to assess activity of compounds at mGlu$_1$ and mGlu$_5$, as previously described in Engers et al (*J. Med. Chem.* 2009, 52, 4115-4118). Calcium assays at mGlu3 were performed as described for mGlu$_5$ with the exception that TREx293 mGlu3 G$_{\alpha15}$ cells were treated with tetracycline at 20 ng/mL for 20 h prior to assay.

Compound activity at the group II (mGlu2 and mGlu3) and group III (mGlu$_4$, mGlu$_6$, mGlu$_7$, and mGlu$_8$) was assessed using thallium flux through GIRK channels, a method that has been described in detail. Briefly, cells were plated into 384-well, black-walled, clear-bottomed poly-D-lysine-coated plates at a density of 15,000 cells/20 µL/well in DMEM containing 10% dialyzed FBS, 20 mM HEPES, and 100 units/mL penicillin/streptomycin (assay media). Plated cells were incubated overnight at 37° C. in the presence of 5% CO$_2$. The following day, the medium was exchanged from the cells to assay buffer [Hanks' balanced salt solution (Invitrogen) containing 20 mM HEPES, pH 7.3] using an FLX405 microplate washer (BioTek), leaving 20 µL/well, followed by the addition of 20 µL/well FluoZin2-AM (330 nM final concentration) indicator dye (Invitrogen; prepared as a stock in DMSO and mixed in a 1:1 ratio with Pluronic acid F-127) in assay buffer. Cells were incubated for 1 h at room temperature, and the dye exchanged to assay buffer using an ELX405, leaving 20 µL/well. Test compounds were diluted to 2 times their final desired concentration in assay buffer (0.3% DMSO final concentration). Agonists were diluted in thallium buffer [125 mM sodium bicarbonate (added fresh the morning of the experiment), 1 mM magnesium sulfate, 1.8 mM calcium sulfate, 5 mM glucose, 12 mM thallium sulfate, and 10 mM HEPES, pH 7.3] at 5 times the final concentration to be assayed. Cell plates and compound plates were loaded onto a kinetic imaging plate reader (FDSS 6000 or 7000; Hamamatsu Corporation, Bridgewater, N.J.). Appropriate baseline readings were taken (10 images at 1 Hz; excitation, 470±20 nm; emission, 540±30 nm) and test compounds were added in a 20 µL volume and incubated for approximately 2.5 min before the addition of 10 µL of thallium buffer with or without agonist. After the addition of agonist, data were collected for approximately an additional 2.5 min. Data were analyzed using Excel (Microsoft Corp, Redmond, Wash.). The slope of the fluorescence increase beginning 5 s after thallium/agonist addition and ending 15 s after thallium/agonist addition was calculated, corrected to vehicle and maximal agonist control slope values, and plotted in using either XLfit (ID Business Solutions Ltd) or Prism software (GraphPad Software, San Diego, Calif.) to generate concentration-response curves. Potencies were calculated from fits using a four-point parameter logistic equation. For concentration-response curve experiments, compounds were serially diluted 1:3 into 10 point concentration response curves and were transferred to daughter plates using an Echo acoustic plate reformatter (Labcyte, Sunnyvale, Calif.). Test compounds were applied and followed by EC$_{20}$ concentrations of glutamate. For selectivity experiments, full concentration-response curves of glutamate or L-AP4 (for mGlu$_7$) were performed in the presence of a 10 µM concentration of compound and compounds that affected the concentration-response by less than 2 fold in terms of potency or efficacy were designated as inactive.

Example B2

TREx293 mGlu3 G$_{\alpha15}$ Cell Line Creation

In order to generate a tetracycline (Tet)-inducible rat mGlu3 stable cell line to be used for a calcium mobilization assay, TREx293 cells (Invitrogen) were transfected with mouse G$_{\alpha15}$-pCMV6 plasmid (Origene) using Fugene6 (Promega). The cells were selected for G$_{\alpha15}$ expression with 1 mg/mL G418 in the presence of 10 µg/ml blasticidin to maintain Tet Repressor expression. Two weeks after the selection, polyclonal TREx293 G$_{\alpha15}$ cells were obtained. The entire coding sequence of rat mGlu3 was amplified by polymerase chain reaction (PCR) and cloned into the Tet-inducible expression plasmid pcDNA5/TO (Invitrogen). Rat mGlu3-pcDNA5/TO was transfected into TREx293 G$_{\alpha15}$ cells and selected for mGlu3 expression with 200 µg/ml hygromycin in the presence of G418 and blasticidin. The resulting polyclonal TREx293 mGlu3 $G_{\alpha 15}$ cells were plated for monoclonal selection and positive monoclones were identified in the calcium mobilization assay. Cells were in maintained in Growth Media containing DMEM, 10% Tet-tested FBS (Atlanta Biogicals), 20 mM HEPES, 2 mM L-glutamine, antibiotic/antimycotic, non-essential amino acids, 500 μg/ml G418, 100 μg/mL hygromycin, and 5 μg/mL blasticidin S at 37° C. in the presence of 5% $CO_2$.

Example B3

HEK293A mGlu2 $G_{\alpha 15}$ Cell Line Creation

In order to generate a rat mGlu2 stable cell line to be used for a calcium mobilization assay, HEK293A cells (ATCC) were transfected with mouse $G_{\alpha 15}$-pCMV6 plasmid (Origene) using Fugene6 (Promega). The cells were selected for $G_{\alpha 15}$ expression with 1 mg/mL G418. Two weeks after the selection, polyclonal HEK293A $G_{\alpha 15}$ cells were obtained. The entire coding sequence of rat mGlu2 was amplified by PCR and cloned into the expression plasmid pIRESpuro3 (Invitrogen). Rat mGlu2-pIRESpuro3 was transfected into HEK293A $G_{\alpha 15}$ cells and selected for mGlu2 expression with 0.6 μg/mL puromycin in the presence of G418. The resulting polyclonal HEK293A mGlu2 $G_{\alpha 15}$ cells were then utilized for calcium mobilization assays. Cells were maintained in Growth Media containing DMEM, 10% FBS, 20 mM HEPES, 2 mM L-glutamine, antibiotic/antimycotic, non-essential amino acids, 700 μg/ml G418, and 0.6 μg/mL puromycin at 37° C. in the presence of 5% $CO_2$.

Example B4

Western Blotting

Western blotting was performed as detailed previously (Sheffler, D. J.; Conn, P. J. *Glutamate-based Therapies for Psychiatric Disorders*, Skolnick, P., Ed. Birkhäuser Basel: 2010; pp 101-116) utilizing 10% polyacrylamide gels and a rabbit polyclonal mGlu2/3 antibody (Millipore, Catalog #06-676) for detection of mGlu3.

Representative in vitro biochemical data is presented in Tables 5.

TABLE 5

In vitro potency and efficacy data at mGlu2 or mGlu3 receptors for PAMs.[a]

| Cmpd | mGlu2 PAM $EC_{50}$ (μM) | mGlu2 PAM Max (%) | mGlu3 PAM $EC_{50}$ (μM) | mGlu3 PAM Max (%) |
|---|---|---|---|---|
| 5 | 2.449 ± 0.272 | 83.1 ± 3.2 | >30 | 15.2 ± 2.7 |
| 6 | >10 | 45.2 ± 6.9 | >30 | 27.8 ± 1.6 |
| 14 | >30 | 15.9 ± 2.4 | >30 | 27.3 ± 2.3 |
| 15 | >30 | 14.1 ± 2.1 | >30 | 24.2 ± 3.2 |
| 16 | >30 | 16.4 ± 2.7 | >30 | 22.7 ± 2.3 |
| 17 | >30 | 12.2 ± 2.4 | >30 | 22.0 ± 2.1 |
| 18 | >30 | 19.0 ± 4.5 | >30 | 16.6 ± 0.3 |
| 19 | >30 | 16.2 ± 2.9 | >30 | 12.2 ± 1.5 |
| 20 | 0.122 ± 0.022 | 88.0 ± 1.6 | 2.724 ± 0.294 | 51.9 ± 5.8 |
| 21 | 0.824 ± 0.071 | 82.6 ± 1.0 | >10 | 26.7 ± 1.7 |
| 22 | >30 | 12.1 ± 2.5 | >30 | 18.3 ± 1.9 |
| 23 | >30 | 22.4 ± 6.7 | >30 | 16.5 ± 1.2 |
| 24 | 0.222 ± 0.031 | 84.5 ± 3.0 | 1.434 ± 0.136 | 69.9 ± 4.5 |
| 25 | 0.451 ± 0.035 | 80.6 ± 2.8 | 3.400 ± 0.783 | 92.9 ± 8.9 |
| 26 | 0.976 ± 0.041 | 76.2 ± 6.3 | >30 | 30.7 ± 2.3 |
| 27 | 2.581 ± 0.157 | 67.1 ± 7.2 | >30 | 28.0 ± 3.1 |
| 28 | 0.415 ± 0.070 | 92.4 ± 9.6 | >30 | 28.1 ± 3.2 |
| 29 | 0.335 ± 0.028 | 98.8 ± 8.0 | >30 | 32.9 ± 3.3 |
| 30 | >10 | 33.1 ± 7.0 | >30 | 12.0 ± 3.9 |
| 31 | 2.415 ± 0.188 | 61.8 ± 8.3 | >10 | 35.5 ± 1.1 |
| 32 | 0.151 ± 0.006 | 80.5 ± 1.1 | 2.048 ± 0.289 | 49.5 ± 2.6 |
| 33 | 0.510 ± 0.057 | 80.8 ± 2.4 | 2.247 ± 0.081 | 40.0 ± 4.8 |
| 34 | >30 | 15.8 ± 4.1 | >30 | 13.8 ± 3.1 |
| 35 | >30 | 14.6 ± 2.8 | >30 | 12.6 ± 1.5 |
| 36 | 0.153 ± 0.010 | 84.5 ± 1.2 | 0.920 ± 0.071 | 81.7 ± 4.2 |
| 37 | 0.699 ± 0.121 | 81.0 ± 2.8 | 2.492 ± 0.401 | 98.4 ± 9.9 |
| 38 | 0.454 ± 0.054 | 76.9 ± 5.5 | >10 | 29.4 ± 2.8 |
| 39 | 1.290 ± 0.265 | 67.5 ± 4.7 | >10 | 26.9 ± 2.4 |
| 40 | 0.192 ± 0.017 | 83.9 ± 3.2 | 1.853 ± 0.356 | 42.1 ± 4.1 |
| 41 | 0.608 ± 0.039 | 84.6 ± 4.4 | >10 | 28.4 ± 2.3 |
| 42 | 0.102 ± 0.015 | 85.0 ± 2.5 | 1.417 ± 0.061 | 67.7 ± 4.3 |
| 43 | 0.639 ± 0.054 | 83.8 ± 3.9 | >10 | 31.2 ± 2.3 |
| 44 | 0.040 ± 0.006 | 85.7 ± 2.5 | 0.614 ± 0.098 | 73.9 ± 6.0 |
| 45 | 0.228 ± 0.046 | 95.4 ± 2.7 | 1.905 ± 1.131 | 46.9 ± 6.2 |
| 46 | 0.096 ± 0.020 | 99.5 ± 0.9 | 1.140 ± 0.010 | 62.9 ± 2.4 |
| 47 | 0.237 ± 0.006 | 82.2 ± 3.4 | >10 | 27.4 ± 2.3 |
| 48 | 0.173 ± 0.038 | 93.3 ± 1.5 | 3.907 ± 1.972 | 41.9 ± 4.0 |
| 49 | 0.564 ± 0.039 | 83.6 ± 2.5 | >10 | 23.7 ± 2.6 |
| 50 | 0.155 ± 0.029 | 89.7 ± 1.7 | 0.737 ± 0.085 | 100.1 ± 5.2 |
| 51 | 0.425 ± 0.078 | 91.8 ± 2.8 | 1.021 ± 0.091 | 67.6 ± 1.5 |
| 52 | 0.161 ± 0.075 | 86.3 ± 1.1 | >30 | 26.3 ± 2.2 |
| 53 | 1.091 ± 0.048 | 70.7 ± 8.5 | >30 | 34.8 ± 3.1 |
| 54 | 0.200 ± 0.050 | 79.2 ± 2.4 | >30 | 17.1 ± 8.0 |
| 55 | 0.259 ± 0.084 | 75.5 ± 6.1 | >30 | 16.8 ± 7.3 |
| 56 | 0.050 ± 0.012 | 83.1 ± 4.3 | >30 | 25.4 ± 5.2 |
| 57 | 0.114 ± 0.054 | 86.5 ± 1.1 | >30 | 25.9 ± 6.2 |
| 58 | 0.162 ± 0.055 | 72.6 ± 7.5 | 6.359 ± 3.655 | 62.5 ± 5.3 |

TABLE 5-continued

In vitro potency and efficacy data at mGlu2 or mGlu3 receptors for PAMs.[a]

| Cmpd | mGlu2 PAM EC$_{50}$ (μM) | mGlu2 PAM Max (%) | mGlu3 PAM EC$_{50}$ (μM) | mGlu3 PAM Max (%) |
|---|---|---|---|---|
| 59 | 0.062 ± 0.011 | 71.3 ± 6.7 | >30 | 16.3 ± 6.0 |
| 60 | 0.124 ± 0.020 | 66.6 ± 5.3 | >30 | 18.4 ± 4.5 |
| 61 | 0.082 ± 0.016 | 86.6 ± 6.0 | >30 | 22.7 ± 5.6 |
| 62 | 0.113 ± 0.046 | 73.1 ± 6.9 | >30 | 25.6 ± 3.8 |
| 63 | 0.116 ± 0.024 | 66.6 ± 2.3 | 0.588 ± 0.104 | 59.9 ± 1.8 |
| 64 | 0.149 ± 0.056 | 66.9 ± 2.1 | >30 | 27.1 ± 1.6 |
| 65 | 0.171 ± 0.029 | 74.1 ± 2.1 | >10 | 31.3 ± 6.5 |
| 66 | 0.234 ± 0.030 | 76.9 ± 3.2 | >30 | 25.2 ± 8.8 |
| 67 | 0.034 ± 0.004 | 85.5 ± 0.6 | 1.830 ± 0.380 | 61.9 ± 3.8 |
| 68 | 0.103 ± 0.026 | 82.8 ± 4.8 | 0.496 ± 0.076 | 64.2 ± 3.2 |
| 69 | 0.052 ± 0.025 | 82.4 ± 6.4 | >10 | 53.0 ± 3.9 |
| 70 | 0.074 ± 0.014 | 87.5 ± 2.4 | 0.438 ± 0.020 | 56.9 ± 3.9 |
| 71 | 0.104 ± 0.014 | 79.3 ± 6.0 | >10 | 40.5 ± 7.8 |
| 72 | 0.184 ± 0.033 | 96.0 ± 2.2 | 0.151 ± 0.028 | 105.5 ± 2.9 |
| 73 | 0.047 ± 0.009 | 98.6 ± 4.7 | 0.310 ± 0.029 | 109.4 ± 1.8 |
| 74 | 0.136 ± 0.032 | 95.8 ± 3.5 | 0.300 ± 0.054 | 108.8 ± 2.3 |
| 75 | 0.208 ± 0.036 | 94.6 ± 2.1 | 0.258 ± 0.063 | 101.7 ± 4.1 |
| 76 | >30 | ND | >30 | ND |
| 77 | >30 | ND | >30 | ND |
| 78 | >10 | ND | >30 | ND |
| 79 | >30 | ND | >30 | ND |
| 80 | >10 | ND | >30 | ND |
| 81 | >30 | ND | >30 | ND |
| 82 | >30 | ND | >30 | ND |
| 83 | >30 | ND | >30 | ND |
| 84 | >30 | ND | >30 | ND |
| 85 | >10 | ND | >30 | ND |
| 86 | >10 | ND | >30 | ND |
| 87 | >10 | 49.5 ± 3.5 | >30 | 24.9 ± 9.6 |
| 88 | 2.419 ± 0.278 | 86.4 ± 2.6 | 5.455 ± .184 | 53.5 ± 10.6 |
| 89 | 4.129 ± 0.590 | 84.6 ± 1.9 | >10 | 81.6 ± 7.2 |
| 90 | 3.889 ± 0.317 | 82.4 ± 3.4 | 6.598 ± 1.454 | 78.7 ± 6.2 |
| 91 | >10 | 48.2 ± 7.4 | >30 | 33.7 ± 7.4 |
| 92 | 0.350 ± 0.030 | 91.2 ± 1.1 | 0.848 ± 0.195 | 96.7 ± 4.0 |
| 93 | 0.250 ± 0.055 | 98.1 ± 1.1 | 0.265 ± 0.050 | 110.0 ± 1.3 |
| 94 | 3.990 ± 0.557 | 83.9 ± 3.4 | 7.051 ± 0.611 | 94.0 ± 3.8 |
| 95 | 3.010 ± 0.988 | 27.5 ± 2.7 | >30 | 26.2 ± 11.7 |
| 96 | 0.955 ± 0.094 | 88.6 ± 0.9 | 1.068 ± 0.061 | 95.3 ± 5.0 |
| 97 | >10 | 57.2 ± 1.4 | >30 | 24.4 ± 4.7 |
| 98 | 0.681 ± 0.090 | 101.1 ± 2.9 | 1.227 ± 0.185 | 102.2 ± 4.7 |
| 99 | 1.035 ± 0.070 | 81 ± 1.8 | 1.147 ± 0.307 | 63.6 ± 5.0 |
| 100 | 2.224 ± 0.709 | 68.1 ± 0.9 | >30 | 33.9 ± 10.1 |
| 101 | 0.875 ± 0.003 | 112.9 ± 1.2 | 0.741 ± 0.006 | 132.2 ± 5.0 |
| 102 | 5.160 ± 0.082 | 70.9 ± 2.3 | >10 | 39.2 ± 5.2 |
| 103 | 0.608 ± 0.010 | 96.4 ± 2.1 | 0.497 ± 0.006 | 111.0 ± 3.4 |
| 104 | >30 | 23.1 ± 1.4 | >30 | 27.0 ± 3.4 |
| 105 | >10 | 67.4 ± 1.9 | >10 | 49.7 ± 3.9 |
| 106 | >10 | 74.8 ± 5.9 | 5.050 ± 0.177 | 97.4 ± 9.4 |
| 107 | >30 | 22.1 ± 1.1 | >30 | 22.9 ± 1.5 |
| 108 | >10 | 38.6 ± 1.1 | >30 | 33.4 ± 5.3 |
| 109 | 0.765 ± 0.005 | 101.5 ± 0.9 | 0.578 ± 0.012 | 106.2 ± 5.1 |
| 110 | 6.404 ± 0.3888 | 48.4 ± 5.5 | >30 | 31.7 ± 8.5 |
| 111 | >10 | ND | >30 | ND |
| 112 | >10 | 35.0 ± 5.8 | >30 | 40.3 ± 1.6 |
| 113 | 0.872 ± 0.004 | 101.9 ± 2.9 | 1.080 ± 0.021 | 109.4 ± 3.5 |
| 114 | >30 | ND | >30 | ND |
| 115 | >30 | ND | >30 | ND |
| 116 | >30 | ND | >30 | ND |
| 117 | >30 | ND | >30 | ND |
| 118 | >30 | ND | >30 | ND |
| 119 | >30 | ND | >30 | ND |
| 120 | >30 | ND | >30 | ND |
| 121 | >30 | ND | >30 | ND |
| 122 | >30 | ND | >30 | ND |
| 123 | >30 | ND | >30 | ND |
| 124 | >30 | ND | >30 | ND |
| 125 | 0.238 ± 0.051 | 82.7 ± 7.2 | >30 | 13.9 ± 3.1 |
| 126 | >10 | ND | >30 | ND |
| 127 | 0.219 ± 0.043 | 91.1 ± 2.6 | 0.343 ± 0.040 | 104.4 ± 2.4 |
| 128 | 0.035 ± 0.013 | 57.9 ± 6.6 | 1.288 ± 0.781 | 67.8 ± 8.7 |
| 129 | 0.616 ± 0.217 | 97.5 ± 9.0 | 3.561 ± 1.941 | 94.0 ± 10.1 |
| 130 | 0.142 ± 0.029 | 92.9 ± 10.7 | 1.684 ± 0.753 | 81.0 ± 14.8 |
| 131 | 0.222 ± 0.082 | 83.2 ± 12.3 | 1.749 ± 0.891 | 55.0 ± 24.4 |
| 132 | 0.561 ± 0.063 | 90.5 ± 13.8 | 1.638 ± 0.487 | 57.5 ± 20.9 |
| 133 | 0.433 ± 0.099 | 90.2 ± 4.1 | 1.706 ± 0.888 | 70.9 ± 3.6 |

TABLE 5-continued

In vitro potency and efficacy data at mGlu2 or mGlu3 receptors for PAMs.[a]

| Cmpd | mGlu2 PAM EC$_{50}$ (μM) | mGlu2 PAM Max (%) | mGlu3 PAM EC$_{50}$ (μM) | mGlu3 PAM Max (%) |
|---|---|---|---|---|
| 134 | 0.118 ± 0.002 | 89.6 ± 2.9 | 0.324 ± 0.094 | 76.4 ± 5.4 |
| 135 | 0.208 ± 0.020 | 88.5 ± 3.8 | 0.587 ± 0.129 | 74.4 ± 5.0 |
| 136 | 0.308 ± 0.040 | 93.3 ± 2.1 | 0.496 ± 0.086 | 77.4 ± 7.1 |
| 137 | 0.181 ± 0.028 | 85.8 ± 3.7 | 0.642 ± 0.151 | 76.8 ± 8.0 |
| 138 | 0.643 ± 0.137 | 42.1 ± 7.1 | >10 | 23.5 ± 4.6 |
| 139 | 0.436 ± 0.084 | 88.2 ± 5.1 | 1.098 ± 0.33 | 85.6 ± 5.5 |
| 140 | 0.489 ± 0.073 | 86.1 ± 6.1 | 8.409 ± 4.842 | 67.2 ± 13.3 |
| 141 | 0.391 ± 0.103 | 67.0 ± 6.4 | 0.656 ± 0.265 | 54.9 ± 9.7 |
| 142 | 3.176 ± 0.626 | 97.1 ± 8.2 | 2.204 ± 0.753 | 88.7 ± 9.5 |
| 143 | 0.571 ± 0.138 | 87.0 ± 11.7 | 3.057 ± 0.624 | 78.3 ± 21.1 |
| 144 | 0.232 ± 0.016 | 59.6 ± 4.0 | 0.701 ± 0.176 | 46.9 ± 5.6 |
| 145 | 1.361 ± 0.259 | 93.4 ± 11.4 | 3.942 ± 1.317 | 79.1 ± 15.0 |
| 146 | 0.564 ± 0.156 | 98.7 ± 5.9 | 2.129 ± 0.812 | 74.5 ± 11.7 |
| 147 | 0.460 ± 0.158 | 98.6 ± 5.7 | 2.282 ± 0.827 | 81.4 ± 9.7 |
| 148 | 2.114 ± 0.215 | 100 ± 3.9 | 2.579 ± 0.272 | 101.7 ± 2.7 |
| 149 | 0.23 ± 0.002 | 107.8 ± 1.2 | 0.203 ± 0.001 | 111.5 ± 3.8 |
| 150 | 0.345 ± 0.002 | 107.3 ± 2.6 | 0.345 ± 0.009 | 107.2 ± 6.3 |
| 151 | >10 | 50.2 ± 7.4 | >10 | 35.5 ± 3.8 |
| 152 | 0.793 ± 0.024 | 102.7 ± 1.8 | 1.882 ± 0.069 | 98.9 ± 3.7 |
| 153 | 0.209 ± 0.003 | 105.6 ± 3.9 | 0.158 ± 0.002 | 106.6 ± 5.5 |
| 154 | >30 | ND | >30 | ND |
| 155 | >30 | ND | >30 | ND |
| 156 | 0.620 ± 0.007 | 105.2 ± 2.1 | 1.177 ± 0.008 | 103.1 ± 1.7 |
| 157 | 0.657 ± 0.027 | 111.1 ± 6.6 | 1.131 ± 0.066 | 105.1 ± 2.8 |
| 158 | 0.328 ± 0.00 | 105.5 ± 3.8 | 0.421 ± 0.005 | 109.9 ± 3.9 |
| 159 | 0.929 ± 0.012 | 104.2 ± 2.5 | 0.967 ± 0.008 | 115.2 ± 2.1 |
| 160 | 0.159 ± 0.003 | 10.7.4 ± 0.2 | 0.3 ± 0.012 | 110.1 ± 2.4 |
| 161 | 1.878 ± 0.017 | 98.2 ± 5.2 | 3.185 ± 0.068 | 113.8 ± 3.9 |
| 162 | 1.726 ± 0.015 | 102.2 ± 3.5 | 3.236 ± 0.063 | 105.6 ± 6.4 |
| 163 | 1.452 ± 0.015 | 105.4 ± 1.6 | 0.268 ± 0.005 | 113.0 ± 5.4 |
| 164 | 0.254 ± 0.007 | 101.1 ± 2.8 | 0.253 ± 0.013 | 103.3 ± 1.9 |
| 165 | 1.658 ± 0.008 | 85.6 ± 1.3 | 1.414 ± 0.034 | 95.0 ± 2.5 |
| 169 | 0.278 ± 0.049 | 77.6 ± 1.8 | 2.99 ± 0.359 | 76.1 ± 5.1 |
| 170 | 0.815 ± 0.05 | 70.2 ± 2.9 | >30 | ND |
| 171 | >30 | 12.3 ± 1.2 | >30 | 10.7 ± 1.0 |
| 172 | 0.763 ± 0.040 | 73.7 ± 1.2 | >10 | ND |
| 174 | >30 | ND | >30 | ND |
| 175 | >30 | ND | >30 | ND |
| 176 | >10 | ND | >30 | ND |
| 177 | >30 | ND | >30 | ND |
| 178 | 0.409 ± 0.105 | 81.4 ± 10.1 | 2.872 ± 1.124 | 67.7 ± 11.7 |
| 179 | 0.848 ± 0.009 | 100.1 ± 2.9 | 1.015 ± 0.020 | 101.8 ± 3.5 |
| 180 | 1.457 ± 0.020 | 88.4 ± 1.5 | >30 | 30.6 ± 9.2 |
| 181 | 2.134 ± 0.008 | 105.2 ± 3.4 | 4.280 ± 0.064 | 105.7 ± 2.1 |
| 182 | >30 | ND | >30 | ND |
| 183 | >10 | ND | >30 | ND |
| 184 | >10 | ND | >30 | ND |
| 185 | 2.793 ± 0.102 | 66.3 ± 0.6 | >30 | 22.4 ± 4.3 |
| 186 | >10 | ND | >30 | ND |
| 187 | 1.575 ± 0.297 | 93.4 ± 3.4 | 3.072 ± 0.632 | 74.1 ± 7.8 |
| 188 | >30 | ND | >30 | ND |
| 189 | >30 | ND | >30 | ND |
| 190 | 0.372 ± 0.034 | 64.9 ± 5.1 | >30 | 12.1 ± 12.8 |
| 191 | 0.256 ± 0.101 | 43.8 ± 5.4 | >30 | 0.1 ± 7.7 |
| 192 | 1.409 ± 0.238 | 82.0 ± 5.1 | 2.916 ± 0.785 | 62.6 ± 9.7 |
| 193 | 0.313 ± 0.02 | 79.5 ± 20.8 | 0.45 ± 0.104 | 74.0 ± 9.5 |
| 194 | >10 | ND | >30 | ND |

[a] mGlu2 PAM EC$_{50}$ μM data and % Glutamate Max data represent the mean ± SEM for at least three independent experiments performed in triplicate.
ND = Not Determined.

Representative in vitro biochemical data selectivity data is presented in Table 6.

TABLE 6

| | mGlu Receptor Subtype Selectivity[a] | | | | | | |
|---|---|---|---|---|---|---|---|
| Comp. | 20 | 25 | 33 | 44 | 67 | 72 | 73 |
| mGlu$_1$ | inactive[b] | inactive[b] | inactive[b] | inactive[b] | Antagonist FS = 0.3 E$_{min}$ = 3% E$_{max}$ = 79% | inactive[b] | inactive[b] |

TABLE 6-continued mGlu Receptor Subtype Selectivity[a]

| | Comp. 20 | 25 | 33 | 44 | 67 | 72 | 73 |
|---|---|---|---|---|---|---|---|
| mGlu$_2$ | Ago-PAM<br>FS = 3.2<br>E$_{min}$ = 54%<br>E$_{max}$ = 77% | Ago-PAM<br>FS = 12.5<br>E$_{min}$ = 45%<br>E$_{max}$ = 71% | Ago-PAM<br>FS = 13.3<br>E$_{min}$ = 54%<br>E$_{max}$ = 77% | Ago-PAM<br>FS = ND<br>E$_{min}$ = 90%<br>E$_{max}$ = 95% | Ago-PAM<br>FS = ND<br>E$_{min}$ = 79%<br>E$_{max}$ = 92% | Ago-PAM<br>FS = ND<br>E$_{min}$ = 72%<br>E$_{max}$ = 95% | Ago-PAM<br>FS = ND<br>E$_{min}$ = 79%<br>E$_{max}$ = 92% |
| mGlu$_3$ | PAM<br>FS = 2.7<br>E$_{min}$ = 9%<br>E$_{max}$ = 153% | PAM<br>FS = 4.5<br>E$_{min}$ = 6%<br>E$_{max}$ = 143% | PAM<br>FS = 2.5<br>E$_{min}$ = 10%<br>E$_{max}$ = 143% | PAM<br>FS = 3.9<br>E$_{min}$ = 4%<br>E$_{max}$ = 116% | PAM<br>FS = 2.9<br>E$_{min}$ = 1%<br>E$_{max}$ = 88% | Ago-PAM<br>FS = 7.1<br>E$_{min}$ = 54%<br>E$_{max}$ = 95% | Ago-PAM<br>FS = 8.9<br>E$_{min}$ = 30%<br>E$_{max}$ = 99% |
| mGlu$_4$ | inactive[b] | inactive[b] | inactive[b] | inactive[b] | Antagonist<br>FS = 1.9<br>E$_{min}$ = 0%<br>E$_{max}$ = 74% | inactive[b] | inactive[b] |
| mGlu$_5$ | inactive[b] | inactive[b] | inactive[b] | inactive[b] | inactive[b] | inactive[b] | inactive[b] |
| mGlu$_6$ | inactive[b] | inactive[b] | inactive[b] | inactive[b] | inactive[b] | inactive[b] | PAM<br>FS = 2.0<br>E$_{min}$ = 8%<br>E$_{max}$ = 93% |
| mGlu$_7$ | inactive[b] | inactive[b] | inactive[b] | inactive[b] | inactive[b] | inactive[b] | inactive[b] |
| mGlu$_8$ | inactive[b] | inactive[b] | inactive[b] | inactive[b] | inactive[b] | inactive[b] | inactive[b] |

[a]In these selectivity experiments, for all receptors a full concentration-response of agonist was performed once in triplicate in the presence and absence of a 10 μM final concentration of each compound. This allows determination of positive allosteric modulator (PAM) (left-shift of the agonist concentration response curve), antagonist (right-shift of the agonist concentration response with a possible decrease in maximal agonist response), and agonist (increase in baseline response) activity in a single experiment. General activity for each compound at each mGlu is listed (PAM, antagonist, Ago-PAM, inactive) followed by the fold-shift (FS) of the agonist concentration-response obtained. Where tested compounds demonstrate activity toward an mGlu receptor subtype, the maximal (E$_{max}$) and minimal (E$_{min}$) responses of the concentration-response of agonist are indicated. Where 10 μM test compound induced greater than a 2-fold shift (FS) of the glutamate concentration-response curve (L-AP4 in the case of mGlu$_7$), full compound concentration-response curves were performed in triplicate on three different days to assess compound potency. Compound 67 showed weak antagonist/NAM activity (IC$_{50}$ >10 μM) at mGlu$_1$ and mGlu$_4$, and compound 73 showed weak PAM activity at mGlu$_6$ (EC$_{50}$ >10 μM).
[b]Inactive compounds show no ability to left or right shift the agonist concentration response curve at 10 μM.

Example B5

CNS Receptors Panel

As a representative of this series, compound 72 was profiled against a representative panel of CNS receptors through the NIMH Psychoactive Drug Screening Program (PDSP; see http://pdsp.med.unc.edu/indexR.html for details). As shown in Table 7, at a concentration of 10 μM, no binding activity was detected for compound 72 at forty-five CNS receptors, suggesting that the new mGlu2/3 PAMs have a low likelihood of off-target activity.

TABLE 7

Off-target profiling data for compound 72.[a]

| Receptor/Target | Species | Cpd 72% inhibition[b] |
|---|---|---|
| Adrenergic α1A | Human | −10.5 |
| Adrenergic α1B | Human | −17.1 |
| Adrenergic α1D | Human | −3.6 |
| Adrenergic α2A | Human | −7.7 |
| Adrenergic α2B | Human | 11.5 |
| Adrenergic α2C | Human | 0.6 |
| Adrenergic β1 | Human | −7.3 |
| Adrenergic β2 | Human | 0.7 |
| Adrenergic β3 | Human | 24.8 |
| Benzodiazepine (brain, [3H]Flunitrazepam) | Rat | −11.2 |
| Dopamine D1 | Human | 1.9 |
| Dopamine D2 | Human | 1.0 |
| Dopamine D3 | Human | −28.2 |
| Dopamine D4 | Human | −2.9 |
| Dopamine D5 | Human | −0.9 |
| GABAA (brain, [3H]Muscimol) | Rat | 11.0 |
| Histamine H1 | Human | 0.2 |
| Histamine H2 | Human | (>10 μM) |
| Histamine H3 | Guinea pig | −5.2 |
| Histamine H4 | Human | (>10 μM) |

TABLE 7-continued

Off-target profiling data for compound 72.[a]

| Receptor/Target | Species | Cpd 72% inhibition[b] |
|---|---|---|
| Muscarinic M1 | Human | −6.6 |
| Muscarinic M2 | Human | −1.0 |
| Muscarinic M3 | Human | 8.3 |
| Muscarinic M4 | Human | −0.9 |
| Muscarinic M5 | Human | −3.8 |
| Opiate δ (OP1, DOP) | Human | 13.7 |
| Opiate κ (OP2, KOP) | Human | 31.2 |
| Opiate L (OP3, MOP) | Human | 11.1 |
| Peripheral benzodiazepine receptor ([3H]PK11195) | Rat | 1.0 |
| Serotonin (5-Hydroxytryptamine) 5-HT1A | Human | −10.2 |
| Serotonin (5-Hydroxytryptamine) 5-HT1B | Human | 16.2 |
| Serotonin (5-Hydroxytryptamine) 5-HT1D | Human | 60.7 (>10 μM) |
| Serotonin (5-Hydroxytryptamine) 5-HT1E | Human | −5.2 |
| Serotonin (5-Hydroxytryptamine) 5-HT2A | Human | −0.6 |
| Serotonin (5-Hydroxytryptamine) 5-HT2B | Human | 7.9 |
| Serotonin (5-Hydroxytryptamine) 5-HT2C | Human | 20.2 |
| Serotonin (5-Hydroxytryptamine) 5-HT3 | Human | −15.3 |
| Serotonin (5-Hydroxytryptamine) 5-HT5A | Human | 4.5 |
| Serotonin (5-Hydroxytryptamine) 5-HT6 | Human | −1.1 |
| Serotonin (5-Hydroxytryptamine) 5-HT7 | Human | 1.8 |
| Sigma σ1 | Rat | −11.3 |
| Sigma σ2 | Rat | 6.6 |
| Transporter, Dopamine (DAT) | Human | −7.7 |
| Transporter, Norepinephrine (NET) | Human | −4.8 |
| Transporter, Serotonin (5-Hydroxytryptamine) (SERT) | Human | 0.3 |
| Adrenergic α1A | Human | −10.5 |
| Adrenergic α1B | Human | −17.1 |
| Adrenergic α1D | Human | −3.6 |
| Adrenergic α2A | Human | −7.7 |
| Adrenergic α2B | Human | 11.5 |
| Adrenergic α2C | Human | 0.6 |
| Adrenergic β1 | Human | −7.3 |
| Adrenergic β2 | Human | 0.7 |
| Adrenergic β3 | Human | 24.8 |
| Benzodiazepine (brain, [3H]Flunitrazepam) | Rat | −11.2 |

TABLE 7-continued

Off-target profiling data for compound 72.[a]

| Receptor/Target | Species | Cpd 72% inhibition[b] |
|---|---|---|
| Dopamine D1 | Human | 1.9 |
| Dopamine D2 | Human | 1.0 |
| Dopamine D3 | Human | −28.2 |
| Dopamine D4 | Human | −2.9 |
| Dopamine D5 | Human | −0.9 |
| GABAA (brain, [3H]Muscimol) | Rat | 11.0 |
| Histamine H1 | Human | 0.2 |
| Histamine H2 | Human | (>10 μM) |
| Histamine H3 | Guinea Pig | −5.2 |

[a] Compound 72 was tested for displacement of radioligand binding activity at 10 μM. Assays were performed by the NIMH Psychoactive Drug Screening Program (UNC Chapel Hill) unless otherwise noted.
[b] Inhibition at 10 μM as a percentage of displacement of the respective radioligand at each target. IC$_{50}$ values where applicable are shown in parentheses.

Example B6

Microsomal Stability In Vitro Assay

Pooled rat liver microsomes (BD Biosciences, #452701) were preincubated with test compounds at 37.5° C. for 5 min in the absence of NADPH. The reaction was initiated by addition of NADPH and incubated under the same conditions. The final incubation concentrations were 4 μM test compound, 2 mM NADPH, and 1 mg/mL (total protein) liver microsomes in phosphate-buffered saline (PBS) at pH 7.4. One aliquot (100 μL) of the incubation mixture was withdrawn at 15 min time points and combined immediately with 100 μL of ACN/MeOH. After mixing, the sample was centrifuged at approximately 13000 rpm for 12 min. The supernatant was filtered and transferred into an autosampler vial and the amount of test compound was quantified using a Shimadzu LCMS 2010EV mass spectrometer. The change of the AUC (area under the curve) of the parent compound as a function of time was used as a measure of microsomal stability. Test compounds were run in duplicate with a positive control. See table 8 for results.

Example B7

Plasma Stability In Vitro Assay

A 20 μL aliquot of a 10 mM solution in DMSO of the test compound was added to 2.0 mL of heparinized rat plasma (Lampire, P1-150N) to obtain a 100 μM final solution. The mixture was incubated for 1 h at 37.5° C. Aliquots of 100 μL were taken at 15 min intervals and diluted with 100 μL of MeOH/ACN. After mixing, the sample was centrifuged at approximately 13000 rpm for 12 min. The supernatant was filtered and transferred into an autosampler vial and the amount of test compound was quantified using the Shimadzu LCMS-2010EV system. The change of the AUC of the parent compound in function of time was used as a measure of plasma stability. See table 8 for results.

Example B8

Parallel Artificial Membrane Permeation Assay (PAMPA)

A 96-well microtiter plate (Millipore, # MSSACCEPTOR) was filled with 300 μL aqueous buffer solution (in general phosphate pH 7.2 buffer was used) and covered with a microtiter filterplate (Millipore, # MAIPNTR10) to create a sort of sandwich construction. The hydrophobic filter material was impregnated with a 10% solution of polar brain lipid extract in chloroform (Avanti) as the artificial membrane, and the organic solvent was allowed to completely evaporate. Permeation studies were started by the transfer of 150 μL of a 100 μM test compound solution on top of the filter plate. The maximum DMSO content of the stock solutions was <1.5%. In parallel, an equilibrium solution lacking a membrane was prepared using the exact concentrations and specifications but lacking the membrane. The concentrations of the acceptor and equilibrium solutions were determined using the Shimadzu LCMS-2010EV and AUC methods. The Acceptor plate and equilibrium plate concentrations were used to calculate the permeability rate (Log $P_e$) of the compounds. The log $P_e$ values were calculated using the following equation:

$$\text{Log } P_e = \log\{C \cdot -\ln(1-[\text{Drug}]_{Acceptor}/[\text{Drug}]_{Equilibrium})\}$$

$$C = (V_D \cdot V_A)/((V_D + V_A)\text{Area·time}))$$

In this equation, $V_D$ (cm$^3$) is the donor volume (0.150 cm$^3$), $V_A$ (cm$^3$) is the acceptor volume (0.300 cm$^3$), Area (cm$^2$) is the accessible filter area (0.168 cm$^2$), and time (s) is the incubation time. [Drug]$_{Acceptor}$ and [Drug]$_{Equilibrium}$ are concentration of the test drug for the sample (Acceptor) and reference (Equilibrium) solutions in the acceptor compartment. See table 8 for results.

Representative in vitro ADME data for Group II mGlu PAMs is presented in Table 8.

TABLE 8

| Cmpd | PAMPA (LogPapp)[a] | Plasma Stability[b] | Microsomal stability[c] |
|---|---|---|---|
| 20 | −5.17 | 95 | 66 |
| 22 | −5.47 | 106 | 29 |
| 24 | −5.19 | 100 | 51 |
| 25 | −4.99 | 99 | 55 |
| 26 | −4.69 | 99 | 9 |
| 33 | −5.33 | 97 | 67 |
| 36 | −5.43 | 101 | 59 |
| 38 | −7.94 | 96 | 21 |
| 39 | −6.73 | 100 | 9 |
| 40 | −4.92 | 100 | 41 |
| 41 | −6.54 | 99 | 59 |
| 42 | −7.18 | 106 | 57 |
| 43 | −5.93 | 97 | 66 |
| 44 | −6.36 | 99 | 43 |
| 45 | −6.54 | 100 | 31 |
| 46 | −7.94 | 123 | 61 |
| 47 | −8.54 | 120 | 21 |
| 48 | −8.24 | 101 | 57 |
| 49 | −6.82 | 114 | 55 |
| 50 | −6.12 | 99 | 5 |
| 51 | −7.28 | 103 | 14 |
| 60 | −5.12 | 96 | 35 |
| 65 | −5.30 | 83 | 60 |
| 68 | −5.24 | 78 | 1 |
| 72 | −5.42 | 63 | 39 |
| 73 | −5.46 | 48 | 49 |
| 74 | −5.63 | 89 | 51 |
| 75 | −5.66 | 83 | 58 |

[a] Permeability is monitored by measuring the amount of compound that can diffuse through a polar brain lipid membrane to predict BBB permeability.
[b,c] Percent remaining after incubation for 60 min. at 37.5° C.

Example B9

Pharmacokinetic (PK) Profile

Compounds 20, 36, 44, and 50 were selected for in vivo assessment of pharmacokinetic (PK) properties in rats. For this initial evaluation, the PK properties of the compounds by oral (p.o.) and intravenous (i.v.) routes of administration as shown in Tables 9 and 10 respectively, was determined. The PAMs were found to be systemically bioavailable with half-life ($t_{1/2}$) values of greater than 90 min when dosed p.o. and demonstrate a range of maximal plasma levels from a low of 1.05 µM (50) to a high of 12.46 µM (36) (Table 9). All compounds had moderate volume of distribution at steady state (Vdss) and medium to high clearance (CL) values, indicating moderate metabolism with a primary distribution in plasma and extracellular fluids, suggesting that one or more of the PAMs might have promise as candidates for in vivo studies. The four compounds exhibited low (20) to good oral bioavailability (50) (% F) albeit at the relatively high oral dose of 20 mg/kg; however, the brain levels of 20, 36 and 44 were low, resulting in low brain:plasma ratios. Although the brain:plasma ratios of these compounds are low, the total brain concentration of 20 and 44 are 9-fold and 18-fold above the in vitro $EC_{50}$ for mGlu2 respectively and close to the in vitro $EC_{50s}$ for mGlu3.

providing $EC_{50}$ values for each curve. Data were obtained from three separate experiments performed in triplicate, normalized to the response to 100 µM glutamate in each experiment, and are expressed as the mean±SEM.

The nature of the GIRK assay requires that each compound is screened for a single mode of pharmacology at a time since activity is only detected through the GIRK channel when thallium is added to the assay. The data presented in Table 5 represent compounds screened for activity in "PAM Mode," where a test compound is added, followed 2.5 min later by an $EC_{20}$ concentration of glutamate in the presence of thallium. It was noted that the response of 44 in "PAM Mode" toward mGlu2 decreased slightly at higher concentrations of test compound (FIG. 1A). This decrease could be caused by either receptor desensitization or intrinsic agonist activity of 44 that was not detected due to the mode in which the functional assay was performed. To investigate this further, the same experiments was carried out in the absence of an $EC_{20}$ concentration of agonist (Agonist Mode). For these experiments, test compounds were added in the presence of thallium and GIRK

TABLE 9

In vivo PK data for mGlu2/mGlu3 PAMs in rats following p.o. administration (20 mg/kg)[a]

| Cmpd | $C_{max}$ (µM) | $T_{max}$ (min) | AUC (0→t) (µmol/L) * min | $T_{1/2}$ (min) | F (%) | Brain (µM) | Plasma (µM) | Brain:Plasma ratio |
|---|---|---|---|---|---|---|---|---|
| 20 | 2.57 ± 0.45 | 135 ± 15 | 544.8 ± 75.4 | 303 ± 55 | 23.5 | 1.12 ± 0.43 | 5.29 ± 1.98 | 0.20 ± 0.03 |
| 36 | 12.46 ± 6.42 | 30 ± 0 | 720.5 ± 283.4 | 89 ± 17 | 58.2 | 0.23 ± 0.06 | 4.23 ± 1.19 | 0.06 ± 0.03 |
| 44 | 2.75 ± 0.47 | 90 ± 17 | 1274.6 ± 246.3 | 471 ± 89 | 41.9 | 0.81 ± 0.17 | 16.38 ± 1.1 | 0.05 ± 0.01 |
| 50 | 1.05 ± 0.15 | 96 ± 40 | 466.2 ± 105.2 | 569 ± 199 | 60.4 | ND | ND | ND |

[a]$C_{max}$: maximum concentration of the compound detected in plasma. $T_{max}$: time at $C_{max}$. AUC: area under the curve. $t_{1/2}$: terminal half-life. F: oral bioavailability.
[b]Brains and plasma were harvested at or near the $T_{max}$.
Compounds were dosed in a volume of 2 mL/kg p.o. (n = 3-4) at 20 mg/kg in 0.6% Tween 80.
ND = Not Determined.

TABLE 10

In vivo PK data for mGlu2/mGlu3 PAMs in rats after i.v. administration (2 mg/kg).[a]

| Cmpd | $C_{max}$ (µM) | CL (mL*min−1*kg−1) | Vdss (L*kg−1) | $AUC_{(0→t)}$ (µmol/L)*min | $T_{1/2}$ (min) |
|---|---|---|---|---|---|
| 20 | 5.00 ± 0.60 | 21.09 ± 3.66 | 0.81 ± 0.14 | 231.7 ± 42.12 | 30 ± 2 |
| 36 | 3.52 ± 0.13 | 38.78 ± 2.55 | 0.89 ± 0.03 | 123.7 ± 7.7 | 18 ± 3 |
| 44 | 6.43 ± 0.39 | 14.58 ± 1.18 | 0.55 ± 0.04 | 304.6 ± 25.8 | 28 ± 0 |
| 50 | 2.15 ± 0.14 | 58.29 ± 7.98 | 2.87 ± 0.60 | 77.2 ± 8.0 | 57 ± 12 |

[a]$C_{max}$: maximum concentration of the compound detected in plasma.
AUC: area under the curve.
$t_{1/2}$: terminal half-life.
CL: Clearance.
Vdss: steady state volume of distribution.
Compounds were injected in a volume of 1 mL/kg i.v. (n = 3-4) through an i.v. catheter at 2 mg/kg in 0.6% Tween 80 or in 1M NaOH, pH adjusted to ~7.

Example B10

Comprehensive In Vitro Pharmacology

Figure 1B:
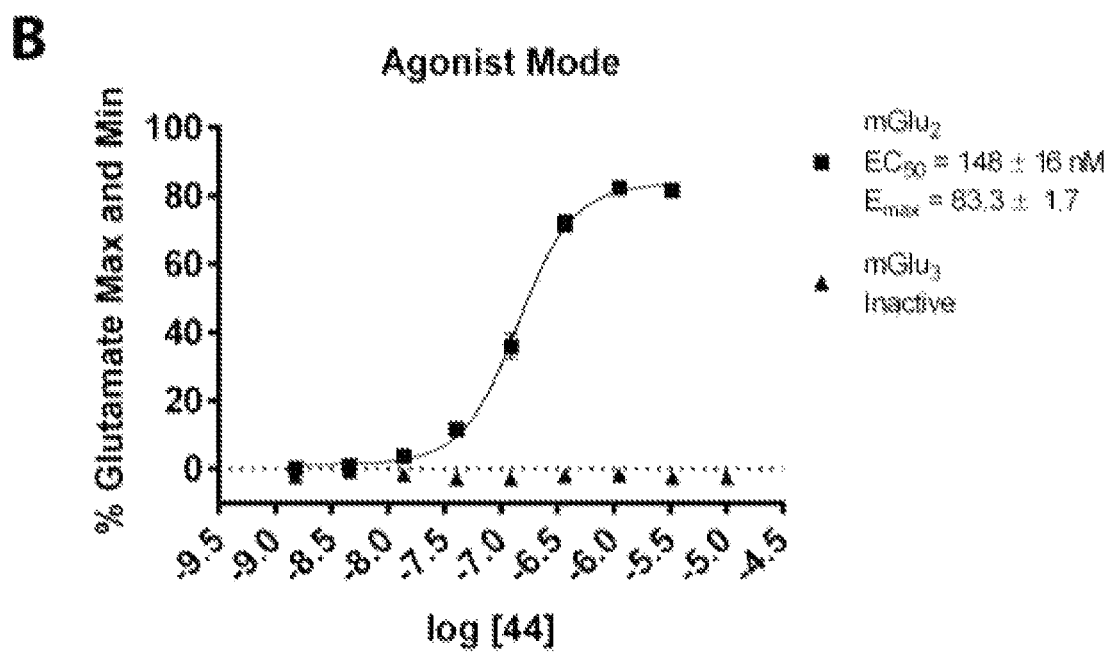
FIG. 1B shows Compound 44 displaying Ago-PAM activity toward mGlu2 and PAM activity toward mGlu3 in a G protein-coupled inwardly rectifying potassium (GIRK) channel thallium-flux assays. A concentration-response of 44 was performed in the absence of an $EC_{20}$ of glutamate in either the mGlu2 GIRK assay (squares) or mGlu3 GIRK assay (triangles).

Compound 44 displays Ago-PAM activity toward mGlu2 and PAM activity toward mGlu3 in GIRK thallium-flux assays. A concentration-response of 44 was performed in the presence (FIG. 1A) and absence (FIG. 1B) of an $EC_{20}$ of glutamate in either the mGlu2 GIRK assay (squares) or mGlu3 GIRK assay (triangles). In the mGlu2 assay, 44 displays both Agonist and PAM activity and is characterized as an Ago-PAM. In the mGlu3 assay, only PAM activity is detected. Data were analyzed using nonlinear regression, activity was immediately monitored. Compound 44 was found to display intrinsic agonist activity towards $mGlu_2$, but not mGlu3 in the GIRK assay (FIG. 1B). Thus, this compound is best characterized as having mGlu2 agonist-PAM activity and mGlu3 PAM activity in the GIRK thallium flux assays.

Figure 2A:
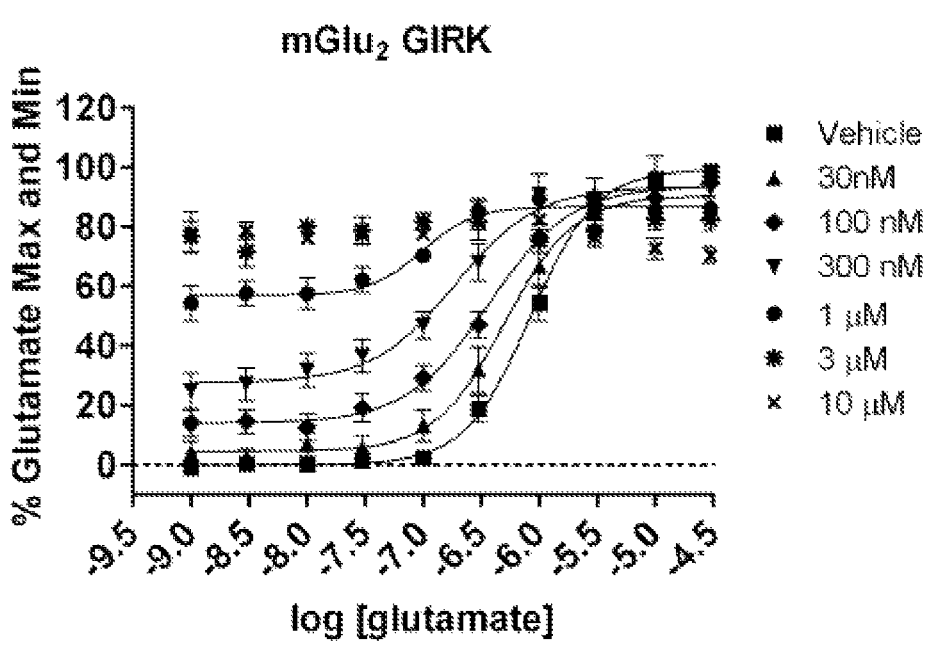
FIG. 2A shows Compound 44 dose-dependently inducing a leftward shift in the glutamate concentration response of mGlu2 in GIRK thallium flux assays.
Figure 2B:
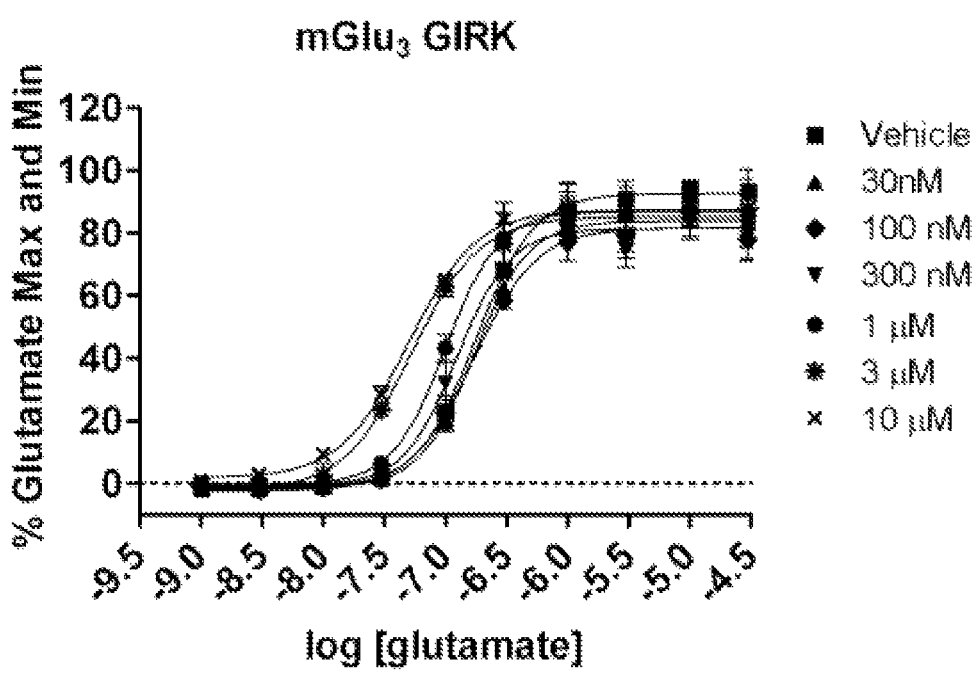
FIG. 2B shows Compound 44 dose-dependently inducing a leftward shift in the glutamate concentration response of mGlu3 in GIRK thallium flux assays.

Compound 44 was evaluated next in a fold-shift assay, another measure of the potentiating activity of a PAM toward the orthosteric ligand glutamate (FIGS. 2A and 2B). Fold-shift values were calculated by determining the ratio of the potency of the orthosteric agonist glutamate in the presence and absence of increasing concentrations of an allosteric modulator. Increasing fixed concentrations of 44 dose-dependently shifted the glutamate concentration-response of mGlu2 (FIG. 2A) and mGlu3 (FIG. 2B) to the left, consistent with an enhancement of glutamate responses. For these assays, the Ago-PAM activity toward mGlu2 is readily apparent as the increase in baseline at low concentrations of glutamate (FIG. 2A). These data are in contrast with the results for mGlu3 (FIG. 2B), which does not show a change in baseline of the glutamate dose-response. The increase in baseline in the mGlu2 GIRK assay at higher concentrations of 44 is due to the Ago-PAM activity of this compound. The leftward shifts induced by 44 indicate a potentiation of the response of mGlu2 and mGlu3 to glutamate. The maximal fold-shift at mGlu2 is 4.50±0.96 and was derived from the test concentration of 44 (300 nM) due to Ago-PAM activity. The maximal fold-shift at mGlu3 is 5.48±0.27 for the 10 µM test concentration. Concentration-response relationships were generated by adding a fixed concentration of 44 to cells as indicated, followed by increasing concentrations of glutamate. Data were analyzed using nonlinear regression, providing $EC_{50}$ values for each curve. Data were obtained from three separate experiments performed in duplicate, normalized to the response to 100 µM glutamate in each experiment, and are expressed as the mean±SEM.

Figure 3A:
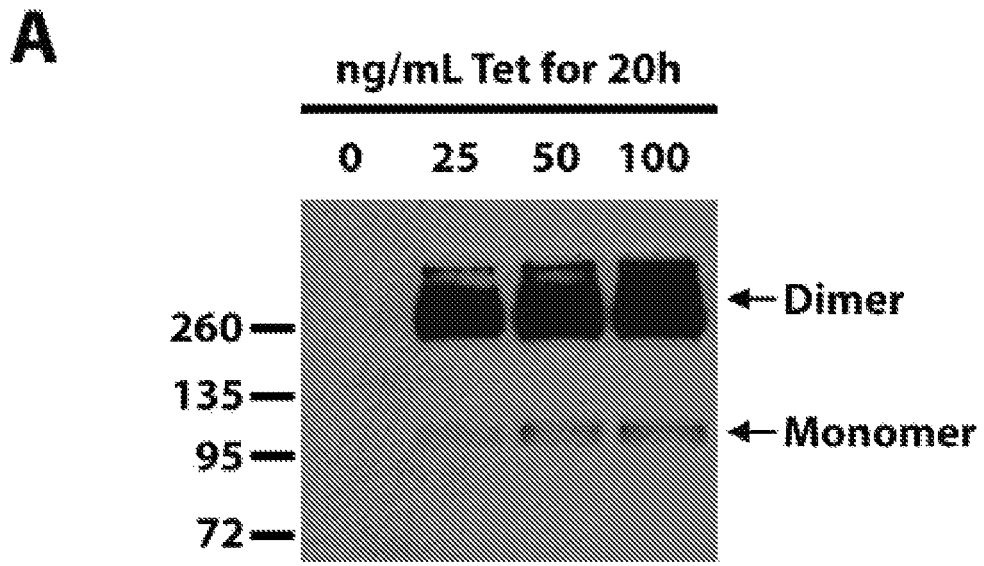
FIG. 3A shows the development of a cell line with inducible mGlu3 expression coupled to calcium mobilization via the promiscuous G protein $G_{\alpha 15}$. mGlu2/3 expression was detected by Western blot.
Figure 3B:
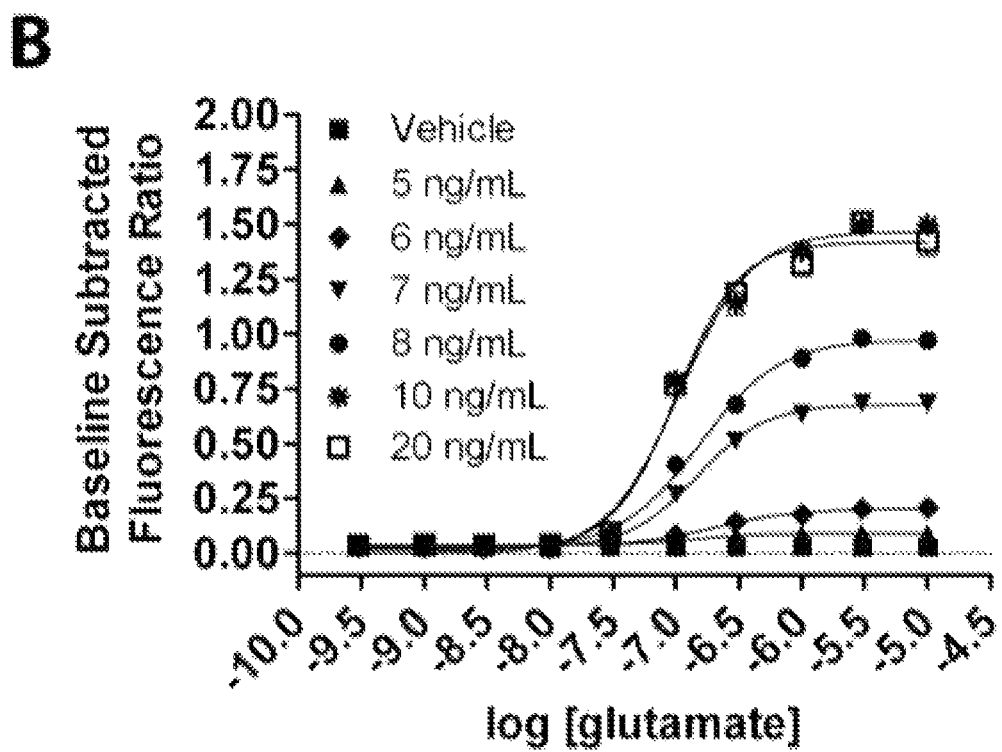
FIG. 3B shows the development of a cell line with inducible mGlu3 expression coupled to calcium mobilization via the promiscuous G protein $G_{\alpha 15}$. Tetracycline dose-dependently induced a glutamate-simulated calcium response.

Compound 44 was evaluated in an orthogonal assay of mGlu3 and mGlu2 activity. For mGlu3 the TREx tetracycline-inducible system (Invitrogen) was utilized. A cell line in which the expression of mGlu3 is dose-dependently induced by tetracycline (Tet) and functionally coupled to calcium mobilization by the promiscuous G protein $G_{\alpha 15}$ (FIGS. 3A and 3B) was developed. In the absence of Tet, no measurable expression of mGlu3 is detected either by Western blot (FIG. 3A) or by functional response to calcium mobilization (FIG. 3B). The optimal calcium mobilization response for this cell line was achieved at 20 ng/mL Tet for 20 h prior to assay. Tet dose-dependently induced a glutamate-simulated calcium response that was maximal at 20 ng/mL Tet. Data were analyzed using nonlinear regression. Data were obtained from three separate experiments performed in triplicate, normalized to the response to 100 µM glutamate in each experiment, and are expressed as the mean±SEM. This concentration of Tet was then utilized for further characterization of 44 in the TREx293 mGlu3 $G_{\alpha 15}$ calcium assay (FIG. 4B), which shows that 44 demonstrates mGlu3 PAM activity in this orthogonal assay whereas the mGlu2 selective PAM BINA remains inactive.

Figure 4A:
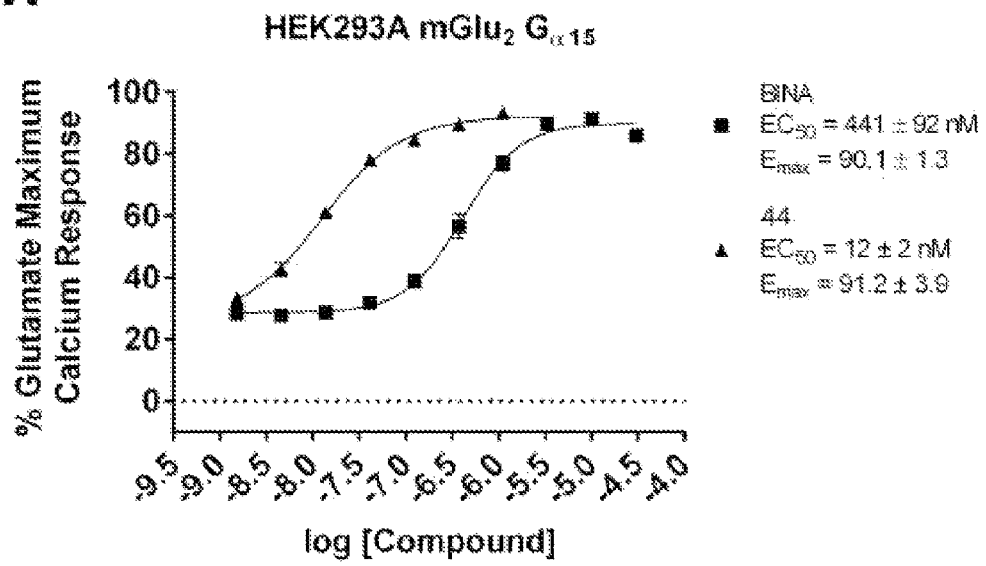
FIG. 4A shows Compound 44 displaying PAM activity toward mGlu2 and mGlu3 in calcium assays utilizing the promiscuous G protein $G_{\alpha 15}$. A concentration-response of 44 (triangles) and the control mGlu2 selective PAM BINA (squares) was performed in the presence of an $EC_{20}$ of glutamate in the HEK293A mGlu2 $G_{\alpha 15}$ calcium assay.
Figure 4B:
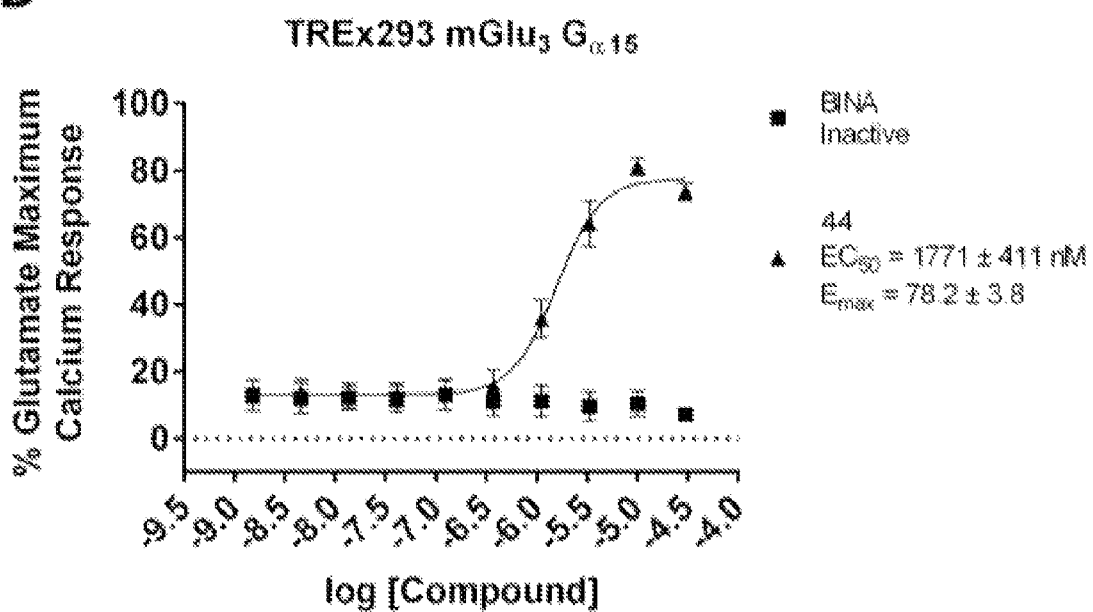
FIG. 4B shows Compound 44 displaying PAM activity toward mGlu2 and mGlu3 in calcium assays utilizing the promiscuous G protein $G_{\alpha 15}$. A concentration-response of 44 (triangles) and the control mGlu2 selective PAM BINA (squares) was performed in the presence of an $EC_{20}$ of glutamate in the TREx293 mGlu3 $G_{\alpha 15}$ calcium assay.

Compound 44 and BINA were also evaluated in calcium assays utilizing HEK293A mGlu2 $G_{\alpha 15}$ cells as shown in FIG. 4A. Unlike in the mGlu2 GIRK assay where it displays Ago-PAM activity, compound 44 behaves as a PAM in the calcium assay. Compound 44 displays PAM activity toward mGlu2 and mGlu3 in calcium assays utilizing the promiscuous G protein $G_{\alpha 15}$. A concentration-response of 44 (triangles) and the control mGlu2 selective PAM BINA (squares) was performed in the presence of an $EC_{20}$ of glutamate in either the (FIG. 4A) HEK293A mGlu2 $G_{\alpha 15}$ calcium assay or (FIG. 4B) TREx293 mGlu3 $G_{\alpha 15}$ calcium assay. In both assays, 44 displays PAM activity. BINA displays PAM activity in the mGlu2 calcium assay but is inactive in the mGlu3 calcium assay. For this assay, mGlu3 expression was induced with 20 ng/mL Tet for 20 h prior to assay. Data were analyzed using nonlinear regression, providing $EC_{50}$ values for each curve. Data were obtained from three separate experiments performed in triplicate, normalized to the response to 100 µM glutamate in each experiment, and are expressed as the mean±SEM.

Example B11

Efficacy Studies in Rat

A member of this series was evaluated in efficacy studies in rats. Given the low brain levels achieved by p.o. dosing for compounds 20, 36, 44, and 50 nine compounds were evaluated by intraperitoneal (i.p.) dosing in order to avoid first pass metabolism and to cast a wider net for a compound suitable for rat efficacy studies (Table 11). All compound plasma levels were determined, but only those with the highest plasma concentrations (i.e. 44, 73, 74, and 75) were evaluated for brain levels. Based on its combination of potency, selectivity, and PK properties, compound 74 was selected for efficacy studies in rats.

TABLE 11

In vivo PK for mGlu2 PAMs in rats following i.p. administration (10 mg/kg)[a]

| Cmpd ID | Plasma (µM)[a] | Plasma $t_{1/2}$ (min) | Brain (µM)[a] | Brain: Plasma |
|---|---|---|---|---|
| 44 | 10.57 ± 2.52 | 43 | 0.23 ± 0.10 | 0.03 ± 0.01 |
| 50 | 3.29 ± 1.27 | 20 | ND | ND |
| 60 | 4.49 ± 0.49 | 22 | ND | ND |
| 65 | 5.44 ± 2.92 | 30 | ND | ND |
| 68 | 2.18 ± 0.58 | 28 | ND | ND |
| 72 | 2.44 ± 2.19 | 27 | ND | ND |
| 73 | 6.81 ± 0.84 | 132 | 0.47 ± 0.35 | 0.02 ± 0.01 |
| 74 | 17.05 ± 0.19 | 106 | 0.56 ± 0.10 | 0.03 ± 0.01 |
| 75 | 6.52 ± 0.54 | 80 | 0.22 ± 0.04 | 0.01 ± 0.01 |

[a]Maximum concentration of the compound detected in plasma or brain.
$t_{1/2}$: terminal half-life.
Compounds were dosed i.p. (n = 3) at 10 mg/kg in 10% EtOH/1% Tween 80, pH adjusted to ~7.
Brains and plasma were harvested at the $T_{max}$ (30 min for all tested).
ND = Not Determined.

Example B12

Behavioral Assessments

Subjects. Male Wistar rats (Charles River Laboratories, Raleigh, N.C.) weighing 300-350 g at the beginning of each experiment were housed in pairs in standard rat Plexiglas cages with food and water available ad libitum, except during food training and the food self-administration experiment (see below). Rats were maintained in a climate-controlled room at 21° C. on a 12 h reverse light/dark cycle and all experiments were conducted during the dark (i.e., active) phase (7:00 h-19:00 h) of the cycle under dim red lighting. All procedures were conducted in accordance with the guidelines from the National Institutes of Health and the Association for the Assessment and Accreditation of Laboratory Animal Care and were approved by the Institutional Animal Care and Use Committee.

Drugs. Cocaine hydrochloride (National Institute on Drug Abuse, Bethesda, Md.) was dissolved in sterile physiological saline and filtered through a 0.22 µm syringe filter (Fisher Scientific, Pittsburgh, Pa.) for sterilization purposes. Compound 74 was mixed into a 10% EtOH, 1% Tween 80 solution.

Food Training. Details regarding the experimental procedures have been described previously.[37] All rats were placed under food restriction (20 g food/day) and trained during daily 1 hr sessions to lever press for 45 mg food pellets (Research Diets, New Brunswick, N.J.) under a fixed ratio 1 reinforcement schedule with a 1 s time-out period (FR1

TO1s). Successful responses were followed by illumination of a cue light for the duration of the time-out period, when lever presses had no consequence. Successful acquisition of food responding, defined as earning 100 pellets during each session, resulted in progression of the training program to FR1 TO10s and FR1 TO20s. Training lasted approximately 5 days.

Cocaine Self-Administration Experiment. After successful acquisition of food training, rats (n=11) were fed ad libitum, surgically prepared with intravenous catheters inserted into the right jugular vein under isoflurane anesthesia (1-1.5% isoflurane/oxygen mixture) and allowed 7 days to recover (see Jin et al. 2010 for details). Rats were then trained to self-administer cocaine under a FR1 TO20s reinforcement schedule during daily 1 hr sessions. Each response at the active lever resulted in an intravenous infusion of cocaine (0.5 mg/kg/infusion) over a 2 s period in a volume of 0.05 μl. Rats were trained for approximately 10 days until responding for cocaine stabilized (i.e., >10 infusions/session; <20% variability in number of infusions over three consecutive sessions). After stabilization of responding, rats were administered Compound 74 (0, 10, 20, 40 mg/kg; i.p.; 3 ml/kg volume; 60 min pretreatment time) according to a within-subjects Latin-square design. At least 4 days elapsed between drug/vehicle injections to re-establish stable self-administration behavior (<20% variability over three consecutive sessions).

Food Self-Administration Experiment. To assess non-specific actions of Compound 74, after successful acquisition of food training and stabilization of responding (<20% variability over three consecutive sessions), rats (n=8) were administered Compound 74 (0, 10, 20, 40 mg/kg; i.p.; 3 ml/kg volume; 60 min pretreatment time) according to a within-subjects Latin-square design. All test parameters, including the FR1 TO20s reinforcement schedule, were identical to the parameters under which cocaine was self-administered.

Statistical Analyses. The number of cocaine infusions/food pellets earned during test sessions with Compound 74 was calculated as a percentage of the average number of infusions/pellets earned during the prior 3 baseline sessions. Data were then analyzed with a mixed design analysis of variance (ANOVA) with Compound 74 dose (within-subjects) and self-administration (i.e., cocaine vs. food; between-subjects) as factors. Significant effects were further analyzed with Tukey post hoc tests. The level of significance was set at α=0.05.

Figure 5:
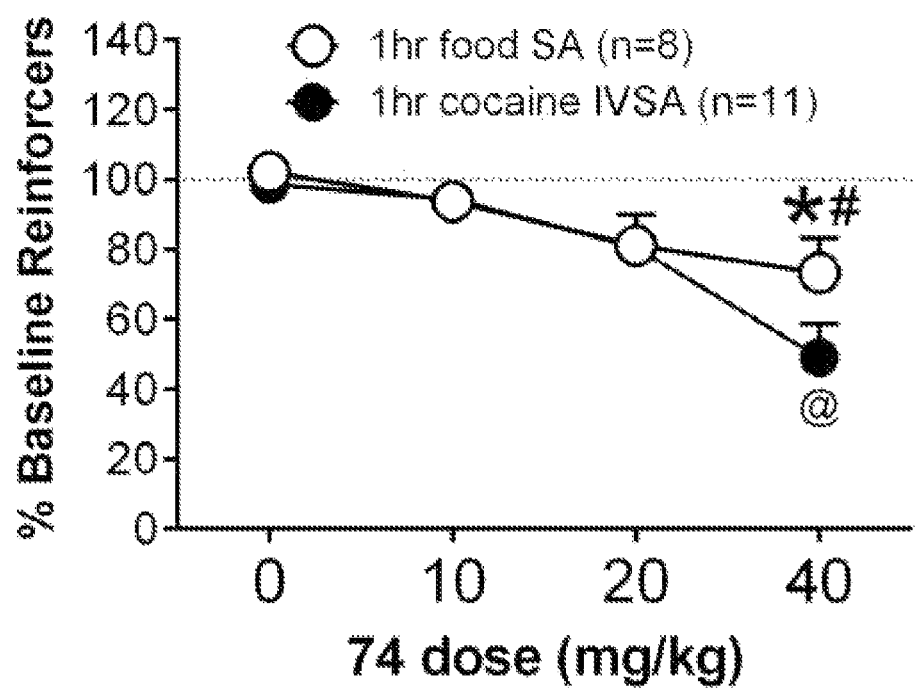
FIG. 5 shows Compound 74 decreasing cocaine-maintained responding, and to a lesser extent food-maintained responding, in rats. At the highest dose tested (40 mg/kg), cocaine-maintained responding was significantly lower than food-maintained responding. The 40 mg/kg dose decreased responding for food compared to vehicle only, whereas the same dose decreased responding for cocaine compared to all other doses tested.

When assessed in vivo, compound 74 dose-dependently decreased cocaine- and food-maintained responding [compound 74 dose main effect: $F_{3,51}$=14.55; p<0.0001]. However, cocaine-maintained responding was decreased to a greater extent than food-maintained responding at the highest dose tested (40 mg/kg; p<0.05) (See FIG. 5). Due to the within-subjects design of the dose response (i.e., each rat received each dose of compound 74 using a Latin-square design), it was not possible to collect brain samples to determine brain concentrations of compound 74 at 40 mg/kg during behavioral testing. It is unlikely that brain concentrations of compound 74 differed between cocaine- and food-maintained rats at this dose, suggesting that the observed differences in behavior were not a function of group differences in brain pharmacokinetic properties of compound 74. The mGlu2/3 receptor agonist LY379268 has previously been shown to similarly decrease both cocaine- and food-maintained responding (Jin, X. et al. *Neuropsychopharmacology* 2010, 35, 2021-2036). Moreover, the selective mGlu2 receptor PAM BINA decreased only cocaine-maintained responding while having no effect on food-maintained responding. Morishima et al. have demonstrated that mGlu2 receptor knockout mice exhibited increased conditioned place preference for cocaine (Morishima, Y. et al. *Proc. Natl. Acad. Sci. U.S.A* 2005, 102, 4170-4175). While these prior studies focused only on the role of mGlu2 receptors in responding for drug and natural rewards, the present findings begin to delineate the individual roles of mGlu2 and mGlu3 receptors in reward processing. These patterns of results possibly suggest that activation of mGlu2 receptors selectively modulates drug-reinforced behavior, whereas activation of mGlu3 receptors either selectively modulates responding for natural rewards or non-selectively modulates responding for both drug and natural rewards. Use of an mGlu2/3 receptor PAM, as reported herein, provides an initial tool by which to indirectly test these hypotheses. Moreover, increasing mGlu2/3 receptor activity using a PAM compared to a receptor agonist may affect behaviors reinforced by natural rewards to a lesser extent relative to drug-reinforced behaviors. Thus, targeting mGlu2 receptors with a PAM may be an effective strategy for treating drug dependence without affecting other motivated behaviors.

What is claimed is:

1. A compound, or a pharmaceutically acceptable salt thereof, having the structure of formula (I):

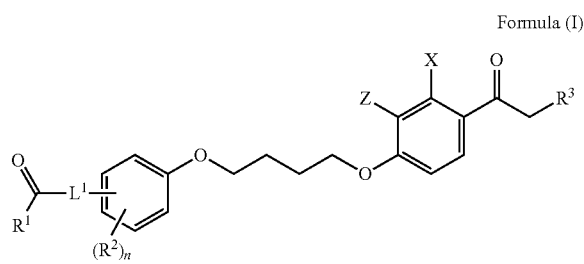

Formula (I)

wherein:
$R^1$ is —OH, —NHOR$^5$, —NHSO$_2$R$^4$, —NR$^4$R$^5$ or R$^4$;
$L^1$ is absent;
$R^2$ is hydrogen, halogen, nitro, —CN, —OH, —OR$^4$, substituted or unsubstituted $C_1$-$C_6$alkyl, substituted or unsubstituted $C_1$-$C_6$fluoroalkyl, or substituted or unsubstituted $C_3$-$C_6$cycloalkyl;
n is 0, 1, 2, 3, or 4;
$R^3$ is substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;
X is —OH, —OR$^4$, halogen, substituted or unsubstituted $C_1$-$C_6$alkyl, substituted or unsubstituted $C_1$-$C_6$fluoroalkyl, or substituted or unsubstituted $C_3$-$C_6$cycloalkyl;
Z is —OH, —OR$^4$, halogen, substituted or unsubstituted $C_1$-$C_6$alkyl, substituted or unsubstituted $C_1$-$C_6$fluoroalkyl, or substituted or unsubstituted $C_3$-$C_6$cycloalkyl;
$R^4$ is substituted or unsubstituted $C_1$-$C_6$alkyl, substituted or unsubstituted $C_3$-$C_6$cycloalkyl substituted or unsubstituted aryl or substituted or unsubstituted heteroaryl; and
$R^5$ is hydrogen, substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;

or $R^4$ and $R^5$ taken together with the nitrogen to which they are attached to form a substituted or unsubstituted $C_2$-$C_8$heterocycloalkyl.

2. The compound of claim 1, or a pharmaceutically acceptable salt thereof, wherein:

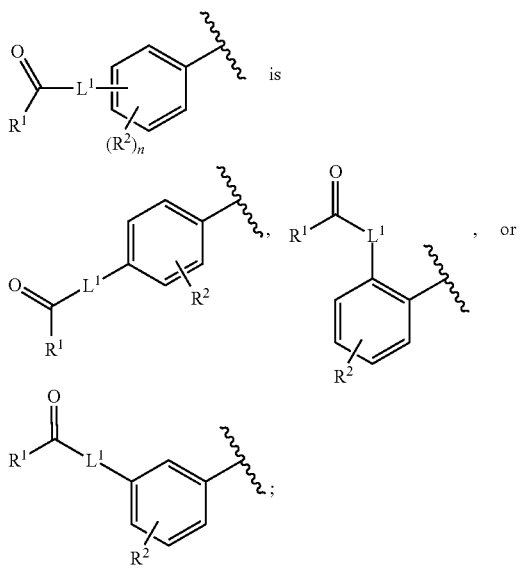

$L^1$ is absent; and
Z is halogen, or $C_1$-$C_6$alkyl.

3. The compound of claim 2, or a pharmaceutically acceptable salt thereof, wherein:
$L^1$ is absent; and
Z is —$CH_3$, or —$CH_2CH_3$.

4. The compound of claim 1, or a pharmaceutically acceptable salt thereof, having the structure of formula (Ia) or formula (Ib):

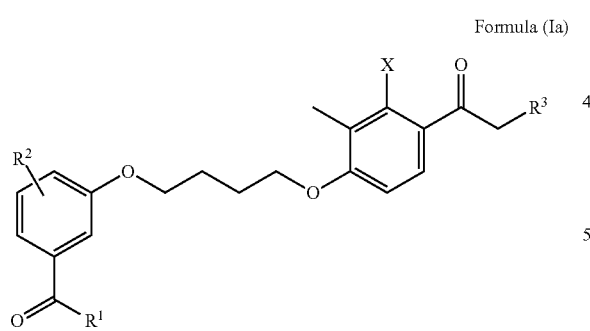

Formula (Ia)

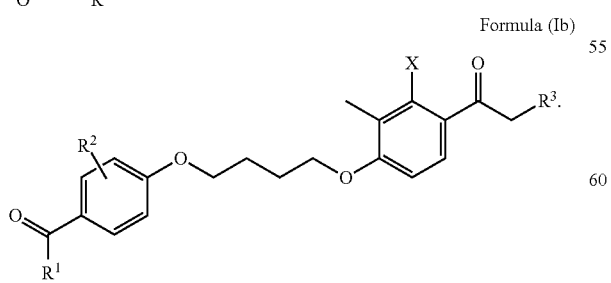

Formula (Ib)

5. The compound of claim 4, or a pharmaceutically acceptable salt thereof, wherein:

$R^1$ is —OH or —$NR^4R^5$;

X is —OH, —$OR^4$, $C_1$-$C_6$alkyl, or $C_1$-$C_6$fluoroalkyl;

$R^2$ is hydrogen, halogen, —CN, —OH, —$OR^4$, substituted or unsubstituted $C_1$-$C_6$alkyl, or substituted or unsubstituted $C_1$-$C_6$fluoroalkyl; and $R^3$ is $C_1$-$C_6$alkyl, or $C_3$-$C_6$cycloalkyl.

6. The compound of claim 5, or a pharmaceutically acceptable salt thereof, wherein:
$R^3$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, cyclopropyl, cyclobutyl, cyclopentyl, or cyclohexyl.

7. The compound of claim 6, or a pharmaceutically acceptable salt thereof, wherein:
$R^1$ is —OH;
$R^2$ is F, Cl, —$CH_3$, or —$OCH_3$;
X is —OH; and
$R^3$ is —$CH(CH_3)_2$, —$C(CH_3)_3$, or cyclopentyl.

8. The compound of claim 1, or a pharmaceutically acceptable salt thereof, selected from the group consisting of:

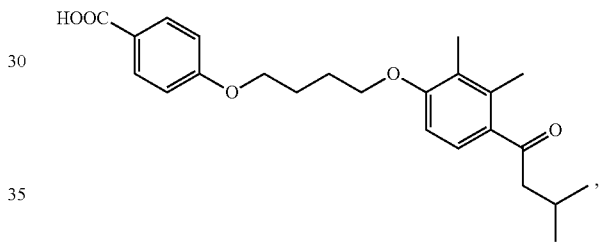

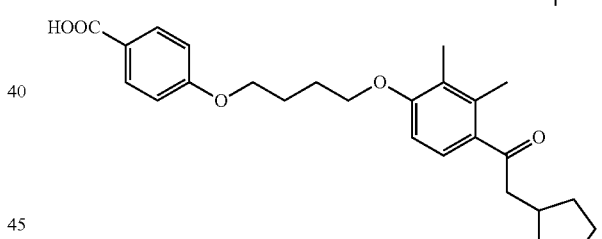

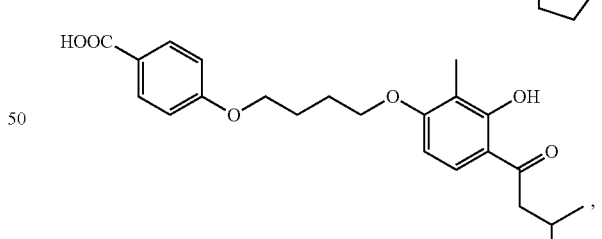

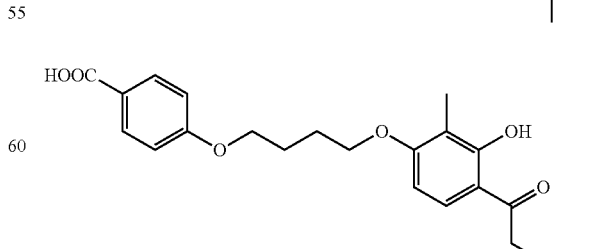

187
-continued
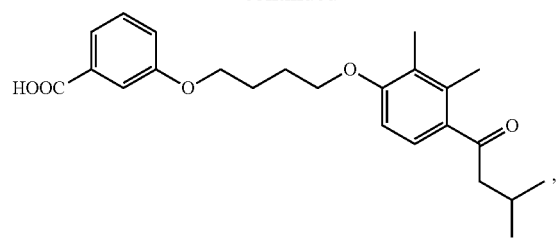
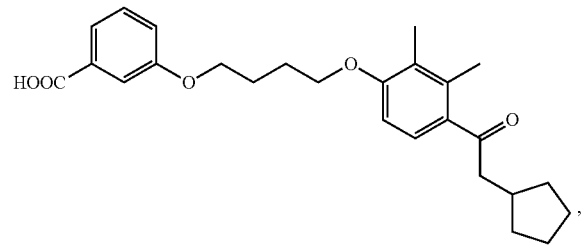
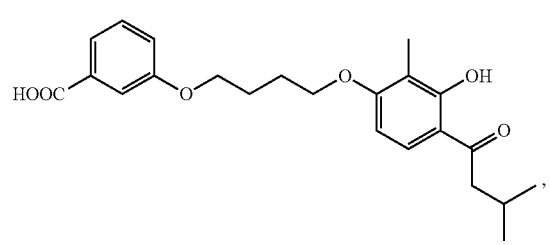
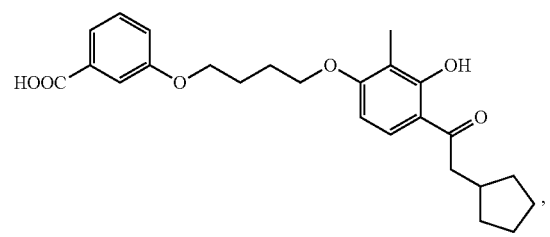
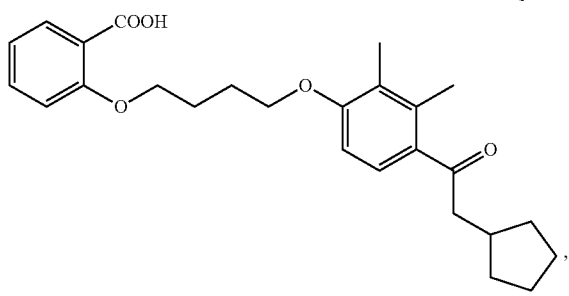
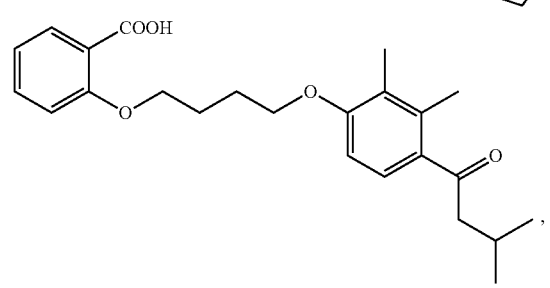
188
-continued
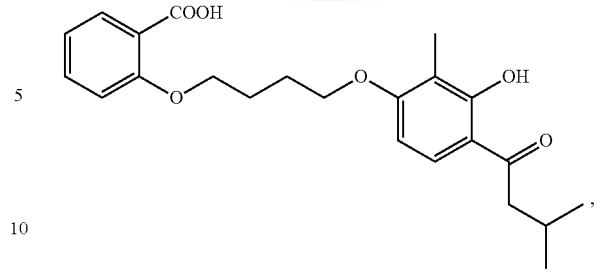
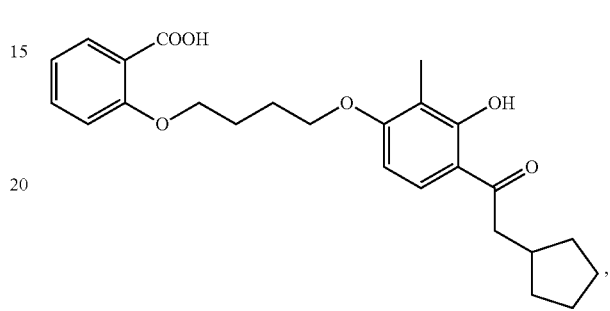
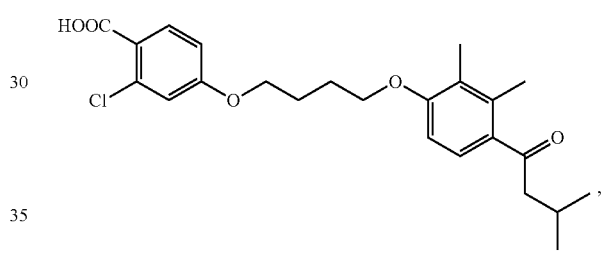
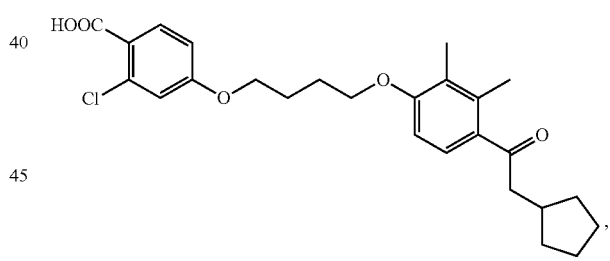
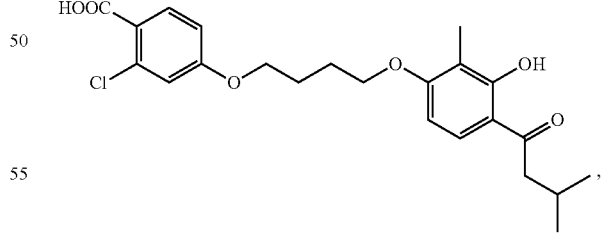
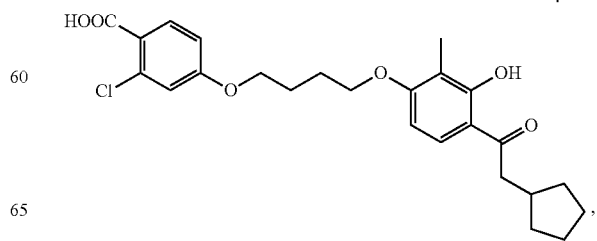

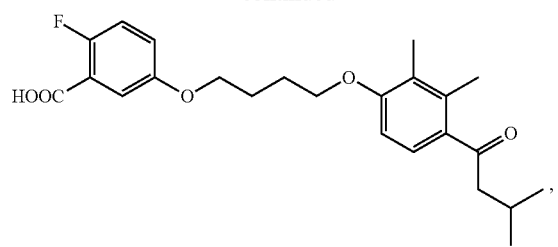
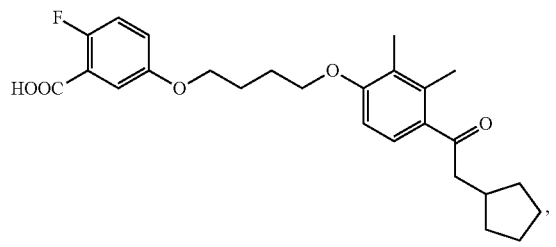
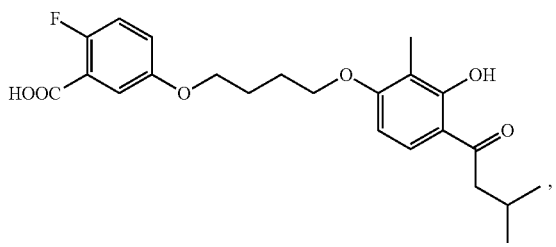
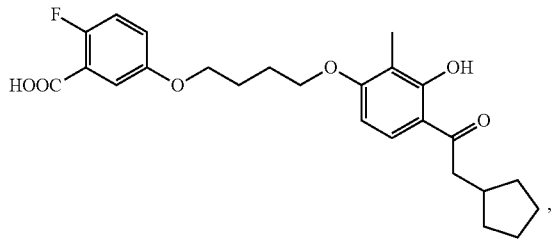
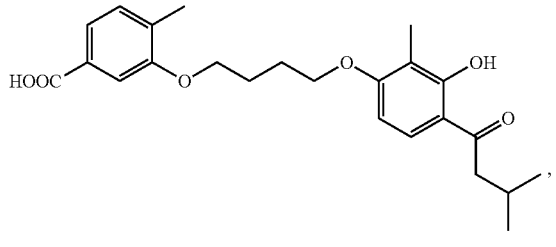
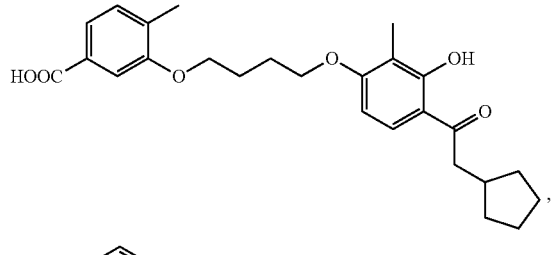
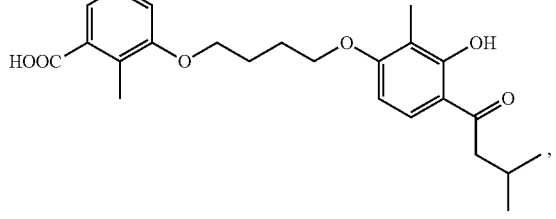
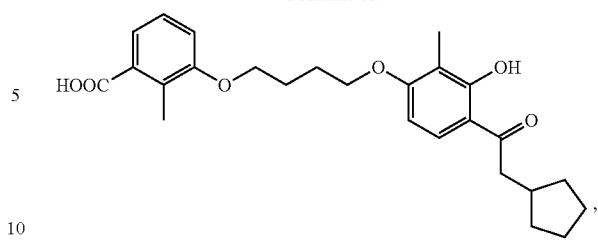
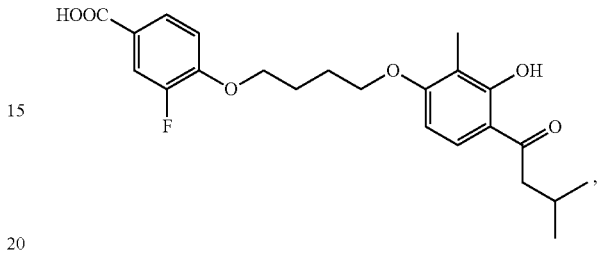
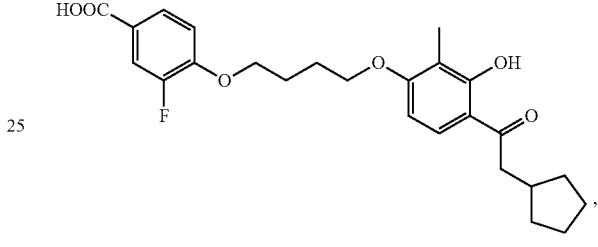
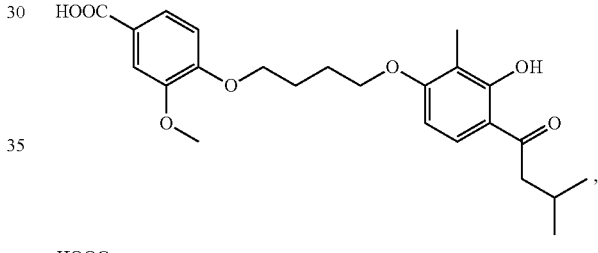
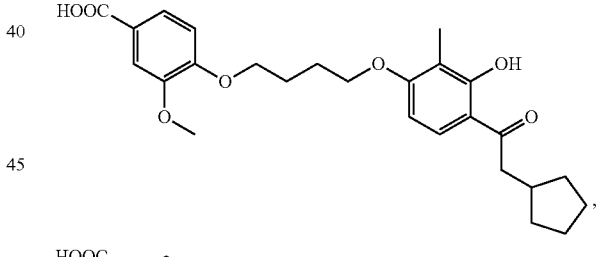
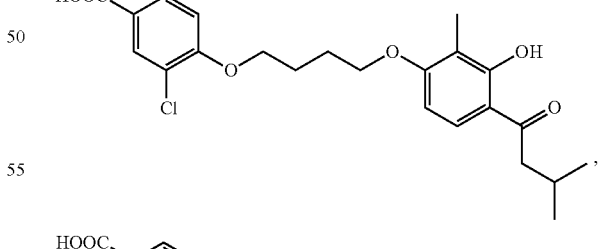
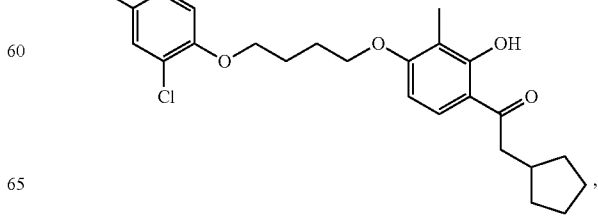

191
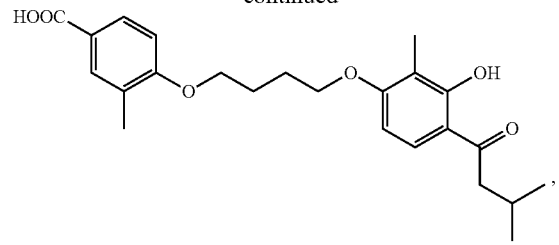
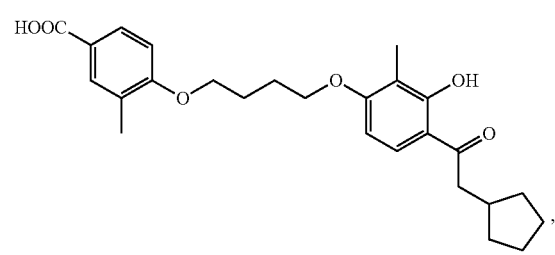
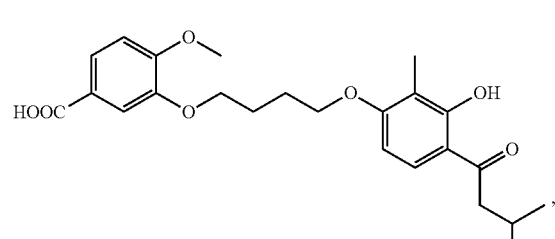
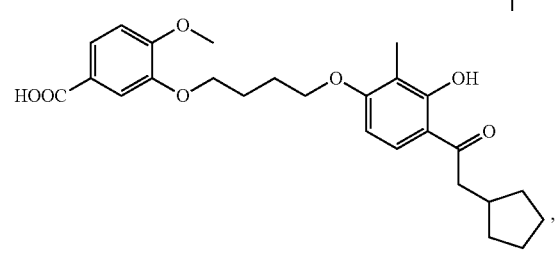
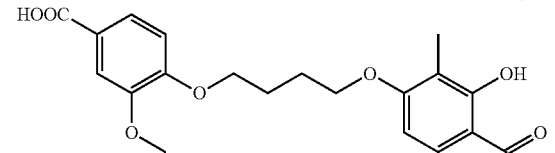
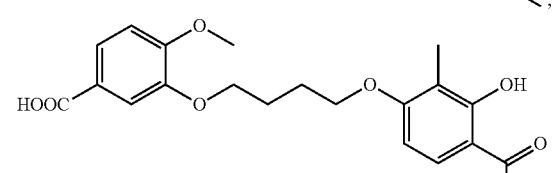
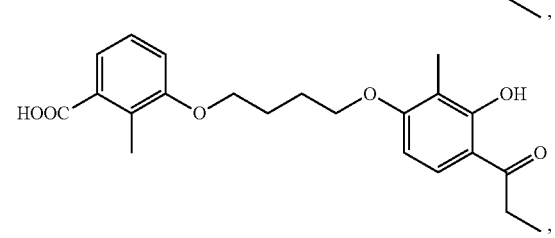
192
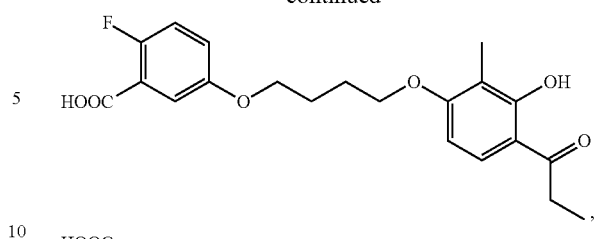
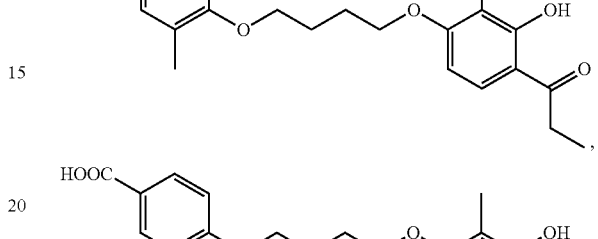
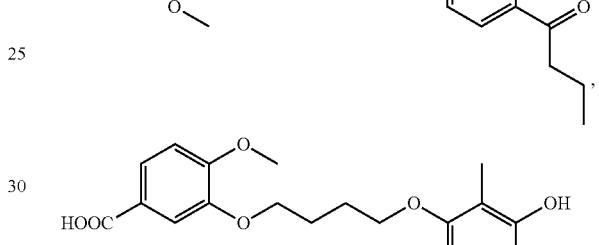
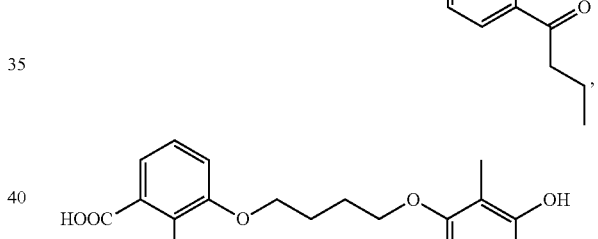
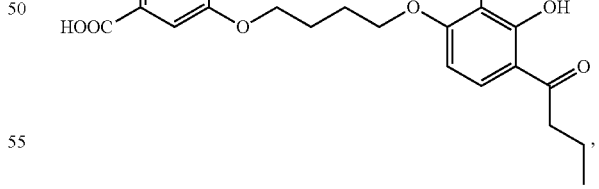
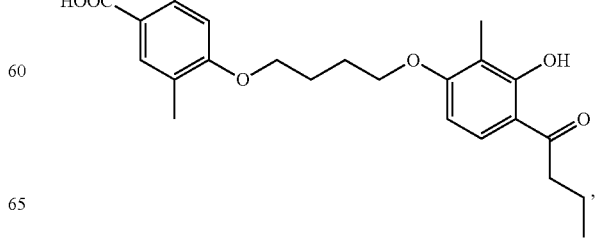

-continued
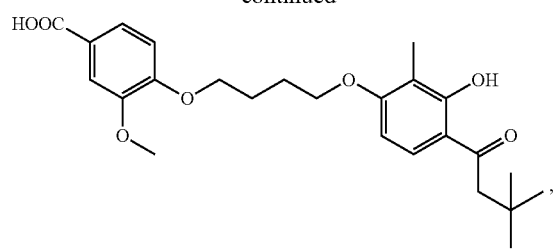
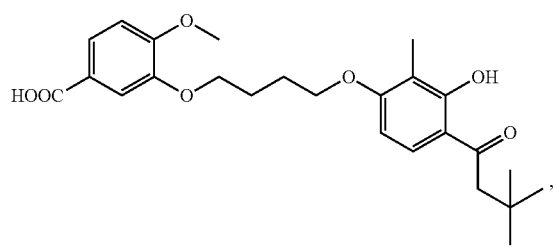
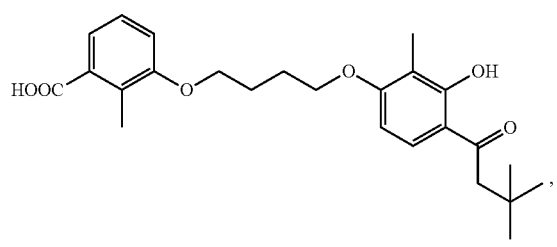
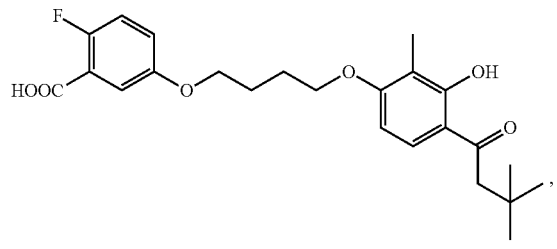
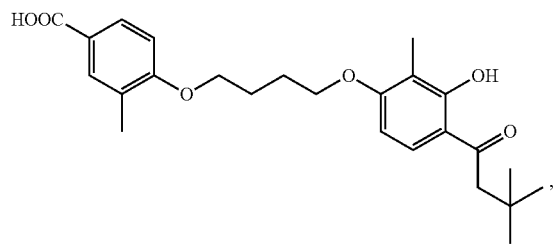
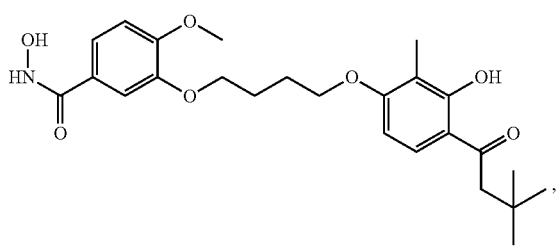
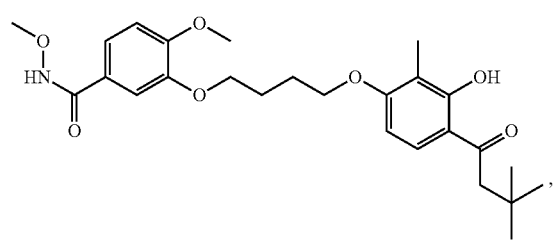
-continued
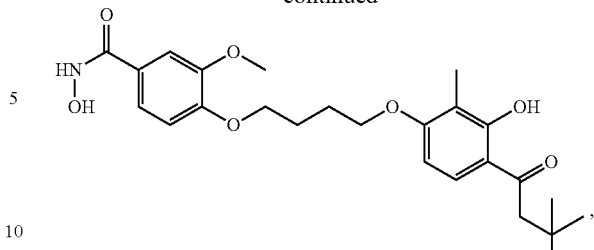
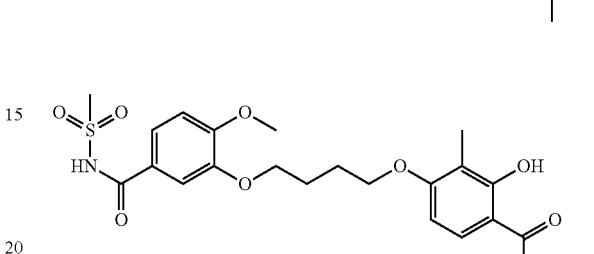
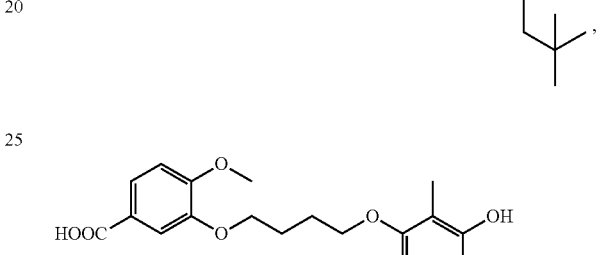
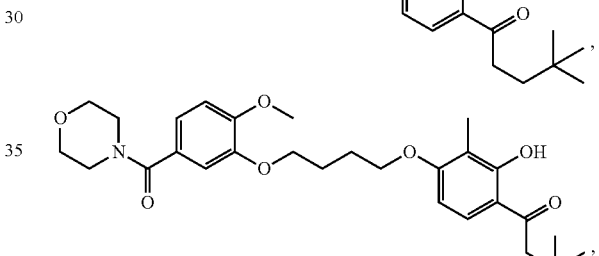
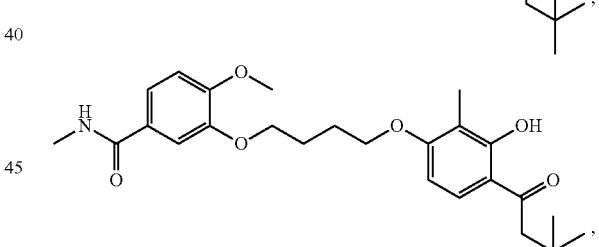
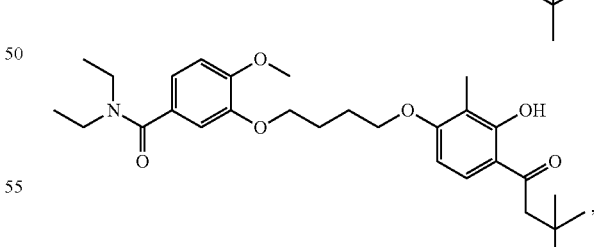
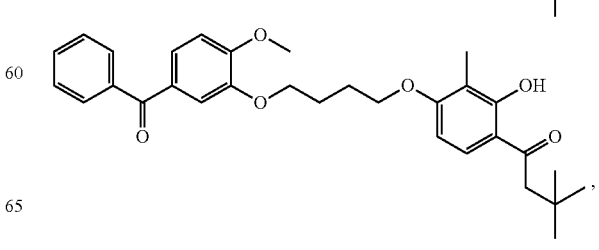

-continued

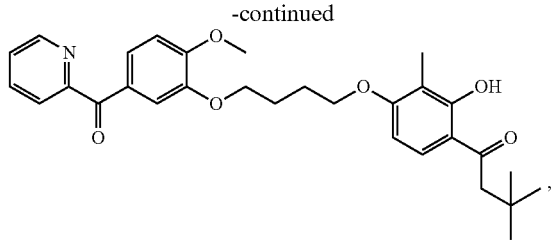

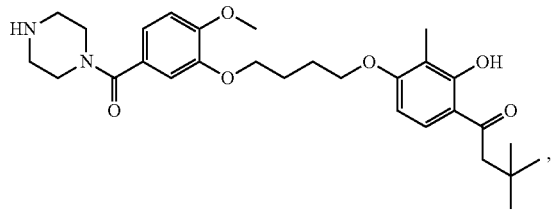

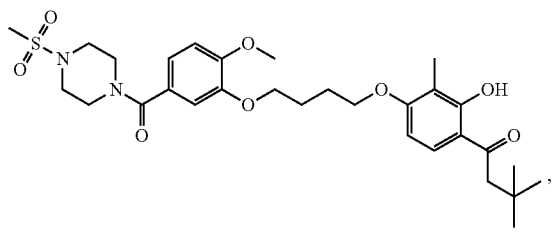

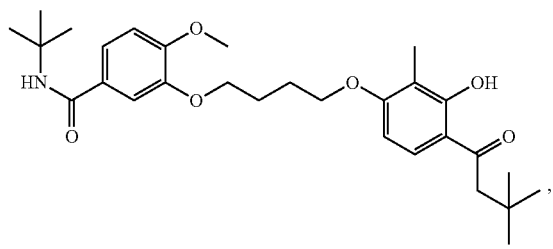

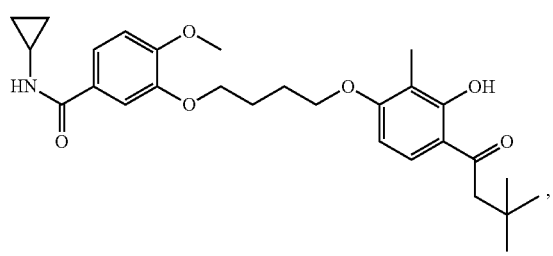

and

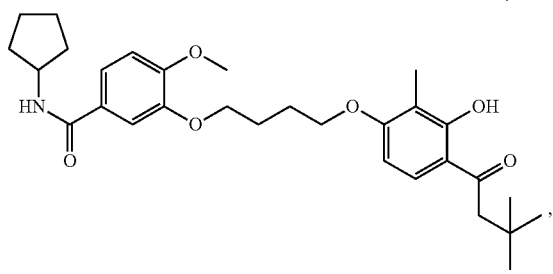

-continued

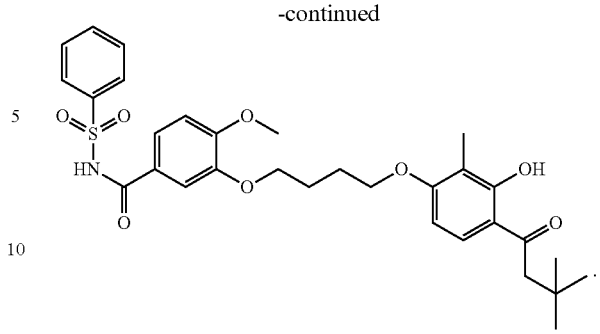

9. A compound, or a pharmaceutically acceptable salt thereof, having the structure of formula (II):

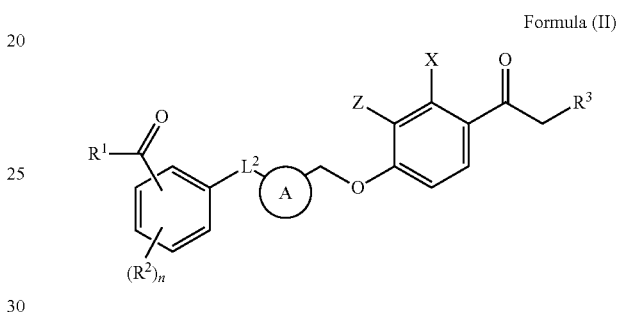

Formula (II)

wherein:
R¹ is —OH, —OR⁴, —NHOR⁵, —NHSO₂R⁴, —NR⁴R⁵ or R⁴;
or —C(=O)R¹ is a carboxylic acid bioisostere having the structure

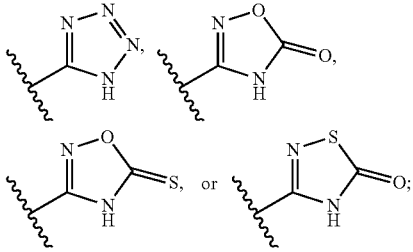

Ring A is a substituted or unsubstituted monocyclic 5-, or 6- heteroaryl selected from the group consisting of: furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl;

L² is absent, —O—(C₁-C₆alkylene)—, —S—, or —S—(C₁-C₆alkylene)—;

R² is hydrogen, halogen, nitro, —CN, —OH, —OR⁴, substituted or unsubstituted C₁-C₆alkyl, substituted or unsubstituted C₁-C₆fluoroalkyl, or substituted or unsubstituted C₃-C₆cycloalkyl;

n is 0, 1, 2, 3, or 4;

R³ is substituted or unsubstituted C₁-C₆alkyl, substituted or unsubstituted C₁-C₆fluoroalkyl, substituted or unsubstituted C₃-C₆cycloalkyl, or substituted or unsubstituted aryl;

X is —OH, —OR⁴, halogen, substituted or unsubstituted $C_1$-$C_6$alkyl, substituted or unsubstituted $C_1$-$C_6$fluoroalkyl, or substituted or unsubstituted $C_3$-$C_6$cycloalkyl;

Z is halogen, or $C_1$-$C_6$alkyl;

$R^4$ is substituted or unsubstituted $C_1$-$C_6$alkyl, substituted or unsubstituted $C_3$-$C_6$cycloalkyl substituted or unsubstituted aryl, or substituted or unsubstituted heteroaryl; and $R^5$ is hydrogen, substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;

or $R^4$ and $R^5$ taken together with the nitrogen to which they are attached to form a substituted or unsubstituted $C_2$-$C_8$heterocycloalkyl.

10. The compound of claim 9, or a pharmaceutically acceptable salt thereof, wherein:

Z is —$CH_3$, or —$CH_2CH_3$; and $L^2$ is absent, —O—($CH_2$)—, or —S—($CH_2$)—.

11. A compound, or a pharmaceutically acceptable salt thereof, having the following structure:

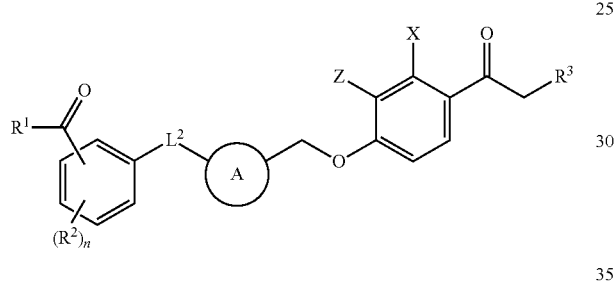

wherein:

$R^1$ is —OH, —OR⁴, —NHOR⁵, —NHSO₂R⁴, —NR⁴R⁵ or $R^4$;

or —C(=O)$R^1$ is a carboxylic acid bioisostere having the structure

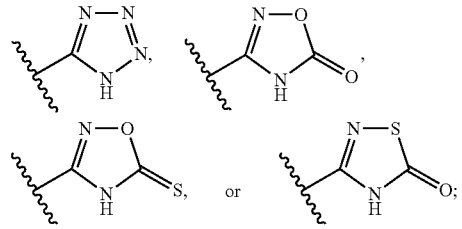

Ring A is selected from a group consisting of:

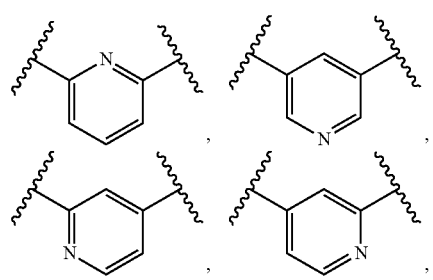

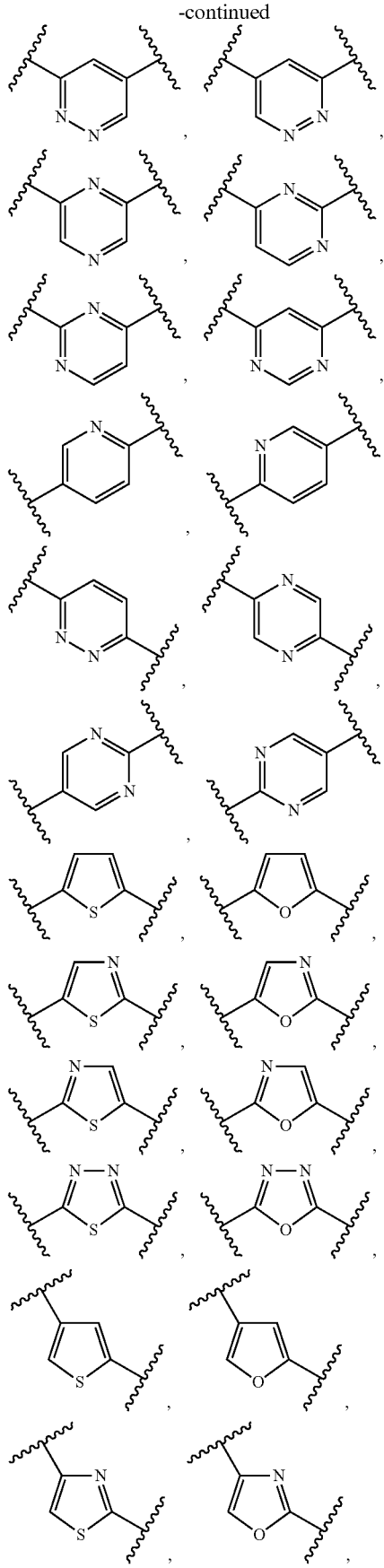

-continued

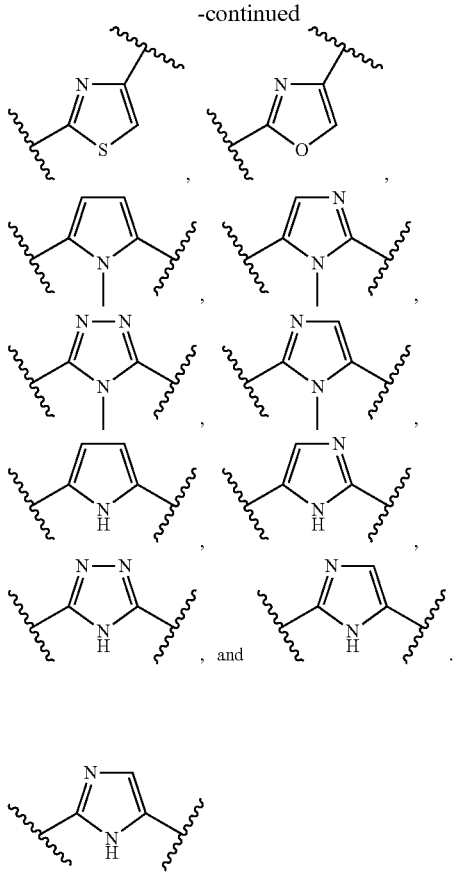

, and

L² is absent, —O—(CH₂)—, or —S—(CH₂)—;
R² is hydrogen, halogen, nitro, —CN, —OH, —OR⁴, substituted or unsubstituted $C_1$-$C_6$alkyl, substituted or unsubstituted $C_1$-$C_6$fluoroalkyl, or substituted or unsubstituted $C_3$-$C_6$cycloalkyl;
n is 0, 1, 2, 3, or 4;
R³ is substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;
X is —OH, —OR⁴, halogen, substituted or unsubstituted $C_1$-$C_6$alkyl, substituted or unsubstituted $C_1$-$C_6$fluoroalkyl, or substituted or unsubstituted $C_3$-$C_6$cycloalkyl;
Z is —CH₃, or —CH₂CH₃;
R⁴ is substituted or unsubstituted $C_1$-$C_6$alkyl, substituted or unsubstituted $C_3$-$C_6$cycloalkyl substituted or unsubstituted aryl, or substituted or unsubstituted heteroaryl; and
R⁵ is hydrogen, substituted or unsubstituted $C_1$-$C_6$alkyl, substituted or unsubstituted $C_1$-$C_6$fluoroalkyl, substituted or unsubstituted $C_3$-$C_6$cycloalkyl, or substituted or unsubstituted aryl;
or R⁴ R⁵ taken together with the nitrogen to which they are attached to form a substituted or unsubstituted $C_2$-$C_8$heterocycloalkyl.

12. The compound of claim 11, or a pharmaceutically acceptable salt thereof, wherein:
R¹ is —OH, —OCH₃, —OCH₂CH₃, or —N(R⁴R⁵);
X is —OH, —OR⁴, $C_1$-$C_6$alkyl, or $C_1$-$C_6$fluoroalkyl;
R² is hydrogen, halogen, —CN, —OH, —OR⁴, substituted or unsubstituted $C_1$-$C_6$alkyl, or substituted or unsubstituted $C_1$-$C_6$fluoroalkyl; and
R³ is $C_1$-$C_6$alkyl, or $C_3$-$C_6$cycloalkyl.

13. The compound of claim 12, or a pharmaceutically acceptable salt thereof, wherein:
R² is F, Cl, —CH₃, or —OCH₃; and
R³ is —CH₃, —CH₂CH₃, —CH₂CH₂CH₃, —CH(CH₃)₂, —CH₂CH₂CH₂CH₃, —CH(CH₃)CH₂CH₃, —CH₂CH(CH₃)₂, —C(CH₃)₃, cyclopropyl, cyclobutyl, cyclopentyl, or cyclohexyl.

14. The compound of claim 13, or a pharmaceutically acceptable salt thereof, wherein:
R³ is —CH(CH₃)₂, —C(CH₃)₃, or cyclopentyl.

15. The compound of claim 11, or a pharmaceutically acceptable salt thereof, selected from the group consisting of:

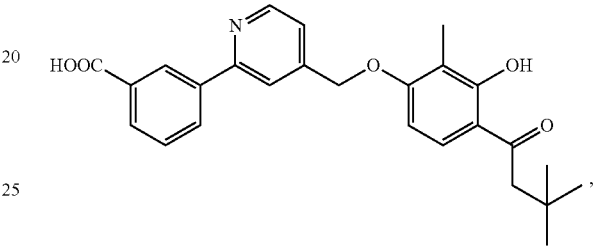

,

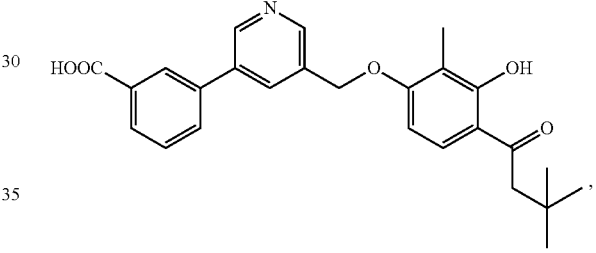

,

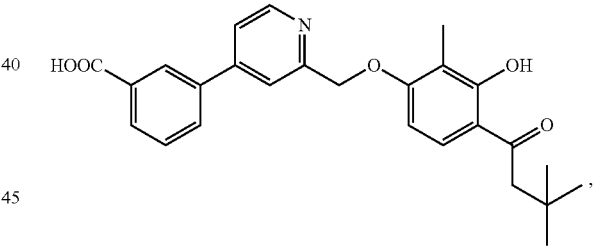

,

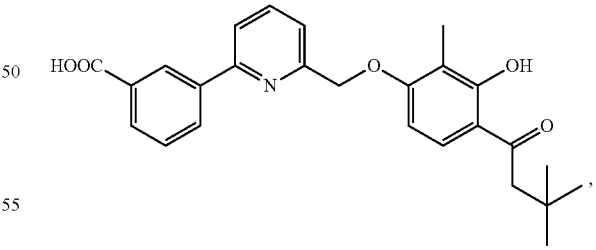

,

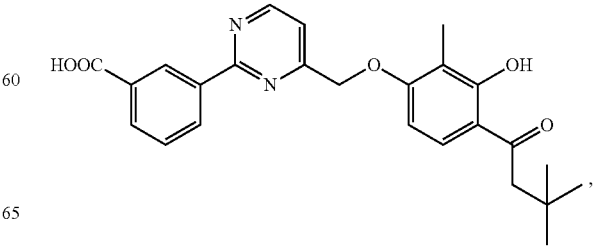

,

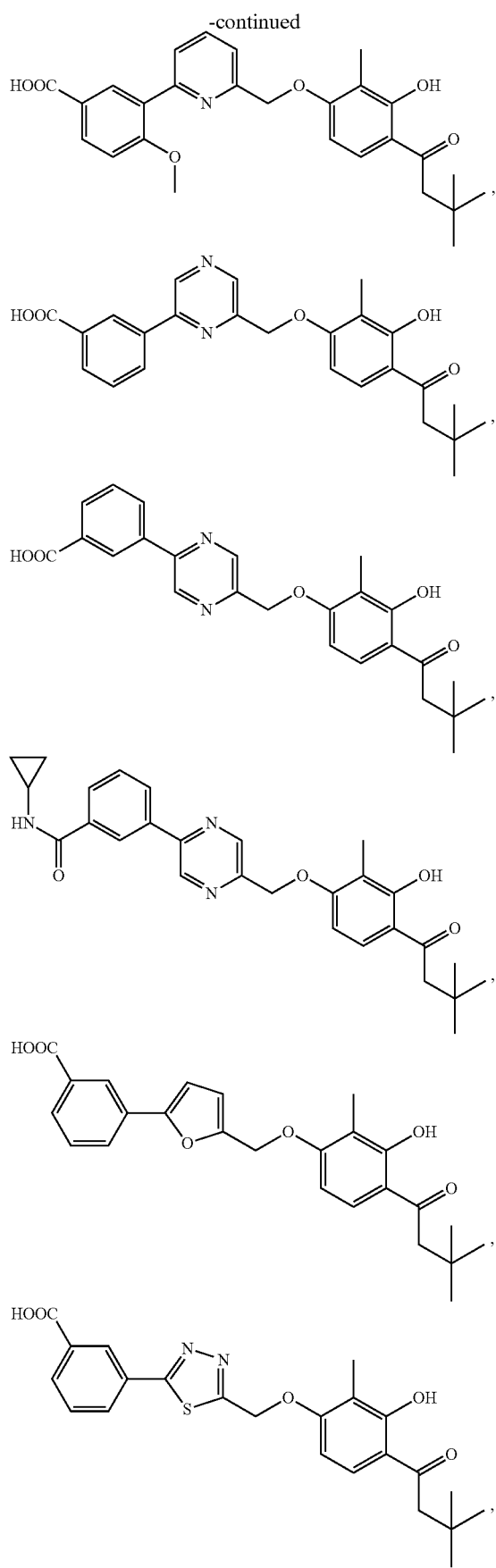

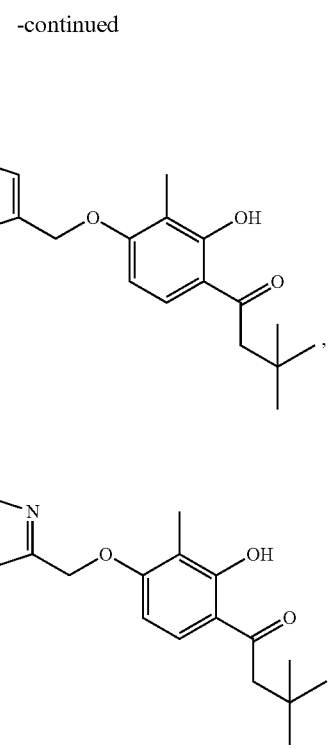

and

16. A pharmaceutical composition comprising a compound of claim 1, or a pharmaceutically acceptable salt thereof, and at least one pharmaceutically acceptable excipient.

17. A method of treating Alzheimer's disease, Parkinson's disease, Huntington's disease, Lou Gehrig's disease, or an addictive disorder in a subject, the method comprising the step of administering to a subject in need thereof a compound of claim 1, or a pharmaceutically acceptable salt thereof.

18. The method of claim 17, wherein the addictive disorder is nicotine addiction, alcohol addiction, opiate addiction, amphetamine addiction, methamphetamine addiction, or cocaine addiction.

19. A method of treating Alzheimer's disease, Parkinson's disease, Huntington's disease, Lou Gehrig's disease, or an addictive disorder in a subject, the method comprising the step of administering to a subject in need thereof a compound of claim 9, or a pharmaceutically acceptable salt thereof.

20. The method of claim 19, wherein the addictive disorder is nicotine addiction, alcohol addiction, opiate addiction, amphetamine addiction, methamphetamine addiction, or cocaine addiction.

21. A pharmaceutical composition comprising a compound of claim 9, or a pharmaceutically acceptable salt thereof, and at least one pharmaceutically acceptable excipient.

22. A method of treating Alzheimer's disease, Parkinson's disease, Huntington's disease, Lou Gehrig's disease, or an addictive disorder in a subject, the method comprising the step of administering to a subject in need thereof a compound of claim 11, or a pharmaceutically acceptable salt thereof.

23. The method of claim 22, wherein the addictive disorder is nicotine addiction, alcohol addiction, opiate addiction, amphetamine addiction, methamphetamine addiction, or cocaine addiction.

24. A pharmaceutical composition comprising a compound of claim 11, or a pharmaceutically acceptable salt thereof, and at least one pharmaceutically acceptable excipient.

* * * * *

UNITED STATES PATENT AND TRADEMARK OFFICE
CERTIFICATE OF CORRECTION

PATENT NO. : 10,099,993 B2
APPLICATION NO. : 15/301697
DATED : October 16, 2018
INVENTOR(S) : Raveendra Panickar Dhanya et al.

Page 1 of 1

It is certified that error appears in the above-identified patent and that said Letters Patent is hereby corrected as shown below:

In the Claims

Claim 11: Column 199, Lines 21-34:

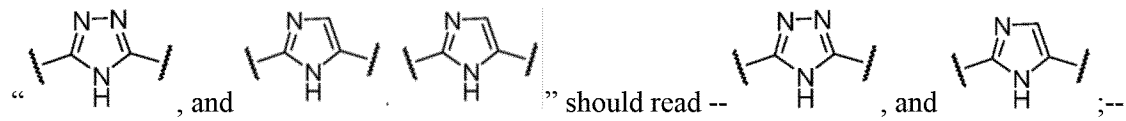

Signed and Sealed this
Fourteenth Day of May, 2019

Andrei Iancu
*Director of the United States Patent and Trademark Office*